US006881402B2

(12) United States Patent
Wold

(10) Patent No.: US 6,881,402 B2
(45) Date of Patent: Apr. 19, 2005

(54) INHIBITING APOPTOSIS WITH ADENOVIRUS RID PROTEIN

(75) Inventor: William S. M. Wold, Chesterfield, MO (US)

(73) Assignee: Saint Louis University, St. Louis, MO (US)

( * ) Notice: Subject to any disclaimer, the term of this patent is extended or adjusted under 35 U.S.C. 154(b) by 110 days.

(21) Appl. No.: 09/111,911

(22) Filed: Jul. 8, 1998

(65) Prior Publication Data

US 2003/0096768 A1 May 22, 2003

Related U.S. Application Data

(60) Provisional application No. 60/088,993, filed on Jul. 9, 1997.

(51) Int. Cl.[7] ......................... A61K 35/00; C12N 15/63

(52) U.S. Cl. ................... 424/93.6; 424/93.2; 435/320.1

(58) Field of Search ............................... 424/93.2, 93.6; 435/320.1, 69.1; 536/23.5; 514/44

(56) References Cited

U.S. PATENT DOCUMENTS 4,963,481 A * 10/1990 de Villiers ................. 435/69.1
6,156,306 A 12/2000 Brownlee et al. ........ 424/93.21

OTHER PUBLICATIONS

Deonarain, MP., "Ligand–targeted receptor–mediated vectors for gene delivery." Exp. Opin. ther. Patents, vol. 8 (1): 53–69, 1998.*

Crystal, RG., "Transfer of genes to humans: Early lessons and obstacles to success." Science, vol. 270 : 404–410, 1995.*

Miller et al., "Targeted vectors for gene therapy." FASEB, vol. 9: 190–199, Feb. 1995.*

Eck et al., "Gene–based Therapy," Goodman & Gilman's The Pharmacological Basis of Therapeutics– Ninth Edition, McGraw–Hill: 77–101, 1996.*

Deigner et al., "Modulating Apoptosis: Current Applications and Prospects for Future Drug Development." Current Medicinal Chemistry, vol. 6: 399–414, 1999.*

Tio et al., "Gene therapy to prevent restenosis, the Boston experience." Semin Intervent Cardiol, vol. 3: 205–210, 1998.*

Blau et al., "Molecular Medicine–Gene therapy– a Novel Form of Drug Delivery." The New England Journal of Medicine, vol. 333 (18): 1204–1207, Nov. 1995.*

Special News Report, "Gene Therapy's Growing Pains." Science, vol. 269: 1050–1055, Aug. 1995.*

Anderson, F., "Human Gene Therapy." Nature, vol. 392 supp: 25–30, Apr. 1998.*

Verma et al., "Gene therapy—promises, problems and prospects." Nature, vol. 389: 239–242, Sep. 1997.*

Carlin et al., Epidermal Growth Factor Receptor is Down–Regulated by a 10,400 MW Protein Encoded by the E3 Region of Adenovirus, *Cell*, 57:135–144 (1989(.

Clark et al., Molecular Pathways of CTL–mediated Cytotoxity, *Immunological Reviews*, 146:33–44 (1995).

Dimitrov et al., Adenovirus E3–10.4K/14.5K Protein Complex Inhjibits Tumor Necrosis Factor–Induced Translocation of Cytosolic Phospholipase $A_2$ to Membranes, *J. of Virol.*, 71:2830–2837 (1997).

Efrat et al., Prolonged survival of pancreatic islet allografts mediated by adenovirus immunoregulatory transgenes, *Proc. Natl. Acad. Sci. USA*, 92:6947–6951 (1995).

Fejer et al., Characterization of Transgenic Mice Containing Adenovirus Early Region 3 Genomic , DNA, *J. of Virol.*, 68:5871–5881 (1994).

French et al., Thyroiditis and hepatitis: Fas on the road to disease, *Nature Med.*, 3(4):387–388 (1997).

Friesen et al., Involvement of the CD95 (APO–1/Fas) receptor/ligand system in drug–induced apoptosis in leukemia cells, *Nature Med.*, 2(5):574–577 (1996).

Giordano et al., Potential Involvement of Fas and Its Ligand in the Pathogenesis of Hashimoto's Thyroiditis, *Science*, 275:960–963 (1997).

Hahne et al., Melanoma Cell Expression of Fas(Apo–1/CD95) Ligand: Implications for Tumor Immune Escape, *Science*, 274:1363–1366 (1996).

Hermiston et al., The Adenovirus E3–10.4K/14.5K Heterodimer, Renamed RID (Receptor Internalization and Degradation), Inhibits TNF–induced Apoptosis, Arachidonic Acid Release, Translocation of $cPLA_2$ to Membranes, and Fas–induced Apoptosis, and it Down–regulates Cell Surface Fas and EGF Receptor, Abstract presented at Small DNA Tumor Viruses Meeting, Jul. 9–14, 1996.

(Continued)

*Primary Examiner*—Ram R. Shukla
(74) *Attorney, Agent, or Firm*—Thompson Coburn, LLP

(57) ABSTRACT

A method for inhibiting apoptosis of a cell expressing a death receptor of the TNFR family is disclosed. The method involves treating the cell with a Receptor Internalization and Degradation (RID) protein complex containing RIDα (10.4K) and RIDβ (14.5K) proteins encoded by the E3 region of adenovirus. The cell can be treated by administering to the cell a polynucleotide expressing the RID complex or by administering to the cell a composition containing the RID complex. Compositions containing a RID complex are also disclosed. The compositions and method are useful in the treatment of cancer, degenerative and immune disorders, as well as in promoting survival of tissue transplants. An adenovirus vector for delivering the RID complex to cells is also disclosed.

6 Claims, 89 Drawing Sheets

(9 of 89 Drawing Sheet(s) Filed in Color)

OTHER PUBLICATIONS

Hermiston et al., Deletion Mutation Analysis of the Adenvirus Type 2 E3–gp19K Protein: Identification of Sequences within the Endoplasmic Reticulum Lumenal Domain That Are Required for Class I Antigen Binding and Protection from Adenovirus–Specific Cytotoxic T Lymphocytes, *Journal of Virology*, 67(9):5289–5298 (1993).

Herrath et al., Expression of adenoviral E3 transgenes in β cells prevents autoimmune diabetes, *Proc. Natl. Acad. Sci. USA*, 94:9808–9813 (1997).

Ilan et al., Insertion of the adenoviral E3 region into a recombinant viral vector prevents antiviral humoral and cellular immune responses and permits long–term gene expression, *Proc. Natl. Acad. Sci. USA*, 94:2587–2592 (1997).

Kondo et al., Essential roles of the Fas Ligand in the development of hepatitis, *Nature Medicine*, 3(4):409–413 (1997).

Krajcsi et al., The Adenovirus E3–14.7K Protein and the E3–10.4K/14.5K Complex of Proteins, Which Independently Inhibit Tumor Necrosis Factor (TNF)–Induced Apoptosis, Also Independently Inhibit TNF–Induced Release of Arachidonic Acid, *J. of Virol*, 70(8):4904–4913 (1996).

Lau et al., Prevention of Islet Allograft Rejection with Engineered Myoblasts Expressing FasL in Mice, *Science*, 273:109–112 (1996).

Lenardo, Fas and the Art of Lymphocyte Maintenance, *The Journal of Experimental Medicine*, 183:721–724 (1996).

Nagata, Fas ligand and immune evasion, *Nature Med.*, 2(12):1306–1307 (1996).

Nagata, Apoptosis by Death Factor, *Cell*, 88:355–365 (1997).

O'Connell et al., The Fas Counterattack: Fas–mediated T Cell Killing by Colon Cancer Cells Expressing Fas Ligand, *J. Exp. Med.*, 184:1075–1082 (1996).

Shisler et al., The Adenovirus E3–10.4K/14.5K Complex Mediates Loss of Cell Surface Fas (CD95) and Resistance to Fas–Induced Apoptosis, *J. of Virol.*, 71:8299–8306 (1997).

Sparer et al., The Role of Human Adenovirus Early Region 3 Proteins (gp19K, 10.4K, 14.5K, and 14.7K) in a Murine Pneumonia Model, *J. of Virol.*, 70:2431–2439 (1996).

Stewart et al., The Adenovirus E3 10.4K and 14.5K Proteins, Which Function to Prevent Cytolysis by Tumor Necrosis Factor and To Down–Regulate the Epidermal Growth Factor Receptor, Are Localized in the Plasma Membrane, *J. of Virol.*, 69:172–181 (1995).

Strand et al., Lymphocyte apoptosis induced by CD95 (APO–1/Fas) ligand–expressing tumor cells —A mechanism of immune evasion?, *Nature Medicine*, 2(12):1361–1366 (1996).

Tanaka et al., Fas ligand in human serum, *Nature Medicine*, 2(3): 317–322 (1996).

Tollefson et al., Forced degradation of Fas inhibits apoptosis in adenovirus–infected cells, *Nature*, 392:726–730 (1998).

Tollefson et al., The 10,400– and 14,500–Dalton Proteins Encoded by Region E3 of Adenovirus Form a Complex and Function togetehr to Down–Regulate the Epidermal Growth Factor Receptor, *J. of Virol.*, 65:3095–3105 (1991).

Williams, Tumor Cells Fight Back to Beat Immune System, *Science*, 274:1302 (1996).

Williams, Thyroid Disease: A Case of Cell Suicide?, Science, 275:926 (1997).

Wold, NIH Grant RO1 CA58538 pp. 1–2, 45–81 (Funded Jul. 18, 1997).

* cited by examiner

RID COMPLEX

RIDα-L (10.4K-L)

```
                10                  20
M I P R V L I L L T L V A L F C A C S T L A A V A H I E
        signal sequence

 30                 40                  50
V D C I P P F T V Y L L Y G F V T L I L I C S L V T V V
    *                                  transmembrane

   60                   70                  80
I A F I Q F I D W V C V R I A Y L R H H P Q Y R D R T I

       90
A D L L R I L
```

RIDα-S (10.4K-S)

```
                10                  20
A V A H I E V D C I P P F T V Y L L Y G F V T L I L I C
                *                          transmembrane

 30                 40                  50
S L V T V V I A F I Q F I D W V C V R I A Y L R H H P Q

     60
Y R D R T I A D L L R I L
```

Pre-RIDβ (14.5K)

```
                    10                      20
        M K F T V T F L L I I C T L S A F C S P T S K P Q R H I
            signal sequence

          30                    40                    50
        S C R F T R I W N I P S C Y N E K S D L S E A W L Y A I

          60                    70                    80
        I S V M V F C S T I L A L A I Y P Y L D I G W N A I D A
            Transmembrane

          90                   100                   110
        M N H P T F P A P A M L P L Q Q V V A G G F V P A N Q P

                   120                   130
        R P P S P T P T E I S Y F N L T G G D D
             *                     *
```

Figure 4C

Mature-RIDβ (14.5K)

```
                    10                      20
        S P T S K P Q R H I S C R F T R I W N I P S C Y N E K S

          30                    40                    50
        D L S E A W L Y A I I S V M V F C S T I L A L A I Y P Y
                  Transmembrane

          60                    70                    80
        L D I G W N A I D A M N H P T F P A P A M L P L Q Q V V

          90                   100                   110
        A G G F V P A N Q P R P P S P T P T E I S Y F N L T G G
                              *                     *

        D D
```

FIGURE 6A
A. *rec*700, anti-DPB
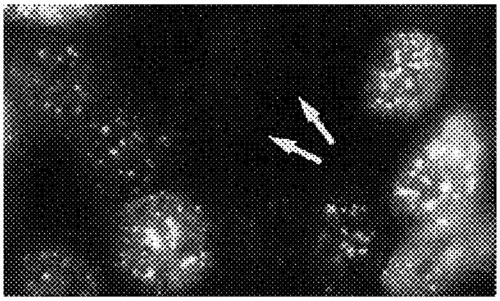
FIGURE 6B
B. *rec*700, DAPI
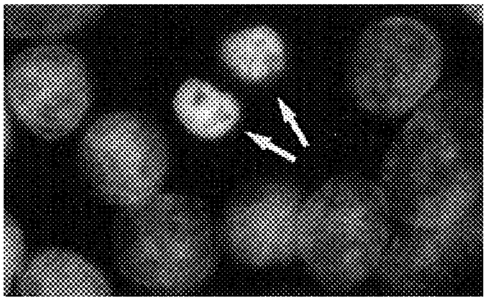
C. RID, anti-RIDβ
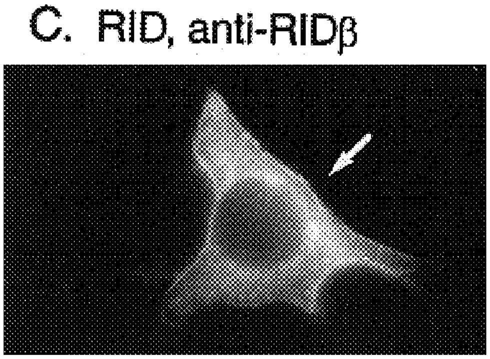
FIGURE 6C
D. RID, DAPI
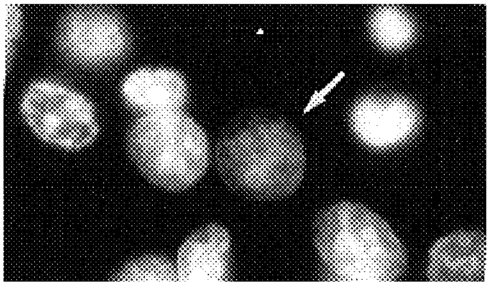
FIGURE 6D FIGURE 11A
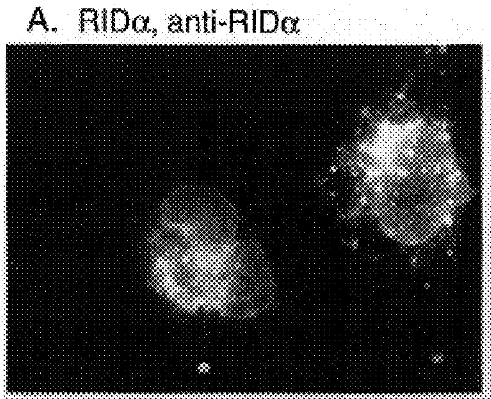
FIGURE 11B
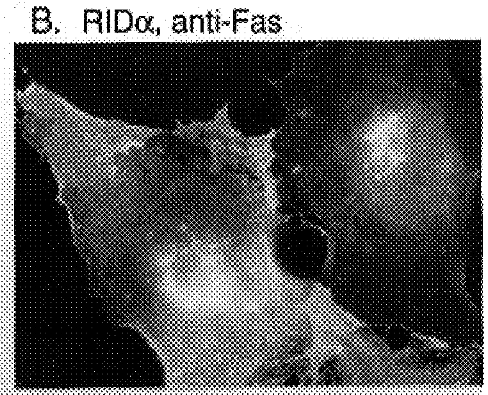
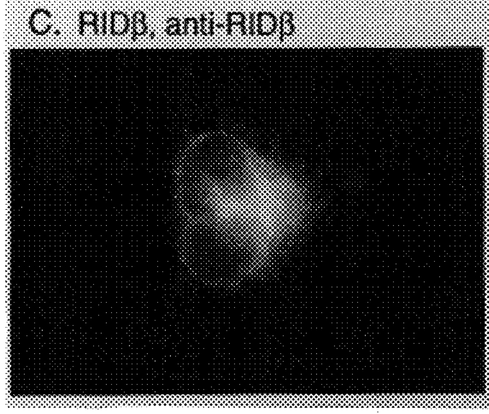
FIGURE 11C
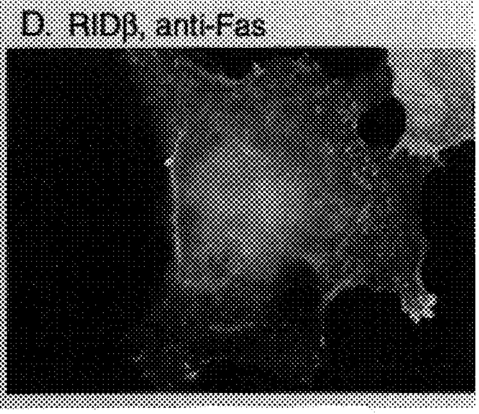
FIGURE 11D Mock - 93%
*rec*700 (Wild type) - 16%
*dl*712 (↑ RID) - 18%
Unstained control - 1.5%

Mock - 100%
*rec*700 (Wild type) - 11%
*dl*712 (↑ RID) - 14%
Unstained control - 1.5%

Mock - 93%
231-10 ($E3^+$ vector) 24 hr. p.i. - 35%
231-10 ($E3^+$ vector) 48hr. p.i. - 11%

```
      catcatcaataatataccttattttggattgaagccaatatgataatgagggggtggagt
    1 ---------+---------+---------+---------+---------+---------+ 60
      gtagtagttattatatggaataaaacctaacttcggttatactattactcccccacctca

                                                        EciI
                                                         |
      ttgtgacgtggcgcggggcgtgggaacggggcgggtgacgtagtagtgtggcggaagtgt
   61 ---------+---------+---------+---------+---------+---------+ 120
      aacactgcaccgcgccccgcacccttgccccgcccactgcatcatcacaccgccttcaca

                      AflIII
                    BspLU11I
                  EciI      |NspI
                      |     |   |
      gatgttgcaagtgtggcggaacacatgtaagcgacggatgtggcaaaagtgacgtttttg
  121 ---------+---------+---------+---------+---------+---------+ 180
      ctacaacgttcacaccgccttgtgtacattcgctgcctacaccgttttcactgcaaaaac

            BsrGI
       BsrFI    |
       SgrAI TatI                                 EciI
           |    |                                    |
      gtgtgcgccggtgtacacaggaagtgacaattttcgcgcggttttaggcggatgttgtag
  181 ---------+---------+---------+---------+---------+---------+ 240
      cacacgcggccacatgtgtccttcactgttaaaagcgcgccaaaatccgcctacaacatc

                                HaeI
                                MscI
   ApoI                       EaeI |
      |                          | |
      taaatttgggcgtaaccgagtaagatttggccattttcgcgggaaaactgaataagagga
  241 ---------+---------+---------+---------+---------+---------+ 300
      atttaaacccgcattggctcattctaaaccggtaaaagcgccctttgacttattctcct

                                                              ApoI
                                             HindIII         EcoRI
                                           ClaI    |   EcoRV     |
                                               |   |       |     |
      agtgaaatctgaataattttgtgttactcatagcgcgtaatatcgataagcttgatatcg
  301 ---------+---------+---------+---------+---------+---------+ 360
      tcactttagacttattaaaacacaatgagtatcgcgcattatagctattcgaactatagc

            BciVI
           PstI |
       SfcI   | |         Eco57I                        BssHII
         |    | |              |                            |
      aattcctgcagccctatggatacacggggttgaaggtatcttcagacggtcttgcgcgct
  361 ---------+---------+---------+---------+---------+---------+ 420
      ttaaggacgtcgggatacctatgtgccccaacttccatagaagtctgccagaacgcgcga

               TaqII
                   |
      tcatctgcaacaacatgaagatagtgggtgcggatggacaggaacaggaggaaactgaca
  421 ---------+---------+---------+---------+---------+---------+ 480
      agtagacgttgttgtacttctatcacccacgcctacctgtccttgtcctcctttgactgt

           XcmI                          AceIII
              |                               |
      ttccatttagattgtggagaaagtttgcagccaggaggaagctgcaataccagagctggg
  481 ---------+---------+---------+---------+---------+---------+ 540
      aaggtaaatctaacacctctttcaaacgtcggtcctccttcgacgttatggtctcgaccc

               BseRI            BspGI  ApoI
                   |                |     |
      aggagggcaaggaggtgctgctgaataaactggacagaaatttgctaactgattttaagt
  541 ---------+---------+---------+---------+---------+---------+ 600
      tcctcccgttcctccacgacgacttatttgacctgtctttaaacgattgactaaaattca

                                               BsaI
                                            BglII |
                                            BstYI |          HgiEII
                                                | |               |
      aagtgatgctttattatttttttttattagttaaagggaataagatctttgagaccgcac
  601 ---------+---------+---------+---------+---------+---------+ 660
      ttcactacgaaataataaaaaaaaataatcaatttcccttattctagaaactctggcgtg
```

Figure 28A

```
                                 Eco0109I
                                 Psp5II
                                 Sse8647I
                       BstYI       |    |   BsgII                  BsmI
                           |       |    |     ||                      |
     agggtcttaataagggtgcagagatcctcaggtccttgacaaggtgagtgaatgcagcct
661  ---------+---------+---------+---------+---------+---------+ 720
     tcccagaattattcccacgtctctaggagtccaggaactgttccactcacttacgtcgga

     tcggtttctaccgagtgctgagttatggtaatgggcttttctcccaccatgaccaccaat
721  ---------+---------+---------+---------+---------+---------+ 780
     agccaaagatggctcacgactcaataccattacccgaaaagagggtggtactggtggtta

                                 Bpu10I      BsaWI          Pfl1108I
                                   |           |                  |
     ttctgacgcttggttggcaacttgtagctaaggcggtgtccggtggtattactgtcgtag
781  ---------+---------+---------+---------+---------+---------+ 840
     aagactgcgaaccaaccgttgaacatcgattccgccacaggccaccataatgacagcatc

                                                          HincII
        HaeI                                              HpaI
          |                                                   |
     gtgactttggcctgctttaccagacaaaagataccccttttgcactggtgcaagttaacc
841  ---------+---------+---------+---------+---------+---------+ 900
     cactgaaaccggacgaaatggtctgttttctatggggaaaacgtgaccacgttcaattgg

                                                MspA1I
                                               BsiEI |
          BanII                                 EaeI | |
        BsiHKAI                                 EagI | |
       Bsp1286I                                GdiII | |
  PflMI     SacI                                   | | |
     |         |                                   | | |
     atgtcttggagctcttgattcatgcgctgttgctcggccgctgccctgcgtctttctagc
901  ---------+---------+---------+---------+---------+---------+ 960
     tacagaacctcgagaactaagtacgcgacaacgagccggcgacgggacgcagaaagatcg

   HaeII                                BglII
  AlwNI|                                BstYI
 BstAPI|                              XbaI |        BseRI
     ||                                  | |           |
     aggcgctgctctgtaataattccgtccatttctagatctagggtgtcagtcatctcctcc
961  ---------+---------+---------+---------+---------+---------+ 1020
     tccgcgacgagacattattaaggcaggtaaagatctagatcccacagtcagtagaggagg

     tgttagattaaagtagctgatttcagtgggggtgggagaagtggggcgaggctgattggc
1021 ---------+---------+---------+---------+---------+---------+ 1080
     acaatctaatttcatcgactaaagtcacccccaccctcttcaccccgctccgactaaccg

          BsrFI
        NgoAIV                   BtsI                TaqII
               |                    |                    |
     tgggacaaagccgccggcaacaacttgttgcagtggaagcatagcgggcgcggggaaagt
1081 ---------+---------+---------+---------+---------+---------+ 1140
     accctgtttcggcggccgttgttgaacaacgtcaccttcgtatcgcccgcgcccctttca

      DrdII       Bsp24I                              Bsp24I
          |            |                                   |
     tgggtggttcatggcatctattcgtttccagccaatgtcaaggtagggatatatagctag
1141 ---------+---------+---------+---------+---------+---------+ 1200
     acccaccaagtaccgtagataagcaaaggtcggttacagttccatccctatatatcgatc

                  PstI
              SfcI   |
                 |   |
     ggctaagatggtactgcagaacaccataacagagatgattgcatataaccaggcttcgga
1201 ---------+---------+---------+---------+---------+---------+ 1260
     ccgattctaccatgacgtcttgtggtattgtctctactaacgtatattggtccgaagcct

                                        SspI
                                           |
     aagatcgctttttttcattgtagcaacttggaatattccatatacgagtgaatctgcatga
1261 ---------+---------+---------+---------+---------+---------+ 1320
     ttctagcgaaaaaagtaacatcgttgaaccttataaggtatatgctcacttagacgtact

     tatatgtctttgaggcttggaggtcggggaacaaaacgcagatagggtgcaaataatcag
1321 ---------+---------+---------+---------+---------+---------+ 1380
     atatacagaaactccgaacctccagccccttgttttgcgtctatcccacgtttattagtc

                                       ApoI
                  ApoI                EcoRI                SfcI
                     |                    |                   |
     cagaaaagtcacagtaaatttcataattaaagaattctgagaagatcagctatagtcctg
1381 ---------+---------+---------+---------+---------+---------+ 1440
     gtcttttcagtgtcatttaaagtattaatttcttaagactcttctagtcgatatcaggac

                   Bsu36I            BsrDI
                 BanI   |            FspI|           BmrI
                    |   |               ||              |
     tctctgtattgcggatggtgcctgaggtacgcaatgcgcacacaaacccagtcaatgaac
1441 ---------+---------+---------+---------+---------+---------+ 1500
```

Figure 28B

```
     agagacataacgcctaccacggactccatgcgttacgcgtgtgtttgggtcagttacttg

                                  PstI
             SfcI          SfcI    |                        BspMI
              |             |      |                          |
     tgaatgaaggcgatgactacagtgacgaggctgcagatgaggataagggtgacaaatccg
1501 ---------+---------+---------+---------+---------+---------+ 1560
     acttacttccgctactgatgtcactgctccgacgtctactcctattcccactgtttaggc

                                                          EaeI
                                                          GdiII
                                                          SacII
                                                        MspA1I|
                                                        BsiEI ||
                                                        BstDSI ||
                                                             | ||
     taaagcaggtaaactgtgaaaggtgggatgcaatctacttcgatgtgagcgaccgcggcc
1561 ---------+---------+---------+---------+---------+---------+ 1620
     atttcgtccatttgacactttccaccctacgttagatgaagctacactcgctggcgccgg

                                                      AvaI
       BsiHKAI                                        SmlI
       Bsp1286I                                       XhoI
             |                                          |
     aatgtagagcacgcacagaaaagcgcaacaagggtcaataatataagaactcgaggaatc
1621 ---------+---------+---------+---------+---------+---------+ 1680
     ttacatctcgtgcgtgtcttttcgcgttgttcccagttattatattcttgagctccttag

                   EarI                                    ApoI
                     |                                        |
     atgtctcatttaatcatactgtaaaagaagagaacatggtttcagaccgtccaatctatg
1681 ---------+---------+---------+---------+---------+---------+ 1740
     tacagagtaaattagtatgacattttcttctcttgtaccaaagtctggcaggttagatac

                                        SfcI
    RleAI              BsiHKAI      HaeI |     HaeIV
     XmnI             Bsp1286I      StuI |     Hin4I
       |                    |          | |       |
     aatttttcattgtgtgggttgagcacaatgataggcctatagatgggggtctggcgcg
1741 ---------+---------+---------+---------+---------+---------+ 1800
     ttaaaaagtaacacacccaactcgtgttactatccggatatctacccccagaccgcgc

                                                         Bsp24I
                                                        HaeII |
                                                     Tth111II |
                                                   Eco47III | |
                                                          | | |
     tctgcgctttaggcaacaaataagccacataataataaggcaaacaaacataagcgctat
1801 ---------+---------+---------+---------+---------+---------+ 1860
     agacgcgaaatccgttgtttattcggtgtattattattccgtttgtttgtattcgcgata

                             Bsp24I
Tth111II                     BmrI |                          ApoI
     |                          | |                             |
     ggaaaaccaccacaagtccaagctcgcccagtcattgacaaaggcatgaacttggggtaa
1861 ---------+---------+---------+---------+---------+---------+ 1920
     ccttttggtggtgttcaggttcgagcgggtcagtaactgtttccgtacttgaaccccatt

                                          RleAI
                BsaWI       BtsI   BsbI     |
                  |           |      |      |
     atttagggcagatgttagtccggtagcagtggtgttgcgatagtccgttgtgggcgcgat
1921 ---------+---------+---------+---------+---------+---------+ 1980
     taaatcccgtctacaatcaggccatcgtcaccacaacgctatcaggcaacacccgcgcta

                                                    Eco57I
           HincII                                         
     BsrFI   |                          BpmI  BclI  ApoI  |  BtsI
       |     |                            |     |    |    |   |
     ggttgagccggtcaactctggagcaggcaagctgaagctgggtttgatcaaatttgcagt
1981 ---------+---------+---------+---------+---------+---------+ 2040
     ccaactcggccagttgagacctcgtccgttcgacttcgacccaaactagtttaaacgtca

      HaeII              HaeII
     AlwNI|          BsgI   |   BspGI            RleAI
         ||             |   |     |                |
     gcaggcgctggcagaaatcaggcgctaacgtccaggaaagtttgatttgaaggttgtggg
2041 ---------+---------+---------+---------+---------+---------+ 2100
     cgtccgcgaccgtctttagtccgcgattgcaggtcctttcaaactaaacttccaacaccc

                                                BspGI
                                      BpmI  RleAI |
                                        |      | |
     tataatcttgcccgcctggagcatatcccacatagagtaaattgtccaggggaatacaag
2101 ---------+---------+---------+---------+---------+---------+ 2160
     atattagaacgggcggacctcgtatagggtgtatctcatttaacaggtccccttatgttc

         Tth111II
             |
     caagcggaaaatcaaggcatttttcttttcatcaataaaactgcgtctgcttttgtatttg
2161 ---------+---------+---------+---------+---------+---------+ 2220
```

Figure 28C

```
     gttcgcctttagttccgtaaaagaaaagtagttattttgacgcagacgaaaacataaac

                                   HaeII
                              Eco47III |            BsrBI             BanI
                                     | |               |                 |
     agataaagtaaggtacataccaaagcaagcgctgtaataagcagagcggtggaacaaaag
2221 ---------+---------+---------+---------+---------+---------+ 2280
     tctatttcattccatgtatggtttcgttcgcgacattattcgtctcgccaccttgttttc

                                                              MslI
                                                          BsrGI |
            RleAI     MslI      Tth111II TatI             TatI  |
                |        |             |    |               | |
     gtgccagtgttctctaaacacttttgtgggggccacaacttgtactgtttgctcatgtac
2281 ---------+---------+---------+---------+---------+---------+ 2340
     cacggtcacaagagatttgtgaaaacacccccggtgttgaacatgacaaacgagtacatg

                                  ApoI
                                     |
     atggtaatatcgcacatttcataaaatggaaatttatacataaaagttttacgattttca
2341 ---------+---------+---------+---------+---------+---------+ 2400
     taccattatagcgtgtaaagtattttacctttaaatatgtattttcaaaatgctaaaagt

StyI          BbsI     DrdI
   |             |        |
     ccttggaagactgtgacattatagtcgttagtgtcacctggctgccaaatagcatataca
2401 ---------+---------+---------+---------+---------+---------+ 2460
     ggaaccttctgacactgtaatatcagcaatcacagtggaccgacggtttatcgtatatgt

                                     HindIII
                                         |
     gcatacttgccaattttgtctttgtggcgaataataagcttttcatgttctgtggtgcat
2461 ---------+---------+---------+---------+---------+---------+ 2520
     cgtatgaacggttaaaacagaaacaccgcttattattcgaaaagtacaagacaccacgta

                                       DraI
             BsmI                      SwaI   BsrDI          DrdII
                |                        |        |              |
     tttataagagtagtgcattcattagcttctgatttaaatgtaacattgcaagctggttcc
2521 ---------+---------+---------+---------+---------+---------+ 2580
     aaatattctcatcacgtaagtaatcgaagactaaatttacattgtaacgttcgaccaagg

                          HaeII
                          SfcI
                    Eco47III |PstI            BglI
                           | |   |               |
     ttaaactcaaccttttggcagcgctgcagactgccgcaagggcgagcaagcctaaaatc
2581 ---------+---------+---------+---------+---------+---------+ 2640
     aatttgagttggaaaaaccgtcgcgacgtctgacggcgttcccgctcgttcggattttag

                                        DraI     BaeI
                                           |        |
     atgtacctcatcttggatgttgcccccagcgtttaaaaagctgacaataggtacaaacgt
2641 ---------+---------+---------+---------+---------+---------+ 2700
     tacatggagtagaacctacaacgggggtcgcaaatttttcgactgttatccatgtttgca

                          BsgI
                    Bsu36I |
             BaeI        | |      MslI
                |        | |         |
     gcgtgcagcaggcggcaaccctaaggcacagaagtgctagtataagaataaacagaatta
2701 ---------+---------+---------+---------+---------+---------+ 2760
     cgcacgtcgtccgccgttgggattccgtgtcttcacgatcatattcttatttgtcttaat

                                                 HindIII
                                                       |
     caagagtaaggataaccccgaccccaattccagaaaaattagacaagcttgtagagttac
2761 ---------+---------+---------+---------+---------+---------+ 2820
     gttctcattcctattggggctggggttaaggtctttttaatctgttcgaacatctcaatg

                       PacI
                          |
     ttgaattgctcatatacttaattaaaaaatcccagcaccccgcaaaatgctttttgacc
2821 ---------+---------+---------+---------+---------+---------+ 2880
     aacttaacgagtatatgaattaatttttttagggtcgtggggcgttttacgaaaaaactgg

                    BanII
                  BslHKAI
                 Bsp1286I
                     Hin4I
              Hin4I SacI           BplI BplI
                  |    |               |   |
     tgagttccgggagttgagctcacctcctgtttttggaaaaatgggagtaatgtctggttac
2881 ---------+---------+---------+---------+---------+---------+ 2940
     actcaaggccctcaactcgagtggaggacaaaaaccttttttaccctcattacagaccaatg

         SfcI                    BsaWI
    RleAI  |                     BsrFI           BspMI
Bpu10I |   |                     PinAI        SunI |           AarI
     | |   |                         |           | |              |
```

Figure 28D

```
     gctcaggctgtaggtgtgggcgcagcaaccggtgacgcactcgtacgttcccggcaggtg
2941 ---------+---------+---------+---------+---------+---------+ 3000
     cgagtccgacatccacacccgcgtcgttggccactgcgtgagcatgcaagggccgtccac

                 BseRI
                   |
     aggagggtggtggtggtggtgtttttcttgacggtgtagttgaagccgagaaggttgtgt
3001 ---------+---------+---------+---------+---------+---------+ 3060
     tcctcccaccaccaccaccacaaaaagaactgccacatcaacttcggctcttccaacaca

                                               EarI
                         BsmBI                 SapI
                           |                     |
     ggcaaacttacttcgtctcgctggaaactgttgtaaattacaaatgaagagccgttaaag
3061 ---------+---------+---------+---------+---------+---------+ 3120
     ccgtttgaatgaagcagagcgacctttgacaacatttaatgtttacttctcggcaatttc

     HgiEII
  SexAI  |                           BsaWI    BsaXI         TaqII
     |   |                               |        |             |
     taccaggtaaggtacttattggcccgcttgtgcaaaccggaggtgaggtttgctttggtc
3121 ---------+---------+---------+---------+---------+---------+ 3180
     atggtccattccatgaataaccgggcgaacacgtttggcctccactccaaacgaaaccag

                                                           BmrI
                                                       BanII |
                                                       BsaXI |
                                                   Bsp1286I  |
                                                           | |
     tgctttgggtgggtaaaaacggtggcgttcacaggatggcgacaggagccccagtagatt
3181 ---------+---------+---------+---------+---------+---------+ 3240
     acgaaacccacccatttttgccaccgcaagtgtcctaccgctgtcctcggggtcatctaa

                                               BglII
                                   MslI        BstYI
                                     |           |
     ctaatttctgtatttattatactcagcacagagatgacaacaaagatcttgatgtaatcc
3241 ---------+---------+---------+---------+---------+---------+ 3300
     gattaaagacataaataatatgagtcgtgtctctactgttgtttctagaactacattagg

                                   EcoO109I
                                    Psp5II
                  BstDSI             SanDI   BsrBI BsrBI
                     |                   |      |     |
     agggttaggacagttgcaaaccacggtcagaacacagggaccccgctcccgctccactag
3301 ---------+---------+---------+---------+---------+---------+ 3360
     tcccaatcctgtcaacgtttggtgccagtcttgtgtccctggggcgagggcgaggtgatc

                                     BsaAI
        HaeII                      AflIII|TaqII
          |                             ||    |
     cagggggcgcttggtaaactcccgaatcaggctacgtgtaagctctacctgggtggtgag
3361 ---------+---------+---------+---------+---------+---------+ 3420
     gtcccccgcgaaccatttgagggcttagtccgatgcacattcgagatggacccaccactc

                        ApaI
                       BanII
                    Bsp1286I
                        BmgI |
                       BseSI |
   BsaHI            EcoO109I||                EarI
                                              SapI
      |                   || |                  |
     ccggacgccgtgcgccgggccctcgatatgctcttcgggcaattcaaagtaacaaaactc
3421 ---------+---------+---------+---------+---------+---------+ 3480
     ggcctgcggcacgcggcccgggagctatacgagaagcccgttaagtttcattgttttgag

            SacII
         MspA1I|
 BsaWI BstDSI ||                     BtsI
     |     |  ||                       |
     accggagccgcgggcaaagcacttgtggcggcggcagtggtcgaggtgtgtcaggcgcag
3481 ---------+---------+---------+---------+---------+---------+ 3540
     tggcctcggcgcccgtttcgtgaacaccgccgccgtcaccagctccacacagtccgcgtc

                              Pfl1108I     EciI
                                  |          |
     tcgctctgcctctccactggtcattcagtcgtagccgtccgccgagtctttcaccgcgtc
3541 ---------+---------+---------+---------+---------+---------+ 3600
     agcgagacggagaggtgaccagtaagtcagcatcggcaggcggctcagaaagtggcgcag

                                 EaeI
                                GdiII      BspGI
                                  |          |
     aaagttgggaataaactggtccgggtagtggccgggaggtccagaaaaggggttgaagta
3601 ---------+---------+---------+---------+---------+---------+ 3660
     tttcaacccttatttgaccaggcccatcaccggccctccaggtcttttccccaacttcat

                                                  BsaWI
       BseRI                                      BspEI    Hin4I
         |                                          |        |
```

Figure 28E

```
     aaccgaaggcacgaactcctcaataaattgtagagttccaatgcctccggagcgcggctc
3661 ---------+---------+---------+---------+---------+---------+ 3720
     ttggcttccgtgcttgaggagttatttaacatctcaaggttacggaggcctcgcgccgag

     Tch111I BplI SfcI PstI Hin4I EarI SapI EaeI GdiII BsrBI
     cgaggacgaggtctgcagagttaggatcgcctgacggggcgtaaatgaagagcggccagc
3721 ---------+---------+---------+---------+---------+---------+ 3780
     gctcctgctccagacgtctcaatcctagcggactgccccgcatttacttctcgccggtcg

     HaeII BspEI BsaWI BsaI Hin4I Bsp1286I BsiHKAI BanII SacI AceIII BseRI
     gccgccgatctgaaatgtcccgtccggacggagaccaagagaggagctcaccgactcgtc
3781 ---------+---------+---------+---------+---------+---------+ 3840
     cggcggctagactttacagggcaggcctgcctctggttctctcctcgagtggctgagcag

     BplI AvaI SmaI BamHI BstYI
     gttgagctgaatacctcgccctctgattttcaggtgagttataccctgcccgggggGGAT
3841 ---------+---------+---------+---------+---------+---------+ 3900
     caactcgacttatggagcgggagactaaaagtccactcaatatgggacgggcccccCCTA

     Hin4I Bsp1286I BsiHKAI BanII SacI BanI KpnI HindIII AflII SmlI
     Bsp24I DraI PmeI NheI BsaI SfcI Bsp24I
     CCGAGCTCGGTACCAAGCTTAAGTTTAAACGCTAGCCAGCTTGGGTCTCCCTATAGTGAG
3901 ---------+---------+---------+---------+---------+---------+ 3960
     GGCTCGAGCCATGGTTCGAATTCAAATTTGCGATCGGTCGAACCCAGAGGGATATCACTC

     VspI BtsI BanII BsiHKAI Bsp1286I SacI
     TCGTATTAATTTCGATAAGCCAGTAAGCAGTGGGTTCTCTAGTTAGCCAGAGAGCTCTGC
3961 ---------+---------+---------+---------+---------+---------+ 4020
     AGCATAATTAAAGCTATTCGGTCATTCGTCACCCAAGAGATCAATCGGTCTCTCGAGACG

     EciI
     TTATATAGACCTCCCACCGTACACGCCTACCGCCCATTTGCGTCAATGGGGCGGAGTTGT
4021 ---------+---------+---------+---------+---------+---------+ 4080
     AATATATCTGGAGGGTGGCATGTGCGGATGGCGGGTAAACGCAGTTACCCCGCCTCAACA

     BanI BsaHI AatII
     TACGACATTTTGGAAAGTCCCGTTGATTTTGGTGCCAAAACAAACTCCCATTGACGTCAA
4081 ---------+---------+---------+---------+---------+---------+ 4140
     ATGCTGTAAAACCTTTCAGGGCAACTAAAACCACGGTTTTGTTTGAGGGTAACTGCAGTT

     TatI
     TGGGGTGGAGACTTGGAAATCCCCGTGAGTCAAACCGCTATCCACGCCCATTGATGTACT
4141 ---------+---------+---------+---------+---------+---------+ 4200
     ACCCCACCTCTGAACCTTTAGGGGCACTCAGTTTGGCGATAGGTGCGGGTAACTACATGA

     BstDSI NcoI StyI MslI BsaAI SnaBI TatI
     GCCAAAACCGCATCACCATGGTAATAGCGATGACTAATACGTAGATGTACTGCCAAGTAG
4201 ---------+---------+---------+---------+---------+---------+ 4260
     CGGTTTTGGCGTAGTGGTACCATTATCGCTACTGATTATGCATCTACATGACGGTTCATC

     TatI BmrI Bsp24I BglI BsaHI
     GAAAGTCCCATAAGGTCATGTACTGGGCATAATGCCAGGCGGGCCATTTACCGTCATTGA
4261 ---------+---------+---------+---------+---------+---------+ 4320
     CTTTCAGGGTATTCCAGTACATGACCCGTATTACGGTCCGCCCGGTAAATGGCAGTAACT

     AatII Bsp24I NdeI TatI BglI
```

Figure 28F

```
     CGTCAATAGGGGGCGTACTTGGCATATGATACACTTGATGTACTGCCAAGTGGGCAGTTT
4321 ---------+---------+---------+---------+---------+---------+ 4380
     GCAGTTATCCCCCGCATGAACCGTATACTATGTGAACTACATGACGGTTCACCCGTCAAA

                            TaqII
                       AatII    |
                  BsaHI  |      |
                      |  |      |
     ACCGTAAATAGTCCACCCATTGACGTCAATGGAAAGTCCCTATTGGCGTTACTATGGGAA
4381 ---------+---------+---------+---------+---------+---------+ 4440
     TGGCATTTATCAGGTGGGTAACTGCAGTTACCTTTCAGGGATAACCGCAATGATACCCTT

              AatII
          BsaHI  |                              BglI
              |  |                                |
     CATACGTCATTATTGACGTCAATGGGCGGGGGTCGTTGGGCGGTCAGCCAGGCGGGCCAT
4441 ---------+---------+---------+---------+---------+---------+ 4500
     GTATGCAGTAATAACTGCAGTTACCCGCCCCCAGCAACCCGCCAGTCGGTCCGCCCGGTA

     TTACCGTAAGTTATGTAACGCGGAACTCCATATATGGGCTATGAACTAATGACCCCGTAA
4501 ---------+---------+---------+---------+---------+---------+ 4560
     AATGGCATTCAATACATTGCGCCTTGAGGTATATACCCGATACTTGATTACTGGGGCATT

                                     AflIII
                                       MluI
        VspI  SpeI                HincII |
           |     |                     | |
     TTGATTACTATTAATAACTAGTCAATAATCAATGTCAACGCGTATATCTGGCCCGTACAT
4561 ---------+---------+---------+---------+---------+---------+ 4620
     AACTAATGATAATTATTGATCAGTTATTAGTTACAGTTGCGCATATAGACCGGGCATGTA

                                                          HincII
                                                   Bsp24I   AccI|
    NruI                    Bpu10I                HindIII  SalI||
     |                         |                        |     |||
     CGCGAAGCAGCGCAAAACGCCTAACCCTAAGCAGATTCTTCATGCAATTcaagcttgtcg
4621 ---------+---------+---------+---------+---------+---------+ 4680
     GCGCTTCGTCGCGTTTTGCGGATTGGGATTCGTCTAAGAAGTACGTTAAgttcgaacagc

                        Bsp24I
    BglII         AflII     |
    BstYI          SmlI     |
       |              |     |
     acagatcttgggcgtggcttaagggtgggaaagaatatataaggtgggggtcttatgtag
4681 ---------+---------+---------+---------+---------+---------+ 4740
     tgtctagaacccgcaccgaattcccacccttcttatatattccacccccagaatacatc

                                      BsiHKAI
                                     Bsp1286I
                                            |
     ttttgtatctgttttgcagcagccgccgccgccatgagcaccaactcgtttgatggaagc
4741 ---------+---------+---------+---------+---------+---------+ 4800
     aaaacatagacaaaacgtcgtcggcggcggcggtactcgtggttgagcaaactaccttcg

                                  BstDSI
        BanII                       NcoI
      BsiHKAI                       StyI
     Bsp1286I                   NspI   |
         SacI                   SphI   |            BpmI
            |                      |   |               |
     attgtgagctcatatttgacaacgcgcatgcccccatgggccggggtgcgtcagaatgtg
4801 ---------+---------+---------+---------+---------+---------+ 4860
     taacactcgagtataaactgttgcgcgtacgggggtacccggccccacgcagtcttacac

                                                        Pfl1108I
       BanII                                              BsaI  |
    Bsp1286I                                          Bsp24I|   |
           |                                                ||  |
     atgggctccagcattgatggtcgccccgtcctgcccgcaaactctactaccttgacctac
4861 ---------+---------+---------+---------+---------+---------+ 4920
     tacccgaggtcgtaactaccagcggggcaggacgggcgtttgagatgatggaactggatg

                                     PstI
    Tth111I                       Eco57I|                  SfcI
      Hin4I|                        SfcI ||              AlwNI|
    MmeI  ||                  Bsp24I  |  ||  EciI       MspA1I|PstI
       |  ||                       |  |  ||    |            ||   |
     gagaccgtgtctggaacgccgttggagactgcagcctccgccgccgcttcagccgctgca
4921 ---------+---------+---------+---------+---------+---------+ 4980
     ctctggcacagaccttgcggcaacctctgacgtcggaggcggcggcgaagtcggcgacgt

          SacII                            BanII
        MspA1I|                         Bsp1286I       BstAPI
       BstDSI ||                    Bpu10I     |         BtsI
            | ||                         |     |            |
     gccaccgcccgcgggattgtgactgactttgctttcctgagcccgcttgcaagcagtgca
4981 ---------+---------+---------+---------+---------+---------+ 5040
     cggtggcgggcgccctaacactgactgaaacgaaaggactcgggcgaacgttcgtcacgt

                BsgI
```

Figure 28G

```
Tth111II   EciI  HincII   MunI
     gcttcccgttcatccgcccgcgatgacaagttgacggctcttttggcacaattggattct
5041                                                                 5100
     cgaagggcaagtaggcgggcgctactgttcaactgccgagaaaaccgtgttaacctaaga

SmaI AvaI  MmeI  AlwNI MspA1I PvuII  BstYI  BspMI
     ttgacccgggaacttaatgtcgtttctcagcagctgttggatctgcgccagcaggtttct
5101                                                                 5160
     aactgggcccttgaattacagcaaagagtcgtcgacaacctagacgcggtcgtccaaaga

BglI  Eco57I  DraI  Bsp24I  Tth111II  XcmI  AlwNI
     gccctgaaggcttcctcccctcccaatgcggtttaaaacataaataaaaaaccagactct
5161                                                                 5220
     cgggacttccgaaggaggggagggttacgccaaattttgtatttatttttggtctgaga

BsaBI  Bsp24I  Tth111II  BssHII  BssHII
     gtttggatttggatcaagcaagtgtcttgctgtctttatttaggggttttgcgcgcgcgg
5221                                                                 5280
     caaacctaaacctagttcgttcacagaacgacagaaataaatccccaaaacgcgcgcgcc

AvaI SmaI TaqII AhdI MspA1I HaeIV Hin4II  BsaI BsiEI  PspSII Eco0109I  PflMI
     taggcccgggaccagcggtctcggtcgttgagggtcctgtgtatttttccaggacgtgg
5281                                                                 5340
     atccgggccctggtcgccagagccagcaactcccaggacacataaaaaggtcctgcacc

BsmBI
     taaaggtgactctggatgttcagatacatgggcataagcccgtctctggggtggaggtag
5341                                                                 5400
     atttccactgagacctacaagtctatgtacccgtattcgggcagagaccccacctccatc

BtsI SfcI PstI  BsbI  Pfl1108I
     caccactgcagagcttcatgctgcggggtggtgttgtagatgatccagtcgtagcaggag
5401                                                                 5460
     gtggtgacgtctcgaagtacgacgccccaccacaacatctactaggtcagcatcgtcctc

Eco47III HaeII  BanI  Eco0109I  StyI
     cgctgggcgtggtgcctaaaaatgtctttcagtagcaagctgattgccaggggcaggccc
5461                                                                 5520
     gcgacccgcaccacggatttttacagaaagtcatcgttcgactaacggtccccgtccggg

TaqII  BsaAI
     ttggtgtaagtgtttacaaagcggttaagctgggatgggtgcatacgtggggatatgaga
5521                                                                 5580
     aaccacattcacaaatgtttcgccaattcgaccctacccacgtatgcacccctatactct

NsiI
     tgcatcttggactgtattttaggttggctatgttcccagccatatccctccggggattc
5581                                                                 5640
     acgtagaacctgacataaaaatccaaccgatacaagggtcggtatagggaggcccctaag

DrdII  BsgI  BsaWI  ApaLI  BseSI  Bsp1286I  BsiHKAI  BciVI  ApoI
     atgttgtgcagaaccaccagcacagtgtatccggtgcacttgggaaatttgtcatgtagc
5641                                                                 5700
     tacaacacgtcttggtggtcgtgtcacataggccacgtgaaccctttaaacagtacatcg

BsmBI  BsaHI  BsmI
     ttagaaggaaatgcgtggaagaacttggagacgcccttgtgacctccaagattttccatg
5701                                                                 5760
     aatcttcctttacgcaccttcttgaacctctgcgggaacactggaggttctaaaaggtac
```

Figure 28H

```
                                  ApaI
                                 BanII
                              Bsp1286I
                                BstDSI
                                 BmgI |
                  BstXI         BseSI |
     NsiI         MslI |        BsrDI |
     |            |  |             |  |
     cattcgtccataatgatggcaatgggcccacgggcggcggcctgggcgaagatatttctg
5761 ---------+---------+---------+---------+---------+---------+ 5820
     gtaagcaggtattactaccgttacccgggtgcccgccgccggacccgcttctataaagac

                      MslI                             HaeI
                        |                               |
     ggatcactaacgtcatagttgtgttccaggatgagatcgtcataggccatttttacaaag
5821 ---------+---------+---------+---------+---------+---------+ 5880
     cctagtgattgcagtatcaacacaaggtcctactctagcagtatccggtaaaaatgtttc

      EciI  BanI                     DrdII
        |     |                         |
     cgcgggcggagggtgccagactgcggtataatggttccatccggcccaggggcgtagtta
5881 ---------+---------+---------+---------+---------+---------+ 5940
     gcgcccgcctcccacggtctgacgccatattaccaaggtaggccgggtccccgcatcaat

                                                           AccI
                                                             |
     ccctcacagatttgcatttcccacgctttgagttcagatggggggatcatgtctacctgc
5941 ---------+---------+---------+---------+---------+---------+ 6000
     gggagtgtctaaacgtaaagggtgcgaaactcaagtctacccccctagtacagatggacg

                                                 BspMI
                                              MspA1I |
                                               PvuII |
      BspMI                                        |  |
        |
     ggggcgatgaagaaaacggtttccggggtaggggagatcagctgggaagaaagcaggttc
6001 ---------+---------+---------+---------+---------+---------+ 6060
     ccccgctacttcttttgccaaaggccccatcccctctagtcgacccttctttcgtccaag

                                       ApaI
                                      BanII
                                   Bsp1286I
        MspA1I            BsrFI       BmgI |
Bpu10I   PvuII          HgiEII|      BseSI |
     |     |                  ||         |  |
     ctgagcagctgcgacttaccgcagccggtgggcccgtaaatcacacctattaccgggtgc
6061 ---------+---------+---------+---------+---------+---------+ 6120
     gactcgtcgacgctgaatggcgtcggccacccgggcatttagtgtggataatggcccacg

                                MspA1I
                                 PvuII
                                 PstI|
     AceIII              SfcI     ||      Bpu10I
         |                  |     ||         |
     aactggtagttaagagagctgcagctgccgtcatccctgagcagggggggccacttcgtta
6121 ---------+---------+---------+---------+---------+---------+ 6180
     ttgaccatcaattctctcgacgtcgacggcagtagggactcgtcccccccggtgaagcaat

      NspI             NspI                 EciI        HaeII
        |                |                    |            |
     agcatgtccctgactcgcatgttttccctgaccaaatccgccagaaggcgctcgccgccc
6181 ---------+---------+---------+---------+---------+---------+ 6240
     tcgtacagggactgagcgtacaaaagggactggtttaggcggtcttccgcgagcggcggg

           BstAPI                       BsaI          EciI
              |                           |              |
     agcgatagcagttcttgcaaggaagcaaagtttttcaacggtttgagaccgtccgccgta
6241 ---------+---------+---------+---------+---------+---------+ 6300
     tcgctatcgtcaagaacgttccttcgtttcaaaaagttgccaaactctggcaggcggcat

                                                           RleAI
      NspI                              TaqII           AceIII|
      SphI                            Tth111II      BstEII AarI||
        |                                  |            |    |||
     ggcatgcttttgagcgtttgaccaagcagttccaggcggtcccacagctcggtcacctgc
6301 ---------+---------+---------+---------+---------+---------+ 6360
     ccgtacgaaaactcgcaaactggttcgtcaaggtccgccagggtgtcgagccagtggacg

   BspMI          BseRI
     |               |
     tctacggcatctcgatccagcatatctcctcgtttcgcgggttggggcggctttcgctgt
6361 ---------+---------+---------+---------+---------+---------+ 6420
     agatgccgtagagctaggtcgtatagaggagcaaagcgcccaaccccgccgaaagcgaca

                      BspGI
                BsiHKAI  |                    BstDSI       Eco0109I
               Bsp1286I  |                   BcgI  |        Psp5II
                      |  |                      |  |             |
     acggcagtagtcggtgctcgtccagacgggccagggtcatgtctttccacgggcgcaggg
6421 ---------+---------+---------+---------+---------+---------+ 6480
```

Figure 28I

```
      tgccgtcatcagccacgagcaggtctgcccggtcccagtacagaaaggtgcccgcgtccc

                                                             HaeI
                                                             MscI
                  BcgI                           BssHII  EaeI |
                    |                                 |     | |
      tcctcgtcagcgtagtctgggtcacggtgaaggggtgcgctccgggctgcgcgctggcca
6481  ---------+---------+---------+---------+---------+---------+ 6540
      aggagcagtcgcatcagacccagtgccacttccccacgcgaggcccgacgcgcgaccggt

                                          BsrFI
                                       HaeII |
                                       BbsI| |
                                  Eco47III|| |
         SmlI              Bce83I      ||| |      Eco57I
            |                   |      ||| |           |
      gggtgcgcttgaggctggtcctgctggtgctgaagcgctgccggtcttcgccctgcgcgt
6541  ---------+---------+---------+---------+---------+---------+ 6600
      cccacgcgaactccgaccaggacgaccacgacttcgcgacggccagaagcgggacgcgca

                             DrdI
                       BstDSI  |                  SacII
  EaeI                   NcoI  |              MspA1I|         BssHII
  GdiII                  StyI  |      BspGI  BstDSI ||     StyI     |
   |                        |  |          |       | ||        |     |
      cggccaggtagcatttgaccatggtgtcatagtccagcccctccgcggcgtggcccttgg
6601  ---------+---------+---------+---------+---------+---------+ 6660
      gccggtccatcgtaaactggtaccacagtatcaggtcggggaggcgccgcaccgggaacc

                                   BseRI
                                BssSI |
                             HaeII  | |
                          BsaHI  |  | |
                           NarI  |  | |
                 StyI      BanI| |  | |    BtsI
                    |         || |  | |       |
      cgcgcagcttgcccttggaggaggcgccgcacgaggggcagtgcagactttgagggcgt
6661  ---------+---------+---------+---------+---------+---------+ 6720
      gcgcgtcgaacgggaacctcctccgcggcgtgctccccgtcacgtctgaaactcccgca

  BsgI                               Hin4I        EcoO109I
   |                                     |               |
      agagcttgggcgcgagaaataccgattccggggagtaggcatccgcgccgcaggccccgc
6721  ---------+---------+---------+---------+---------+---------+ 6780
      tctcgaacccgcgctctttatggctaaggcccctcatccgtaggcgcggcgtccggggcg

                                    EaeI
                                   GdiII
                                  BanII |
                                BsiHKAI |
                               Bsp1286I |
             BsaI                   SacI |
             BsmI BssSI         XcmI  | |                SexAI
                |     |            |  | |                    |
      agacggtctcgcattccacgagccaggtgagctctggccgttcggggtcaaaaaccaggt
6781  ---------+---------+---------+---------+---------+---------+ 6840
      tctgccagagcgtaaggtgctcggtccactcgagaccggcaagccccagtttttggtcca

                                                   Hin4I
                                               BsrFI |
                                                   | |
      ttcccccatgctttttgatgcgtttcttacctctggtttccatgagccggtgtccacgct
6841  ---------+---------+---------+---------+---------+---------+ 6900
      aagggggtacgaaaaactacgcaaagaatggagaccaaaggtactcggccacaggtgcga

                                                             Bce83I
                                                             BsrBI|
                                                        AvaI    ||
                            BstZ17I           HaeI      SmlI    ||
                              AccI|   SmlI    StuI      XhoI    ||
                                 ||      |       |         |    ||
      cggtgacgaaaaggctgtccgtgtccccgtatacagacttgagaggcctgtcctcgagcg
6901  ---------+---------+---------+---------+---------+---------+ 6960
      gccactgcttttccgacaggcacaggggcatatgtctgaactctccggacaggagctcgc

        SacII
      MspA1I|
    BstDSI ||
    BseRI| ||                                  Hin4I       BspGI
        || ||                                      |           |
      gtgttccgcggtcctcctcgtatagaaactcggaccactctgagacaaaggctcgcgtcc
6961  ---------+---------+---------+---------+---------+---------+ 7020
      cacaaggcgccaggaggagcatatctttgagcctggtgagactctgtttccgagcgcagg

   HaeI              BsaXI                BsiEI        BpmI
      |                  |                    |           |
      aggccagcacgaaggaggctaagtgggaggggtagcggtcgttgtccactagggggtcca
7021  ---------+---------+---------+---------+---------+---------+ 7080
      tccggtcgtgcttcctccgattcaccctccccatcgccagcaacaggtgatcccccaggt
```

Figure 28J

```
     NspI, BbsI, PshAI, AflIII, BspLU11I, EarI
7081 ctcgctccagggtgtgaagacacatgtcgccctcttcggcatcaaggaaggtgattggtt 7140
     gagcgaggtcccacacttctgtgtacagcgggagaagccgtagttccttccactaaccaa

     BsaAI, PmlI, HaeI, Eco57I
7141 tgtaggtgtaggccacgtgaccgggtgttcctgaaggggggctataaaagggggtggggg 7200
     acatccacatccggtgcactggcccacaaggacttccccccgatattttcccccaccccc

     PflMI, MspA1I, PvuII, ScaI, TatI, EarI
7201 cgcgttcgtcctcactctcttccgcatcgctgtctgcgagggccagctgttggggtgagt 7260
     gcgcaagcaggagtgagagaaggcgtagcgacagacgctcccggtcgacaaccccactca

7261 actccctctgaaaagcgggcatgacttctgcgctaagattgtcagtttccaaaaacgagg 7320
     tgagggagacttttcgcccgtactgaagacgcgattctaacagtcaaaggtttttgctcc

     SacII, MspA1I, BstDSI, BseRI, EaeI, GdiII
7321 aggatttgatattcacctggcccgcggtgatgcctttgagggtggccgcatccatctggt 7380
     tcctaaactataagtggaccgggcgccactacggaaactcccaccggcgtaggtagacca

     HindIII, MmeI
7381 cagaaaagacaatctttttgttgtcaagcttggtggcaaacgacccgtagagggcgttgg 7440
     gtcttttctgttagaaaaacaacagttcgaaccaccgtttgctgggcatctcccgcaacc

     BssHII, BsiEI, PvuI, NruI, BsgI, EaeI, GdiII, StyI
7441 acagcaacttggcgatggagcgcagggtttggtttttgtcgcgatcggcgcgctccttgg 7500
     tgtcgttgaaccgctacctcgcgtcccaaaccaaaaacagcgctagccgcgcgaggaacc

     BsaAI, BssHII
7501 ccgcgatgtttagctgcacgtattcgcgcgcaacgcaccgccattcgggaaagacggtgg 7560
     ggcgctacaaatcgacgtgcataagcgcgcgttgcgtggcggtaagccctttctgccacc

     BsiHKAI, Bsp1286I, BseSI, ApaLI, BstAPI, DraIII, Bsp1286I, SexAI,
     BmgI, BseSI, BanII, SacII, MspA1I, BstDSI, Tth111I, HincII
7561 tgcgctcgtcgggcaccaggtgcacgcgccaaccgcggttgtgcagggtgacaaggtcaa 7620
     acgcgagcagcccgtggtccacgtgcgcggttggcgccaacacgtcccactgttccagtt

     BsiEI, EaeI, EagI, GdiII, NotI, BsgI, HaeII, BspGI
7621 cgctggtggctacctctccgcgtaggcgctcgttggtccagcagaggcggccgcccttgc 7680
     gcgaccaccgatggagaggcgcatccgcgagcaaccaggtcgtctccgccggcgggaacg

     BsmBI, BstDSI
7681 gcgagcagaatggcggtagggggtctagctgcgtctcgtccggggggtctgcgtccacgg 7740
     cgctcgtcttaccgccatcccccagatcgacgcagagcaggccccccagacgcaggtgcc
```

Figure 28K

```
             SmaI
          AvaI |       BssHII
             | |            |
      taaagaccccgggcagcaggcgcgcgtcgaagtagtctatcttgcatccttgcaagtcta
 7741 ---------+---------+---------+---------+---------+---------+ 7800
      atttctggggcccgtcgtccgcgcgcagcttcatcagatagaacgtaggaacgttcagat

                                                          BstDSI
                                                   Eco0109I    |
                                  BssHII            Psp5II NcoI
     HaeII                     BssHII |              SanDI StyI
         |                          | |                  |    |
      gcgcctgctgccatgcgcgggcggcaagcgcgcgctcgtatgggttgagtgggggacccc
 7801 ---------+---------+---------+---------+---------+---------+ 7860
      cgcggacgacggtacgcgcccgccgttcgcgcgcgagcatacccaactcaccccctgggg

       PflMI
  TaqII |                           NspI                      Hin4I
      | |                             |                           |
      atggcatggggtgggtgagcgcggaggcgtacatgccgcaaatgtcgtaaacgtagaggg
 7861 ---------+---------+---------+---------+---------+---------+ 7920
      taccgtaccccacccactcgcgcctccgcatgtacggcgtttacagcatttgcatctccc

                                               SacII
    BanII                                   MspA1I|
 Bsp1286I            BplI                BstDSI ||      BssHII
        |               |                     | ||           |
      gctctctgagtattccaagatatgtagggtagcatcttccaccgcggatgctggcgcgca
 7921 ---------+---------+---------+---------+---------+---------+ 7980
      cgagagactcataaggttctatacatcccatcgtagaaggtggcgcctacgaccgcgcgt

 BsaAI                                        BseRI       TaqII
     |                                            |           |
      cgtaatcgtatagttcgtgcgaggggagcgaggaggtcgggaccgaggttgctacgggcgg
 7981 ---------+---------+---------+---------+---------+---------+ 8040
      gcattagcatatcaagcacgctcccctcgctcctccagccctggctccaacgatgcccgcc

                            MmeI          NspI
                       BbsI    |       MmeI |   Eco57I
                          |    |          | |        |
      gctgctctgctcggaagactatctgcctgaagatggcatgtgagttggatgatatggttg
 8041 ---------+---------+---------+---------+---------+---------+ 8100
      cgacgagacgagccttctgatagacggacttctaccgtacactcaacctactataccaac

                               BsaI
                  BbsI     BsaHI |
                     |         | |
      gacgctggaagacgttgaagctggcgtctgtgagacctaccgcgtcacgcacgaaggagg
 8101 ---------+---------+---------+---------+---------+---------+ 8160
      ctgcgaccttctgcaacttcgaccgcagacactctggatggcgcagtgcgtgcttcctcc

                           BsgI      AceIII       BspMI
                    HincII  |   BstEII  |   DrdI   |
                          | |        |  |      |   |
      cgtaggagtcgcgcagcttgttgaccagctcggcggtgacctgcacgtctagggcgcagt
 8161 ---------+---------+---------+---------+---------+---------+ 8220
      gcatcctcagcgcgtcgaacaactggtcgagccgccactggacgtgcagatcccgcgtca

   BspGI
       |
      agtccagggtttccttgatgatgtcatacttatcctgtcccttttttttccacagctcgc
 8221 ---------+---------+---------+---------+---------+---------+ 8280
      tcaggtcccaaaggaactactacagtatgaatagga cagggaaaaaaaaggtgtcgagcg

                                    ScaI
   AceIII              EarI      TatI |
        |                 |         | |
      ggttgaggacaaactcttcgcggtctttccagtactcttggatcggaaacccgtcggcct
 8281 ---------+---------+---------+---------+---------+---------+ 8340
      ccaactcctgtttgagaagcgccagaaaggtcatgagaacctagcctttgggcagccgga

                          NspI     HincII      BglI
                             |          |         |
      ccgaacggtaagagcctagcatgtagaactggttgacggcctggtaggcgcagcatcccct
 8341 ---------+---------+---------+---------+---------+---------+ 8400
      ggcttgccattctcggatcgtacatcttgaccaactgccggaccatccgcgtcgtaggga

                                        TaqII
                                    RleAI |
                                  BsaWI | |
                          BglI  BspEI | | |
                             |      | | | |
      tttctacgggtagcgcgtatgcctgcgcggccttccggagcgaggtgtgggtgagcgcaa
 8401 ---------+---------+---------+---------+---------+---------+ 8460
      aaagatgcccatcgcgcatacggacgcgccggaaggcctcgctccacacccactcgcgtt

                                                            EciI
                                                               |
      aggtgtccctgaccatgactttgaggtactggtatttgaagtcagtgtcgtcgcatccgc
```

Figure 28L

```
8461 ---------+---------+---------+---------+---------+---------+ 8520
     tccacagggactggtactgaaactccatgaccataaacttcagtcacagcagcgtaggcg

     cctgctcccagagcaaaaagtccgtgcgcttttggaacgcggatttggcagggcgaagg
8521 ---------+---------+---------+---------+---------+---------+ 8580
     ggacgagggtctcgtttttcaggcacgcgaaaaccttgcgcctaaaccgtcccgcttcc

                                                        Eco0109I
                                                          Psp5II
      EarI                                                 SanDI
        |                                                      |
     tgacatcgttgaagagtatctttcccgcgcgaggcataaagttgcgtgtgatgcggaagg
8581 ---------+---------+---------+---------+---------+---------+ 8640
     actgtagcaacttctcatagaaagggcgcgctccgtatttcaacgcacactacgccttcc

                                            BsiHKAI
      BanI                                 Bsp1286I
        |                                       |
     gtcccggcacctcggaacggttgttaattacctgggcggcgagcacgatctcgtcaaagc
8641 ---------+---------+---------+---------+---------+---------+ 8700
     cagggccgtggagccttgccaacaattaatggacccgccgctcgtgctagagcagtttcg

                                 RleAI
                                   |
     cgttgatgttgtggcccacaatgtaaagttccaagaagcgcgggatgcccttgatggaag
8701 ---------+---------+---------+---------+---------+---------+ 8760
     gcaactacaacaccgggtgttacatttcaaggttcttcgcgccctacgggaactaccttc

                                                        BsiHKAI
                                                       Bsp1286I
                          BanII               BanII          |
                        BsiHKAI            Bsp1286I          |
                       Bsp1286I     Bpu1102I      |          |
             Pfl1108I       SacI EarI       |     |          |
           Eco57I   |  AceIII   | SapI      |     |          |
                |   |       |   |   |       |     |          |
     gcaatttttaagttcctcgtaggtgagctcttcaggggagctgagcccgtgctctgaaa
8761 ---------+---------+---------+---------+---------+---------+ 8820
     cgttaaaaaattcaaggagcatccactcgagaagtcccctcgactcgggcacgagacttt

       BmrI
      ApaI|
     BanII|
  Bsp1286I|
     MmeI||
     BmgI|||
    BseSI|||                             BanII
Eco0109I ||||                           BsiHKAI
                                       Bsp1286I
                                           SacI
      | ||||                                  |
     gggcccagtctgcaagatgagggttggaagcgacgaatgagctccacaggtcacgggcca
8821 ---------+---------+---------+---------+---------+---------+ 8880
     cccgggtcagacgttctactcccaaccttcgctgcttactcgaggtgtccagtgcccggt

                            Eco0109I
                              Psp5II
                            Sse8647I                 HaeI
BspMI           AarI  NruI         |                 MscI
    |              |     |         |            EaeI  |
     ttagcatttgcaggtggtcgcgaaaggtcctaaactggcgacctatggccatttttctg
8881 ---------+---------+---------+---------+---------+---------+ 8940
     aatcgtaaacgtccaccagcgctttccaggatttgaccgctggataccggtaaaaagac

                                   MspA1I         StyI
                                        |            |
     gggtgatgcagtagaaggtaagcgggtcttgttcccagcggtcccatccaaggttcgcgg
8941 ---------+---------+---------+---------+---------+---------+ 9000
     cccactacgtcatcttccattcgcccagaacaagggtcgccagggtaggttccaagcgcc

          BsaI                          EciI    RcaI     AceIII
            |                              |       |          |
     ctaggtctcgcgcggcagtcactagaggctcatctccgccgaacttcatgaccagcatga
9001 ---------+---------+---------+---------+---------+---------+ 9060
     gatccagagcgcgccgtcagtgatctccgagtagaggcggcttgaagtactggtcgtact

       BstAPI
 Bsp1286I   |
    BssSI|  |
     BmgI||  |                                   Pfl1108I
    BseSI||  |      Eco0109I                 BsaI       | BsmBI
        |||  |             |                    |       |     |
     agggcacgagctgcttcccaaaggcccccatccaagtataggtctctacatcgtaggtga
9061 ---------+---------+---------+---------+---------+---------+ 9120
     tcccgtgctcgacgaagggtttccgggggtaggttcatatccagagatgtagcatccact

                                                BsaXI
                                                AloI|
                                   BsiEI       BstYI|
                                    PvuI       UbaLI|          MunI
                                       |           ||             |
     caaagagacgctcggtgcgaggatgcgagccgatcgggaagaactggatctcccgccacc
```

Figure 28M

```
9121 ---------+---------+---------+---------+---------+---------+ 9180
     gtttctctgcgagccacgctcctacgctcggctagcccttcttgacctagagggcggtgg

     PflMI             BseRI                                  BssSI
     |                 |                                      |
     aattggaggagtggctattgatgtggtgaaagtagaagtccctgcgacgggccgaacact
9181 ---------+---------+---------+---------+---------+---------+ 9240
     ttaacctcctcaccgataactacaccactttcatcttcagggacgctgcccggcttgtga

                                             BsiHKAI
                                            Bsp1286I
                                               BsgI|
                               ScaI          BseSI||
                            TatI |        ApaLI ||| BsrGI
                         FspI | |   MspA1I | ||| TatI
                            | | |        | | |||   |
     cgtgctggctttgtaaaaacgtgcgcagtactggcagcggtgcacgggctgtacatcct
9241 ---------+---------+---------+---------+---------+---------+ 9300
     gcacgaccgaaaacattttgcacgcgtcatgaccgtcgccacgtgcccgacatgtagga

BssSI                                               BanII
EcoNI  HincII      BsiEI               ApoI  Bsp1286I
    |      |           |                  |         |
     gcacgaggttgacctgacgaccgcgcacaaggaagcagagtgggaatttgagcccctcgc
9301 ---------+---------+---------+---------+---------+---------+ 9360
     cgtgctccaactggactgctggcgcgtgttccttcgtctcacccttaaactcggggagcg

                                                              AvaI
                                                              SmlI
           BbsI    Tth111II                                   XhoI
              |          |                                       |
     ctggcgggtttggctggtggtcttctacttcggctgcttgtccttgaccgtctggctgct
9361 ---------+---------+---------+---------+---------+---------+ 9420
     gaccgcccaaaccgaccaccagaagatgaagccgacgaacaggaactggcagaccgacga

                                             BanII   MmeI
       BsaXI                          Bsp1286I BspGI|   BssHII
           |                                 |    ||       |
     cgaggggagttacggtggatcggaccaccacgccgcgcgagcccaaagtccagatgtccg
9421 ---------+---------+---------+---------+---------+---------+ 9480
     gctcccctcaatgccacctagcctggtggtgcggcgcgctcgggtttcaggtctacaggc

                                                  BstDSI
                                                   NcoI
       BsiEI              AceIII                   StyI PflMI
           |                   |                       |     |
     cgcgcggcggtcggagcttgatgacaacatcgcgcagatgggagctgtccatggtctgga
9481 ---------+---------+---------+---------+---------+---------+ 9540
     gcgcgccgccagcctcgaactactgttgtagcgcgtctaccctcgacaggtaccagacct

           BsaHI
         SacII |
       MspA1I| |
     BstDSI || |
    BanII | || |                         SfcI
  BsiHKAI | || |                   BanII |
 Bsp1286I | || |                 BsiHKAI |
    SacI  | || |               Bsp1286I |PstI
          | || |     BpmI     BspMI SacI |SbfI
          | || |        |         |    |  |   |
     gctcccgcggcgtcaggtcaggcgggagctcctgcaggtttacctcgcatagacgggtca
9541 ---------+---------+---------+---------+---------+---------+ 9600
     cgagggcgccgcagtccagtccgccctcgaggacgtccaaatggagcgtatctgcccagt

                                               XcmI
                                             AlwNI|
         BstYI                               PflMI|      BsaHI
             |                                    ||          |
     gggcgcgggctagatccaggtgatacctaatttccaggggctggttggtggcggcgtcga
9601 ---------+---------+---------+---------+---------+---------+ 9660
     cccgcgcccgatctaggtccactatggattaaaggtccccgaccaaccaccgccgcagct

                          SacII
                        MspA1I|
                       BstDSI ||
                                          KpnI
            Hin4I      BaeI| ||     BanI    |          BaeI
                |          || ||       |    |             |
     tggcttgcaagaggccgcatccccgcggcgcgactacggtaccgcgcggcgggcggtggg
9661 ---------+---------+---------+---------+---------+---------+ 9720
     accgaacgttctccggcgtaggggcgccgcgctgatgccatggcgcgccgcccgccaccc

   SacII                     NsiI
 MspA1I|             HaeIV    |                    BanII
 BstDSI ||     StyI   Hin4I   |                 Bsp1286I
      | ||        |       |   |                        |
     ccgcggggtgtccttggatgatgcatctaaaagcggtgacgcgggcgagcccccggagg
9721 ---------+---------+---------+---------+---------+---------+ 9780
     ggcgccccacaggaacctactacgtagattttcgccactgcgcccgctcgggggcctcc

                                                    AceIII
                                                    BssHII
```

Figure 28N

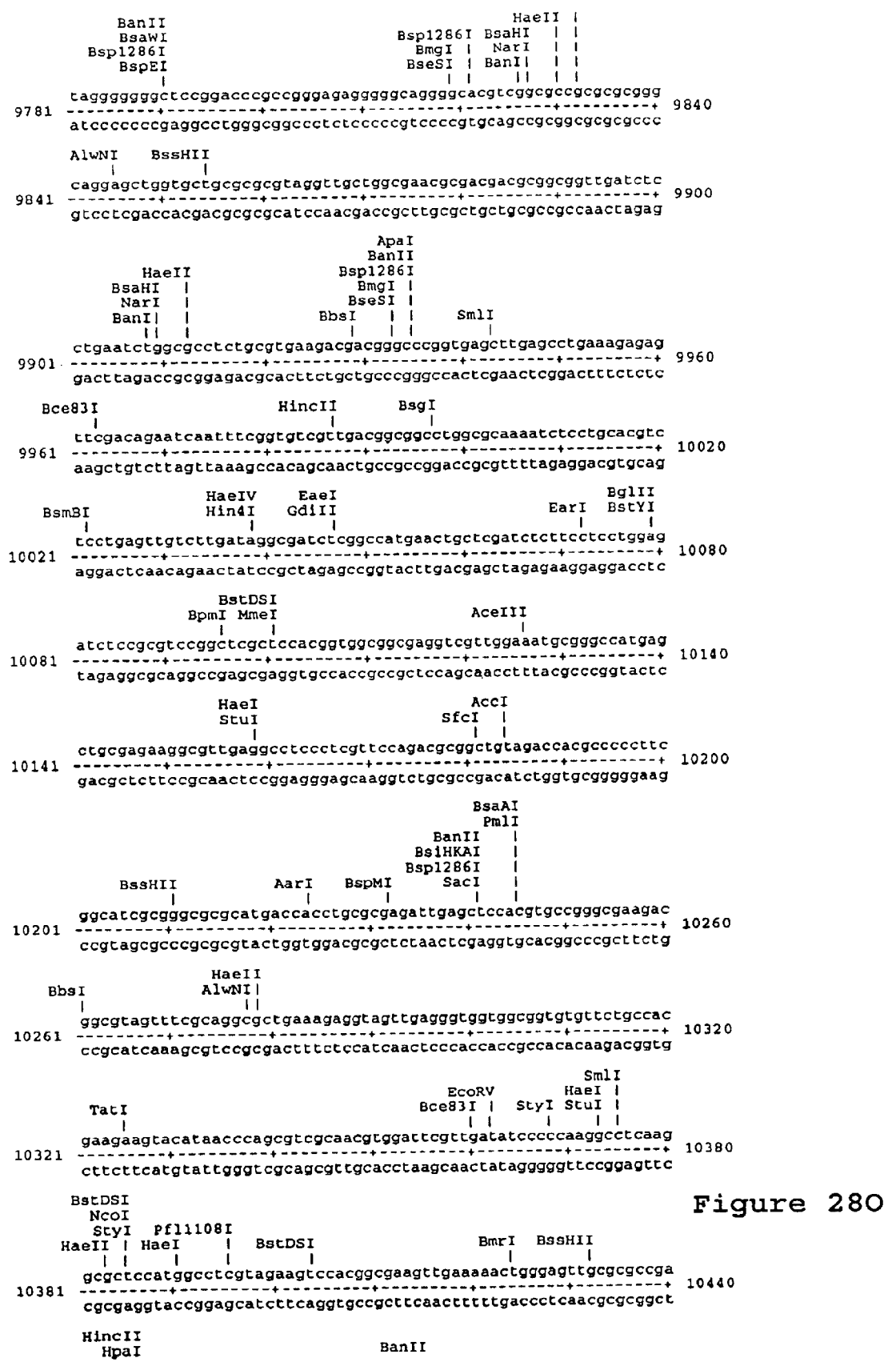

```
BanII
BsaWI
Bsp1286I
BspEI
                                        HaeII
                                Bsp1286I BsaHI
                                BmgI     NarI
                                BseSI    BanII
      tagggggggctccggacccgccgggagaggggcaggggcacgtcggcgccgcgcgcggg
 9781 ---------+---------+---------+---------+---------+---------+ 9840
      atcccccccgaggcctgggcggccctctccccgtccccgtgcagccgcggcgcgcgccc

AlwNI BssHII
      caggagctggtgctgcgcgcgtaggttgctggcgaacgcgacgacgcggcggttgatctc
 9841 ---------+---------+---------+---------+---------+---------+ 9900
      gtcctcgaccacgacgcgcgcatccaacgaccgcttgcgctgctgcgccgccaactagag

                            ApaI
                            BanII
    HaeII                   Bsp1286I
  BsaHI                     BmgI
  NarI                      BseSI
  BanI                 BbsI           SmlI
      ctgaatctggcgcctctgcgtgaagacgacgggcccggtgagcttgagcctgaaagagag
 9901 ---------+---------+---------+---------+---------+---------+ 9960
      gacttagaccgcggagacgcacttctgctgcccgggccactcgaactcggactttctctc

Bce83I                HincII     BsgI
      ttcgacagaatcaatttcggtgtcgttgacggcggcctggcgcaaaatctcctgcacgtc
 9961 ---------+---------+---------+---------+---------+---------+ 10020
      aagctgtcttagttaaagccacagcaactgccgccggaccgcgttttagaggacgtgcag

                 HaeIV  EaeI                            BglII
BsmBI            Hin4I  GdiII                    EarI  BstYI
      tcctgagttgtcttgataggcgatctcggccatgaactgctcgatctcttcctcctggag
10021 ---------+---------+---------+---------+---------+---------+ 10080
      aggactcaacagaactatccgctagagccggtacttgacgagctagagaaggaggacctc

                 BstDSI
              BpmI MmeI                  AceIII
      atctccgcgtccggctcgctccacggtggcggcgaggtcgttggaaatgcgggccatgag
10081 ---------+---------+---------+---------+---------+---------+ 10140
      tagaggcgcaggccgagcgaggtgccaccgccgctccagcaacctttacgcccggtactc

                 HaeI                        AccI
                 StuI                   SfcI
      ctgcgagaaggcgttgaggcctccctcgttccagacgcggctgtagaccacgcccccttc
10141 ---------+---------+---------+---------+---------+---------+ 10200
      gacgctcttccgcaactccggagggagcaaggtctgcgccgacatctggtgcgggggaag

                                             BsaAI
                                             PmlI
                                       BanII
                                       BsiHKAI
                                       Bsp1286I
       BssHII         AarI     BspMI   SacI
      ggcatcgcgggcgcgcatgaccacctgcgcgagattgagctccacgtgccgggcgaagac
10201 ---------+---------+---------+---------+---------+---------+ 10260
      ccgtagcgcccgcgcgtactggtggacgcgctctaactcgaggtgcacggcccgcttctg

                 HaeII
BbsI             AlwNI
      ggcgtagtttcgcaggcgctgaaagaggtagttgagggtggtggcggtgtgttctgccac
10261 ---------+---------+---------+---------+---------+---------+ 10320
      ccgcatcaaagcgtccgcgactttctccatcaactcccaccaccgccacacaagacggtg

                                                          SmlI
                                        EcoRV        HaeI
TatI                                  Bce83I   StyI  StuI
      gaagaagtacataacccagcgtcgcaacgtggattcgttgatatcccccaaggcctcaag
10321 ---------+---------+---------+---------+---------+---------+ 10380
      cttcttcatgtattgggtcgcagcgttgcacctaagcaactatagggggttccggagttc
```

Figure 280

```
BstDSI
NcoI
StyI   Pfl1108I
HaeII  HaeI       BstDSI                BmrI  BssHII
      gcgctccatggcctcgtagaagtccacggcgaagttgaaaaactgggagttgcgcgccga
10381 ---------+---------+---------+---------+---------+---------+ 10440
      cgcgaggtaccggagcatcttcaggtgccgcttcaactttttgaccctcaacgcgcggct

HincII
HpaI                            BanII
```

```
              BseRI      |                         BsiHKAI
         BpmI |  |                         Bsp1286I
         BseRI|  |  BsaXI              BbsI   SacI  Tth111I
             |||  |   |                   |    |      |
         cacggttaactcctcctccagaagacggatgagctcggcgacagtgtcgcgcacctcgcg
10441    ---------+---------+---------+---------+---------+---------+  10500
         gtgccaattgaggaggaggtcttctgcctactcgagccgctgtcacagcgcgtggagcgc

              Eco0109I              BseRI              Eco0109I
              SfcI    |              EarI |              EarI   |
                 ||   |                 | |                 |  |
         ctcaaaggctacaggggcctcttcttcttcttcaatctcctcttccataagggcctcccc
10501    ---------+---------+---------+---------+---------+---------+  10560
         gagtttccgatgtccccggagaagaagaagaagttagaggagaaggtattcccggagggg

         ttcttcttcttctggcggcggtgggggagggggacacggcggcgacgacggcgcaccgg
10561    ---------+---------+---------+---------+---------+---------+  10620
         aagaagaagaagaccgccgccacccctccccctgtgccgccgctgctgccgcgtggcc

               HincII                      SacII
               AccI|                       MspA1I|
               BsiEI|       HaeII          BstDSI ||
               SalI||Eco47III |            Bsp24I |  ||          BsaI
                 |||    |     |               |   |  ||            |
         gaggcggtcgacaaagcgctcgatcatctccccgcggcgacggcgcatggtctcggtgac
10621    ---------+---------+---------+---------+---------+---------+  10680
         ctccgccagctgtttcgcgagctagtagaggggcgccgctgccgcgtaccagagccactg

               BsiEI
               MmeI
               EaeI  |
               EagI  |
               GdiII |                       BbsI
         Bsp24I|  |  |                       BsaHI   |
             | |  |  |                        |      |
         ggcgcggccgttctcgcgggggcgcagttggaagacgccgcccgtcatgtcccggttatg
10681    ---------+---------+---------+---------+---------+---------+  10740
         ccgcgccggcaagagcgccccccgcgtcaaccttctgcggcgggcagtacagggccaatac

                            BciVI         HaeII      NsiI     MunI
                              |             |         |        |
         ggttggcgggggctgccatgcggcagggatacggcgctaacgatgcatctcaacaattg
10741    ---------+---------+---------+---------+---------+---------+  10800
         ccaaccgccccccgacggtacgccgtccctatgccgcgattgctacgtagagttgttaac

                              Bpu10I
                              Eco0109I  |                      BsiEI
                   EciI       Psp5II    |       Hin4I           BsaWI|
                     |          |       |         |               | |
         ttgtgtaggtactccgccgccgagggacctgagcgagtccgcatcgaccggatcggaaaa
10801    ---------+---------+---------+---------+---------+---------+  10860
         aacacatccatgaggcggcggctccctggactcgctcaggcgtagctggcctagccttt

                                                       BstDSI
                                                       BsiHKAI|
               AvaI                                    Bsp1286I|
               SmlI       BsaHI                        Bsp24I  ||
               XhoI       Bsp24I                       Bpu1102I| ||
                |            |                            |   | ||
         cctctcgagaaaggcgtctaaccagtcacagtcgcaaggtaggctgagcaccgtggcggg
10861    ---------+---------+---------+---------+---------+---------+  10920
         ggagagctctttccgcagattggtcagtgtcagcgttccatccgactcgtggcaccgccc

            MspA1I     BsiEI             EciI
              |          |                 |
         cggcagcgggcggcggtcggggttgtttctggcggaggtgctgctgatgatgtaattaaa
10921    ---------+---------+---------+---------+---------+---------+  10980
         gccgtcgcccgccgccagcccaacaaagaccgcctccacgacgactactacattaattt

                             Bce83I
                SmlI         HincII |
                BsmBI        AccI   |                         BstXI
                Bsp24II|    EciI SalI||    | Bsp24I            StyI|
                  || |       |  |||  |     |   |                 ||
         gtaggcggtcttgagacggcggatggtcgacagaagcaccatgtccttgggtccggcctg
10981    ---------+---------+---------+---------+---------+---------+  11040
         catccgccagaactctgccgcctaccagctgtcttcgtggtacaggaacccaggccggac

                      EaeI
                BsmI  GdiII
                FspI| BsiEI|                    BspMI
                  ||   ||                         |
         ctgaatgcgcaggcggtcggccatgccccaggcttcgtttgacatcggcgcaggtctt
11041    ---------+---------+---------+---------+---------+---------+  11100
         gacttacgcgtccgccagccggtacggggtccgaagcaaaactgtagccgcgtccagaaa

                       BsrFI
                         |
         gtagtagtcttgcatgagcctttctaccggcacttcttcttctccttcctcttgtcctgc
11101    ---------+---------+---------+---------+---------+---------+  11160
```

Figure 28P

```
          catcatcagaacgtactcggaaagatggccgtgaagaagaagaggaaggagaacaggacg

                                                             HaeII
                                                         BsaHI |
                                             EaeI         NarI |
       BstAPI                       EciI  GdiII          BanI|  |      EarI
          |                           |       |            ||  |         |
          atctcttgcatctatcgctgcggcggcggcggagtttggccgtaggtggcgccctcttcc
  11161   ---------+---------+---------+---------+---------+---------+   11220
          tagagaacgtagatagcgacgccgccgccgcctcaaaccggcatccaccgcgggagaagg

            MslI                                               Eco57I
              |                                                   |
          tcccatgcgtgtgaccccgaagcccctcatcggctgaagcagggctaggtcggcgacaac
  11221   ---------+---------+---------+---------+---------+---------+   11280
          agggtacgcacactggggcttcggggagtagccgacttcgtcccgatccagccgctgttg

                                         BspMI
                                     EcoNI   |        AhdI
                                     MslI |  |      HaeIV|
            BsgI       HaeI          AarI | |  |AccI  Hin4II|
              |          |             | | |  |   |     ||
          gcgctcggctaatatggcctgctgcacctgcgtgagggtagactggaagtcatccatgtc
  11281   ---------+---------+---------+---------+---------+---------+   11340
          cgcgagccgattataccggacgacgtggacgcactcccatctgaccttcagtaggtacag

                                                         HaeI
                                                         MscI
                             BsbI                    EaeI |          BsgI
                               |                       | |             |
          cacaaagcggtggtatgcgcccgtgttgatggtgtaagtgcagttggccataacggacca
  11341   ---------+---------+---------+---------+---------+---------+   11400
          gtgtttcgccaccatacgcgggcacaactaccacattcacgtcaaccggtattgcctggt

                                          BsmBI
                                      BanII  |
                                    BsiHKAI  |                    AvaI
       HincII                      Bsp1286I  |                    SmlI
         HpaI  BstEII                  SacI  |                    XhoI
            |      |                      |  |                       |
          gttaacggtctggtgacccggctgcgagagctcggtgtacctgagacgcgagtaagccct
  11401   ---------+---------+---------+---------+---------+---------+   11460
          caattgccagaccactgggccgacgctctcgagccacatggactctgcgctcattcggga

              BsaAI                       AlwNI
              SnaBI            SexAI     PflMI          BciVI
                  |                |         |               |
          cgagtcaaatacgtagtcgttgcaagtccgcaccaggtactggtatcccaccaaaaagtg
  11461   ---------+---------+---------+---------+---------+---------+   11520
          gctcagtttatgcatcagcaacgttcaggcgtggtccatgaccatagggtggtttttcac

                                          EaeI      BanII      BglII
                                         GdiII   Bsp1286I      BstYI
                                             |         |           |
          cggcggcggctggcggtagaggggccagcgtagggtggccggggctccgggggcgagatc
  11521   ---------+---------+---------+---------+---------+---------+   11580
          gccgccgccgaccgccatctccccggtcgcatcccaccggccccgaggcccccgctctag

                                                              BsrFI
                     EcoRV     MmeI       BspGI    MslI  NgoAIV
                         |        |           |       |        |
          ttccaacataaggcgatgatatccgtagatgtacctggacatccaggtgatgccggcggc
  11581   ---------+---------+---------+---------+---------+---------+   11640
          aaggttgtattccgctactataggcatctacatggacctgtaggtccactacggccgccg

                                                          MspA1I
             BssHII                                     FspI |   BstAPI
                 |                                        |  |        |
          ggtggtggaggcgcgcggaaagtcgcggacgcggttccagatgttgcgcagcggcaaaaa
  11641   ---------+---------+---------+---------+---------+---------+   11700
          ccaccacctccgcgcgcctttcagcgcctgcgccaaggtctacaacgcgtcgccgttttt

     BstDSI
       NcoI
       StyI                     BsrFI     BssHII
   BsiHKAI|                   EaeI |   BssHII |
  Bsp1286I|                  GdiII |   BglI  | |         HincII   XbaI
          ||                     | |      |  | |              |      |
          gtgctccatggtcgggacgctctggccggtcaggcgcgcgcaatcgttgacgctctagac
  11701   ---------+---------+---------+---------+---------+---------+   11760
          cacgaggtaccagccctgcgagaccggccagtccgcgcgcgttagcaactgcgagatctg

                               Bsp1286I
                                   BmgI |     EarI
                  BsaXI           BseSI |BstDSI|            ApoI
                      |               | |    ||               |
          cgtgcaaaaggagagcctgtaagcgggcactcttccgtggtctggtggataaattcgcaa
  11761   ---------+---------+---------+---------+---------+---------+   11820
          gcacgttttcctctcggacattcgcccgtgagaaggcaccagaccacctatttaagcgtt
```

Figure 28Q

```
                                                      EciI
                                                 BciVI |
                                             BsiEI   | |
                                         EaeI   |    | |
                                  BanII  EagI   |    | |
            EciI   BsiEI    Bsp1286I    GdiII   |    | |
               |       |           |        |   |    | |
       gggtatcatggcggacgaccggggttcgagccccgtatccggccgtccgccgtgatccat
11821  ---------+---------+---------+---------+---------+---------+ 11880
       cccatagtaccgcctgctggccccaagctcggggcataggccggcaggcggcactaggta

                                         AatII            BsiHKAI
BstEII                              BsaHI  |             Bsp1286I
   |                                    |  |                    |
       gcggttaccgcccgcgtgtcgaacccaggtgtgcgacgtcagacaacgggggagtgctcc
11881  ---------+---------+---------+---------+---------+---------+ 11940
       cgccaatggcgggcgcacagcttgggtccacacgctgcagtctgttgccccctcacgagg

                                             HaeI     BssHII
                                             MscI EaeI     |
                                   NheI  EaeI |GdiII       |
                                      |     | |     |      |
       ttttggcttccttccaggcgcggcggctgctgcgctagctttttggccactggccgcgc
11941  ---------+---------+---------+---------+---------+---------+ 12000
       aaaaccgaaggaaggtccgcgccgccgacgacgcgatcgaaaaaccggtgaccggcgcg

                                                    SfcI
                                                      |
       gcagcgtaagcggttaggctggaaagcgaaagcattaagtggctcgctccctgtagccgg
12001  ---------+---------+---------+---------+---------+---------+ 12060
       cgtcgcattcgccaatccgacctttcgctttcgtaattcaccgagcgagggacatcggcc

                                                         BsiEI
                                                      EaeI  |
                                                      EagI  |
                             Eco0109I                GdiII  |
                              Psp5II              BsrFI |   |
          StyI                 SanDI  AloI       RsrII |  |   |
             |                     |     |           | |  |   |
       agggttatttccaagggttgagtcgcgggaccccggttcgagtctcggaccggccgga
12061  ---------+---------+---------+---------+---------+---------+ 12120
       tcccaataaaaggttcccaactcagcgccctggggccaagctcagagcctggccggcct

                                                         BsaWI
                                                    ApoI BspEI
                                                       |     |
       ctgcggcgaacgggggtttgcctccccgtcatgcaagaccccgcttgcaaattcctccgg
12121  ---------+---------+---------+---------+---------+---------+ 12180
       gacgccgcttgcccccaaacggaggggcagtacgttctggggcgaacgtttaaggaggcc

                                        BstAPI
             BanII                    BsaWI |
          Bsp1286I                    NsiI| |          BseRI
                 |                       || |              |
       aaacagggacgagccccttttttgcttttcccagatgcatccggtgctgcggcagatgcg
12181  ---------+---------+---------+---------+---------+---------+ 12240
       tttgtccctgctcggggaaaaaacgaaaagggtctacgtaggccacgacgccgtctacgc

                                                 Bsp1286I
                                                   BseRI|
                                                    BmgI||
                                                   BseSI||
     BbvCI                                          BanI|||
    Bpu10I MspA1I           MspA1I       NspI      ||||
         |      |                |          |      ||||
       cccccctcctcagcagcggcaagagcaagagcagcggcagacatgcagggcaccctcccc
12241  ---------+---------+---------+---------+---------+---------+ 12300
       ggggggaggagtcgtcgccgttctcgttctcgtcgccgtctgtacgtcccgtgggagggg

                                   HincII
                                 SacII  |
                               MspA1I|  |
                              BstDSI ||  |
                                   | ||  |
       tcctcctaccgcgtcaggaggggcgacatccgcggttgacgcggcagcagatggtgatta
12301  ---------+---------+---------+---------+---------+---------+ 12360
       aggaggatggcgcagtcctccccgctgtaggcgccaactgcgccgtcgtctaccactaat

                  ApaI
                 BanII
              Bsp1286I
                 BmgI |
                BseSI |
           HaeII    | |
          BsaHI |   | |
           NarI |   | |
          BanI| |   | |
        SacII|| |   | |
       MspA1I||| |   | |                                BseRI
     BstDSI |||| |   | |      BspGI         Eco0109I      |
```

Figure 28R 12361 cgaacccccgcggcgccgggcccggcactacctggacttggaggagggcgagggcctggc 12420
gcttgggggcgccgcggcccgggccgtgatggacctgaacctcctcccgctcccggaccg BanI, BsrBI, StyI, MspA1I, BsgI, HaeII, Bpu10I, KpnI, PvuII, AflIII, MluI 12421 gcggctaggagcgccctctcctgagcggtacccaagggtgcagctgaagcgtgatacgcg 12480
cgccgatcctcgcgggagaggactcgccatgggttcccacgtcgacttcgcactatgcgc SacII, MspA1I, BstDSI, BsaAI, SunI, Eco57I, AlwNI, BsiEI, NruI, BanII, Bsp1286I, AvaI 12481 tgaggcgtacgtgccgcggcagaacctgtttcgcgaccgcgagggagaggagcccgagga 12540
actccgcatgcacggcgccgtcttggacaaagcgctggcgctccctctcctcgggctcct HaeIV, Hin4I, AloI, BseRI, BseRI, AceIII, HaeI, NruI, BsrBI 12541 gatgcgggatcgaaagttccacgcagggcgcgagctgcggcatggcctgaatcgcgagcg 12600
ctacgccctagctttcaaggtgcgtcccgcgctcgacgccgtaccggacttagcgctcgc BanII, Bsp1286I, BseRI, BssHII, BssHII 12601 gttgctgcgcgaggaggactttgagcccgacgcgcgaaccgggattagtcccgcgcgcgc 12660
caacgacgcgctcctcctgaaactcgggctgcgcgcttggccctaatcagggcgcgcgcg BsiEI, EaeI, EagI, GdiII, BsaAI, PmlI, AflIII, NotI, SexAI, BstEII, DrdII 12661 acacgtggcggccgccgacctggtaaccgcatacgagcagacggtgaaccaggagattaa 12720
tgtgcaccgccggcggctggaccattggcgtatgctcgtctgccacttggtcctctaatt SunI, BsaAI, HindIII, PmlI, BssHII, SfcI 12721 ctttcaaaaaagctttaacaaccacgtgcgtacgcttgtggcgcgcgaggaggtggctat 12780
gaaagttttttcgaaattgttggtgcacgcatgcgaacaccgcgcgctcctccaccgata RleAI, BseRI, NsiI, BssHII, BpmI 12781 aggactgatgcatctgtgggactttgtaagcgcgctggagcaaaacccaaatagcaagcc 12840
tcctgactacgtagacaccctgaaacattcgcgcgacctcgttttgggtttatcgttcgg MspA1I, BsmI, BsrBI, PvuII, BsgI 12841 gctcatggcgcagctgttccttatagtgcagcacagcagggacaacgaggcattcaggga 12900
cgagtaccgcgtcgacaaggaatatcacgtcgtgtcgtccctgttgctccgtaagtccct BanII, Bsp1286I, AvaI, MspA1I, BsaBI, SfcI 12901 tgcgctgctaaacatagtagagcccgagggccgctggctgctcgatttgataaacatcct 12960
acgcgacgatttgtatcatctcgggctcccggcgaccgacgagctaaactatttgtagga

Figure 28S

Bce83I, EaeI, PstI, MslI, SmlI, BsgI, GdiII 12961 gcagagcatagtggtgcaggagcgcagcttgagcctggctgacaaggtggccgccatcaa 13020
cgtctcgtatcaccacgtcctcgcgtcgaactcggaccgactgttccaccggcggtagtt XcmI
Bpu1102I 13021 ctattccatgcttagcctgggcaagttttacgcccgcaagatataccataccccttacgt 13080
gataaggtacgaatcggacccgttcaaaatgcgggcgttctatatggtatggggaatgca FspI MslI NspI HaeII 13081 tcccatagacaaggaggtaaagatcgaggggttctacatgcgcatggcgctgaaggtgct 13140
agggtatctgttcctccatttctagctccccaagatgtacgcgtaccgcgacttccacga SmlI Eco57I Bce83I 13141 taccttgagcgacgacctgggcgtttatcgcaacgagcgcatccacaaggccgtgagcgt 13200
atggaactcgctgctggacccgcaaatagcgttgctcgcgtaggtgttccggcactcgca BsrFI NgoAIV
BanII BsiHKAI Bsp1286I SacI AceIII Bpu1102I BsiEI
BstAPI
ApaI BanII Bsp1286I BmgI BseSI EcoO109I EcoO109I 13201 gagccggcggcgcgagctcagcgaccgcgagctgatgcacagcctgcaaagggccctggc 13260
ctcggccgccgcgctcgagtcgctggcgctcgactacgtgtcggacgtttcccgggaccg MspA1I Hin4I Bsp24I HaeII 13261 tggcacgggcagcggcgatagagaggccgagtcctactttgacgcgggcgctgacctgcg 13320
accgtgcccgtcgccgctatctctccggctcaggatgaaactgcgcccgcgactggacgc ApaI BanII Bsp1286I Bsp24I BmgI BseSI EcoO109I BspMI
Bsp24I BglI Bsp24I MspA1I PvuII Bsp24I BpmI BanI 13321 ctgggccccaagccgacgcgccctggaggcagctggggccggacctgggctggcggtggc 13380
gacccggggttcggctgcgcgggacctccgtcgaccccggcctggacccgaccgccaccg BssHII Bsp24I BssHII 13381 acccgcgcgcgctggcaacgtcggcggcgtggaggaatatgacgaggacgatgagtacga 13440
tgggcgcgcgcgaccgttgcagccgccgcacctccttatactgctcctgctactcatgct ScaI TatI BclI 13441 gccagaggacggcgagtactaagcggtgatgtttctgatcagatgatgcaagacgcaacg 13500
cggtctcctgccgctcatgattcgccactacaaagactagtctactacgttctgcgttgc PstI HaeII SfcI BstDSI 13501 gacccggcggtgcgggcggcgctgcagagccagccgtccggccttaactccacggacgac 13560
ctgggccgccacgcccgccgcgacgtctcggtcggcaggccggaattgaggtgcctgctg HaeII BsaHI NarI BanI PflMI BssHII AflIII MluI 13561 tggcgccaggtcatggaccgcatcatgtcgctgactgcgcgcaatcctgacgcgttccgg 13620
accgcggtccagtacctggcgtagtacagcgactgacgcgcgttaggactgcgcaaggcc

Figure 28T

BsaXI BsrFI HaeI BssHII BssHII cagcagccgcaggccaaccggctctccgcaattctggaagcggtggtcccggcgcgcgca

```
13621 ---------+---------+---------+---------+---------+---------+ 13680
      gtcgtcggcgtccggttggccgagaggcgttaagaccttcgccaccagggccgcgcgcgt

                                BsiEI        EaeI
         BssSI                  PvuI         GdiII
      aaccccacgcacgagaaggtgctggcgatcgtaaacgcgctggccgaaaacagggccatc
13681 ---------+---------+---------+---------+---------+---------+ 13740
      ttggggtgcgtgctcttccacgaccgctagcatttgcgcgaccggcttttgtcccggtag

                           Pfl1108I
                             AccI
                          Eco57I
                       FseI
                BsrFI
               NgoAIV
      cggcccgacgaggccggcctggtctacgacgcgctgcttcagcgcgtggctcgttacaac
13741 ---------+---------+---------+---------+---------+---------+ 13800
      gccgggctgctccggccggaccagatgctgcgcgacgaagtcgcgcaccgagcaatgttg

                              BsrFI
MspA1I                    BspGI   BsgI                 BstDSI
      agcggcaacgtgcagaccaacctggaccggctggtgggggatgtgcgcgaggccgtggcg
13801 ---------+---------+---------+---------+---------+---------+ 13860
      tcgccgttgcacgtctggttggacctggccgaccacccccctacacgcgctccggcaccgc

                                         BstDSI
                                          NcoI
                                          StyI
                                        BanII
                                      Bsp1286I
          BssHII                     BsaXI
        BssHII
      cagcgtgagcgcgcgcagcagcagggcaacctgggctccatggttgcactaaacgccttc
13861 ---------+---------+---------+---------+---------+---------+ 13920
      gtcgcactcgcgcgcgtcgtcgtcccgttggacccgaggtaccaacgtgatttgcggaag

                                SacII
                              MspA1I
   TatI                     BstDSI
      ctgagtacacagcccgccaacgtgccgcggggacaggaggactacaccaactttgtgagc
13921 ---------+---------+---------+---------+---------+---------+ 13980
      gactcatgtgtcgggcggttgcacggcgcccctgtcctcctgatgtggttgaaacactcg

   BtsI
      gcactgcggctaatggtgactgagacaccgcaaagtgaggtgtaccagtctgggccagac
13981 ---------+---------+---------+---------+---------+---------+ 14040
      cgtgacgccgattaccactgactctgtggcgtttcactccacatggtcagacccggtctg

                                 SfcI
                               HaeI             EcoNI
                       AccI    StuI  PstI   Bpu10I
      tattttttccagaccagtagacaaggcctgcagaccgtaaacctgagccaggctttcaaa
14041 ---------+---------+---------+---------+---------+---------+ 14100
      ataaaaaaggtctggtcatctgttccggacgtctggcatttggactcggtccgaaagttt

                                                      Tth111I
                                 BanII                 BsiEI
   RleAI      AlwNI           Bsp1286I         BsiEI RleAI
      aacttgcaggggctgtggggggtgcgggctcccacaggcgaccgcgcgaccgtgtctagc
14101 ---------+---------+---------+---------+---------+---------+ 14160
      ttgaacgtccccgacaccccccacgcccgagggtgtccgctggcgcgctggcacagatcg

    BsaHI                                        HaeII
      ttgctgacgcccaactcgcgcctgttgctgctgctaatagcgcccttcacggacagtggc
14161 ---------+---------+---------+---------+---------+---------+ 14220
      aacgactgcgggttgagcgcggacaacgacgacgattatcgcgggaagtgcctgtcaccg

           SmaI          AvrII
         AvaI            StyI                           HaeI
      agcgtgtcccgggacacatacctaggtcacttgctgacactgtaccgcgaggccataggt
14221 ---------+---------+---------+---------+---------+---------+ 14280
      tcgcacagggccctgtgtatggatccagtgaacgactgtgacatggcgctccggtatcca

          NspI                                       BssHII
      caggcgcatgtggacgagcatactttccaggagattacaagtgtcagccgcgcgctgggg
14281 ---------+---------+---------+---------+---------+---------+ 14340
      gtccgcgtacacctgctcgtatgaaaggtcctctaatgttcacagtcggcgcgcgacccc

                                                     BsrFI
                                         BpmI   BspMI
```

Figure 28U

```
                                                    |       |  |
      caggaggacacgggcagcctggaggcaaccctaaactacctgctgaccaaccggcggcag
14341 ---------+---------+---------+---------+---------+---------+ 14400
      gtcctcctgtgcccgtcggacctccgttgggatttgatggacgactggttggccgccgtc

                          DraI                         BseRI
  BstYI                   PmeI                   BseRI    |BsaAI
      |                   |                          |    |    |
      aagatcccctcgttgcacagtttaaacagcgaggaggagcgcatttgcgctacgtgcag
14401 ---------+---------+---------+---------+---------+---------+ 14460
      ttctaggggagcaacgtgtcaaatttgtcgctcctcctcgcgtaaaacgcgatgcacgtc

                                                          BspGI
                                                       HaeII  |
                BsgI                               XcmI    |  |
                  |                                    |   |  |
      cagagcgtgagccttaacctgatgcgcgacggggtaacgcccagcgtggcgctggacatg
14461 ---------+---------+---------+---------+---------+---------+ 14520
      gtctcgcactcggaattggactacgcgctgccccattgcgggtcgcaccgcgacctgtac

                                               BsiEI
                                             EaeI  |
                                             EagI  |
                                            GdiII  |
   BssHII                   NspI       BsrFI  |    |
        |                      |          |   |    |
      accgcgcgcaacatggaaccgggcatgtatgcctcaaaccggccgtttatcaaccgccta
14521 ---------+---------+---------+---------+---------+---------+ 14580
      tggcgcgcgttgtaccttggcccgtacatacggagtttggccggcaaatagttggcggat

                     BsiEI
                  EaeI  |
                  EagI  |
                 GdiII  |
                  NotI  |          AvaI
                     |  |             |
      atggactacttgcatcgcgcggccgccgtgaaccccgagtatttcaccaatgccatcttg
14581 ---------+---------+---------+---------+---------+---------+ 14640
      tacctgatgaacgtagcgcgccggcggcacttggggctcataaagtggttacggtagaac

                                                      Bsp1286I
                                                         AvaI|
                                                        BmgI||
                                                       BseSI||
                                                     BanI  |||
                                                        |  |||
      aacccgcactggctaccgccccctggtttctacaccggggggattcgaggtgcccgaggt
14641 ---------+---------+---------+---------+---------+---------+ 14700
      ttgggcgtgaccgatggcgggggaccaaagatgtggcccccctaagctccacgggctccca

                                                              AlwNI
                                                             BstAPI
                                                                  |
      aacgatggattcctctgggacgacatagacgacagcgtgtttccccgcaaccgcagacc
14701 ---------+---------+---------+---------+---------+---------+ 14760
      ttgctacctaaggagaccctgctgtatctgctgtcgcacaaaggggcgttggcgtctgg

                                             HaeII     HindIII
                                                 |           |
      ctgctagagttgcaacagcgcgagcaggcagaggcggcgctgcgaaaggaaagcttccgc
14761 ---------+---------+---------+---------+---------+---------+ 14820
      gacgatctcaacgttgtcgcgctcgtccgtctccgccgcgacgctttcctttcgaaggcg

                                               SacII
                                             MspA1I|
    HaeI           Tth111II   HaeII    BstDSI ||
       |                  |         |       |  ||
      aggccaagcagcttgtccgatctaggcgctgcggccccgcggtcagatgctagtagccca
14821 ---------+---------+---------+---------+---------+---------+ 14880
      tccggttcgtcgaacaggctagatccgcgacgccggggcgccagtctacgatcatcgggt

    HindIII      Hin4I    BsaI                              BglI
          |          |      |                                  |
      tttccaagcttgatagggtctcttaccagcactcgcaccacccgcccgcgcctgctgggc
14881 ---------+---------+---------+---------+---------+---------+ 14940
      aaaggttcgaactatcccagagaatggtcgtgagcgtggtgggcgggcgcggacgacccg

                BseRI          PstI
           BseRI    |      SfcI    |                           BspMI
               |    |         |    |                               |
      gaggaggagtacctaaacaactcgctgctgcagccgcagcgcgaaaaaaacctgcctccg
14941 ---------+---------+---------+---------+---------+---------+ 15000
      ctcctcctcatggatttgttgagcgacgacgtcggcgtcgcgctttttttggacggaggc

                                                           BbsI
                                                        SunI  |
                                                           |  |
      gcatttcccaacaacgggatagagagcctagtggacaagatgagtagatggaagacgtac
15001 ---------+---------+---------+---------+---------+---------+ 15060
      cgtaaagggttgttgccctatctctcggatcacctgttctactcatctaccttctgcatg
```

Figure 28V

```
      BsiHKAI
     Bsp1286I           Bsp24I                          BsiEI
            |                |                              |
      gcgcaggagcacagggacgtgccaggcccgcgcccgcccacccgtcgtcaaaggcacgac
15061 ---------+---------+---------+---------+---------+---------+ 15120
      cgcgtcctcgtgtccctgcacggtccgggcgcgggcgggtgggcagcagtttccgtgctg

      RleAI
     MspA1I|
 Bsp24I  ||             Hin4I            DrdI
      |  ||                 |                |
      cgtcagcggggtctggtgtgggaggacgatgactcggcagacgacagcagcgtcctggat
15121 ---------+---------+---------+---------+---------+---------+ 15180
      gcagtcgccccagaccacaccctcctgctactgagccgtctgctgtcgtcgcaggaccta

                     FspI                                DraI
                        |                                   |
      ttgggagggagtggcaacccgtttgcgcaccttcgccccaggctggggagaatgttttaa
15181 ---------+---------+---------+---------+---------+---------+ 15240
      aaccctccctcaccgttgggcaaacgcgtggaagcggggtccgaccccctcttacaaaatt

                                                BanI
                                          BstXI   |
                                        BstDSI|   |
                                          NcoI|   |
                                          StyI|   |
                                   StyI  HaeI||   |
                                      |     |||   |
      aaaaaaaaaagcatgatgcaaaataaaaaactcaccaaggccatggcaccgagcgttggt
15241 ---------+---------+---------+---------+---------+---------+ 15300
      ttttttttttcgtactacgttttattttttgagtggttccggtaccgtggctcgcaacca

                                              Eco0109I
                                                Psp5II
                                              Sse8647I
                  BssHII                    BseRI     |
                       |                        |     |
      tttcttgtattccccttagtatgcggcgcgcggcgatgtatgaggaaggtcctcctccct
15301 ---------+---------+---------+---------+---------+---------+ 15360
      aaagaacataaggggaatcatacgccgcgcgccgctacatactccttccaggaggaggga

                         HaeII
                    BsaHI  |
                     NarI  |
 Pfl1108I           BanI|  |           HaeII
      |                ||  |               |
      cctacgagagtgtggtgagcgcggcgccagtggcggcggcgctgggttctcccttcgatg
15361 ---------+---------+---------+---------+---------+---------+ 15420
      ggatgctctcacaccactcgcgccgcggtcaccgccgccgcgacccaagagggaagctac

                               BanI
                             SacII|
                           MspA1I||
     BspGI              BstDSI |||KpnI    BspMI
         |                   | |||   |        |
      ctcccctggacccgccgtttgtgcctccgcggtacctgcggcctaccgggggggagaaaca
15421 ---------+---------+---------+---------+---------+---------+ 15480
      gaggggacctgggcggcaaacacggaggcgccatggacgccggatggccccccctctttgt

                BanI                   MslI  SexAI
                   |                      |     |
      gcatccgttactctgagttggcaccccctattcgacaccacccgtgtgtacctggtggaca
15481 ---------+---------+---------+---------+---------+---------+ 15540
      cgtaggcaatgagactcaaccgtggggataagctgtggtgggcacacatggaccacctgt

      HincII
    AhdI   |
 HaeIV|    |    HaeIV                                   PshAI
 Hin4I|    |    Hin4I                              BstDSI |
     ||    |        |                                   | |
      acaagtcaacggatgtggcatccctgaactaccagaacgaccacagcaacttctgacca
15541 ---------+---------+---------+---------+---------+---------+ 15600
      tgttcagttgcctacaccgtagggacttgatggtcttgctggtgtcgttgaaagactggt

                                           Tth111II
                           SmaI             HaeIV |
                  SfcI  AvaI |              Hin4I |
                     |     | |                 |  |
      cggtcattcaaaacaatgactacagcccggggggaggcaagcacacagaccatcaatcttg
15601 ---------+---------+---------+---------+---------+---------+ 15660
      gccagtaagttttgttactgatgtcgggcccccctccgttcgtgtgtctggtagttagaac

        BsiEI
      AhdI  |
     BsiEI  |
    BsaWI|  |
    BsrFI|  |
    HaeIV|  |
    Hin4I|  |
```

Figure 28W

```
     PinAI|    |  BmrI                                           NspI
       ||     |     |                                              |
      acgaccggtcgcactggggcggcgacctgaaaccatcctgcataccaacatgccaaatg
15661 ---------+---------+---------+---------+---------+---------+ 15720
      tgctggccagcgtgaccccgccgctggactttggtaggacgtatggttgtacggtttac

        XmnI
          |
      tgaacgagttcatgtttaccaataagtttaaggcgcgggtgatggtgtcgcgcttgccta
15721 ---------+---------+---------+---------+---------+---------+ 15780
      acttgctcaagtacaaatggttattcaaattccgcgcccactaccacagcgcgaacggat

    AceIII            TaqII                            AvaI
        |                 |                              |
      ctaaggacaatcaggtggagctgaaatacgagtgggtggagttcacgctgcccgagggca
15781 ---------+---------+---------+---------+---------+---------+ 15840
      gattcctgttagtccacctcgactttatgctcacccacctcaagtgcgacgggctcccgt

                                                  BsiEI  BsiHKAI
    BsaI                                           PvuI Bsp1286I
      |                                                |      |
      actactccgagaccatgaccatagaccttatgaacaacgcgatcgtggagcactacttga
15841 ---------+---------+---------+---------+---------+---------+ 15900
      tgatgaggctctggtactggtatctggaatacttgttgcgctagcacctcgtgatgaact

                                                   Eco57I
                                                        |
      aagtgggcagacagaacggggttctggaaagcgacatcggggtaaagtttgacacccgca
15901 ---------+---------+---------+---------+---------+---------+ 15960
      ttcacccgtctgtcttgccccaagacctttcgctgtagccccatttcaaactgtgggcgt

          BmrI      Tth111I
            |          |
      acttcagactggggtttgaccccgtcactggtcttgtcatgcctggggtatatacaaacg
15961 ---------+---------+---------+---------+---------+---------+ 16020
      tgaagtctgaccccaaactggggcagtgaccagaacagtacggaccccatatatgtttgc

      aagccttccatccagacatcattttgctgccaggatgcggggtggacttcacccacagcc
16021 ---------+---------+---------+---------+---------+---------+ 16080
      ttcggaaggtaggtctgtagtaaaacgacggtcctacgccccacctgaagtgggtgtcgg

          RleAI
       TaqII  |
   Bpu10I  |  |
      |    |  |
      gcctgagcaacttgttgggcatccgcaagcggcaaccccttccaggagggctttaggatca
16081 ---------+---------+---------+---------+---------+---------+ 16140
      cggactcgttgaacaacccgtaggcgttcgccgttgggaaggtcctcccgaaatcctagt

 Pfl1108I           MmeI          BpmI          BsaHI    BglI
      |                |             |              |       |
      cctacgatgatctggagggtggtaacattcccgcactgttggatgtggacgcctaccagg
16141 ---------+---------+---------+---------+---------+---------+ 16200
      ggatgctactagacctcccaccattgtaagggcgtgacaacctacacctgcggatggtcc

                                                          BtsI
                                                             |
      cgagcttgaaagatgacaccgaacagggcgggggtggcgcaggcggcagcaacagcagtg
16201 ---------+---------+---------+---------+---------+---------+ 16260
      gctcgaactttctactgtggcttgtcccgcccccaccgcgtccgccgtcgttgtcgtcac

                                      SacII    BsrFI
         EarI                       MspA1I|    BsrDI|
   MspA1I  |                     BstDSI ||      MmeI|
      |    |                         |  ||         ||
      gcagcggcgcggaagagaactccaacgcggcagccgcggcaatgcagccggtggaggaca
16261 ---------+---------+---------+---------+---------+---------+ 16320
      cgtcgccgcgccttctcttgaggttgcgccgtcggcgccgttacgtcggccacctcctgt

                                                 BcgI       BseRI
                                            BbvCI  |     BbvCI |
                                           Bpu10I  |    Bpu10I |
           BcgI                          BglI   |  | BssHII  | |
             |                             |    |  |  |      | |
      tgaacgatcatgccattcgcggcgacacctttgccacacgggctgaggagaagcgcgctg
16321 ---------+---------+---------+---------+---------+---------+ 16380
      acttgctagtacggtaagcgccgctgtggaaacggtgtgcccgactcctcttcgcgcgac

              BsiEI
            EaeI  |
            EagI  |
           GdiII  |
         MspA1I|  |                   FspI
               || |          MspA1I  | AvaI
               || |               |  |  |
      aggccgaagcagcggccgaagctgccgcccccgctgcgcaacccgaggtcgagaagcctc
16381 ---------+---------+---------+---------+---------+---------+ 16440
      tccggcttcgtcgccggcttcgacggcgggggcgacgcgttgggctccagctcttcggag

          BsaWI
          BsrFI
```

Figure 28X

```
          PinAI BclI         EcoNI
            |     |            |
      agaagaaaccggtgatcaaacccctgacagaggacagcaagaaacgcagttacaacctaa
16441 ---------+---------+---------+---------+---------+---------+ 16500
      tcttctttggccactagtttggggactgtctcctgtcgttctttgcgtcaatgttggatt

                                     BanI
                                   TaqII|
                                MspA1I ||
                                 PvuII ||
           BsrDI          BmrI  HgiEII| ||KpnI
             |              |        || ||   |
      taagcaatgacagcaccttcacccagtaccgcagctggtaccttgcatacaactacggcg
16501 ---------+---------+---------+---------+---------+---------+ 16560
      attcgttactgtcgtggaagtgggtcatggcgtcgaccatggaacgtatgttgatgccgc

                                                            BspMI
         BsaWI     BsrBI                               BspMI    |
           |         |                                    |     |
      accctcagaccggaatccgctcatggaccctgctttgcactcctgacgtaacctgcggct
16561 ---------+---------+---------+---------+---------+---------+ 16620
      tgggagtctggccttaggcgagtacctgggacgaaacgtgaggactgcattggacgccga

           AccI                                       BsrBI
             |                                           |
      cggagcaggtctactggtcgttgccagacatgatgcaagaccccgtgaccttccgctcca
16621 ---------+---------+---------+---------+---------+---------+ 16680
      gcctcgtccagatgaccagcaacggtctgtactacgttctggggcactggaaggcgaggt

                                 HaeII             BsiHKAI
                              BsaHI |             Bsp1286I
                     AceIII   NarI  |              BseSI |
                 BsaWI   |    BanI| |            ApaLI | |
                     |   |      || |                 |  | |
      cgcgccagatcagcaactttccggtggtgggcgccgagctgttgcccgtgcactccaaga
16681 ---------+---------+---------+---------+---------+---------+ 16740
      gcgcggtctagtcgttgaaaggccaccacccgcggctcgacaacgggcacgtgaggttct

                      AccI
                  DrdI   |               EciI
                     |   |                  |
      gcttctacaacgaccaggccgtctactcccaactcatccgccagtttacctctctgaccc
16741 ---------+---------+---------+---------+---------+---------+ 16800
      cgaagatgttgctggtccggcagatgagggttgagtaggcggtcaaatggagagactggg

 BsaAI
  PmlI                                   AscI
AflIII|                                 BssHII
    ||          AvaI   DrdII  PflMI      |
    ||            |      |       |       |
      acgtgttcaatcgctttcccgagaaccagatttggcgcgcccgccagcccccaccatca
16801 ---------+---------+---------+---------+---------+---------+ 16860
      tgcacaagttagcgaaagggctcttggtctaaaccgcgcgggcggtcgggggtggtagt

                AclI                            MspA1I
                XmnI                        BcgI   |FspI
                  |                            |   |  |
      ccaccgtcagtgaaaacgttcctgctctcacagatcacgggacgctaccgctgcgcaaca
16861 ---------+---------+---------+---------+---------+---------+ 16920
      ggtggcagtcacttttgcaaggacgagagtgtctagtgccctgcgatggcgacgcgttgt

                      BseRI
                   BcgI  |
              BspGI  |   |        BsaHI  BsaHI    AarI   BspMI
                  |   |   |            |      |        |      |
      gcatcggaggagtccagcgagtgaccattactgacgccagacgccgcacctgcccctacg
16921 ---------+---------+---------+---------+---------+---------+ 16980
      cgtagcctcctcaggtcgctcactggtaatgactgcggtctgcggcgtggacggggatgc

   Eco0109I
          |
      tttacaaggccctgggcatagtctcgccgcgcgtcctatcgagccgcactttttgagcaa
16981 ---------+---------+---------+---------+---------+---------+ 17040
      aaatgttccgggacccgtatcagagcggcgcgcaggatagctcggcgtgaaaaactcgtt

      NspI Tth111II                      Eco0109I     Tth111II
         |      |                           |             |
      gcatgtccatccttatatcgcccagcaataacacaggctggggcctgcgcttcccaagca
17041 ---------+---------+---------+---------+---------+---------+ 17100
      cgtacaggtaggaatatagcgggtcgttattgtgtccgaccccggacgcgaagggttcgt

                                                      Bsp1286I
                                                         BmgI |
                                                        BseSI |
                                 HaeII          DraIII    MmeI | |
        Tth111II       Eco47III |       BsbI BmrI|    TaqII | |
               |               | |          |    ||       |  | |
      agatgtttggcggggccaagaagcgctccgaccaacacccagtgcgcgtgcgcgggcact
17101 ---------+---------+---------+---------+---------+---------+ 17160
      tctacaaaccgccccggttcttcgcgaggctggttgtgggtcacgcgcacgcgcccgtga
```

Figure 28Y

```
                                    BcgI
                                    BsiEI
                                  EaeI
                                  EagI
                                  GdiII
  BssHII        BssHII            NotI     BmrI                  BsaHI
       accgcgcgccctggggcgcgcacaaacgcggccgcactgggcgcaccaccgtcgatgacg
17161  ---------+---------+---------+---------+---------+---------+ 17220
       tggcgcgcgggaccccgcgcgtgtttgcgccggcgtgacccgcgtggtggcagctactgc

    XcmI
  BcgI              BssHII      BseRI
       ccatcgacgcggtggtggaggaggcgcgcaactacacgcccacgccgccaccagtgtcca
17221  ---------+---------+---------+---------+---------+---------+ 17280
       ggtagctgcgccaccacctcctccgcgcgttgatgtgcgggtgcggcggtggtcacaggt

     EaeI       BstDSI          BanII               BsmBI
     GdiII      XcmI            Bsp1286I  HaeII     EarI
       cagtggacgcggccattcagaccgtggtgcgcggagcccggcgctatgctaaaatgaaga
17281  ---------+---------+---------+---------+---------+---------+ 17340
       gtcacctgcgccggtaagtctggcaccacgcgcctcgggccgcgatacgattttacttct

   EciI                                   BglI  BtsI
       gacggcggaggcgcgtagcacgtcgccaccgccgccgacccggcactgccgcccaacgcg
17341  ---------+---------+---------+---------+---------+---------+ 17400
       ctgccgcctccgcgcatcgtgcagcggtggcggcggctgggccgtgacggcgggttgcgc

                                        BsiEI
                                      EaeI
                                      EagI
                                      GdiII     EaeI     BglI
                                    BsrFI       GdiII    SfiI  BsrBI
       cggcggcggccctgcttaaccgcgcacgtcgcaccggccgacgggcggccatgcgggccg
17401  ---------+---------+---------+---------+---------+---------+ 17460
       gccgccgccgggacgaattggcgcgtgcagcgtggccggctgcccgccggtacgcccggc

                                                            BsiEI
                                                          EaeI
          SacII                                           EagI
        MspA1I                                            GdiII
      BstDSI                   Bsp1286I                   NotI
     EaeI                      BmgI                       BsrBI
    GdiII                      BseSI        BspGI
       ctcgaaggctggccgcgggtattgtcactgtgccccccaggtccaggcgacgagcggccg
17461  ---------+---------+---------+---------+---------+---------+ 17520
       gagcttccgaccggcgcccataacagtgacacggggggtccaggtccgctgctcgccggc

         EaeI
        GdiII
         SacII
       MspA1I                   AhdI
     BstDSI                     HaeIV       AflIII
                                Hin4I       TaqII
       ccgcagcagccgcggccattagtgctatgactcagggtcgcaggggcaacgtgtattggg
17521  ---------+---------+---------+---------+---------+---------+ 17580
       ggcgtcgtcggcgccggtaatcacgatactgagtcccagcgtccccgttgcacataaccc

                          Bsp1286I
                          BmgI
                          BseSI  FspI
       tgcgcgactcggttagcggcctgcgcgtgcccgtgcgcacccgcccccgcgcaactaga
17581  ---------+---------+---------+---------+---------+---------+ 17640
       acgcgctgagccaatcgccggacgcgcacgggcacgcgtgggcgggggcgcgttgatct

                                                      BssHII
                                                BciVI
                                          MspA1I
       ttgcaagaaaaaactacttagactcgtactgttgtatgtatccagcggcggcggcgcgca
17641  ---------+---------+---------+---------+---------+---------+ 17700
       aacgttctttttttgatgaatctgagcatgacaacatacataggtcgccgccgccgcgcgt

                      EarI                                 BglII
                      BpmI                                 BstYI
       acgaagctatgtccaagcgcaaaatcaaagaagagatgctccaggtcatcgcgccggaga
17701  ---------+---------+---------+---------+---------+---------+ 17760
       tgcttcgatacaggttcgcgttttagtttcttctctacgaggtccagtagcgcggcctct

              EarI
              SapI
       tctatggcccccccgaagaaggaagagcaggattacaagccccgaaagctaaagcgggtca
17761  ---------+---------+---------+---------+---------+---------+ 17820
```

Figure 28Z

```
         agataccggggggcttcttccttctcgtcctaatgttcggggctttcgatttcgcccagt

                                    BsgI
                                       |
         aaaagaaaaagaaagatgatgatgatgaacttgacgacgaggtggaactgctgcacgcta
17821    ---------+---------+---------+---------+---------+---------+  17880
         ttttctttttctttctactactactacttgaactgctgctccaccttgacgacgtgcgat

                               AflIII
                                 MluI
                             HincII |
                               AccI| |
                              SalI|| |     AflIII                BanI
                                 ||| |          |                   |
         ccgcgcccaggcgacgggtacagtggaaaggtcgacgcgtaaaacgtgttttgcgacccg
17881    ---------+---------+---------+---------+---------+---------+  17940
         ggcgcgggtccgctgcccatgtcacctttccagctgcgcattttgcacaaaacgctgggc

                             HaeII
                        Eco47III |
                               | |
         gcaccaccgtagtctttacgcccggtgagcgctccacccgcacctacaagcgcgtgtatg
17941    ---------+---------+---------+---------+---------+---------+  18000
         cgtggtggcatcagaaatgcgggccactcgcgaggtgggcgtggatgttcgcgcacatac

                   Eco0109I
                     Psp5II
                   Sse8647I
              Tth111II     |    SmlI    BspMI  HaeI        HaeII|
                       |     |         |    |    |            ||
                                                      AvaI
                                                    Bce83I
         atgaggtgtacggcgacgaggacctgcttgagcaggccaacgagcgcctcggggagtttg
18001    ---------+---------+---------+---------+---------+---------+  18060
         tactccacatgccgctgctcctggacgaactcgtccggttgctcgcggagcccctcaaac

                                           BspGI
                     NspI         MspA1I   |             BsbI
                        |             |  |                  |
         cctacggaaagcggcataaggacatgctggcgttgccgctggacgagggcaacccaacac
18061    ---------+---------+---------+---------+---------+---------+  18120
         ggatgcctttcgccgtattcctgtacgaccgcaacggcgacctgctcccgttgggttgtg

                                 AlwNI
                                BstAPI
                   BtsI      AarI |
                   SfcI  BstAPI   |
              BspMI   |PstI    |  |
                  |   |    |   |  |
         ctagcctaaagcccgtaacactgcagcaggtgctgcccgcgcttgcaccgtccgaagaaa
18121    ---------+---------+---------+---------+---------+---------+  18180
         gatcggatttcgggcattgtgacgtcgtccacgacgggcgcgaacgtggcaggcttcttt

                                                       BanI
                                                   TaqII |
                                               MspA1I  | |
                               BanI            PvuII   | |KpnI
                                  |                |   | |   |
         agcgcggcctaaagcgcgagtctggtgacttggcacccaccgtgcagctgatggtaccca
18181    ---------+---------+---------+---------+---------+---------+  18240
         tcgcggtcgctgaccttctacagaaccttttttactggcaccttggacccgacctcgggc

                                                          BanII
        HaeII AlwNI                                    Bsp1286I
       BsgI | PflMI                  BstDSI               AvaI|
          | |     |                        |                  ||
         agcgccagcgactggaagatgtcttggaaaaaatgaccgtggaacctgggctggagcccg
18241    ---------+---------+---------+---------+---------+---------+  18300
         tcgcggtcgctgaccttctacagaaccttttttactggcaccttggacccgacctcgggc

                                 Tth111II
                                 HaeII  |
              BspMI           BsaHI |   |
              BpmI |           NarI |   |
              EaeI |           BanI||   |
             GdiII |        AarI || |   |BmrI       BstDSI
                 | |           | || |   |   |            |
         aggtccgcgtgcggccaatcaagcaggtggcgccgggactgggcgtgcagaccgtggacg
18301    ---------+---------+---------+---------+---------+---------+  18360
         tccaggcgcacgccggttagttcgtccaccgcggccctgacccgcacgtctggcacctgc

          BsgI                                          XcmI
            |                                              |
         ttcagatacccactaccagtagcaccagtattgccaccgccacagagggcatggagacac
18361    ---------+---------+---------+---------+---------+---------+  18420
         aagtctatgggtgatggtcatcgtggtcataacggtggcggtgtctcccgtacctctgtg

                                                              BsgI
                                                           BsiEI |
                                    SacII                  EaeI | |
                  MspA1I          MspA1I|                  EagI | |
                BbvCI   |        BstDSI ||                GdiII | |
```

Figure 28AA

```
DrdI    Bpu10I    EciI    BsiEI    NotI
aaacgtccccggttgcctcagcggtggcggatgccgcggtgcaggcggtcgctgcggccg
18421                                                        18480
tttgcaggggccaacggagtcgccaccgcctacggcgccacgtccgccagcgacgccggc

BstDSI
cgtccaagacctctacggaggtgcaaacggacccgtggatgtttcgcgtttcagcccccc
18481                                                        18540
gcaggttctggagatgcctccacgtttgcctgggcacctacaaagcgcaaagtcgggggg

HaeII BsaHI NarI BanII    HaeII BsaHI NarI BanII BssHII
ggcgcccgcgcggttcgaggaagtacggcgccgccagcgcgctactgcccgaatatgccc
18541                                                        18600
ccgcgggcgcgccaagctccttcatgccgcggcggtcgcgcgatgacgggcttatacggg

BsrDI
tacatccttccattgcgcctacccccggctatcgtggctacacctaccgccccagaagac
18601                                                        18660
atgtaggaaggtaacgcggatgggggccgatagcaccgatgtggatggcggggtcttctg

BbsI    BsaHI    DrdII
gagcaactacccgacgccgaaccaccactggaacccgccgccgccgtcgccgtcgccagc
18661                                                        18720
ctcgttgatgggctgcggcttggtggtgaccttgggcggcggcggcagcggcagcggtcg

BcgI    FspI    NruI BcgI    Eco0109I Psp5II
ccgtgctggccccgatttccgtgcgcagggtggctcgcgaaggaggcaggaccctggtgc
18721                                                        18780
ggcacgaccggggctaaaggcacgcgtcccaccgagcgcttcctccgtcctgggaccacg

BssHII    DraI    BsrFI    DrdII
tgccaacagcgcgctaccaccccagcatcgtttaaaagccggtctttgtggttcttgcag
18781                                                        18840
acggttgtcgcgcgatggtggggtcgtagcaaattttcggccagaaacaccaagaacgtc

AarI    BspMI    BanI    BsmI
atatggccctcacctgccgcctccgtttcccggtgccgggattccgaggaagaatgcacc
18841                                                        18900
tataccgggagtggacggcggaggcaaagggccacggccctaaggctccttcttacgtgg

BstDSI FseI EaeI GdiII BsrFI NgoAIV EaeI GdiII    BglI    NspI SphI    FspI    BsrFI SgrAI
gtaggaggggcatggccggccacggcctgacgggcggcatgcgtcgtgcgcaccaccggc
18901                                                        18960
catcctccccgtaccggccggtgccggactgcccgccgtacgcagcacgcgtggtggccg

BssHII    NspI SphI    BciVI
ggcggcgcgcgtcgcaccgtcgcatgcgcggcggtatcctgcccctccttattccactga
18961                                                        19020
ccgccgcgcgcagcgtggcagcgtacgcgccgccataggacggggaggaataaggtgact

Bsp1286I BmgI BseSI HaeII SacII MspA1I BstDSI BsaHI NarI BanI    BstDSI HaeI BglI
tcgccgcggcgattggcgccgtgcccggaattgcatccgtggccttgcaggcgcagagac
19021                                                        19080
agcggcgccgctaaccgcggcacgggccttaacgtaggcaccggaacgtccgcgtctctg

NspI    BspGI
actgattaaaaacaagttgcatgtggaaaaatcaaaataaaaagtctggactctcacgct
19081                                                        19140
tgactaatttttgttcaacgtacacctttttagttttattttcagacctgagagtgcga
```

Figure 28BB

```
                                                BbsI          BsmBI
                                                   |             |
      cgcttggtcctgtaactattttgtagaatggaagacatcaactttgcgtctctggccccg
19141 ---------+---------+---------+---------+---------+---------+ 19200
      gcgaaccaggacattgataaaacatcttaccttctgtagttgaaacgcagagaccggggc

                                                     BanI            BsrBI
                                              EcoRV    |     Eco57I     |
                                                  |    |          |     |
      cgacacggctcgcgcccgttcatgggaaactggcaagatatcggcaccagcaatatgagc
19201 ---------+---------+---------+---------+---------+---------+ 19260
      gctgtgccgagcgcgggcaagtaccctttgaccgttctatagccgtggtcgttatactcg

        HaeII           BanII
      BsaHI |        Bsp1286I
       NarI |MspA1I        |
      BanI| | PvuII        |       BsrBI      ApoI
         || |     |        |           |         |
      ggtggcgccttcagctggggctcgctgtggagcggcattaaaatttcggttccaccgtt
19261 ---------+---------+---------+---------+---------+---------+ 19320
      ccaccgcggaagtcgaccccgagcgacacctcgccgtaattttaaagccaaggtggcaa

                                                    BbvCI
                  HaeI                             Bpu10I
                  StuI                   HaeI     AlwNI|
                     |                      |         ||
      aagaactatggcagcaaggcctggaacagcagcacaggccagatgctgagggataagttg
19321 ---------+---------+---------+---------+---------+---------+ 19380
      ttcttgataccgtcgttccggaccttgtcgtcgtgtccggtctacgactccctattcaac

                                                 HaeI
                                                MmeI|
         ApoI                            HaeI      ||
            |                               |      ||
      aaagagcaaaatttccaacaaaaggtggtagatggcctggcctctggcattagcggggtg
19381 ---------+---------+---------+---------+---------+---------+ 19440
      tttctcgttttaaaggttgttttccaccatctaccggaccggagaccgtaatcgccccac

          HaeI
          MscI
         EaeI |   BglI BtsI                  HindIII
            | |      |    |                        |
      gtggacctggccaaccaggcagtgcaaaataagattaacagtaagcttgatccccgccct
19441 ---------+---------+---------+---------+---------+---------+ 19500
      cacctggaccggttggtccgtcacgttttattctaattgtcattcgaactaggggcggga

                       BpmI
                      BsiEI
                     BstDSI
                     BseRI|       BsaXI
                     EaeI ||     Hin4II|
                     EagI ||  Tth111II||
                    GdiII ||     BsaXI|||
                   BsrFI | ||     Hin4I||||
                       | | ||         ||||
      cccgtagaggagcctccaccggccgtggagacagtgtctccagaggggcgtggcgaaaag
19501 ---------+---------+---------+---------+---------+---------+ 19560
      gggcatctcctcggaggtggccggcacctctgtcacagaggtctccccgcaccgcttttc

                                                        Hin4I  SunI
                                                            |     |
      cgtccgcgccccgacagggaagaaactctggtgacgcaaatagacgagcctccctcgtac
19561 ---------+---------+---------+---------+---------+---------+ 19620
      gcaggcgcggggctgtcccttctttgagaccactgcgtttatctgctcggagggagcatg

                    BstAPI                          Bsp24I
                     HaeI|                      BstDSI |
                     StuI|                        NcoI |
                  Bsp24I ||                       StyI |
        BplI   BseRI | ||                       XcmI | |BsaWI
           |       | | ||                          | | |   |
      gaggaggcactaaagcaaggcctgcccaccacccgtcccatcgcgcccatggctaccgga
19621 ---------+---------+---------+---------+---------+---------+ 19680
      ctcctccgtgatttcgttccggacgggtggtgggcagggtagcgcgggtaccgatggcct

                                  BspGI       BspMI
                                      |           |
      gtgctgggccagcacacacccgtaacgctggacctgcctcccccgccgacacccagcag
19681 ---------+---------+---------+---------+---------+---------+ 19740
      cacgacccggtcgtgtgtgggcattgcgacctggacggagggggcggctgtgggtcgtc

       TaqII           BsiEI
           |               |
      aaacctgtgctgccaggcccgaccgccgttgttgtaacccgtcctagccgcgcgtccctg
19741 ---------+---------+---------+---------+---------+---------+ 19800
      tttggacacgacggtccgggctggcggcaacaacattgggcaggatcggcgcgcagggac

              RsrII    BsiEI
          MspA1I |     PvuI
```

Figure 28CC

```
              | |        |
      cgccgcgccgccagcggtccgcgatcgttgcggcccgtagccagtggcaactggcaaagc
19801 ---------+---------+---------+---------+---------+---------+ 19860
      gcggcgcggcggtcgccaggcgctagcaacgccgggcatcggtcaccgttgaccgtttcg

                                              HaeII       Eco57I
                                                  |            |
      acactgaacagcatcgtgggtctgggggtgcaatccctgaagcgccgacgatgcttctga
19861 ---------+---------+---------+---------+---------+---------+ 19920
      tgtgacttgtcgtagcacccagacccccacgttagggacttcgcggctgctacgaagact

       AflIII                              AceIII          Bpu1102I
          |                                    |                  |
      atagctaacgtgtcgtatgtgtgtcatgtatgcgtccatgtcgccgccagaggagctgct
19921 ---------+---------+---------+---------+---------+---------+ 19980
      tatcgattgcacagcatacacacagtacatacgcaggtacagcggcggtctcctcgacga

        BssHII
     BseRI  |                                        BtsI
         |  |                                           |
      gagccgccgcgcgcccgctttccaagatggctaccccttcgatgatgccgcagtggtctt
19981 ---------+---------+---------+---------+---------+---------+ 20040
      ctcggcggcgcgcgggcgaaaggttctaccgatggggaagctactacggcgtcaccagaa

                                                  SmaI
                                                AvaI |
                                               BanII |
                                           Bsp1286I  |
      NspI  AvaI       BsaHI       Bpu10I         |   |
         |     |           |           |         | | |
      acatgcacatctcgggccaggacgcctcggagtacctgagccccgggctggtgcagtttg
20041 ---------+---------+---------+---------+---------+---------+ 20100
      tgtacgtgtagagcccggtcctgcggagcctcatggactcggggcccgaccacgtcaaac

                                                            HaeII
                                                        BsaHI  |
      BsmBI                                              NarI  |
    Eco57I||  BsgI                            BstDSI    BanI|| |
         ||     |                                  |        || |
      cccgcgccaccgagacgtacttcagcctgaataacaagtttagaaaccccacggtggcgc
20101 ---------+---------+---------+---------+---------+---------+ 20160
      gggcgcggtggctctgcatgaagtcggacttattgttcaaatctttggggtgccaccgcg

                       BsaWI
                       BsrFI
         DraIII        PinAI                                MslI
              |            |                                   |
      ctacgcacgacgtgaccacagaccggtcccagcgtttgacgctgcggttcatccctgtgg
20161 ---------+---------+---------+---------+---------+---------+ 20220
      gatgcgtgctgcactggtgtctggccagggtcgcaaactgcgacgccaagtagggacacc

                                           TaqII
    BciVI                                RleAI |
        |                                    | |
      accgtgaggatactgcgtactcgtacaaggcgcggttcaccctagctgtgggtgataacc
20221 ---------+---------+---------+---------+---------+---------+ 20280
      tggcactcctatgacgcatgagcatgttccgcgccaagtgggatcgacacccactattgg

                                                              ApaI
                                                             BanII
                                                          Bsp1286I
                                                              BmgI |
                                                             BseSI |
                                          SacII        Eco0109I|   |
                                        MspA1I|       Eco0109I||   |
         BspGI          BsaAI        BstDSI || BspGI          |||  |
             |              |             | ||     |          |||  |
      gtgtgctggacatggcttccacgtactttgacatccgcggcgtgctggacaggggcccta
20281 ---------+---------+---------+---------+---------+---------+ 20340
      cacacgacctgtaccgaaggtgcatgaaactgtaggcgccgcacgacctgtccccgggat

                                                   Bsp1286I
                                                       BmgI |
                                                      BseSI |
                       BtsI                 StyI BanI     | |
                          |                    |    |     | |
      cttttaagccctactctggcactgcctacaacgccctggctcccaagggtgccccaaatc
20341 ---------+---------+---------+---------+---------+---------+ 20400
      gaaaattcgggatgagaccgtgacggatgttgcgggaccgagggttcccacggggtttag

                                              EarI
                                                 |
      cttgcgaatgggatgaagctgctactgctcttgaaataaacctagaagaagaggacgatg
20401 ---------+---------+---------+---------+---------+---------+ 20460
      gaacgcttaccctacttcgacgatgacgagaactttatttggatcttcttctcctgctac

                                                             BsaHI
                 AccI                                         NarI
              BbsI  |        Bpu1102I          BsaAI         BanI|
                 |  |              |               |            ||
```

Figure 28DD

```
      acaacgaagacgaagtagacgagcaagctgagcagcaaaaaactcacgtatttgggcagg
20461 ---------+---------+---------+---------+---------+---------+ 20520
      tgttgcttctgcttcatctgctcgttcgactcgtcgtttttgagtgcataaacccgtcc

    HaeII              SspI
      |                  |
      cgccttattctggtataaatattacaaaggagggtattcaaataggtgtcgaaggtcaaa
20521 ---------+---------+---------+---------+---------+---------+ 20580
      gcggaataagaccatatttataatgtttcctcccataagtttatccacagcttccagttt

          Tth111II                        EcoNI
              |                             |
      cacctaaatatgccgataaaacatttcaacctgaacctcaaataggagaatctcagtggt
20581 ---------+---------+---------+---------+---------+---------+ 20640
      gtggatttatacggctattttgtaaagttggacttggagtttatcctcttagagtcacca

                     MspA1I
             VspI    PvuII
              |        |
      acgaaactgaaattaatcatgcagctgggagagtccttaaaaagactaccccaatgaaac
20641 ---------+---------+---------+---------+---------+---------+ 20700
      tgctttgactttaattagtacgtcgaccctctcaggaatttttctgatggggttactttg

              NdeI                        RleAI    BsmI
              |                             |        |
      catgttacggttcatatgcaaaacccacaaatgaaaatggagggcaaggcattcttgtaa
20701 ---------+---------+---------+---------+---------+---------+ 20760
      gtacaatgccaagtatacgttttgggtgtttacttttacctcccgttccgtaagaacatt

      agcaacaaaatggaaagctagaaagtcaagtggaaatgcaatttttctcaactactgagg
20761 ---------+---------+---------+---------+---------+---------+ 20820
      tcgttgttttacctttcgatctttcagttcacctttacgttaaaaagagttgatgactcc

                                           BsrGI
   BsiEI       BsrDI                       TatI
      |          |                           |
      cgaccgcaggcaatggtgataacttgactcctaaagtggtattgtacagtgaagatgtag
20821 ---------+---------+---------+---------+---------+---------+ 20880
      gctggcgtccgttaccactattgaactgaggatttcaccataacatgtcacttctacatc

                                    NspI                 BssSI
                                     |                      |
      atatagaaaccccagacactcatatttcttacatgcccactattaaggaaggtaactcac
20881 ---------+---------+---------+---------+---------+---------+ 20940
      tatatctttggggtctgtgagtataaagaatgtacgggtgataattccttccattgagtg

                                    HaeI
                                    StuI
                                BglI |    BsrDI
                                 |   |     |
      gagaactaatgggccaacaatctatgcccaacaggcctaattacattgcttttagggaca
20941 ---------+---------+---------+---------+---------+---------+ 21000
      ctcttgattacccggttgttagatacgggttgtccggattaatgtaacgaaaatccctgt

                           TaqII
                             |
      attttattggtctaatgtattacaacagcacgggtaatatgggtgttctggcgggccaag
21001 ---------+---------+---------+---------+---------+---------+ 21060
      taaaataaccagattacataatgttgtcgtgcccattatacccacaagaccgcccggttc

               BsmI
      Tth111II  |                               Tth111II
           |    |                                   |
      catcgcagttgaatgctgttgtagatttgcaagacagaaacacagagctttcataccagc
21061 ---------+---------+---------+---------+---------+---------+ 21120
      gtagcgtcaacttacgacaacatctaaacgttctgtctttgtgtctcgaaagtatggtcg

                       DrdII
                       SexAI                             HincII
                         |                                  |
      ttttgcttgattccattggtgatagaaccaggtacttttctatgtggaatcaggctgttg
21121 ---------+---------+---------+---------+---------+---------+ 21180
      aaaacgaactaaggtaaccactatcttggtccatgaaaagatacaccttagtccgacaac

      acagctatgatccagatgttagaattattgaaaatcatggaactgaagatgaacttccaa
21181 ---------+---------+---------+---------+---------+---------+ 21240
      tgtcgatactaggtctacaatcttaataacttttagtaccttgacttctacttgaaggtt

   Eco57I       BmrI        VspI                 StyI
      |           |           |                    |
      attactgctttccactgggaggtgtgattaatacagagactcttaccaaggtaaaaccta
21241 ---------+---------+---------+---------+---------+---------+ 21300
      taatgacgaaaggtgaccctccacactaattatgtctctgagaatggttccattttggat

  EcoNI                             SfcI ApoI  MmeI
      |                               |    |     |
      aaacaggtcaggaaaatggatgggaaaaagatgctacagaatttcagataaaaatgaaa
21301 ---------+---------+---------+---------+---------+---------+ 21360
      tttgtccagtcctttttacctaccctttttctacgatgtcttaaagtctatttttacttt
```

Figure 28EE

```
                   BstDSI
                    NcoI
                    StyI                            PflMI    ApoI
                     |                                |        |
      taagagttggaaataatttgccatggaaatcaatctaaatgccaacctgtggagaaatt
21361 ---------+---------+---------+---------+---------+---------+ 21420
      attctcaaccttattaaaacggtacctttagttagatttacggttggacacctctttaa

                   HaeII
 TatI       Eco47III |          MmeI      TatI
  |               | |            |          |
      tcctgtactccaacatagcgctgtatttgcccgacaagctaaagtacagtccttccaacg
21421 ---------+---------+---------+---------+---------+---------+ 21480
      aggacatgaggttgtatcgcgacataaacgggctgttcgatttcatgtcaggaaggttgc

                              Tth111II                    SmaI
 ApoI          MmeI Pfl1108I     |                    AvaI |
  |              |       |       |                       | |
      taaaaatttctgataacccaaacacctacgactacatgaacaagcgagtggtggctcccg
21481 ---------+---------+---------+---------+---------+---------+ 21540
      atttttaaagactattgggtttgtggatgctgatgtacttgttcgctcaccaccgagggc

                              BsiHKAI
                        StyI Bsp1286I                Tth111I
                         |        |                      |
      ggttagtggactgctacattaaccttggagcacgctggtcccttgactatatggacaacg
21541 ---------+---------+---------+---------+---------+---------+ 21600
      ccaatcacctgacgatgtaattggaacctcgtgcgaccagggaactgatatacctgttgc

                        XcmI    HaeI
 HincII            MslI |BsrDI |       BsrBI
  |                    | |    | |        |
      tcaacccatttaaccaccaccgcaatgctggcctgcgctaccgctcaatgttgctgggca
21601 ---------+---------+---------+---------+---------+---------+ 21660
      agttgggtaaattggtggtggcgttacgaccggacgcgatggcgagttacaacgacccgt

              Bsp1286I
                BmgI |          BanI
 BsrDI         BseSI |      MslI |
  |                | |         | |
      atggtcgctatgtgcccttccacatccaggtgcctcagaagttctttgccattaaaaacc
21661 ---------+---------+---------+---------+---------+---------+ 21720
      taccagcgatacacgggaaggtgtaggtccacggagtcttcaagaaacggtaatttttgg

                        Pfl1108I
                     Eco57I |
                 BanII     |  |                   HincII
              Bsp1286I     |  |                     HpaI  DrdII
                     |     |  |                        |    |
      tccttctcctgccgggctcatacacctacgagtggaacttcaggaaggatgttaacatgg
21721 ---------+---------+---------+---------+---------+---------+ 21780
      aggaagaggacggcccgagtatgtggatgctcaccttgaagtccttcctacaattgtacc

              AvrII
               StyI
             BanII |
            BsiHKAI |
           Bsp1286I |
           PstI   | |
 SfcI   |  SacI |           Bsu36I  HincII
  |     |     | |              |       |
      ttctgcagagctccctaggaaatgacctaagggttgacggagccagcattaagtttgata
21781 ---------+---------+---------+---------+---------+---------+ 21840
      aagacgtctcgagggatcctttactggattcccaactgcctcggtcgtaattcaaactat

                       BstDSI
                        NcoI            BsaXI       SmlI
                        StyI        BsbI   |  RleAI  |  HaeI
                         |            |   |     |  |    |
      gcatttgcctttacgccaccttcttccccatggcccacaacaccgcctccacgcttgagg
21841 ---------+---------+---------+---------+---------+---------+ 21900
      cgtaaacggaaatgcggtggaagaaggggtaccgggtgttgtggcggaggtgcgaactcc

                                            BsaXI
             Bce83I                       Hin4II  EciI
                |                            ||     |
      ccatgcttagaaacgacaccaacgaccagtcctttaacgactatctctccgccgccaaca
21901 ---------+---------+---------+---------+---------+---------+ 21960
      ggtacgaatctttgctgtggttgctggtcaggaaattgctgatagagaggcggcggttgt

                                Bsp1286I
                                  BmgI |
 NspI                            BseSI |              BmrI
  |                                  | |                 |
      tgctctaccctatacccgccaacgctaccaacgtgcccatatccatcccctcccgcaact
21961 ---------+---------+---------+---------+---------+---------+ 22020
      acgagatgggatatgggcggttgcgatggttgcacgggtataggtaggggagggcgttga

              SacII
            MspA1I|                AflII
```

Figure 28FF

```
        BstDSI ||                SmlI                          BmrI
               | ||                 |                              |
        gggcggctttccgcggctgggccttcacgcgccttaagactaaggaaaccccatcactgg
  22021 ---------+---------+---------+---------+---------+---------+ 22080
        cccgccgaaaggcgccgacccggaagtgcgcggaattctgattcctttggggtagtgacc

         Pf11108I
   BanII       |
Bsp1286I       |
   AvaI|       |
        ||     |
        gctcgggctacgaccccttattacacctactctggctctataccctacctagatggaacct
  22081 ---------+---------+---------+---------+---------+---------+ 22140
        cgagcccgatgctgggaataatgtggatgagaccgagatatgggatggatctaccttgga

                                  HaeI                MspA1I
                                  MscI             EarI     |HaeI
                                EaeI |            DrdI |PvuII   |
                                   | |               | |     |  |
        tttacctcaaccacacctttaagaaggtggccattacctttgactcttctgtcagctggc
  22141 ---------+---------+---------+---------+---------+---------+ 22200
        aaatggagttggtgtggaaattcttccaccggtaatggaaactgagaagacagtcgaccg

                                                   HaeII
           BsrDI                              Eco47III |HincII
               |                                     | |     |
        ctggcaatgaccgcctgcttacccccaacgagtttgaaattaagcgctcagttgacgggg
  22201 ---------+---------+---------+---------+---------+---------+ 22260
        gaccgttactggcggacgaatgggggttgctcaaactttaattcgcgagtcaactgcccc

                                               DrdII
           AclI     BmrI              PflMI      |           NheI
              |        |                  |      |              |
        agggttacaacgttgcccagtgtaacatgaccaaagactggttcctggtacaaatgctag
  22261 ---------+---------+---------+---------+---------+---------+ 22320
        tcccaatgttgcaacgggtcacattgtactggtttctgaccaaggaccatgtttacgatc

                                                                NspI
                                                              TatI|
                                                                  ||
        ctaactacaacattggctaccagggcttctatatcccagagagctacaaggaccgcatgt
  22321 ---------+---------+---------+---------+---------+---------+ 22380
        gattgatgttgtaaccgatggtcccgaagatatagggtctctcgatgttcctggcgtaca

                Bsp24I                              Bsp24I
                     |                                   |
        actccttctttagaaacttccagcccatgagccgtcaggtggtggatgatactaaataca
  22381 ---------+---------+---------+---------+---------+---------+ 22440
        tgaggaagaaatctttgaaggtcgggtactcggcagtccaccacctactatgatttatgt

             PflMI            BsbI
                 |               |
        aggactaccaacaggtgggcatcctacaccaacacaacaactctggatttgttggctacc
  22441 ---------+---------+---------+---------+---------+---------+ 22500
        tcctgatggttgtccacccgtaggatgtggttgtgttgttgagacctaaacaaccgatgg

                                HaeI
                                StuI
                                   |
        ttgcccccaccatgcgcgaaggacaggcctaccctgctaacttcccctatccgcttatag
  22501 ---------+---------+---------+---------+---------+---------+ 22560
        aacgggggtggtacgcgcttcctgtccggatgggacgattgaaggggataggcgaatatc

                                                  BsiEI
                                                  PvuI
             HincII                               SgfI     BpmI
                  |                                  |        |
        gcaagaccgcagttgacagcattacccagaaaaagtttcttgcgatcgcaccctttggc
  22561 ---------+---------+---------+---------+---------+---------+ 22620
        cgttctggcgtcaactgtcgtaatgggtctttttcaaagaaacgctagcgtgggaaaccg

                                BstDSI
                                  NcoI
                                  StyI
                                     |
        gcatcccattctccagtaactttatgtccatgggcgcactcacagacctgggccaaaacc
  22621 ---------+---------+---------+---------+---------+---------+ 22680
        cgtagggtaagaggtcattgaaatacaggtacccgcgtgagtgtctggacccggttttgg

                                                       BstDSI
                                                  BamHI NcoI
           BsaXI  EciI                            BstYI StyI
               |     |                                |     |
        ttctctacgccaactccgcccacgcgctagacatgacttttgaggtggatcccatggacg
  22681 ---------+---------+---------+---------+---------+---------+ 22740
        aagagatgcggttgaggcgggtgcgcgatctgtactgaaaactccacctagggtacctgc

                                                              BsiEI
                                                           EaeI |
                                                           EagI |
```

Figure 28GG

```
                                                          GdiII   |
                                                        BsiHKAI |  |
                                                       Bsp1286I |  |
                Tth111II                                  BsrFI |  |
        BanII          |                                BseSI | |  |
      Bsp1286I         |                Tth111I     ApaLI | | | |  |
             |         |                      |         | | | | |  |
        agcccacccttctttatgttttgtttgaagtctttgacgtggtccgtgtgcaccggccgc
  22741 ---------+---------+---------+---------+---------+---------+ 22800
        tcgggtgggaagaaatacaaaacaaacttcagaaactgcaccaggcacacgtggccggcg

                                                      BsiEI
                                                     BsrFI|
          BsaHI                                     NgoAIV|
         SacII |                                    EaeI ||
       MspA1I| |                       BspMI        EagI ||
      BstDSI || |                 FspI    |        GdiII ||
           | || |                    |    |            | ||
        accgcggcgtcatcgaaaccgtgtacctgcgcacgcccttctcggccggcaacgccacaa
  22801 ---------+---------+---------+---------+---------+---------+ 22860
        tggcgccgcagtagctttggcacatggacgcgtgcgggaagagccggccgttgcggtgtt

                                                    BanII
                           MspA1I              Bsp1286I
                            PvuII BstDSI             |
                            BpmI|  NcoI              |
                       Tth111II||  StyI              |          AlwNI
                              |||     |              |              |
        cataaagaagcaagcaacatcaacaacagctgccgccatgggctccagtgagcaggaact
  22861 ---------+---------+---------+---------+---------+---------+ 22920
        gtatttcttcgttcgttgtagttgttgtcgacggcggtacccgaggtcactcgtccttga

                                                    Bsp1286I
                 BglII                                 BmgI |
                 BstYI                                BseSI |
                 RleAI                                BanI| |     Eco47III
                     |                                    || |           |
        gaaagccattgtcaaagatcttggttgtgggccatattttttgggcacctatgacaagcg
  22921 ---------+---------+---------+---------+---------+---------+ 22980
        ctttcggtaacagtttctagaaccaacacccggtataaaaaacccgtggatactgttcgc

                                                                  NruI
                                                              BsiEI |
                                                          BsiEI   | |
                                                         BsrFI|   | |
                                                         EaeI ||  | |
                                                         EagI ||  | |
      HaeII                                             GdiII ||  | |
          |                                                 | ||  | |
        ctttccaggctttgtttctccacacaagctcgcctgcgccatagtcaatacggccggtcg
  22981 ---------+---------+---------+---------+---------+---------+ 23040
        gaaaggtccgaaacaaagaggtgtgttcgagcggacgcggtatcagttatgccggccagc

           BmrI                HaeI             UbaLI           NspI
              |                   |                 |               |
        cgagactgggggcgtacactggatggcctttgcctggaacccgcactcaaaaacatgcta
  23041 ---------+---------+---------+---------+---------+---------+ 23100
        gctctgacccccgcatgtgacctaccggaaacggaccttgggcgtgagtttttgtacgat

            BanII                         SmlI
          Bsp1286I  Bce83I         BspMI     |          Tth111II   Hin4I
                 |       |             |    |                |       |
        cctctttgagccctttggctttctgaccagcgactcaagcaggtttaccagtttgagta
  23101 ---------+---------+---------+---------+---------+---------+ 23160
        ggagaaactcgggaaaccgaaagactggtcgctgagttcgtccaaatggtcaaactcat

                             BsrDI                  MspA1I
                             HaeII                  BsiEI |
                                 |                      | |
        cgagtcactcctgcgccgtagcgccattgcttcttcccccgaccgctgtataacgctgga
  23161 ---------+---------+---------+---------+---------+---------+ 23220
        gctcagtgaggacgcggcatcgcggtaacgaagaagggggctggcgacatattgcgacct

                               ApaI
                              BanII
                            Bsp1286I
                                BmgI |    BsiEI
                               BseSI |  EaeI   |
                          EcoO109I | |  EagI   |
                              TaqII | | GdiII  |
                                  | | |    | |
        aaagtccacccaaagcgtacagggggcccaactcggccgcctgtggactattctgctgcat
  23221 ---------+---------+---------+---------+---------+---------+ 23280
        tttcaggtgggtttcgcatgtccccgggttgagccggcggacacctgataagacgacgta

                                       BstDSI
                                        NcoI
       NspI                             StyI                BaeI
          |                                |                   |
        gtttctccacgcctttgccaactggccccaaactcccatggatcacaaccccaccatgaa
```

Figure 28HH

```
23281 ---------+---------+---------+---------+---------+---------+ 23340
      caaagaggtgcggaaacggttgaccggggtttgagggtacctagtgttggggtggtactt

                 KpnI
             BanI   |          BaeI          Bsp24I
              |     |            |             |
      ccttattaccggggtacccaactccatgctcaacagtccccaggtacagcccaccctgcg
23341 ---------+---------+---------+---------+---------+---------+ 23400
      ggaataatggccccatgggttgaggtacgagttgtcaggggtccatgtcgggtgggacgc

                    SfcI           HaeII
             Bsp24I   |  AceIII    Hin4I|              BpmI BplI
                |     |     |         ||                 |    |
      tcgcaaccaggaacagctctacagcttcctggagcgccactcgccctacttccgcagcca
23401 ---------+---------+---------+---------+---------+---------+ 23460
      agcgttggtccttgtcgagatgtcgaaggacctcgcggtgagcgggatgaaggcgtcggt

                                                         NspI
                                                 AflIII   |
        FspI             HaeII                  BspLU11I  |      TatI
         |                 |                           |  |        |
      cagtgcgcagattaggagcgccacttctttttgtcacttgaaaaacatgtaaaaataatg
23461 ---------+---------+---------+---------+---------+---------+ 23520
      gtcacgcgtctaatcctcgcggtgaagaaaaacagtgaactttttgtacatttttattac

                                             BsrGI
                                              TatI     AvaI
                                               |        |
      tactagagacactttcaataaaggcaaatgcttttatttgtacactctcgggtgattatt
23521 ---------+---------+---------+---------+---------+---------+ 23580
      atgatctctgtgaaagttatttccgtttacgaaaataaacatgtgagagcccactaataa

                                DraI                          MslI
                                 |                              |
      taccccccacccttgccgtctgcgccgtttaaaaatcaaaggggttctgccgcgcatcgct
23581 ---------+---------+---------+---------+---------+---------+ 23640
      atgggggtgggaacggcagacgcggcaaatttttagtttccccaagacggcgcgtagcga

                     BaeI                         BsiHKAI
                 AflIII|                          Bsp1286I   BaeI
                       ||                              |       |
      atgcgccactggcagggacacgttgcgatactggtgtttagtgctccacttaaactcagg
23641 ---------+---------+---------+---------+---------+---------+ 23700
      tacgcggtgaccgtccctgtgcaacgctatgaccacaaatcacgaggtgaatttgagtcc

                SacII
              MspA1I|                                       AflIII
           BstDSI ||             AceIII              FspI   BspMI
                  |  ||                |                  |   MluI
      cacaaccatccgcggcagctcggtgaagttttcactccacaggctgcgcaccatcaccaa
23701 ---------+---------+---------+---------+---------+---------+ 23760
      gtgttggtaggcgccgtcgagccacttcaaaagtgaggtgtccgacgcgtggtagtggtt

                         EcoRV
                    HaeII   |
                BsaHI   |   |                                 BssHII
                 NarI   |   |                              BssHII |
                BanI|   |   |            EcoO109I    EciI      |  |
                   ||   |   |                 |        |       |  |
      cgcgtttagcaggtcgggcgccgatatcttgaagtcgcagttggggcctccgccctgcgc
23761 ---------+---------+---------+---------+---------+---------+ 23820
      gcgcaaatcgtccagcccgcggctatagaacttcagcgtcaaccccggaggcgggacgcg

                                                               MmeI
                                                          BsiHKAI|
                                                         Bsp1286I|
                                                          BseSI ||
                                                HaeII  ApaLI |  ||
                                                  |        | |  ||
      gcgcgagttgcgatacacagggttgcagcactggaacactatcagcgccgggtggtgcac
23821 ---------+---------+---------+---------+---------+---------+ 23880
      cgcgctcaacgctatgtgtcccaacgtcgtgaccttgtgatagtcgcggcccaccacgtg

                                          EcoO109I
        HaeI                               Psp5II
        MscI                  BstYI      Sse8647I
      EaeI |                Hin4I |      BspGI |          Bpu10I
         | |                    | |          | |             |
      gctggccagcacgctcttgtcggagatcagatccgcgtccaggtcctccgcgttgctcag
23881 ---------+---------+---------+---------+---------+---------+ 23940
      cgaccggtcgtgcgagaacagcctctagtctaggcgcaggtccaggaggcgcaacgagtc

                                                 Bsp1286I
                                                   BmgI |
          HincII                                  BseSI |
             |                                        | |
      ggcgaacggagtcaactttggtagctgccttcccaaaaagggcgcgtgcccaggctttga
23941 ---------+---------+---------+---------+---------+---------+ 24000
      ccgcttgcctcagttgaaaccatcgacggaagggtttttcccgcgcacgggtccgaaact
```

Figure 28II

```
                                   Bsp1286I
                                     BmgI |
                                    BseSI |
 Hin4I        MslI    BplI  BstEII  HgiEII |     BciVI
     |           |      |      |        | |        |
     gttgcactcgcaccgtagtggcatcaaaaggtgaccgtgcccggtctgggcgttaggata
24001 ---------+---------+---------+---------+---------+---------+ 24060
     caacgtgagcgtggcatcaccgtagttttccactggcacgggccagacccgcaatcctat

     AlwNI                                 Bpu10I
     HaeII                                Eco57I|
        |                                     ||
     cagcgcctgcataaaagccttgatctgcttaaaagccacctgagcctttgcgccttcaga
24061 ---------+---------+---------+---------+---------+---------+ 24120
     gtcgcggacgtattttcggaactagacgaattttcggtggactcggaaacgcggaagtct

                                                            MmeI
                                                       BsiHKAI|
                                                      Bsp1286I|
                                   EaeI     BglI        BseSI ||
         NspI    BstAPI           GdiII     SfiI       ApaLI | ||
            |         |               |        |           | | ||
     gaagaacatgccgcaagacttgccggaaaactgattggccggacaggccgcgtcgtgcac
24121 ---------+---------+---------+---------+---------+---------+ 24180
     cttcttgtacggcgttctgaacggccttttgactaaccggcctgtccggcgcagcacgtg

                          BglII                 BsaWI
                          BstYI                 BsrFI
             BsgI    BsbI     |                 PinAI
                |       |     |                     |
     gcagcaccttgcgtcggtgttggagatctgcaccacatttcggccccaccggttcttcac
24181 ---------+---------+---------+---------+---------+---------+ 24240
     cgtcgtggaacgcagccacaacctctagacgtggtgtaaagccggggtggccaagaagtg

       Eco57I                BssHII
       HaeI |              BssHII |
          | |                   | |
     gatcttggccttgctagactgctccttcagcgcgcgctgcccgttttcgctcgtcacatc
24241 ---------+---------+---------+---------+---------+---------+ 24300
     ctagaaccggaacgatctgacgaggaagtcgcgcgcgacgggcaaaagcgagcagtgtag

             BsiHKAI
            Bsp1286I
          BsaAI     |                                AflII
           PmlI     |                           AccI  SmlI
              |     |                              |     |
     catttcaatcacgtgctccttatttatcataatgcttccgtgtagacacttaagctcgcc
24301 ---------+---------+---------+---------+---------+---------+ 24360
     gtaaagttagtgcacgaggaataaatagtattacgaaggcacatctgtgaattcgagcgg

                                                 BanII
                                              Bsp1286I
                                                BssSI|
                                           Tth111II ||
                                               BsgI | ||
             MspA1I                          BstDSI| | ||
                  |                              || | ||
     ttcgatctcagcgcagcggtgcagccacaacgcgcagcccgtgggctcgtgatgcttgta
24361 ---------+---------+---------+---------+---------+---------+ 24420
     aagctagagtcgcgtcgccacgtcggtgttgcgcgtcgggcacccgagcactacgaacat

                                         PstI
                                 PstI    SbfI
 BstEII       BspMI     SfcI     |   SfcI   |
      |           |        |   |       |   |
     ggtcacctctgcaaacgactgcaggtacgcctgcaggaatcgccccatcatcgtcacaaa
24421 ---------+---------+---------+---------+---------+---------+ 24480
     ccagtggagacgtttgctgacgtccatgcggacgtccttagcggggtagtagcagtgttt

                                          BsiHKAI
                                         Bsp1286I
                                      SacII     |
                                    MspA1I|     |
                            MspA1I BstDSI ||    |
                             PvuII BseRI| ||    |
                                 |    || ||    |
     ggtcttgttgctggtgaaggtcagctgcaacccgcggtgctcctcgttcagccaggtctt
24481 ---------+---------+---------+---------+---------+---------+ 24540
     ccagaacaacgaccacttccagtcgacgttgggcgccacgaggagcaagtcggtccagaa

       BsiEI
      EaeI |
      EagI |
     GdiII |
         | |
     gcatacggccgccagagcttccacttggtcaggcagtagtttgaagttcgcctttagatc
24541 ---------+---------+---------+---------+---------+---------+ 24600
     cgtatgccggcggtctcgaaggtgaaccagtccgtcatcaaacttcaagcggaaatctag

                              BssHII
```

Figure 28JJ

```
BsaAI                 BssHII |
BsaBI      PmlI                 BssHII | |
  |         |                         | | |
         gttatccacgtggtacttgtccatcagcgcgcgcgcagcctccatgccccttctccccacgc
24601 ---------+---------+---------+---------+---------+---------+ 24660
         caataggtgcaccatgaacaggtagtcgcgcgcgcgtcggaggtacgggaagagggtgcg

          BsiEI
          PvuI       MspA1I
           |           |
         agacacgatcggcacactcagcgggttcatcaccgtaatttcactttccgcttcgctggg
24661 ---------+---------+---------+---------+---------+---------+ 24720
         tctgtgctagccgtgtgagtcgcccaagtagtggcattaaagtgaaaggcgaagcgaccc

  BanII EarI                                  BmrI
Bsp1286I SapI   EarI                          BbsI|
  |       |      |                             ||
         ctcttcctcttcctcttgcgtccgcataccacgcgccactgggtcgtcttcattcagccg
24721 ---------+---------+---------+---------+---------+---------+ 24780
         gagaaggagaaggagaacgcaggcgtatggtgcgcggtgacccagcagaagtaagtcggc

                                              BsaWI
                                              BsrFI
                                              PinAI
                   Tth111II                   SgrAI
                       |                        |
         ccgcactgtgcgcttacctcctttgccatgcttgattagcaccggtgggttgctgaaacc
24781 ---------+---------+---------+---------+---------+---------+ 24840
         ggcgtgacacgcgaatggaggaaacggtacgaactaatcgtggccacccaacgactttgg

              HaeII
                |
         caccatttgtagcgccacatcttctctttcttcctcgctgtccacgattacctctggtga
24841 ---------+---------+---------+---------+---------+---------+ 24900
         gtggtaaacatcgcggtgtagaagagaaagaaggagcgacaggtgctaatggagaccact

                                                            BsrDI
                                                            HaeI|
         AvaI                                               MscI|
         HaeII                  HaeII                    EaeI ||
           |                      |                         | ||
         tggcgggcgctcgggcttgggagaagggcgcttctttttcttcttgggcgcaatggccaa
24901 ---------+---------+---------+---------+---------+---------+ 24960
         accgcccgcgagcccgaaccctcttcccgcgaagaaaaagaagaacccgcgttaccggtt

                    SacII
                  MspA1I|
                 BstDSI ||
               TaqII | ||
               EaeI| | ||
  EciI        GdiII| | ||              BanI             BbsI
    |              || | ||               |                 |
         atccgccgccgaggtcgatggccgcgggctgggtgtgcgcggcaccagcgcgtcttgtga
24961 ---------+---------+---------+---------+---------+---------+ 25020
         taggcggcggctccagctaccggcgcccgacccacacgcgccgtggtcgcgcagaacact

                                                             SmaI
                                                          AvaI |
                                                         HaeII |
                                                       BsaHI | |
                                                        NarI | |
         Hin4I              BplI                       BanI| | |
           |                  |                          || | |
         tgagtcttcctcgtcctcggactcgatacgccgcctcatccgctttttgggggcgcccg
25021 ---------+---------+---------+---------+---------+---------+ 25080
         actcagaaggagcaggagcctgagctatgcggcggagtaggcgaaaaacccccgcgggc

                                 BstDSI
                             BsaXI   |
                            Hin4I|   |
                            AhdI ||  |
                         AflIII| ||  |
                          HaeIV| || NcoI            AatII
                          Hin4I| || StyI        BsaHI   |
                              || ||   |             |   |
         gggaggcggcggcgacggggacggggacgacacgtcctccatggttgggggacgtcgcgc
25081 ---------+---------+---------+---------+---------+---------+ 25140
         ccctccgccgccgctgcccctgcccctgctgtgcaggaggtaccaacccccctgcagcgcg

                                                    HaeI
                                                    MscI
                AvaI          BseRI          EarI  EaeI |
                  |             |              |    | |
         cgcaccgcgtccgcgctcgggggtggtttcgcgctgctcctcttcccgactggccatttc
25141 ---------+---------+---------+---------+---------+---------+ 25200
         gcgtggcgcaggcgcgagcccccaccaaagcgcgacgaggagaagggctgaccggtaaag

          SfcI
           |
         cttctcctataggcagaaaaagatcatggagtcagtcgagaagaaggacagcctaaccgc
```

Figure 28KK

```
25201 ---------+---------+---------+---------+---------+---------+ 25260
      gaagaggatatccgtcttttctagtacctcagtcagctcttcttcctgtcggattggcg

      cccctctgagttcgccaccaccgcctccaccgatgccgccaacgcgcctaccaccttccc
25261 ---------+---------+---------+---------+---------+---------+ 25320
      ggggagactcaagcggtggtggcggaggtggctacggcggttgcgcggatggtggaaggg

                                          Eco0109I
                                     Bce83I    |
                                      BseRI    |
         BanI       SmlI         BseRI  |  Psp5II
          |          |              |   |      |
      cgtcgaggcaccccccgcttgaggaggaggaagtgattatcgagcaggacccaggttttgt
25321 ---------+---------+---------+---------+---------+---------+ 25380
      gcagctccgtggggggcgaactcctcctccttcactaatagctcgtcctgggtccaaaaca

                      BsrBI
           BbsI Hin4I  |          BplI
              |    |   |            |
      aagcgaagacgacgaggaccgctcagtaccaacagaggataaaaagcaagaccaggacaa
25381 ---------+---------+---------+---------+---------+---------+ 25440
      ttcgcttctgctgctcctggcgagtcatggttgtctcctatttttcgttctggtcctgtt

                                                   RleAI   BsmBI
                                                       |       |
      cgcagaggcaaacgaggaacaagtcgggcgggggggacgaaaggcatggcgactacctaga
25441 ---------+---------+---------+---------+---------+---------+ 25500
      gcgtctccgtttgctccttgttcagcccgccccccctgctttccgtaccgctgatggatct

                                     HaeII
                                  PstI  |              AflIII
        BsaXI               SfcI   |    |                MluI
           |                   |   |    |                   |
      tgtgggagacgacgtgctgttgaagcatctgcagcgccagtgcgccattatctgcgacgc
25501 ---------+---------+---------+---------+---------+---------+ 25560
      acaccctctgctgcacgacaacttcgtagacgtcgcggtcacgcggtaatagacgctgcg

                 Bsp1286I
                    BmgI |
                  BseSI  |                       Pfl1108I
                       | |                              |
      gttgcaagagcgcagcgatgtgcccctcgccatagcggatgtcagccttgcctacgaacg
25561 ---------+---------+---------+---------+---------+---------+ 25620
      caacgttctcgcgtcgctacacggggagcggtatcgcctacagtcggaacggatgcttgc

                                                           BanII
                                                        Bsp1286I
                                                     NspI      |
                                                           |   |
      ccacctattctcaccgcgcgtacccccccaaacgccaagaaaacggcacatgcgagcccaa
25621 ---------+---------+---------+---------+---------+---------+ 25680
      ggtggataagagtggcgcgcatgggggggtttgcggttcttttgccgtgtacgctcgggtt

                              Tth111II
                                    |
      cccgcgcctcaacttctaccccgtatttgccgtgccagaggtgcttgccacctatcacat
25681 ---------+---------+---------+---------+---------+---------+ 25740
      gggcgcggagttgaagatggggcataaacggcacggtctccacgaacggtggatagtgta

                                                       BsrBI
                                                           |
      ctttttccaaaactgcaagataccccctatcctgccgtgccaaccgcagccgagcggacaa
25741 ---------+---------+---------+---------+---------+---------+ 25800
      gaaaaaggttttgacgttctatggggataggacggcacggttggcgtcggctcgcctgtt

          Tth111II
       HaeI     |
MspA1I    |     |                   Hin4I
 PvuII    |     |      HaeII        EcoRV |
     |    |     |         |             | |
      gcagctggccttgcggcagggcgctgtcatacctgatatcgcctcgctcaacgaagtgcc
25801 ---------+---------+---------+---------+---------+---------+ 25860
      cgtcgaccggaacgccgtcccgcgacagtatggactatagcggagcgagttgcttcacgg

                              BssHII
                                   |
      aaaaatctttgagggtcttggacgcgacgagaagcgcgcggcaaacgctctgcaacagga
25861 ---------+---------+---------+---------+---------+---------+ 25920
      tttttagaaactcccagaacctgcgctgctcttcgcgcgccgtttgcgagacgttgtcct

                                          BpmI
                                      AvaI   |
                             BsaXI    SmlI   |
                              BsbI    XhoI   |      BssHII
                                |        |   |           |
      aaacagcgaaaatgaaagtcactctggagtgttggtggaactcgagggtgacaacgcgcg
25921 ---------+---------+---------+---------+---------+---------+ 25980
      tttgtcgcttttactttcagtgagacctcacaaccaccttgagctcccactgttgcgcgc

                                          BglI
```

Figure 28LL

```
                                 BstEII                    TaqII
                                  |                          |
      cctagccgtactaaaacgcagcatcgaggtcacccactttgcctacccggcacttaacct
25981 ---------+---------+---------+---------+---------+---------+ 26040
      ggatcggcatgattttgcgtcgtagctccagtgggtgaaacggatgggccgtgaattgga

                             RcaI
                            MslI|
                         AceIII ||
                        BsiHKAI ||
     HgiEII            Bsp1286I ||
      StyI   RcaI             | ||                     FspI  AlwNI
       |      |               | ||                       |      |
      acccccaaggtcatgagcacagtcatgagtgagctgatcgtgcgccgtgcgcagccccct
26041 ---------+---------+---------+---------+---------+---------+ 26100
      tgggggttccagtactcgtgtcagtactcactcgactagcacgcggcacgcgtcggggga

                                            Tth111II
               ApoI    BpmI           Eco0109I    |BseRI
                 |       |                |     |   |
      ggagagggatgcaaatttgcaagaacaaacagaggagggcctacccgcagttggcgacga
26101 ---------+---------+---------+---------+---------+---------+ 26160
      cctctccctacgtttaaacgttcttgtttgtctcctcccggatgggcgtcaaccgctgct

       BssHII
     NheI  |                                                BseRI
        |  |                                                    |
      gcagctagcgcgctggcttcaaacgcgcgagcctgccgacttggaggagcgacgcaaact
26161 ---------+---------+---------+---------+---------+---------+ 26220
      cgtcgatcgcgcgaccgaagtttgcgcgctcggacggctgaacctcctcgctgcgtttga

               BsiHKAI                           MspA1I
       EaeI   Bsp1286I           BsaXI        NspI  |
      GdiII   BtsI   |BstDSI     SmlI|        SphI  | Bce83I
         |       |   |     |        ||           |  |     |
      aatgatggccgcagtgctcgttaccgtggagcttgagtgcatgcagcggttctttgctga
26221 ---------+---------+---------+---------+---------+---------+ 26280
      ttactaccggcgtcacgagcaatggcacctcgaactcacgtacgtcgccaagaaacgact

                                                          BsaAI
                                                          SnaBI
                          BsrDI                            SunI
                            |                                 |
      cccggagatgcagcgcaagctagaggaaacattgcactacacctttcgacagggctacgt
26281 ---------+---------+---------+---------+---------+---------+ 26340
      gggcctctacgtcgcgttcgatctcctttgtaacgtgatgtggaaagctgtcccgatgca

                                  BanII
                                 BsiHKAI             MmeI
         HaeI   BglII           Bsp1286I         BsaXI |    StyI
         StuI   BstYI               SacI  SexAI    |  |BsaI  | ApoI
            |      |                   |      |    | |   |  |    |
      acgccaggcctgcaagatctccaacgtggagctctgcaacctggtctcctaccttggaat
26341 ---------+---------+---------+---------+---------+---------+ 26400
      tgcggtccggacgttctagaggttgcacctcgagacgttggaccagaggatggaacctta

                              Bce83I                         AscI
                  StyI       BstAPI|           SmlI        BssHII
                    |             ||             |             |
      tttgcacgaaaaccgccttgggcaaaacgtgcttcattccacgctcaagggcgaggcgcg
26401 ---------+---------+---------+---------+---------+---------+ 26460
      aaacgtgcttttggcggaacccgttttgcacgaagtaaggtgcgagttcccgctccgcgc

                                                          BstDSI
                                                            NcoI
                                                            StyI
                                                        EaeI   |
      Tth111I                                          GdiII   |
         |                                                 |   |
      ccgcgactacgtccgcgactgcgtttacttatttctatgctacacctggcagacggccat
26461 ---------+---------+---------+---------+---------+---------+ 26520
      ggcgctgatgcaggcgctgacgcaaatgaataaagatacgatgtggaccgtctgccggta

                                                          AlwNI
                                                         BstAPI
                      Bce83I          BseRI            PstI   |
      Tth111II   BtsI      |   AceIII  SmlI  |  SfcI       |    |
          |        |       |      |       | |      |     |    |
      gggcgtttggcagcagtgcttggaggagtgcaacctcaaggagctgcagaaactgctaaa
26521 ---------+---------+---------+---------+---------+---------+ 26580
      cccgcaaaccgtcgtcacgaacctcctcacgttggagttcctcgacgtctttgacgattt

                                               EaeI
                                             GdiII
                                          BstDSI |
       Eco0109I                           HaeII | |
         PspSII                      Eco47III | | |
       Sse8647I                         BsaXI| | | |               EciI
              |                            || | | |                  |
      gcaaaacttgaaggacctatggacggccttcaacgagcgctccgtggccgcgcacctggc
```

Figure 28MM

```
26581 ---------+---------+---------+---------+---------+---------+ 26640
      cgttttgaacttcctggatacctgccggaagttgctcgcgaggcaccggcgcgtggaccg

                                              EcoNI    AlwNI
                                                  |        |
      ggacatcatttccccgaacgcctgcttaaaaccctgcaacagggtctgccagacttcac
26641 ---------+---------+---------+---------+---------+---------+ 26700
      cctgtagtaaaggggcttgcggacgaattttgggacgttgtcccagacggtctgaagtg

                                                      Bpu10I
                                                       HaeII
               NspI                              Eco47III |
                  |                                     | |
      cagtcaaagcatgttgcagaactttaggaactttatcctagagcgctcaggaatcttgcc
26701 ---------+---------+---------+---------+---------+---------+ 26760
      gtcagtttcgtacaacgtcttgaaatccttgaaataggatctcgcgagtccttagaacgg

              BsiHKAI
             Bsp1286I
              BseSI |             Bsp1286I
              BspMI |               BmgI |                    EciI
        AarI ApaLI| |              BseSI |               BsmI    |
         |       || |                  | |                  |    |
      cgccacctgctgtgcacttcctagcgactttgtgcccattaagtaccgcgaatgccctcc
26761 ---------+---------+---------+---------+---------+---------+ 26820
      gcggtggacgacacgtgaaggatcgctgaaacacgggtaattcatggcgcttacgggagg

                                  NheI
                                 PstI|
                  BtsI      SfcI   ||
                     |         |   ||
      gccgctttggggccactgctaccttctgcagctagccaactaccttgcctaccactctga
26821 ---------+---------+---------+---------+---------+---------+ 26880
      cggcgaaaccccggtgacgatggaagacgtcgatcggttgatggaacggatggtgagact

                 BsrBI                                BstAPI
               BbsI |        AccI                   BpmI    |
                  | |           |                      |    |
      cataatggaagacgtgagcggtgacggtctactggagtgtcactgtcgctgcaacctatg
26881 ---------+---------+---------+---------+---------+---------+ 26940
      gtattaccttctgcactcgccactgccagatgacctcacagtgacagcgacgttggatac

                                   MspA1I                 BanI
             BsrBI                  PvuII            AceIII  |
                 |                      |                 |  |
      caccccgcaccgctccctggtttgcaattcgcagctgcttaacgaaagtcaaattatcgg
26941 ---------+---------+---------+---------+---------+---------+ 27000
      gtggggcgtggcgagggaccaaacgttaagcgtcgacgaattgctttcagtttaatagcc

                                               SacII
                Eco0109I                     MspA1I|
                  Psp5II                   BstDSI ||
                   SanDI               AhdI     | ||
                  PstI |              HaeIV|    | ||
     KpnI     SfcI   | |              Hin4I|    | ||
        |        |   | |                 ||     | ||
      tacctttgagctgcagggtccctcgcctgacgaaaagtccgcggctccggggttgaaact
27001 ---------+---------+---------+---------+---------+---------+ 27060
      atggaaactcgacgtcccagggagcggactgcttttcaggcgccgaggccccaactttga

                    AatII
                 BsaHI |          ApoI    Bsu36I
                     | |             |         |
      cactccggggctgtggacgtcggcttaccttcgcaaatttgtacctgaggactaccacgc
27061 ---------+---------+---------+---------+---------+---------+ 27120
      gtgaggccccgacacctgcagccgaatggaagcgtttaaacatggactcctgatggtgcg

                    Pfl1108I
   BssSI   UbaLI           |      BbsI
       |       |           |         |
      ccacgagattaggttctacgaagaccaatcccgcccgccaaatgcggagcttaccgcctg
27121 ---------+---------+---------+---------+---------+---------+ 27180
      ggtgctctaatccaagatgcttctggttagggcgggcggtttacgcctcgaatggcggac

                                  MunI
                              HaeI |
                              MscI |
                            EaeI | |
                        BstXI  | | |
                            |  | | |
      cgtcattacccagggccacattcttggccaattgcaagccatcaacaaagcccgccaaga
27181 ---------+---------+---------+---------+---------+---------+ 27240
      gcagtaatgggtcccggtgtaagaaccggttaacgttcggtagttgtttcgggcggttct

                                              BmrI          BanII
                                             AhdI|        BsiHKAI
                                           HaeIV||       Bsp1286I
        Pfl1108I                           Hin4I||           SacI
               |                                |||              |
      gtttctgctacgaaagggacggggggtttacttggacccccagtccggcgaggagctcaa
```

Figure 28NN

```
27241 ---------+---------+---------+---------+---------+---------+ 27300
      caaagacgatgctttccctgccccccaaatgaacctgggggtcaggccgctcctcgagtt

                                                   ApaI
                                                  BanII
                                               Bsp1286I
                                                  BmgI |
                                                 BseSI |
                                            EcoO109I|  |
                                               SacII || |
                                             MspA1I| || |
                                            BstDSI || || |
      BseRI                                        | || || |
      |
      cccaatccccccgccgccgcagccctatcagcagcagccgcgggcccttgcttcccagga
27301 ---------+---------+---------+---------+---------+---------+ 27360
      gggttagggggggcggcggcgtcgggatagtcgtcgtcggcgcccgggaacgaagggtcct

                         MspA1I
                          PvuII
                          PstI|
                        TaqII ||                                BseRI
     BanI               SfcI | ||        BstDSI         TaqII   BmrI  |
      |                    |  | ||          |             |      |    |
      tggcacccaaaaagaagctgcagctgccgccgccacccacggacgaggaggaatactggg
27361 ---------+---------+---------+---------+---------+---------+ 27420
      accgtgggtttttcttcgacgtcgacggcggcggtgggtgcctgctcctccttatgaccc

                                                   BseRI
                                               BseRI  |    BbsI
                           BseRI           BseRI  |   |   BmrI|
                             |               |    |   |     ||
      acagtcaggcagaggaggtttggacgaggaggaggaggacatgatggaagactgggaga
27421 ---------+---------+---------+---------+---------+---------+ 27480
      tgtcagtccgtctcctccaaacctgctcctcctcctcctgtactaccttctgaccctct

           HindIII
      EcoNI     |       EarI                             TaqII BcgI
        |       |         |                                 |     |
      gcctagacgaggaagcttccgaggtcgaagaggtgtcagacgaaacaccgtcaccctcgg
27481 ---------+---------+---------+---------+---------+---------+ 27540
      cggatctgctccttcgaaggctccagcttctccacagtctgctttgtggcagtgggagcc

                       HaeII
                    BsaHI  |
                     NarI  |
                    BanI|  |
                 BsrFI || |
        BsmI    NgoAIV || |                BsaWI
     BsiEI |    SgrAI  || |  BcgI          BsrFI
      | |          |  || |    |            PinAI               BseRI
      | |          |  || |    |              |                    |
      tcgcattcccctcgccggcgccccagaaatcggcaaccggttccagcatggctacaacct
27541 ---------+---------+---------+---------+---------+---------+ 27600
      agcgtaaggggagcggccgcggggtctttagccgttggccaaggtcgtaccgatgttgga

                    BsrFI
                   NgoAIV
                  HaeII |
                BsaHI | |
          Bsu36I    |  | |
        BsrBI |  NarI | |
      BsaXI |  |BanI| | |      BtsI
      | |    |   || | |        |
      ccgctcctcaggcgccgccggcactgcccgttcgccgacccaaccgtagatgggacacca
27601 ---------+---------+---------+---------+---------+---------+ 27660
      ggcgaggagtccgcggcggccgtgacgggcaagcggctgggttggcatctaccctgtggt

                BsrFI
             HgiEII|
      DrdII     ||                   Tth111II
         |      ||                       |
      ctggaaccagggccggtaagtccaagcagccgccgccgttagcccaagagcaacaacagc
27661 ---------+---------+---------+---------+---------+---------+ 27720
      gaccttggtcccggccattcaggttcgtcggcggcggcaatcgggttctcgttgttgtcg

                                      Tth111II
                                Tth111II   |
                         Bsp1286I     |    |
                            BmgI |    |    |
    HaeII                  BseSI |    |    |
     StyI      BsrBI             |    |    |             RleAI
      |          |              ||    |    |               |
      gccaaggctaccgctcatggcgcgggcacaagaacgccatagttgcttgcttgcaagact
27721 ---------+---------+---------+---------+---------+---------+ 27780
      cggttccgatggcgagtaccgcgcccgtgttcttgcggtatcaacgaacgaacgttctga

                                                        HaeI
                                                  DraIII  |
                                                      |   |
      gtgggggcaacatctccttcgcccgccgctttcttctctaccatcacggcgtggccttcc
27781 ---------+---------+---------+---------+---------+---------+ 27840
      cacccccgttgtagaggaagcgggcggcgaaagaagagatggtagtgccgcaccggaagg
```

Figure 2800

SfcI BsgI BsrFI SgrAI MspA1I
27841 cccgtaacatcctgcattactaccgtcatctctacagcccatactgcaccggcggcagcg 27900
gggcattgtaggacgtaatgatggcagtagagatgtcgggtatgacgtggccgccgtcgc MspA1I EaeI GdiII MspA1I BsiEI BsaWI
27901 gcagcggcagcaacagcagcggccacacagaagcaaaggcgaccggatagcaagactctg 27960
cgtcgccgtcgttgtcgtcgccggtgtgtcttcgtttccgctggcctatcgttctgagac MspA1I Eco47III HaeII BseRI BseRI BanI NarI BsaHI
27961 acaaagcccaagaaatccacagcggcggcagcagcaggaggaggagcgctgcgtctggcg 28020
tgtttcgggttctttaggtgtcgccgccgtcgtcgtcctcctcctcgcgacgcagaccgc HaeII
28021 cccaacgaacccgtatcgacccgcgagcttagaaacaggatttttcccactctgtatgct 28080
gggttgcttgggcatagctgggcgctcgaatctttgtcctaaaaagggtgagacatacga AceIII BsaI
28081 atatttcaacagagcaggggccaagaacaagagctgaaaataaaaaacaggtctctgcga 28140
tataaagttgtctcgtccccggttcttgttctcgacttttattttttgtccagagacgct MspA1I PvuII Eco57I
28141 tccctcacccgcagctgcctgtatcacaaaagcgaagatcagcttcggcgcacgctggaa 28200
agggagtgggcgtcgacggacatagtgttttcgcttctagtcgaagccgcgtgcgacctt BbsI EarI BssHII AflII SmlI SpeI
28201 gacgcggaggctctcttcagtaaatactgcgcgctgactcttaaggactagtttcgcgcc 28260
ctgcgcctccgagagaagtcatttatgacgcgcgactgagaattcctgatcaaagcgcgg ApoI BpmI BsaXI EaeI GdiII MspA1I Bsp24I BanI NarI BsaHI HaeII
28261 ctttctcaaatttaagcgcgaaaactacgtcatctccagcggccacacccggcgccagca 28320
gaaagagtttaaattcgcgcttttgatgcagtagaggtcgccggtgtgggccgcggtcgt AlwNI HaeII Bsp24I ApoI AflIII BspLU11I NspI
28321 cctgtcgtcagcgccattatgagcaaggaaattcccacgccctacatgtggagttaccag 28380
ggacagcagtcgcggtaatactcgttcctttaagggtgcgggatgtacacctcaatggtc AceIII BpmI
28381 ccacaaatgggacttgcggctggagctgcccaagactactcaacccgaataaactacatg 28440
ggtgtttaccctgaacgccgacctcgacgggttctgatgagttgggcttatttgatgtac Eco0109I Psp5II SanDI EcoRV AvaI SmaI RleAI HincII ApoI EcoRI
28441 agcgcgggaccccacatgatatcccgggtcaacggaatccgcgcccaccgaaaccgaatt 28500
tcgcgccctggggtgtactatagggcccagttgccttaggcgcgggtggctttggcttaa 28501 ctcttggaacaggcggctattaccaccacacctcgtaataaccttaatccccgtagttgg 28560

Figure 28PP

```
gagaaccttgtccgccgataatggtggtgtggagcattattggaattaggggcatcaacc

                                                 BstXI
MspA1I                              BsrBI    MslI |    BsmBI    BsaHI
  |                                   |       | |       |         |
      cccgctgccctggtgtaccaggaaagtcccgctcccaccactgtggtacttcccagagac
28561 ---------+---------+---------+---------+---------+---------+ 28620
      gggcgacgggaccacatggtcctttcagggcgagggtggtgacaccatgaagggtctctg

      gcccaggccgaagttcagatgactaactcaggggcgcagcttgcgggcggctttcgtcac
28621 ---------+---------+---------+---------+---------+---------+ 28680
      cgggtccggcttcaagtctactgattgagtccccgcgtcgaacgcccgccgaaagcagtg

                   SmaI
                   SrfI
                AvaI |
DraIII  BsiEI     |  |
  |        |      |  |
      agggtgcggtcgcccgggcaggtataactcacctgacaatcagagggcgaggtattcag
28681 ---------+---------+---------+---------+---------+---------+ 28740
      tcccacgccagcgggcccgtcccatattgagtggactgttagtctcccgctccataagtc

                    BanII
                   BsiHKAI
         BseRI    Bsp1286I           BsaWI
      AceIII |       SacI             BspEI
            | |         |          BsaI |
                                       | |
      ctcaacgacgagtcggtgagctcctcgcttggtctccgtccggacgggacatttcagatc
28741 ---------+---------+---------+---------+---------+---------+ 28800
      gagttgctgctcagccactcgaggagcgaaccagaggcaggcctgccctgtaaagtctag

          BsiEI
         EaeI |
         EagI |
        GdiII |
       HaeII| |
      BsrFI|| |
     NgoAIV|| |
     BsaHI ||| |                                         Tth111I
      NarI ||| |                                       PstI   |
     BanI| ||| |                                  SfcI   |    |
      || ||| |                                      |    |    |
      ggcggcgccggccgtccttcattcacgcctcgtcaggcaatcctaactctgcagacctcg
28801 ---------+---------+---------+---------+---------+---------+ 28860
      ccgccgcggccggcaggaagtaagtgcggagcagtccgttaggattgagacgtctggagc

        Hin4I                    BplI     BpmI        TaqII
          |                        |        |            |
      tcctctgagccgcgctctggaggcattggaactctgcaatttattgaggagtttgtgcca
28861 ---------+---------+---------+---------+---------+---------+ 28920
      aggagactcggcgcgagacctccgtaaccttgagacgttaaataactcctcaaacacggt

                         EcoO109I
      AccI                PspSII     EaeI    BsaWI
BseRI  |                AvaI |      GdiII   BspEI
  |    |                  |  |        |       |
      tcggtctactttaaccccttctcgggacctcccggccactatccggatcaatttattcct
28921 ---------+---------+---------+---------+---------+---------+ 28980
      agccagatgaaattggggaagagccctggagggccggtgataggcctagttaaataagga

                          EciI  Pfl1108I
                            |       |
      aactttgacgcggtaaaggactcggcggacggctacgactgaatgttaagtggagaggca
28981 ---------+---------+---------+---------+---------+---------+ 29040
      ttgaaactgcgccatttcctgagccgcctgccgatgctgacttacaattcacctctccgt

                   SexAI
                     |
      gagcaactgcgcctgaaacacctggtccactgtcgccgccacaagtgctttgcccgcgac
29041 ---------+---------+---------+---------+---------+---------+ 29100
      ctcgttgacgcggactttgtggaccaggtgacagcggcggtgttcacgaaacgggcgctg

                                            ApaI
                                           BanII
                                         Bsp1286I
                                            BmgI |
                                           BseSI |
BsaWI                      AvaI        EcoO109I | |     BsaHI
  |                          |                | | |        |
      tccggtgagttttgctactttgaattgcccgaggatcatatcgagggcccggcgcacggc
29101 ---------+---------+---------+---------+---------+---------+ 29160
      aggccactcaaaacgatgaaacttaacgggctcctagtatagctcccgggccgcgtgccg

                                                          HaeII
                                                            |
      gtccggcttaccgcccagggagagcttgcccgtagcctgattcgggagtttacccagcgc
29161 ---------+---------+---------+---------+---------+---------+ 29220
      caggccgaatggcgggtccctctcgaacgggcatcggactaagccctcaaatgggtcgcg

                    EcoO109I
```

Figure 28QQ

```
                         Psp5II
                  BsrBI   SanDI  AloI
                      |        |     |
      cccctgctagttgagcgggacaggggaccctgtgttctcactgtgatttgcaactgtcct
29221 ---------+---------+---------+---------+---------+---------+ 29280
      ggggacgatcaactcgccctgtcccctgggacacaagagtgacactaaacgttgacagga

                                    BglII
                     BglII          BstYI
    StyI             BstYI       PacI  |
      |                  |          |  |
      aaccttggattacatcaagatcTTAATTAAgatcttattccctttaactaataaaaaaa
29281 ---------+---------+---------+---------+---------+---------+ 29340
      ttggaacctaatgtagttctagAATTAATTctagaataagggaaattgattattttttt

                                     ApoI     BspGI
                                         |          |
      ataataaagcatcacttacttaaaatcagttagcaaatttctgtccagtttattcagcag
29341 ---------+---------+---------+---------+---------+---------+ 29400
      tattatttcgtagtgaatgaattttagtcaatcgtttaaagacaggtcaaataagtcgtc

    BseRI                        AceIII
      |                              |
      cacctccttgccctcctcccagctctggtattgcagcttcctcctggctgcaaactttct
29401 ---------+---------+---------+---------+---------+---------+ 29460
      gtggaggaacgggaggagggtcgagaccataacgtcgaaggaggaccgacgtttgaaaga

         XcmI
            |
      ccacaatctaaatggaatgtcagtttcctcctgttcctgtccatccgcacccactatctt
29461 ---------+---------+---------+---------+---------+---------+ 29520
      ggtgttagatttaccttacagtcaaaggaggacaaggacaggtaggcgtgggtgatagaa

    TaqII           BssHII                             Eco57I
      |                  |                                   |
      catgttgttgcagatgaagcgcgcaagaccgtctgaagataccttcaaccccgtgtatcc
29521 ---------+---------+---------+---------+---------+---------+ 29580
      gtacaacaacgtctacttcgcgcgttctggcagacttctatggaagttggggcacatagg

                     BsaXI
                 BsaWI   |
       BciVI     BsrFI   |
   NdeI    |     PinAI   |              BseRI          MmeI
      |    |         |   |                  |              |
      atatgacacggaaaccggtcctccaactgtgcctttcttactcctccctttgtatcccc
29581 ---------+---------+---------+---------+---------+---------+ 29640
      tatactgtgcctttggccaggaggttgacacggaaagaatgaggagggaaacatagggg

    BciVI
      |
      caatgggtttcaagagagtccccctggggtactctctttgcgcctatccgaacctctagt
29641 ---------+---------+---------+---------+---------+---------+ 29700
      gttacccaaagttctctcaggggggaccccatgagagaaacgcggataggcttggagatca

                   NspI                                 BsrFI
  Tth111II         SphI                          BspGI NgoAIV
         |            |                              |      |
      tacctccaatggcatgcttgcgctcaaaatgggcaacggcctctctctggacgaggccgg
29701 ---------+---------+---------+---------+---------+---------+ 29760
      atggaggttaccgtacgaacgcgagttttacccgttgccggagagagacctgctccggcc

                                     BanII
                                  Bsp1286I
       BsaXI                         Hin4I                BplI
          |                              |                   |
      caaccttacctcccaaaatgtaaccactgtgagcccacctctcaaaaaaaccaagtcaaa
29761 ---------+---------+---------+---------+---------+---------+ 29820
      gttggaatggagggttttacattggtgacactcgggtggagagtttttttggttcagttt

    BsgI  Tth111II
      |         |
      cataaacctggaaatatctgcacccctcacagttacctcagaagccctaactgtggctgc
29821 ---------+---------+---------+---------+---------+---------+ 29880
      gtatttggacctttatagacgtggggagtgtcaatggagtcttcgggattgacaccgacg

          HgiEII         BsbI             Eco0109I
                |              |                  |
      cgccgcacctctaatggtcgcgggcaacacactcaccatgcaatcacaggccccgctaac
29881 ---------+---------+---------+---------+---------+---------+ 29940
      gcggcgtggagattaccagcgcccgttgtgtgagtggtacgttagtgtccggggcgattg

    BsiHKAI
  Bsp1286I                       Eco0109I
    BseSI |                        Psp5II
  ApaLI | |          BsrDI       StyI  |        TaqII
      | | |              |          |  |           |
      cgtgcacgactccaaacttagcattgccacccaaggacccctcacagtgtcagaaggaaa
29941 ---------+---------+---------+---------+---------+---------+ 30000
      gcacgtgctgaggtttgaatcgtaacggtgggttcctggggagtgtcacagtcttccttt
```

Figure 28RR

```
                               Tth111II
 NheI            Eco0109I         |                             BtsI
  |                   |           |                               |
      gctagccctgcaaacatcaggccccctcaccaccaccgatagcagtaccctactatcac
30001 ---------+---------+---------+---------+---------+---------+ 30060
      cgatcgggacgtttgtagtccgggggagtggtggtggctatcgtcatgggatgatagtg

                                                          BanII
                                   XcmI                 Bsp1286I
                                     |                       |
      tgcctcacccccctctaactactgccactggtagcttgggcattgacttgaaagagcccat
30061 ---------+---------+---------+---------+---------+---------+ 30120
      acggagtggggggagattgatgacggtgaccatcgaacccgtaactgaactttctcgggta

                                            BanII
                                          Bsp1286I     NspI
                                              |          |
      ttatacacaaaatggaaaactaggactaaagtacggggctcctttgcatgtaacagacga
30121 ---------+---------+---------+---------+---------+---------+ 30180
      aatatgtgttttaccttttgatcctgatttcatgccccgaggaaacgtacattgtctgct

                               BspGI        VspI
                                 |            |
      cctaaacactttgaccgtagcaactggtccaggtgtgactattaataatacttccttgca
30181 ---------+---------+---------+---------+---------+---------+ 30240
      ggatttgtgaaactggcatcgttgaccaggtccacactgataattattatgaaggaacgt

                  StyI          BpmI
                    |             |
      aactaaagttactggagccttgggttttgattcacaaggcaatatgcaacttaatgtagc
30241 ---------+---------+---------+---------+---------+---------+ 30300
      ttgatttcaatgacctcggaacccaaaactaagtgttccgttatacgttgaattacatcg

               Hin4I           BsaHI
                 |               |
      aggaggactaaggattgattctcaaaacagacgccttatacttgatgttagttatccgtt
30301 ---------+---------+---------+---------+---------+---------+ 30360
      tcctcctgattcctaactaagagttttgtctgcggaatatgaactacaatcaataggcaa

                                               ApaI
                                              BanII
                                            Bsp1286I
                                              BmgI |
                                             BseSI |
                                         Eco0109I| |
                                        Eco0109I|| |
                                               ||| |
      tgatgctcaaaaccaactaaatctaagactaggacagggccctctttttataaactcagc
30361 ---------+---------+---------+---------+---------+---------+ 30420
      actacgagttttggttgatttagattctgatcctgtcccgggagaaaaatatttgagtcg

                                   HaeI
       PflMI       RleAI           StuI
         |           |               |
      ccacaacttggatattaactacaacaaaggcctttacttgtttacagcttcaaacaattc
30421 ---------+---------+---------+---------+---------+---------+ 30480
      ggtgttgaacctataattgatgttgtttccggaaatgaacaaatgtcgaagtttgttaag

                                  Tth111II
         SmlI       Bpu10I          StyI |
   Tth111II|    HincII   |      Bce83I|  |
   HindIII ||    HpaI    |      BtsI ||  |               SfcI
         | ||      |     |         | ||  |                 |
      caaaaagcttgaggttaacctaagcactgccaaggggttgatgtttgacgctacagccat
30481 ---------+---------+---------+---------+---------+---------+ 30540
      gtttttcgaactccaattggattcgtgacggttccccaactacaaactgcgatgtcggta

       VspI                      ApoI  DrdII
         |                         |     |
      agccattaatgcaggagatgggcttgaatttggttcacctaatgcaccaaacacaaatcc
30541 ---------+---------+---------+---------+---------+---------+ 30600
      tcggtaattacgtcctctacccgaacttaaaccaagtggattacgtggtttgtgtttagg

                 BstDSI
                   NcoI
                   StyI
                  HaeI|
                  MscI|                                Tth111II
Tth111II         EaeI || HaeI ApoI                      DrdII |EcoNI
   |               |  ||   |    |                          | |   |
      cctcaaaacaaaaattggccatggcctagaatttgattcaaacaaggctatggttcctaa
30601 ---------+---------+---------+---------+---------+---------+ 30660
      ggagttttgtttttaaccggtaccggatcttaaactaagtttgttccgataccaaggatt

            HaeI                BanI
              |                   |
      actaggaactggccttagttttgacagcacaggtgccattacagtaggaaacaaaaataa
30661 ---------+---------+---------+---------+---------+---------+ 30720
      tgatccttgaccggaatcaaaactgtcgtgtccacggtaatgtcatcctttgtttttatt
```

Figure 28SS

```
                                                     AccI
                                                SfcI  |
                          BsaXI         AceIII    |   |
                            |              |      |   |
       tgataagctaactttgtggaccacaccagctccatctcctaactgtagactaaatgcaga
30721  ---------+---------+---------+---------+---------+---------+  30780
       actattcgattgaaacacctggtgtggtcgaggtagaggattgacatctgatttacgtct

                                                           SfcI
                                                             |
       gaaagatgctaaactcactttggtcttaacaaaatgtggcagtcaaatacttgctacagt
30781  ---------+---------+---------+---------+---------+---------+  30840
       ctttctacgatttgagtgaaaccagaattgttttacaccgtcagtttatgaacgatgtca

                                                           BsiHKAI
                                         PflMI             Bsp1286I
                                           |                    |
       ttcagttttggctgttaaaggcagtttggctccaatatctggaacagttcaaagtgctca
30841  ---------+---------+---------+---------+---------+---------+  30900
       aagtcaaaaccgacaatttccgtcaaaccgaggttatagaccttgtcaagtttcacgagt

                                                       BspGI
                                                         |
       tcttattataagatttgacgaaaatggagtgctactaaacaattccttcctggacccaga
30901  ---------+---------+---------+---------+---------+---------+  30960
       agaataatattctaaactgcttttacctcacgatgatttgttaaggaaggacctgggtct

   BstXI               BglII
   SspI|               BstYI            MmeI        Eco57I
      ||                 |                |            |
       atattggaactttagaaatggagatcttactgaaggcacagcctatacaaacgctgttgg
30961  ---------+---------+---------+---------+---------+---------+  31020
       tataaccttgaaatctttacctctagaatgacttccgtgtcggatatgtttgcgacaacc

       atttatgcctaacctatcagcttatccaaaatctcacggtaaaactgccaaaagtaacat
31021  ---------+---------+---------+---------+---------+---------+  31080
       taaatacggattggatagtcgaataggttttagagtgccattttgacggttttcattgta

       tgtcagtcaagtttacttaaacggagacaaaactaaacctgtaacactaaccattacact
31081  ---------+---------+---------+---------+---------+---------+  31140
       acagtcagttcaaatgaatttgcctctgttttgatttggacattgtgattggtaatgtga

                                                            MslI
                                                              |
       aaacggtacacaggaaacaggagacacaactccaagtgcatactctatgtcattttcatg
31141  ---------+---------+---------+---------+---------+---------+  31200
       tttgccatgtgtcctttgtcctctgtgttgaggttcacgtatgagatacagtaaaagtac

             HaeI
             MscI
           EaeI |           VspI      SspI
              | |             |         |
       ggactggtctggccacaactacattaatgaaatatttgccacatcctcttacactttttc
31201  ---------+---------+---------+---------+---------+---------+  31260
       cctgaccagaccggtgttgatgtaattactttataaacggtgtaggagaatgtgaaaaag

   BsrDI                                    AflIII          MunI
       |                                       |               |
       atacattgcccaagaataaagaatcgtttgtgttatgtttcaacgtgtttatttttcaat
31261  ---------+---------+---------+---------+---------+---------+  31320
       tatgtaacgggttcttatttcttagcaaacacaatacaaagttgcacaaataaaaagtta

         ApoI
           |
       tgcagaaaatttcaagtcatttttcattcagtagtatagccccaccaccacatagcttat
31321  ---------+---------+---------+---------+---------+---------+  31380
       acgtcttttaaagttcagtaaaaagtaagtcatcatatcggggtggtggtgtatcgaata

                                                          BspMI
                                                              |
       acagatcaccgtaccttaatcaaactcacagaaccctagtattcaacctgccacctccct
31381  ---------+---------+---------+---------+---------+---------+  31440
       tgtctagtggcatggaattagtttgagtgtcttgggatcataagttggacggtggaggga

       BsbI    TatI                    HaeI
          |      |                       |
       cccaacacacagagtacacagtcctttctccccggctggccttaaaaagcatcatatcat
31441  ---------+---------+---------+---------+---------+---------+  31500
       gggttgtgtgtctcatgtgtcaggaaagaggggccgaccggaatttttcgtagtatagta

       gggtaacagacatattcttaggtgttatattccacacggtttcctgtcgagccaaacgct
31501  ---------+---------+---------+---------+---------+---------+  31560
       cccattgtctgtataagaatccacaatataaggtgtgccaaaggacagctcggtttgcga

                                         AceIII          MspA1I
                          SmaI       AflII  |             PvuII
              VspI        AvaI |      SmlI  |           BspGI |
                 |           | |        |   |               | |
       catcagtgatattaataaactccccgggcagctcacttaagttcatgtcgctgtccagct
31561  ---------+---------+---------+---------+---------+---------+  31620
```

Figure 28TT

```
          gtagtcactataattatttgaggggcccgtcgagtgaattcaagtacagcgacaggtcga

Bpu1102I
  AlwNI|                                           MmeI
      ||                                              |
          gctgagccacaggctgctgtccaacttgcggttgcttaacgggcggcgaaggagaagtcc
31621 ---------+---------+---------+---------+---------+---------+ 31680
          cgactcggtgtccgacgacaggttgaacgccaacgaattgcccgccgcttcctcttcagg

                                                              PstI
                              MslI                        BcgI |
                        Hin4I    |                        SfcI | |
                             |   |                            | | |
          acgcctacatggggggtagagtcataatcgtgcatcaggatagggcggtggtgctgcagca
31681 ---------+---------+---------+---------+---------+---------+ 31740
          tgcggatgtacccccatctcagtattagcacgtagtcctatcccgccaccacgacgtcgt

                                             PstI             BtsI
                                  BcgI       SbfI             MslI |
BssHII                        BsrBI|    SfcI    |        BseRI| |
     |                             ||      |    |            || |
          gcgcgcgaataaactgctgccgccgccgctccgtcctgcaggaatacaacatggcagtgg
31741 ---------+---------+---------+---------+---------+---------+ 31800
          cgcgcgcttatttgacgacggcggcggcgaggcaggacgtccttatgttgtaccgtcacc

                                             HaeII
    BbvCI                                BsaHI    |         Bsp1286I
  Bpu10I                                  NarI    |           BmgI |
    BsaI                                 BanI|    |           BseSI |
       |                                     ||   |              | |
          tctcctcagcgatgattcgcaccgcccgcagcataaggcgccttgtcctccgggcacagc
31801 ---------+---------+---------+---------+---------+---------+ 31860
          agaggagtcgctactaagcgtggcgggcgtcgtattccgcggaacaggaggcccgtgtcg

                                          SfcI
                                      AlwNI|PstI              SspI
                                           ||   |                |
          agcgcaccctgatctcacttaaatcagcacagtaactgcagcacagcaccacaatattgt
31861 ---------+---------+---------+---------+---------+---------+ 31920
          tcgcgtgggactagagtgaatttagtcgtgtcattgacgtcgtgtcgtggtgttataaca

                          RleAI
                         HaeII|        BciVI
                              ||           |
          tcaaaatcccacagtgcaaggcgctgtatccaaagctcatggcggggaccacagaaccca
31921 ---------+---------+---------+---------+---------+---------+ 31980
          agttttagggtgtcacgttccgcgacataggtttcgagtaccgcccctggtgtcttgggt

      HaeI
      MscI
    EaeI |
  BsaAI | |
   PmlI | |    BspMI                                      BspGI
      | | |        |                                          |
          cgtggccatcataccacaagcgcaggtagattaagtggcgacccctcataaacacgctgg
31981 ---------+---------+---------+---------+---------+---------+ 32040
          gcaccggtagtatggtgttcgcgtccatctaattcaccgctggggagtatttgtgcgacc

                                                           KpnI
                              NspI               BanI     |
                                 |                  |     |
          acataaacattacctcttttggcatgttgtaattcaccacctcccggtaccatataaacc
32041 ---------+---------+---------+---------+---------+---------+ 32100
          tgtatttgtaatggagaaaaccgtacaacattaagtggtggagggccatggtatatttgg

                                                  HaeI
                 HaeII                            MscI
               BsaHI |                          EaeI |          BspMI
                NarI |                      MspA1I | |          BsrFI|
               BanI| |                        PvuII | |        NgoAIV|
                   || |                           | | |              ||
          tctgattaaacatggcgccatccaccaccatcctaaaccagctggccaaaacctgcccgc
32101 ---------+---------+---------+---------+---------+---------+ 32160
          agactaatttgtaccgcggtaggtggtggtaggatttggtcgaccggttttggacgggcg

                 PstI
             BtsI  |                                  BanII
             SfcI  |                              Bsp1286I
                |  |                                     |
          cggctatacactgcagggaaccgggactggaacaatgacagtggagagcccaggactcgt
32161 ---------+---------+---------+---------+---------+---------+ 32220
          gccgatatgtgacgtcccttggccctgaccttgttactgtcacctctcgggtcctgagca

  BstDSI                                                   BsaAI
    NcoI                                                    PmlI
    StyI                  RcaI EcoRV          BsbI   AflIII   |
       |                     |    |              |       | |
          aaccatggatcatcatgctcgtcatgatatcaatgttggcacaacacaggcacacgtgca
32221 ---------+---------+---------+---------+---------+---------+ 32280
          ttggtacctagtagtacgagcagtactatagttacaaccgtgttgtgtccgtgtgcacgt
```

Figure 28UU

```
                   BseRI
          Bsu36I     |                          DrdII
               |     |                              |
       tacacttcctcaggattacaagctcctcccgcgttagaaccatatcccagggaacaaccc
 32281 ---------+---------+---------+---------+---------+---------+ 32340
       atgtgaaggagtcctaatgttcgaggagggcgcaatcttggtatagggtcccttgttggg

                                     PstI
                                BtsI   |        BbsI
                                SfcI   |   RleAI  |BsaAI        DraIII
                                   |   |       |  |    |              |
       attcctgaatcagcgtaaatcccacactgcagggaagacctcgcacgtaactcacgttgt
 32341 ---------+---------+---------+---------+---------+---------+ 32400
       taaggacttagtcgcatttagggtgtgacgtcccttctggagcgtgcattgagtgcaaca

                                   MspA1I
                                BpmI   |
                                   |   |
       gcattgtcaaagtgttacattcgggcagcagcggatgatcctccagtatggtagcgcggg
 32401 ---------+---------+---------+---------+---------+---------+ 32460
       cgtaacagtttcacaatgtaagcccgtcgtcgcctactaggaggtcataccatcgcgccc

                         AccI
                           |
       tttctgtctcaaaaggaggtagacgatccctactgtacggagtgcgccgagacaaccgag
 32461 ---------+---------+---------+---------+---------+---------+ 32520
       aaagacagagttttcctccatctgctagggatgacatgcctcacgcggctctgttggctc

            Pfl1108I
         BsbI      |                          Tth111I
            |      |                                |
       atcgtgttggtcgtagtgtcatgccaaatggaacgccggacgtagtcatatttcctgaag
 32521 ---------+---------+---------+---------+---------+---------+ 32580
       tagcacaaccagcatcacagtacggtttaccttgcggcctgcatcagtataaaggacttc

                                                 BsmBI
                                 BglII        BsaWI |
      SexAI        Eco57I        BstYI     Tth111II |     BsaI
          |             |            |            | |        |
       caaaaccaggtgcgggcgtgacaaacagatctgcgtctccggtctcgccgcttagatcgc
 32581 ---------+---------+---------+---------+---------+---------+ 32640
       gttttggtccacgcccgcactgtttgtctagacgcagaggccagagcggcgaatctagcg

                                                     HaeII
                                                      XcmI
                                                  BsaHI  |
                                                   NarI  |
                                                  BanI|  |
                                                     ||  |
       tctgtgtagtagttgtagtatatccactctctcaaagcatccaggcgcccctggcttcg
 32641 ---------+---------+---------+---------+---------+---------+ 32700
       agacacatcatcaacatcatataggtgagagagtttcgtaggtccgcggggaccgaagc

                                 MspA1I
                                      |
       ggttctatgtaaactccttcatgcgccgctgccctgataacatccaccaccgcagaataa
 32701 ---------+---------+---------+---------+---------+---------+ 32760
       ccaagatacatttgaggaagtacgcggcgacgggactattgtaggtggtggcgtcttatt

                                                         BsrBI
                                                         EarI|
                                                         SapI|
                         TaqII                      AceIII  ||
                             |                           |  ||
       gccacacccagccaacctacacattcgttctgcgagtcacacacgggaggagcgggaaga
 32761 ---------+---------+---------+---------+---------+---------+ 32820
       cggtgtgggtcggttggatgtgtaagcaagacgctcagtgtgtgccctcctcgcccttct

                                                                BglII
    BseRI    DrdII                                              BstYI
        |        |                                                  |
       gctggaagaaccatgttttttttttattccaaaagattatccaaaacctcaaaatgaag
 32821 ---------+---------+---------+---------+---------+---------+ 32880
       cgaccttcttggtacaaaaaaaaaaataaggttttctaataggttttggagttttacttc

                              BsaWI                  SfcI
                                  |                     |
       atctattaagtgaacgcgctcccctccggtggcgtggtcaaactctacagccaaagaaca
 32881 ---------+---------+---------+---------+---------+---------+ 32940
       tagataattcacttgcgcgaggggaggccaccgcaccagtttgagatgtcggtttcttgt

       gataatggcatttgtaagatgttgcacaatggcttccaaaaggcaaacggccctcacgtc
 32941 ---------+---------+---------+---------+---------+---------+ 33000
       ctattaccgtaaacattctacaacgtgttaccgaaggttttccgtttgccgggagtgcag

                                    BseRI
        Eco57I                HgiEII |
             |                     | |
       caagtggacgtaaaggctaaacccttcagggtgaatctcctctataaacattccagcacc
```

Figure 28VV

```
33001 ---------+---------+---------+---------+---------+---------+ 33060
      gttcacctgcatttccgatttgggaagtcccacttagaggagatatttgtaaggtcgtgg

      ttcaaccatgcccaaataattctcatctcgccaccttctcaatatatctctaagcaaatc
33061 ---------+---------+---------+---------+---------+---------+ 33120
      aagttggtacgggtttattaagagtagagcggtggaagagttatatagagattcgtttag

                   BpmI
                EaeI  |                           Bce83I
        SspI   GdiII  |                 Eco57I  HaeII             SmlI
          |        |   |                      |       |                |
      ccgaatattaagtccggccattgtaaaaatctgctccagagcgccctccaccttcagcct
33121 ---------+---------+---------+---------+---------+---------+ 33180
      ggcttataattcaggccggtaacatttttagacgaggtctcgcgggaggtggaagtcgga

              Tth111II
             RcaI    |   ApoI
                |    |     |
      caagcagcgaatcatgattgcaaaaattcaggttcctcacagacctgtataagattcaaa
33181 ---------+---------+---------+---------+---------+---------+ 33240
      gttcgtcgcttagtactaacgtttttaagtccaaggagtgtctggacatattctaagttt

                                 Eco0109I             MspA1I  BsgI
                                  Psp5II               PvuII BspMI
                                       |                    |     |
      agcggaacattaacaaaaataccgcgatcccgtaggtcccttcgcagggccagctgaaca
33241 ---------+---------+---------+---------+---------+---------+ 33300
      tcgccttgtaattgtttttatggcgctagggcatccagggaagcgtcccggtcgacttgt

                               EaeI
                              GdiII
    MslI                    BsgI |
       |                       | |
      taatcgtgcaggtctgcacggaccagcgcggccacttccccgccaggaaccttgacaaaa
33301 ---------+---------+---------+---------+---------+---------+ 33360
      attagcacgtccagacgtgcctggtcgcgccggtgaaggggcggtccttggaactgtttt

                   RleAI
                       |
      gaacccacactgattatgacacgcatactcggagctatgctaaccagcgtagccccgatg
33361 ---------+---------+---------+---------+---------+---------+ 33420
      cttgggtgtgactaatactgtgcgtatgagcctcgatacgattggtcgcatcggggctac

HindIII
      |
      taagctttgttgcatgggcggcgatataaaatgcaaggtgctgctcaaaaaatcaggcaa
33421 ---------+---------+---------+---------+---------+---------+ 33480
      attcgaaacaacgtacccgccgctatattttacgttccacgacgagttttttagtccgtt

                        Pf11108I      MslI BspMI
                               |        |    |
      agcctcgcgcaaaaaagaaagcacatcgtagtcatgctcatgcagataaaggcaggtaag
33481 ---------+---------+---------+---------+---------+---------+ 33540
      tcggagcgcgttttttctttcgtgtagcatcagtacgagtacgtctatttccgtccattc

                                                    NspI
  BsaWI                                    AflIII     |
  BspEI DrdII                           BspLU11I    | Tth111II
      |    |                                    |   |      |
      ctccggaaccaccacagaaaaagacaccatttttctctcaaacatgtctgcgggtttctg
33541 ---------+---------+---------+---------+---------+---------+ 33600
      gaggccttggtggtgtctttttctgtggtaaaaagagagtttgtacagacgcccaaagac

                                    DraI
                                       |
      cataaacacaaaataaaataacaaaaaaacatttaaacattagaagcctgtcttacaaca
33601 ---------+---------+---------+---------+---------+---------+ 33660
      gtatttgtgttttattttattgtttttttgtaaatttgtaatcttcggacagaatgttgt

                                              BglI
                                     EaeI  BsrFI|
                                    GdiII NgoAIV|
                                        |      ||
      ggaaaaacaaccccttataagcataagacggactacggccatgccggcgtgaccgtaaaaa
33661 ---------+---------+---------+---------+---------+---------+ 33720
      cctttttgttgggaatattcgtattctgcctgatgccggtacggccgcactggcattttt

                                                 BsaWI
                               TaqII             BspEI
   BstEII                 BseRI  |Hin4I    AceIII    |
       |                      |  |    |           |   |
      aactggtcaccgtgattaaaaagcaccaccgacagctcctcggtcatgtccggagtcata
33721 ---------+---------+---------+---------+---------+---------+ 33780
      ttgaccagtggcactaattttcgtggtggctgtcgaggagccagtacaggcctcagtat

                         TaqII                          BsiEI
                             |                              |
      atgtaagactcggtaaacacatcaggttgattcatcggtcagtgctaaaaagcgaccgaa
33781 ---------+---------+---------+---------+---------+---------+ 33840
      tacattctgagccatttgtgtagtccaactaagtagccagtcacgatttttcgctggctt
```

Figure 28WW

```
          TaqII
       SmaI  |
    AvaI |   |
       |  |  |
       atagcccgggggaatacatacccgcaggcgtagagacaacattacagccccccataggagg
 33841 ---------+---------+---------+---------+---------+---------+ 33900
       tatcgggcccccttatgtatgggcgtccgcatctctgttgtaatgtcggggggtatcctcc

                                                               AvrII
             VspI                                               StyI
              |                                                  |
       tataacaaaattaataggagagaaaaacacataaacacctgaaaaaccctcctgcctagg
 33901 ---------+---------+---------+---------+---------+---------+ 33960
       atattgttttaattatcctctctttttgtgtatttgtggactttttgggaggacggatcc

                                                 HaeII
    BpmI           BsrBI           Eco47III  | MspA1I
      |               |                   |  |     |
       caaaatagcaccctcccgctccagaacaacatacagcgcttcacagcggcagcctaacag
 33961 ---------+---------+---------+---------+---------+---------+ 34020
       gttttatcgtgggagggcgaggtcttgttgtatgtcgcgaagtgtcgccgtcggattgtc

                                                              BanI
                                                                 |
       tcagccttaccagtaaaaaagaaaacctattaaaaaaacaccactcgacacggcaccagc
 34021 ---------+---------+---------+---------+---------+---------+ 34080
       agtcggaatggtcattttttcttttggataatttttttgtggtgagctgtgccgtggtcg

        AceIII                                                BsgI
           |                                                    |
       tcaatcagtcacagtgtaaaaaagggccaagtgcagagcgagtatatataggactaaaaa
 34081 ---------+---------+---------+---------+---------+---------+ 34140
       agttagtcagtgtcacattttttcccggttcacgtctcgctcatatatatcctgattttt

                                                         TaqII
                                                             |
       atgacgtaacggttaaagtccacaaaaaacacccagaaaaccgcacgcgaacctacgccc
 34141 ---------+---------+---------+---------+---------+---------+ 34200
       tactgcattgccaatttcaggtgttttttgtgggtcttttggcgtgcgcttggatgcggg

                                               RleAI
                                                 |
       agaaacgaaagccaaaaaacccacaacttcctcaaatcgtcacttccgttttcccacgtt
 34201 ---------+---------+---------+---------+---------+---------+ 34260
       tctttgctttcggttttttgggtgttgaaggagtttagcagtgaaggcaaaagggtgcaa

  BsaAI
  SnaBI                                         BsbI              EciI
      |                                           |                 |
       acgtaacttcccattttaagaaaactacaattcccaacacatacaagttactccgcccta
 34261 ---------+---------+---------+---------+---------+---------+ 34320
       tgcattgaagggtaaaattcttttgatgttaagggttgtgtatgttcaatgaggcgggat

       aaacctacgtcacccgccccgttcccacgccccgcgccacgtcacaaactccacccccc
 34321 ---------+---------+---------+---------+---------+---------+ 34380
       tttggatgcagtgggcggggcaagggtgcggggcgcggtgcagtgtttgaggtgggggag

       attatcatattggcttcaatccaaaataaggtatattattgatgatg
 34381 ---------+---------+---------+---------+------- 34427
       taatagtataaccgaagttaggttttattccatataataactactac
```

Enzymes that do cut:

| | | | | | | | |
|---|---|---|---|---|---|---|---|
| AarI | AatII | AccI | AceIII | AclI | AflII | AflIII | AhdI |
| AloI | AlwNI | ApaI | ApaLI | ApoI | AscI | AvaI | AvrII |
| BaeI | BamHI | BanI | BanII | BbsI | BbvCI | Bce83I | BcgI |
| BciVI | BclI | BglI | BglII | BmgI | BmrI | BplI | BpmI |
| Bpu10I | Bpu1102I | BsaI | BsaAI | BsaBI | BsaHI | BsaWI | BsaXI |
| BsbI | BseRI | BseSI | BsgI | BsiEI | BsiHKAI | BsmI | BsmBI |
| Bsp24I | Bsp1286I | BspEI | BspGI | BspLU11I | BspMI | BsrBI | BsrDI |
| BsrFI | BsrGI | BssHII | BssSI | BstAPI | BstDSI | BstEII | BstXI |
| BstYI | Bst2171 | Bsu36I | BtsI | ClaI | DraI | DraIII | DrdI |
| DrdII | EaeI | EagI | EarI | EciI | Eco47III | Eco57I | EcoNI |
| EcoO109I | EcoRI | EcoRV | FseI | FspI | GdiII | HaeI | HaeII |
| HaeIV | HgiEII | Hin4I | HincII | HindIII | HpaI | KpnI | MluI |
| MmeI | MscI | MslI | MspA1I | MunI | NarI | NcoI | NdeI |
| NgoAIV | NheI | NotI | NruI | NsiI | NspI | PacI | Pfl1108I |
| PflMI | PinAI | PmeI | PmlI | PshAI | PspSII | PstI | PvuI |
| PvuII | RcaI | RleAI | RsrII | SacI | SacII | SalI | SanDI |
| SapI | SbfI | ScaI | SexAI | SfcI | SfiI | SgfI | SgrAI |
| SmaI | SmlI | SnaBI | SpeI | SphI | SrfI | Sse8647I | SspI |
| StuI | StyI | SunI | SwaI | TaqII | TatI | Tth111I | Tth111II |
| UbaLI | VspI | XbaI | XcmI | XhoI | XmnI | | |

Enzymes that do not cut:

NspV

Figure 28XX gp19K

RIDβ

14.7K

INHIBITING APOPTOSIS WITH ADENOVIRUS RID PROTEIN

RELATED APPLICATION

This application claims priority to U.S. Provisional Application Ser. No. 60/088,993, filed Jul. 9, 1997, which is incorporated herein in its entirety by reference.

REFERENCE TO GOVERNMENT GRANT

This invention was made with government support under Grant Number RO1 CA58538. The government has certain rights in this invention.

BACKGROUND OF THE INVENTION (1) Field of the Invention

This invention relates generally to the regulation of apoptosis and, more particularly, to a method for inhibiting apoptosis using the Adenovirus RID protein and to applications of this method, including promoting survival of tissue transplants, treating autoimmune disease, and promoting tumor destruction in cancer patients.

(2) Description of the Related Art

Apoptosis, or programmed cell death, plays a fundamental role in regulation of the immune system. For review, see White, E. *Genes & Development* 10:1–15, 1996; van Parijs. L. and Abbas, A. K., *Curr. Opin. Immunol.* 8:355–361, 1996; Nagata, S., *Cell* 88:355–365, 1997. In recent years researchers have shown that some members of the tumor necrosis factor (TNF) family of cytokines can induce apoptosis by binding to their specific receptors on target cells. Nagata, supra; Baker, S. J. and Reddy, E. P., *Oncogene* 12:1–9, 1996. The receptors for the TNF family of cytokines belong to a family of proteins referred to as the TNFR family, which is characterized by an extracellular domain of highly conserved cysteine residues contained in cysteine-rich pseudorepeats (Chaudhary et al., *Immunity* 7:821–830, 1997). In addition, several members of the TNFR family possess a conserved cytoplasmic domain of approximately 80 amino acids called the death domain, which functions to initiate an intracellular apoptotic signaling cascade upon binding of the appropriate cytokine. (See Chaudhary et al., supra:; Walczak et al., *EMBO J.* 16:5386–5397, 1997.) TNFR proteins containing death domains comprise a death receptor subfamily which includes: TNFR1 (Tartiglia et al., *Cell* 74:845–853, 1993); Fas (also called CD95 and Apo-1) (Itoh and Nagata, *J. Biol. Chem.* 268:10932–10937, 1993); death receptor 3 (DR3, also called TRAMP, Apo-3, Wsl-1, and LARD) (Chinnaiyan et al., *Science* 274:990–992,1996; Kiston et al., *Nature* 384:372–375, 1996); TRAIL-R1 (also known as DR4) (Pan et al., *Science* 276:111–113, 1997); and TRAIL-R2 (also called DR5) (Pan et al., *Science* 277:815–818, 1997). The death domains of these proteins are shown in FIG. 1.

Fas, the most studied death receptor, is expressed on the surface of most cell types, including epithelial cells, fibroblasts, T and B cells, liver hepatocytes and some tumor cells (Nagata, *Nature Medicine* 2:1306–1307, 1996; French et al., *Nature Medicine* 3:387–388, 1997). However, FasL is primarily expressed by activated leukocytes of the immune system, including cytotoxic T lymphocytes (CTL's) and natural killer (NK) cells (Nagata, *Cell*, supra). It is believed that the Fas ligand (FasL) plays a role in the immune response of these cells to induce apoptosis in target cells expressing Fas. Such target cells include virus-infected cells and tumor cells. On the other hand, leukocytes also express Fas, which can result in down regulation of the immune response due to activated leukocytes killing each other (Nagata, *Cell*, supra).

Recently, it was discovered that FasL is also expressed in immune-privileged sites such as the eye chamber, parts of the nervous system, and testis and it is believed that any activated leukocytes entering such sites are immediately killed through the FasL-Fas apoptotic pathway, thereby preventing a potentially crippling immune response (Nagata, *Cell*, supra). This finding could potentially be applied to preventing transplant rejection and, indeed, one group has reported that islet allografts were protected from immune rejection by cotransplantation with syngeneic myoblasts expressing functional FasL (Lau et al., *Science* 273:109–112, 1996).

The discovery of FasL expression in immune-privileged sites led a number of groups to examine whether the means by which tumor cells avoid destruction is through expression of FasL. A number of tumor cell types were subsequently reported to constitutively express FasL, including Iymphoma and leukemia cells (Tanake, et al., *Nature Med.* 2:317–322, 1996) various nonlymphoid carcinoma cells, including colon cancer (O'Connell, et al., *J. Exp. Med.* 184:1075–1082, 1996), hepatocellular carcinoma (Strand et al., *Nature Med.* 21361–1366, 1996) and melanoma (Hahne et al., *Science* 274:1363–1366, 1996). As a result of expressing FasL, many tumor cells have the ability to kill attacking CTL and NK cells thereby reducing the immune response against the tumor. In addition, it has been reported that some types of tumors become resistant to Fas-mediated apoptosis, either by downregulation of Fas expression or by other unknown mechanisms, and thereby avoid being killed by the infiltrating leukocytes (Nagata, *Nat. Med.*, supra.; Strand et al., supra; Hahne et al., supra). Because alterations in Fas-FasL regulation, including upregulation of FasL expression and downregulation of Fas expression, may be involved in tumor cells avoiding destruction by the immune system, it would be desirable to devise an approach that would reduce the effect of such changes in Fas-FasL regulation. In one such approach it was recently reported that the anticancer drug doxorubicin enhances expression of both Fas and Fasl in tumor cells (Friesen et al., *Nature Med.* 2:574–577, 1996).

Recent reports have associated other disease states with dysfunction of the Fas system, including hypereosinophilic syndromes in humans (Lenardo et al., *J. Exp. Med.* 183:721–724, 1996), hepatitis (Kondo et al., *Nat. Med.* 3:409–413, 1997) and the autoimmune disease Hashimoto's thyToiditis (HT) (Giordano et al., *Science* 175:960–963, 1997). Consequently, it has been suggested that inappropriate upregulation of Fas may be a causal factor in other autoimmune diseases involving tissues which constitutively express FasL (French et al., supra).

Human adenoviruses (used interchangeably herein with Ad), which cause disease in the respiratory tract, conjunctiva, intestine, urinary tract and liver, have evolved elaborate mechanisms to overcome host antiviral defenses, including at least four of the seven known proteins encoded by the early region 3 (E3) transcription unit which have been reported to inhibit the host immune response to Ad-infected cells (Fejer et al., *J. Virol.* 68:5871–5881, 1994; Sparer et al., *J. Virol.* 770:2431–2439, 1996). One of these proteins is a 19 kDa glycoprotein (gp19K), which inhibits CTL-mediated lysis of Ad-infected cells in vitro (Efrat et al., *Proc. Natl. Acad. Sci.* 92:6947–6951, 1995). Three other E3 proteins, the 14.7K protein and 10.4K protein in combination with the 14.5K protein (referenced hereinafter as the 10.4K/14.5K complex), protect adenovirus-infected cells against cytolysis and the inflammatory response induced by tumor necrosis factor-α (TNF-α) both in vitro and in vivo (Sparer et al., supra; Krajcsi et al., *J. Virol.* 70:4904–4913, 1996; Dimitrov et al., *J. Virol.* 71:2830–2837, 1997). Although the exact stoichiometry of 10.4K and 14.5K proteins in this complex is not known, it is believed to consist of one 14.5K polypeptide in physical association with a dimer formed by full-length and short forms of the 10.4K polypeptide joined in disulfide linkage. Stewart et al, supra.

Efrat et al. have reported that the expression of the one of the Ad E3 genes, i.e. the gene encoding the 19 kDa glycoprotein (gp19K), can prolong survival of pancreatic islet allografts. The islets were obtained from transgenic animals prepared to contain the entire E3 genomic DNA from human Ad, however, the gp19K mRNA was prominently expressed with little or no expression of the 10.4K protein which makes up a portion of the 10.4/14.5 complex. The islet allografts survived reportedly due to the expression of the gp19K protein and there was no suggestion in this reference that the 10.4K or 14.5K proteins either separately or in the 10.4K/14.5K complex played any role in the survival of the allografts.

Nevertheless, the 10.4/14.5 complex can protect Ad-infected cells from the inflammatory response in the context of Ad infection (Sparer et al., supra) and, although it has not been heretofore recognized, it is possible that the 10.4K/14.5K complex could also provide a novel basis for modulating the immune system in certain disease processes.

SUMMARY OF THE INVENTION

In accordance with the present invention, the inventor herein has succeeded in discovering that the Ad 10.4K/14.5K complex inhibits apoptosis mediated by death receptors, in particular Fas or TNFR-1, by removing the death receptor from the cell surface. The present invention, thus, provides a method for inhibiting apoptosis of a cell comprising treating the cell with an effective amount of a 10.4K/14.5K complex referenced herein as RID (Receptor Internalization and Death) or as RID complex. The RID complex reduces the number of molecules of one or more death receptors on the surface of the cell. This down-regulation of the death receptor results from internalization of the receptor to endosomes and degradation of the internalized death receptor by lysozymes. The RID complex is obtained from or derived from the RIDα and RIDβ proteins encoded by the Ad E3 region DNA. Other E3 region-encoded proteins, including the gp19K and 14.7K proteins, are not required to remove the death receptor from the cell surface or to induce apoptosis. Due to the similar structure of TNFR death receptors, and in the common pathway by which they mediate apoptosis, it is believed that RID can inhibit apoptosis mediated by all death receptor members of the TNFR family by promoting their removal from the cell surface.

In one embodiment of the present invention, the cell is treated with RID by administering to the cell a polynucleotide encoding the RID complex, through which the RID complex is expressed in the cell. Alternatively, the treating step comprises administering the RID complex to the cell, preferably in a carrier that facilitates delivery of the complex into the cell. The method can be used to inhibit apoptosis of cells expressing one or more death receptors of the TNFR family, including but not limited to Fas, TNFR-1, DR3, TRAIL-R1 and TRAIL-R2. Where the cell comprises a tissue, the method is useful for promoting survival of a tissue transplant in a patient or in promoting survival of a tissue under attack in a patient suffering from a degenerative disease, an immunodeficiency disease, an autoimmune disorder or other diseases associated with disregulation of apoptosis mediated by the TNFR death receptors. The method is also useful in inhibiting apoptosis of leukocytes mediated by tumor cells in cancer patients, thereby promoting leukocyte destruction of the patients tumor cells.

Accordingly, in another embodiment, the present invention provides a method for decreasing apoptosis of target cells in a patient comprising treating the patient with an effective amount of a RID complex. The target cells express a death receptor which is downregulated when RID enters the cells.

In yet another embodiment, the invention provides a method for inhibiting leukocyte apoptosis in a patient comprising withdrawing leukocytes from the patient, treating the leukocytes with an effective amount of a RID complex, and administering the treated leukocytes to the patient.

In another embodiment, the present invention provides a composition comprising a RID complex in a carrier suitable for facilitating entry of the RID complex into a cell. As illustrated in FIG. 3, a RID complex comprises at least three polypeptides: a full-length Ad E3 10.4K protein having two transmembrane domains (RIDα-L)(SEQ ID NO:1), a short form of the 10.4K protein with only one transmembrane domain (RIDα-S)(SEQ ID NO:2), and a 14.5K protein (RIDβ)(SEQ ID NO:4). RID compositions intended for treating humans preferably contain a pharmaceutically acceptable carrier. In one embodiment, the carrier component of the composition comprises a liposome.

The present invention also provides an Ad vector for expressing a RID complex in a cell and to cells transfected with this vector. The vector comprises a nucleotide sequence encoding the RIDα and RIDβ polypeptide components of the complex operably linked to a promoter capable of directing expression of the nucleotide sequence in the cell. A preferred vector consists of 231-10 (SEQ ID NO:5), which expresses functional polypeptides for all of the E3 genes other than adp.

Among the several advantages found to be achieved by the present invention, therefore, may be noted the provision of compositions and methods for inhibiting apoptosis of a cell expressing a death receptor; the provision of compositions and methods for promoting tissue transplant survival in patients; the provision of compositions and methods for treating patients suffering from an autoimmune disease and other disorders associated with dysfunction of apoptosis regulation; and the provision of compositions and methods for promoting tumor destruction in cancer patients.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 illustrates the amino acid sequences and various domains of preferred embodiments of the RIDα and RIDβ polypeptides, showing in FIGS. 4A–4B the long and short forms of the E3 10.4K polypeptides (RIDα-L(SEQ ID NO:1) and RIDα-S(SEQ ID NO:2)) from Ad serotype 2, FIG. 4C the pre-14.5K (RIDβ)(SEQ ID NO:3) polypeptide of Ad serotype 5, and in FIG. 4D the mature 14.5K (RIDβ) (SEQ ID NO :4) polypeptide of Ad serolype 5, with the signal sequences and transmembrane domains underlined and the asterisks indicating sites for disulfide linkage in RIDα or for O-phosphorylation in RIDβ;

FIG. 6 shows photographs of MCF7-Fas cells (FIGS. 6A and 6B) infected with rec700 Ad ("wild-type") or (FIGS. 6C and 6D) transiently transfected with pMT2-RIDα plus pMT2-RIβ which were then treated with an agonist monoclonal antibody to Fas and double-stained for the adenovinis-encoded DNA binding protein (anti-ADP) (FIG. 6A) and for DNA 4, 6-diamidino-2-phenylindole (DAPI) (FIG. 6B) or double-stained for RIDβ (FIG. 6C) and DNA (FIG. 6D), with the photographs taken using a 100× Plan apo objective lens;

FIG. 28 illustrates the nucleotide sequence of the 231-10 genome(SEQ ID NO:5) with the numbering beginning with the first base-pair on the conventional left side of the AdS genome as shown in FIG. 27 and proceeding to the last base-pair at the right side of the genome;

DETAILED DESCRIPTION OF THE INVENTION

Figure 1:
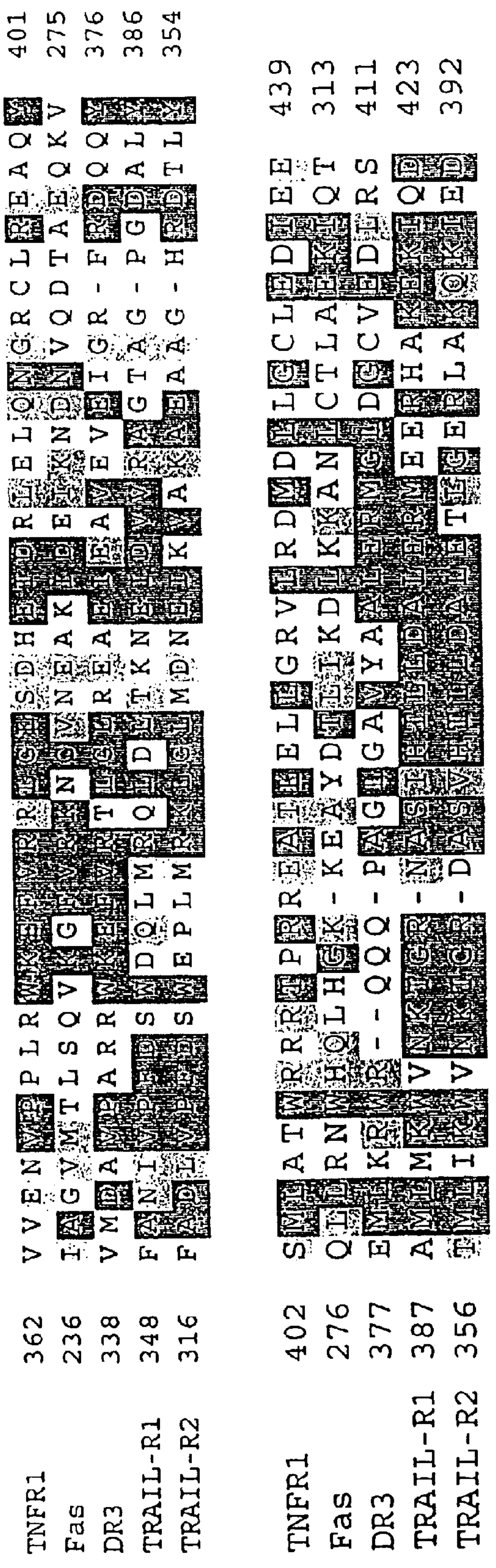
FIG. 1 shows an alignment of the amino acid sequences of the death domains of the death receptor subfamily of TNFR proteins, with residues identical in more than 30% of sequences shaded black and residues conserved in more than 30% of sequences shaded in gray.
Figure 2:
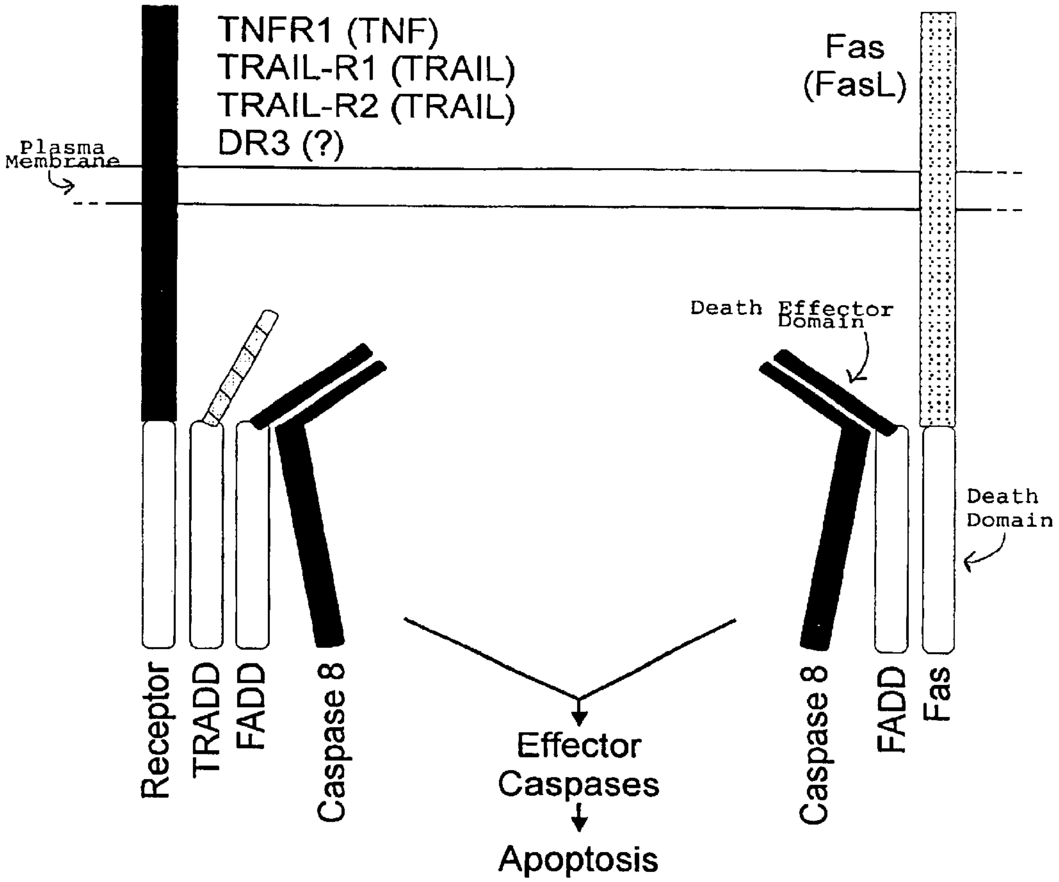
FIG. 2 is a schematic representation of apoptosis mediated by death domain-containing members of the TNF receptor superfamily, with the death receptors Fas, TNFR 1, TRAIL-R1, TRAIL-R2 and DR3 depicted by the bars on the extreme right and left sides of the figure, the ligands for these receptors indicated in parenthesis, and showing the association of the death receptors with intracellular proteins in the apoptotic singling cascade at the bottom of the figure.

The present invention is based on the discovery that the Ad RID complex inhibits apoptosis mediated by death receptors, and in particular by Fas and TNFR1. Some of the molecular events involved in apoptosis induced through death receptors of the TNFR family are illustrated in FIG. 2. Fas (bar on the extreme right) is localized on the cell surface. When FasL engages Fas on the outside of the cell (top of FIG. 2), Fas associates with proteins within the cell (bottom of FIG. 2). First, Fas binds a protein named FADD through their corresponding death domains and then the Fas/FADD complex binds the protein named Caspase 8 through another region in FADD and Caspase 8 named the "death effector" domain. This binding activates the enzymatic activity of Caspase 8, an "initiator" caspase. Activated Caspase 8 cleaves other caspases (effector caspases), which then cleave other proteins, and apoptosis ensues. Apoptosis induced through TNFR is very similar, except that an additional protein, named TRADD, is involved. INF engages TNFR1, causing it to bind TRADD through death domains in TNFR1 and TRADD (left part of FIG. 2). The TNFR1/TRADD complex then binds FADD through their death domains and this is followed by binding to Caspase 8, etc. TRAIL-R1, TRAIL-R2, and DR3 are believed to undergo a similar binding cascade to activate caspases, although the ligand that triggers apoptosis through DR3 is unknonn.

Figure 5:
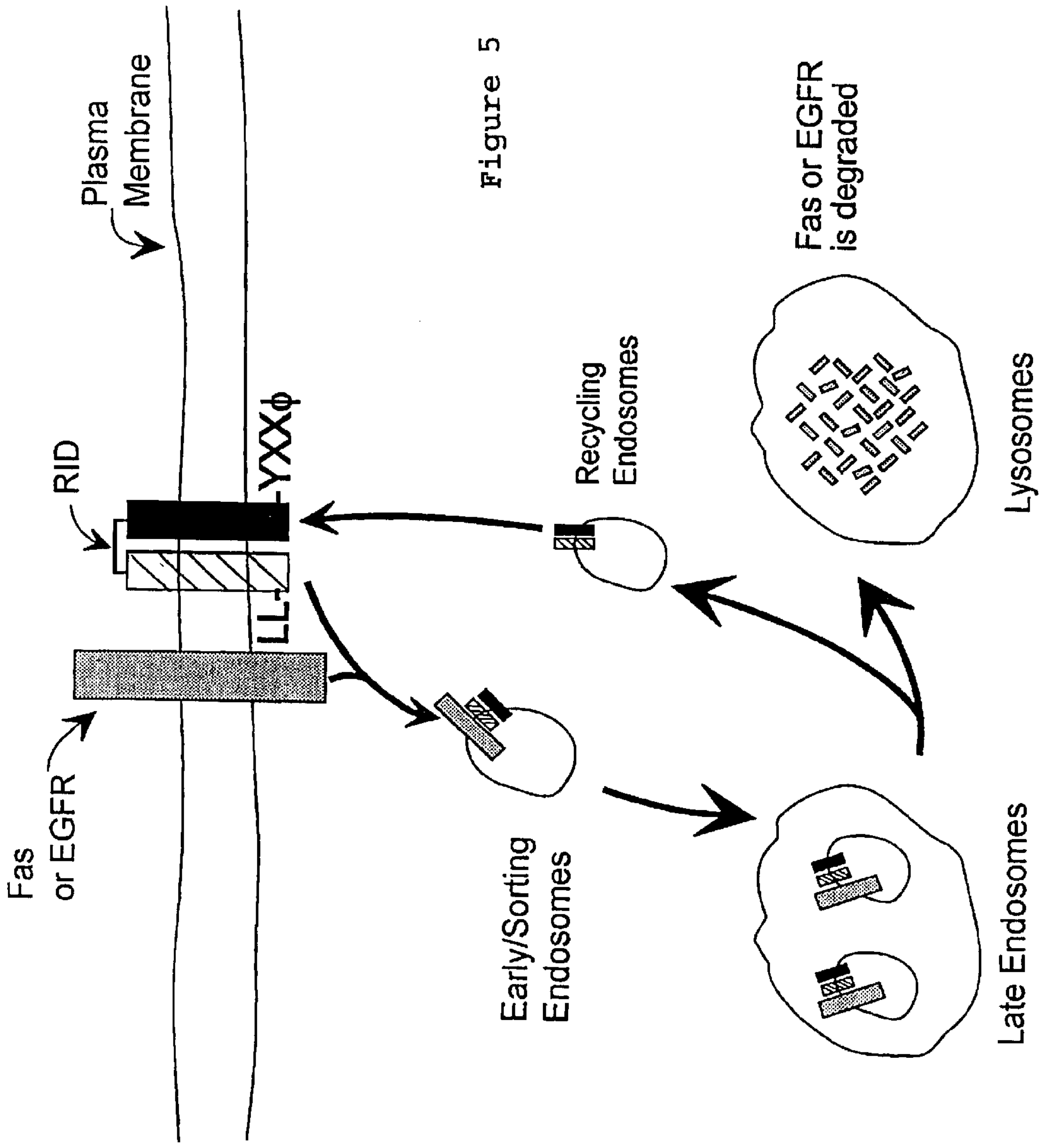
FIG. 5 is a schematic representation of a model for RID-induced internalization and degradation of Fas and TNFR1 death receptors, showing RID and the death receptor in the plasma membrane, entry of RID and the death receptor into endosomes, transport of these endosomes to lysosomes where the death receptor is degraded, and recycling of RID in endosomes to the cell surface, where it can internalize another death receptor molecule.

RID inhibits apoptosis by means of an internalization and degradation mechanism common to all death receptors. As illustrated in FIG. 5, RID shuttles the death receptor from the cell surface to lysosomes where the receptors are degraded. This model is supported in part by the fact that the RID complex has two motifs in its intracellular portion that are known to play a role in the internalization of some cell surface receptors and their transport to lysosomes. These motifs are a dileucine motif (LL), which is present in RIDα, and a tyrosine-based motif in RIDβ, which is YXXϕ, where Y is tyrosine, X is any amino acid, and ϕ is an aromatic or bulky hydrophobic amino acid such as phenylalanine, tyrosine, tryptophan and proline. It is believed that RID acts through the LL and YXXϕ motifs to cause Fas or TNFR1 to be internalized into early/sorting endosomes. Again, acting through the LL and YXXϕ motifs, RID mediates transport of the early endosomes to late endosomes and then to lysosomes where the receptors are degraded. RID then recycles back to the cell surface in endosomes where it repeats this process. Additional evidence supporting this model is as follows: (1) RID co-localizes with Fas on the cell surface as well as in vesicles; (2) degradation of Fas is inhibited by bafilomycin A1, an inhibitor of late endosome function; (3) the RID proteins are very stable, as indicated by pulse-chase experiments, whereas Fas is very unstable in the presence of RID; and (4) mutation of the LL motif severely reduces the function of RID, and conversion of the Y in the YXXϕ motif abolishes the function of RID.

Because of their similar structures and common apoptotic pathway, it is believed that all death receptors of the TNFR family can be removed from the cell surface by RID via internalization into endosomes and subsequent degradation in lysozymes. Thus, RID will inhibit apoptosis mediated by any member of the TNFR death receptor family. As such, RID should be useful to promote survival of cells and tissues in the treatment of diseases such as degenerative diseases, immune disorders including autoimmune disorders, ischemic injury such as caused by myocardial infarction, stroke induced neuron death and reperfusion injury, alcohol-induced hepatitis, diseases caused by viral infection, such as AIDS and fulminant hepatitis, and cancer. RID is also useful in promoting survival of tissue transplants in transplant recipients.

Thus, in one embodiment the invention provides a method for inhibiting apoptosis of a cell comprising treating the cell with an effective amount of a Receptor Internalization and Degradation (RID) complex. Cells which can be treated by this method express one or more death receptors of the TNFR family, which includes Fas, TNFR1, DR3, TRAIL-R1, TRAIL-R2 and any subsequently discovered family member characterized by the presence of a death domain. Cells expressing a death receptor can be identified by methods known in the art, such as incubating the cells with one or more death receptor ligands followed by evaluating the cells for apoptosis, detecting death receptor molecules on the cell surface with an antibody against the death receptor, or detecting mRNA molecules that encode the death receptor. Cell death by apoptosis is readily recognizable and includes cytoplasmic and nuclear condensation, loss of membrane integrity and extensive fragmentation of chromosomal DNA, which forms a characteristic ladder when analyzed by gel electrophoresis. Vaux, D., *Proc. Natl. Acad. Sci* 90:786–789, 1993. Antibodies against the TNFR death receptors are either commercially available or can be readily prepared using standard techniques.

Figure 3:
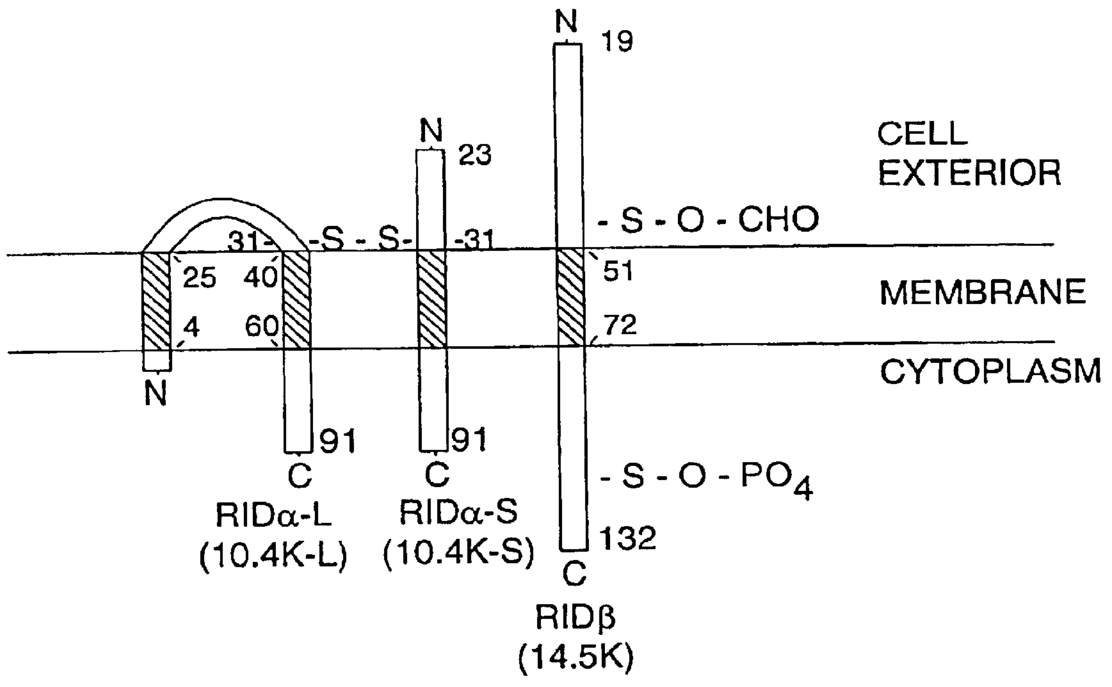
FIG. 3 is a schematic representation of a preferred RID complex showing one mature 14.5K polypeptide having an O-glycosylated residue in the extracellular (or lumenal) domain and an O-phosphorylated residue in the cytoplasmic domain, and two covalently-linked 10.4K polypeptides, one of which is an uncleaved, full-length form of 10.4K (10.4K-L) having two membrane-spanning regions (diagonal stripes) and the other a cleaved, short form of 10.4K (10.4K-S) with only one transmembrane region.

The RID complex used in the method comprises at least one of each of the following polypeptides: a RIDα-L polypeptide(SEQ ID NO:1), a RIDα-S polypeptide(SEQ ID NO:2), and a RIDβ polypeptide. RID α and RIDβ are synonymous with the 10.4K and 14.5K proteins, respectively, which are encoded by two genes in the Ad E3 region. The basic structures of these polypeptides in a membrane are illustrated in FIG. 3. RIDα-L (SEQ ID NO:1) comprises a first transmembrane domain, which is an uncleaved signal sequence, an extracellular domain, an internal transmembrane domain, and a cytoplasmic domain. RIDα-S(SEQ ID NO:2) lacks the signal sequence and thus comprises the extracellular domain, the internal transmembrane domain and the cytoplasmic domain. RIDβ comprises an extracellular domain, which preferably lacks the signal sequence as shown in FIG. 4D, a transmembrane domain and a cytoplasmic domain. When the RID complex is localized in membrane structures and vesicles within the cell, the extracellular domain is located in the lumen of these membranes and vesicles.

In preferred embodiments, the RIDα-S(SEQ ID NO:2) and RIDα-L(SEQ ID NO:1) polypeptides are covalently joined by a disulfide bond between cysteine residues in their extracellular domains which correspond by alignment with the $Cys_{31}$ residue of the Ad2 10.4K protein (FIG. 4A). Also, RIDβ preferably has a mucin type O-linked oligosaccharide attached to one or more amino acids in the extracellular domain and/or is phosphorylated at one or two serines in the cytoplasmic domain. (See Krajcsi et al., *Virol.* 187:492–498, 1992; Krajcsi et al., *Virol.* 188:570–579, 1992.) The location of these residues in RIDβ polypeptides encoded by E3 genes of different Ad serotypes can be determined by alignment with the amino acid sequence for the 14.5K protein of Ad5, which is shown in FIG. 4C.

A RID complex made by Ad in vivo is believed to contain RIDα-L(SEQ ID NO:1), RID-αS(SEQ ID NO:2) and RIDβ (SEQ ID NO:4)(lacking the signal sequence) polypeptides in about a 1:1:1 ratio. However, it is possible that various ratios of these polypeptides will be functional or that in some cases different ratios will be required to provide a functional complex.

The amino acid sequences of the RIDα-L(SEQ ID NO:2), RIDα-β(SEQ ID NO:2) and RIDβ polypeptides comprising the RID complex may be identical to those of naturally-occurring Ad RIDα (10.4K) and RIDβ(14.5K) proteins from any Ad serotype or may comprise functional variants of such naturally-occurring sequences. As stated above, the genes encoding the RIDα and RIDβ proteins are highly conserved among Ad serotypes. These genes are also conserved in Ads from some non-human species. Thus, it is believed that their encoded products should function very similar to the RIDα and RIDβ polypeptides from Ad2 and Ad5, which were used in the experiments described herein. In addition, the invention includes the use of RID complexes in which the RIDα-L(SEQ ID NO:1), RIDα-S(SEQ ID NO:2), and RIDβ polypeptides comprise homologous amino acid sequences, i.e., encoded by the same Ad serotype, or that comprises heterologous sequences, i.e., encoded by two or more Ad serotypes. Thus, for example, a RID complex may comprise (1) a RIDα-L polypeptide comprising the RIDα-L amino acid sequence from Ad2(SEQ ID NO:1), (2) a RIDα-S polypeptide comprising the RIDα-S amino acid sequence from Ad5(SEQ ID NO:2), and (3) a RIDβ polypeptide comprising the RIDβ amino acid sequence from Ad9(SEQ ID NO:4). Preferably, the RID complex comprises polypeptides whose amino acid sequences correspond to serotypes from the same subgroup. More preferably, the RID complex comprises RIDα-S(SEQ ID NO:2) and RIDα-L(SEQ ID NO:1) polypeptides encoded by the RIDα gene of Ad2 and a RIDβ polypeptide encoded by the RIDβ gene of Ad5(SEQ ID NO:4).

A functional variant of a naturally-occurring RIDα or RIDβ sequence contains one or more amino acid substitutions in that sequence which do not destroy the ability of the resulting polypeptide to function in a RID complex to inhibit apoptosis. Preferably, amino acid substitutions in functional variants are conservative amino acid substitutions, which refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H. In addition, conservative amino acid substitutions as used herein is intended to include substitutions which are present at corresponding positions in sequences from different Ad serotypes.

A functional variant as used herein can also include modified sequences in which one or more amino acids have been inserted, deleted, or replaced with a different amino acid or a modified amino acid or unusual amino acid, as well as modifications such as glycosylation or phosphorylation so long as the polypeptide containing the modified sequence retains the biological activity of a RIDα or RIDβ polypeptide. By retaining the biological activity, it is meant that the modified polypeptide can function to form a RID complex with anti-apoptotic activity.

In one embodiment, the cell is treated with the RID complex by administering to the cell a polynucleotide encoding the RID complex. The polynucleotide comprises a nucleotide sequence encoding a RIDα polypeptide and a RIDβ polypeptide operably linked to a promoter that produces expression of the RID complex in the cell. In one variation of this embodiment, the polynucleotide can contain portions of the Ad E3 region in addition to that portion encoding RIDα and RIDβ. However, the polynucleotide predominantly expresses the RIDα and RIDβ proteins over any other Ad proteins. Alternatively, actions on cell apoptosis resulting from expression of the polynucleotide are predominantly due to the RID complex rather than any other protein expressed by the polynucleotide. The polynucleotide can comprise an expression plasmid, a retrovirus vector, an Ad vector, an adenovirus associated vector (AAV) or other vector used in the art to deliver genes into cells. Alternatively, the polynucleotide can be administered to the cell by microinjection.

In embodiments where the cell being treated is in a patient, such as cells comprising a tissue transplant or a tissue involved in an antoimmune disorder, the polynucleotide encoding RID is administered to the patient. Any of the vectors discussed above can be used. It is also contemplated that the RID complex be administered by coinfection with a replication-defective Ad expressing RID and another replication competent Ad that complements the replication defective virus to increase the expression of RID in the infected cells.

Preferably, the polynucleotide is selectively delivered to target cells within the patient so as not to affect apoptosis in other tissues. Targeted delivery of the polynucleotide can be done for example by using delivery vehicles such as polycations, liposomes or viral vectors containing targeting moieties that recognizes and binds a specific marker on the target cell. Such methods are known in the art, see, e.g., U.S. Pat. No. 5,635,383. Another targeted delivery approach uses viral vectors that can only replicate in specific cell types which is accomplished by placing the viral genes necessary for replication under the transcriptional control of a response element for a transcription factor that is only active in the target cell. See, e.g., U.S. Pat. No. 5,698,443.

In other embodiments of the invention, the cell is treated by administering to the cell a composition comprising a RID complex. The RID complex for use in such embodiments can be prepared by a variety of means. For example, the RID complex can be isolated from the membranes of Ad-infected cells or cells transfected with a nucleotide sequence encoding the RIDα and RIDβ polypeptides. Alternatively, the polypeptide components of the complex can be expressed in separate cell cultures, extracted into an appropriate buffer and mixed in vitro. RIDα and RIDβ polypeptides can also be chemically synthesized and mixed to form the complex. The RID zomplex can then be tested for the ability to inhibit apoptosis of a cell expressing a death receptor as described herein for Fas and TNFR1.

Preferably, the RID complex is administered with a carrier that facilitates delivery of the RID complex into the cell, such as liposomes. Where the RID complex is being administered to a patiert, the liposomes can have targeting moieties exposed on the surface such as antibodies, ligands or receptors to specific cell surface molecules to limit delivery of RID to targeted cells. Liposome drug delivery is known in the art (see, e.g., Amselem et al., *Chem. Phys. Lipid* 64:219–237, 1993). Alternatively, one or more of the polypeptides of the complex can be modified to include a specific transit peptide that is capable of delivering the peptide into the cytoplasm of a cell or the complex can be delivered directly into a cell by microinjection.

Compositions comprising a RID complex can be administered by any suitable route known in the art including, for example, intravenous, subcutaneous, intramuscular, transdermal, intrathecal or intracerebral or administration to cells in ex vivo treatment protocols. Administration can be either rapid as by injection or over a period of time as by slow infusion or administration of slow release formulation. For treating tissues in the central nervous system, administration can be by injection or infusion into the cerebrospinal fluid (CSF). When it is intended that the RID complex be administered to cells in the central nervous system, administration can be with one or more agents capable of promoting penetration of the protein complex across the blood-brain barrier.

The RID complex can also be linked or conjugated with agents that provide desirable pharmaceutical or pharmacodynamic properties, including for example, substances known in the art to promote penetration or transport across the blood-brain barrier such as an antibody to the transferrin receptor (Friden et al., *Science* 259:373–377, 1993), a polymer such as polyethylene glycol to obtain desirable properties of solubility, stability, half-life and other pharmaceutically advantageous properties Davis et al. *Enzyme Eng* 4:169–73, 1978; Burnham, *Am J Hosp Pharm* 51:210–218, 1994).

For nonparental administration, the compositions can also include absorption enhancers which increase the pore size of the mucosal membrane. Such absorption enhancers include sodium deoxycholate, sodium glycocholate, dimethyl-β-cyclodextrin, lauroyl-1-lysophosphatidylcholine and other substances having structural similarities to the phospholipid domains of the mucosal membrane.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising the RID complex are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The RID complex is administered to patients in an amount effective to inhibit apoptosis of target cells within the patient. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in cell death assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

The compositions and methods of the invention are contemplated for use in promoting survival of tissue transplants. For example, the tissue can be treated in vitro with the RID complex and the treated tissue then introduced into the transplant. In addition, previously transplanted tissues can be treated with RID by administering the RID complex to the transplant recipient. In either scenario, it is contemplated that the RID complex can be administered as a protein formulation or as a polynucleotide expressing the complex.

In another embodiment, the RID complex is used to promote the survival of leukocytes in cancer patients. The leukocytes can be treated in vivo by administering to the patient a polynucleotide expressing RID or a composition containing the RID complex. Preferably, the polynucleotide or RID complex is targeted to the leukocytes by one of the targeting methods discussed above. For example, cytotoxic T cells could be targeted by using an antibody against the CD8 marker and natural killer cells targeted by use of an antibody against the CD16 marker. Alternatively, the leukocytes can be removed from the patient, treated with the RID complex ex vivo, and the treated leukocytes then returned to the patient.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates inhibition of Fas-mediated apoptosis by adenovirus E1B and E3 proteins.

Human breast adenocarcinoma cells expressing Fas (MCF7-Fas) (Jäättela et al., *Oncogene* 10:2297–2305, 1995) were infected with rec700 or with an adenovirus mutant lacking expression of one or more of the RIDα, RIDβ, E3–14.7K and E1B-19K proteins. rec700 is an Ad5-Ad2-Ad5 "wild-type" recombinant whose genome consists of the Ad5 EcoRI A (map positions 0 to 76), Ad2 EcoRI D (map positions 76 to 83), and Ad5 EcoRI B (map positions 83 to 100) fragments (Wold et al., *Virol.* 148:168–188, 1986). rec700 is the parental virus of E3 mutants with 700 or 7000 numbers. The infected cells were treated with a monoclonal antibody to Fas, CH-11, which acts as an agonist of Fas and induces apoptosis. The cells were then fixed and stained for DNA and for the adenovirus DNA binding protein (DBP). Experimental cetails are provided in the footnote to Table 1.

Examples of apoptotic and non-apoptotic nuclei in rec700-infected cells are shown in FIGS. 6A and 6B. Most cells were infected as indicated by the speckled staining of DBP in the nucleus (FIG. 6A), and these nuclei were non-apoptotic (FIG. 6B). Two uninfected cells were apoptotic (arrows in FIGS. 6A and 6B) as evidenced by the presence of shrunken and irregular nuclei with condensed DNA that often fluoresced very brightly above the plane of focus for non-apoptotic nuclei. The percentage of apoptotic and non-apoptotic nuclei was scored in rec700- or mutant-infected cells staining for DBP and the quantitative results are shown in Table 1 below.

TABLE 1

Fas Agonist-induced Apoptosis in MCF7-Fas Cells Infected with Ad Mutants[1]

| | Ad DNA Binding Protein-Positive Cells[2] | |
|---|---|---|
| Virus Mutant | Apoptotic | Non-apoptotic |
| rec700 (wild type) | 0.1[3] | 99.9[3] |
| pm760 (E1B-19K$^+$, RID$^+$) | 0.7 | 99.3 |
| dl309 (E1B-19K$^+$, RID$^-$) | 0.1 | 99.9 |
| dl748 (E1B-19K$^+$, RID$^-$) | 0.6 | 99.4 |
| dl764 (E1B-19K$^+$, RID$^-$) | 0.2 | 99.8 |
| lp5 (E1B-19K$^-$, RID$^+$) | 9.9 | 90.2 |
| dl250 (E1B-19K$^-$, RID$^+$) | 10.4 | 89.6 |
| dl111 (E1B-19K$^-$, RID$^-$) | 87.2 | 12.8 |
| dl118 (E1B-19K$^-$, RID–) | 94.1 | 5.9 |

[1]MCF7-Fas cells were infected with 250 PFU per cell of virus except for lp5, dl250, dl111, and dl118 where 10 PFU per cell was used. At 21 h post-infection (p.i.), cells were treated for 22 h with the CH-11 agonist mAb to Fas (200 ng/ml) (Panvera, Madison, WI) plus cycloheximide (25 μg/ml). Cells were fixed and stained for the Ad DNA binding protein (DBP) using a rabbit antiserum (obtained from Maurice Green, St. Louis University) and goat anti-rabbit IgG (fluorescein conjugate) and for DNA using 4,6-diamidino-2-phenylindole (DAPI). Typical apoptotic and non-apoptotic nuclei are shown in FIG. 6B, which is from the same experiment. Nuclei of dl111- or dl118-infected cells not treated with Fas agonist were not apoptotic (not shown), indicating that the apoptosis observed was not due to the cyt deg phenotype of E1B-19K-negative mutants (Subramanian et al., J. Virol. 52:336–343, 1984).
[2]At least 1000 DBP-positive cells were counted per sample.
[3]Percent of apoptotic and non-apoptotic nuclei in cells staining for DBP.

In cells infected with rec700 or mutant pm760, which expresses both E1B-19K and RID, very few nuclei were apoptotic. Cells infected with mutants expressing E1B-19K but lacking RIDα and E3-14.7K (dl748), or lacking RIDβ (dl764), or lacking each of RIDα, RIDβ, and E3-14.7K (dl309) also had very few apoptotic nuclei. However, only about 10% of cells infected with lp5 and dl250, which lack E1B-19K but express RID, had apoptotic nuclei, while about 90% of the nuclei were apoptotic in cells infected with dl111 and dl118, which lack expression of RIDα, RIDβ, E3 14.7 K and E1B-19K. These results indicate that adenovirus has two proteins that independently inhibit Fas-induced apoptosis, RID and/or E3-14.7K in the E3 transcription unit and E1B-19K in the EIB transcription unit. This result observed with E1B-19K is consistent with an earlier report (Hashimoto, S., et al., *Int. Immunol.* 3:343–351, 1991. Data below show that RID inhibits Fas-induced apoptosis.

EXAMPLE 2

This example illustrates that the RID complex is sufficient to inhibit apoptosis.

To address whether RID is sufficient to inhibit Fas-induced apoptosis, plasmids expressing RIDα or RIDβ from the Ad major late promoter plus SV40 enhancer were prepared by cloning the gene for RIDα or RIDβ into the pMT2 vector (Mazzarella, R. A. & Green, M. *J. Biol. Chem.* 262: 8875–8883, 1987) to generate pMT2-RIDα and pMT2-RIDβ. MCF7-Fas cells were transiently transfected with pMT2-RIDα plus pMT2-RIDβ, pMT2-RIDβ alone, or pMT2 alone (2.5 μg for each plasmid). After 38 h, cells were treated for 9 h with the CH-11 agonist mAb to Fas (500 ng/ml) plus cycloheximide (25 μg/ml), fixed in methanol with DAPI, and stained for RIDβ using the rabbit P118–132 antipeptide antiserum (Tollefson et al., *Virology* 175:19–29, 1990).

Examples of apoptotic and non-apoptotic nuclei in the cells co-transfected with pMT2-RIDα and pMT2-RIDβ are shown in FIGS. 6C and 6D. The cell transfected with RIDα plus RIDβ (arrow in FIG. 6C) was non apoptotic (arrow in FIG. 6D). RIDβ-negative cells usually had apoptotic nuclei (most cells in FIG. 6D). Of 2000 cells counted in random fields, 173 RIDβ-positive cells were seen, and only 26% of these had apoptotic nuclei. In the transfection with RIDβ alone, and with 2000 cells counted, 101 RIDβ-positive cells were seen, 80% of which had apoptotic nuclei. With pMT2 alone, 62% of the total nuclei were apoptotic. These results indicate that RID (i.e. RIDα plus RIDβ, but not RIDβ alone, is sufficient to inhibit Fas-induced apoptosis.

EXAMPLE 3

This example illustrates that RID down-regulates Fas from the cell-surface of adenovirus-infected human breast carcinoma cells.

To investigate how RID inhibits apoptosis, MCF7-Fas cells were infected with adenovirus serotype 5 (Ad5), rec700, or an Ad mutant lacking expression of one or more of RIDα, RIDβ, and E3-14.7K proteins. At 28 h p.i., cells were detached using 0.025% EDTA, then resuspended in FACS buffer (1× PBS, 2% FBS). Approximately $1\times10^6$ cells were pelleted and resuspended in 50 μl FACS buffer containing antibodies against human Fas (UB2 IgG mAb) (Panvera)(10 μg/ml), the human transferrin receptor (Boehringer/Mannheim, Indianapolis, Ind.) (2.5 μg/ml) and purified mouse IgGγ (PharMingen, San Diego, Calif.)(5 μg/ml) as an iso-type control. In common with Fas, the transferrin receptor is a cell surface receptor. Cells were incubated with the primary antibodies, washed with cold FACS buffer, incubated with 20 μg/ml of goat anti-mouse FITC-conjugated antibody (ICN), washed. then analyzed on a FACScaliber flow cytometer (Becton Dickinson, Mountain View, Calif.). The data were analyzed with Cell Quest software (Becton Dickinson) and are shown in FIG. 7.

Figure 7A:
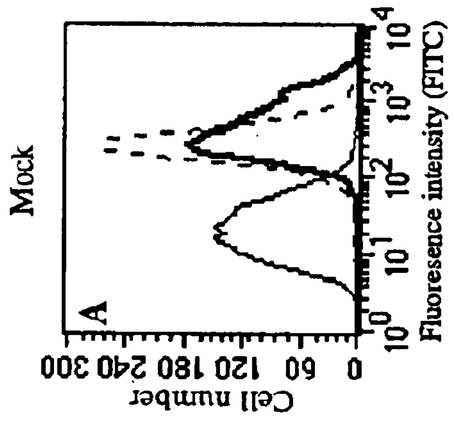
FIG. 7 shows flow cytometry tracings of MCF7-Fas cells which were mock-infected (FIG. 7A) or infected with wild-type Ad (Ad5 and rec700) (FIGS. 7B–7C) or with the indicated Ad E3 mutant (FIGS. 7D–7H) and then incubated with antibodies to Fas (bold trace), transferrin receptor (dashed trace), or control IgG (light trace)
Figure 7B:
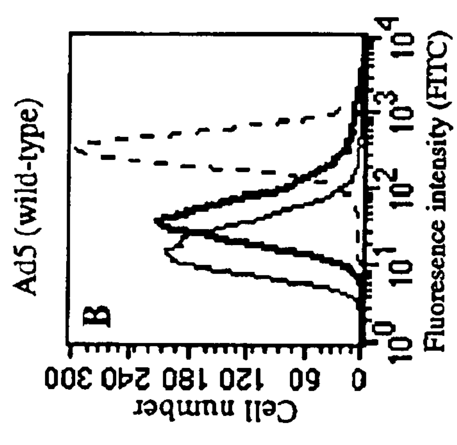
Figure 7C:
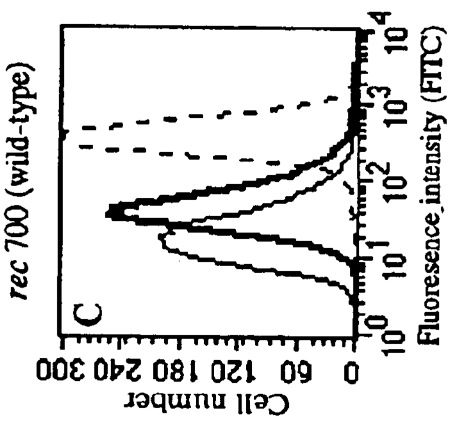
Figure 7D:
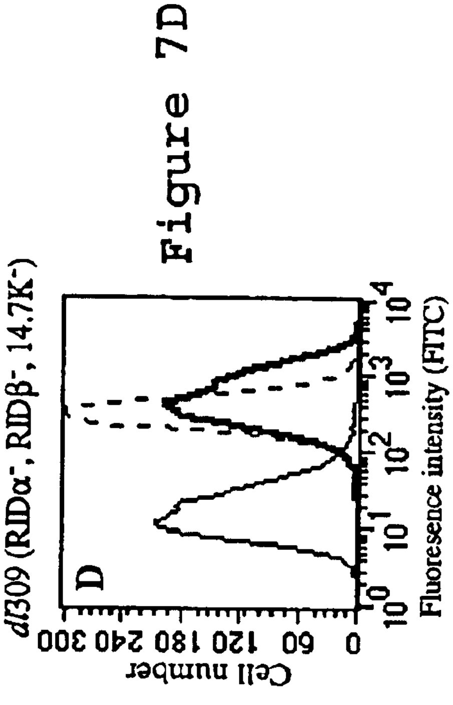
Figures 7E, 7F, 7G, 7H:
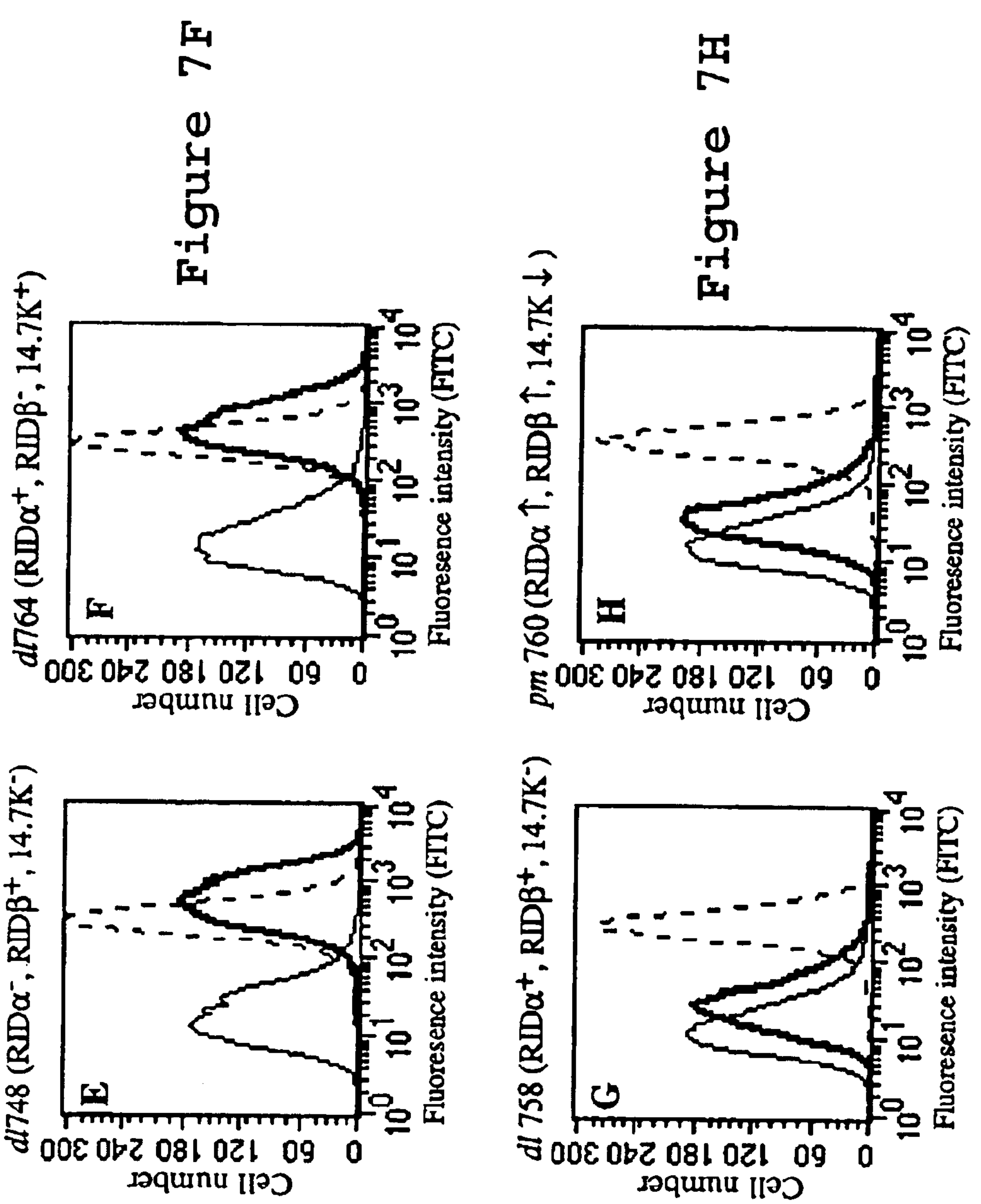

Nearly all Fas (bold trace in FIG. 7) was cleared from cells infected with Ad5 or rec700 (FIGS. 7B, 7C). Transferrin receptor (dashed trace) was not affected. Fas was not cleared from cells infected with mutants lacking RIDα and/or RIDβ, namely dl309 (lacks RIDα, RIDβ, E3-14.7K) (FIG. 7D), dl748 (lacks RIDα)(FIG. 7E), and dl764 (lacks RIDβ) (FIG. 7F). Fas was down-regulated by dl758 (RID-positive, lacks E3-14.7K) (FIG. 7G) and pm760 (overexpresses RIDα and RIDβ) (FIG. 7H). These results indicate that RID (i.e. RIDα and RIDβ) is necessary to clear Fas from the surface of Ad-infected MCF7-Fas cells. Other Ad proteins, including E,3-14.7K and E1B-19K, are not required.

EXAMPLE 4

This example illustrates that RID down-regulates Fas from the cell-surface of adenovirus-infected human lung adenocarcinoma cells.

To determine if RID can remove Fas from the surface of other cell types, the human A549 cell line was exarmined. A549 cells are derived from a human lung adenocarcinoma. A549 cells were mock-infected or infected with rec700. At 26 h p.i., cells were suspended in FACS buffer containing mouse IgG-γ, anti-human-Fas UB2 IgG monoclonal antibody (Panvera), or antibody against the human transferrin receptor (Boehringer/Mannheim), incubated with goat anti-mouse fluorescein isothiocyanate (FITC)-conjugated antibody, and analyzed on a FACScaliber flow cytometer using Cell Quest software (Becton Dickinson). The results are shown in FIG. 8.

Figure 8:
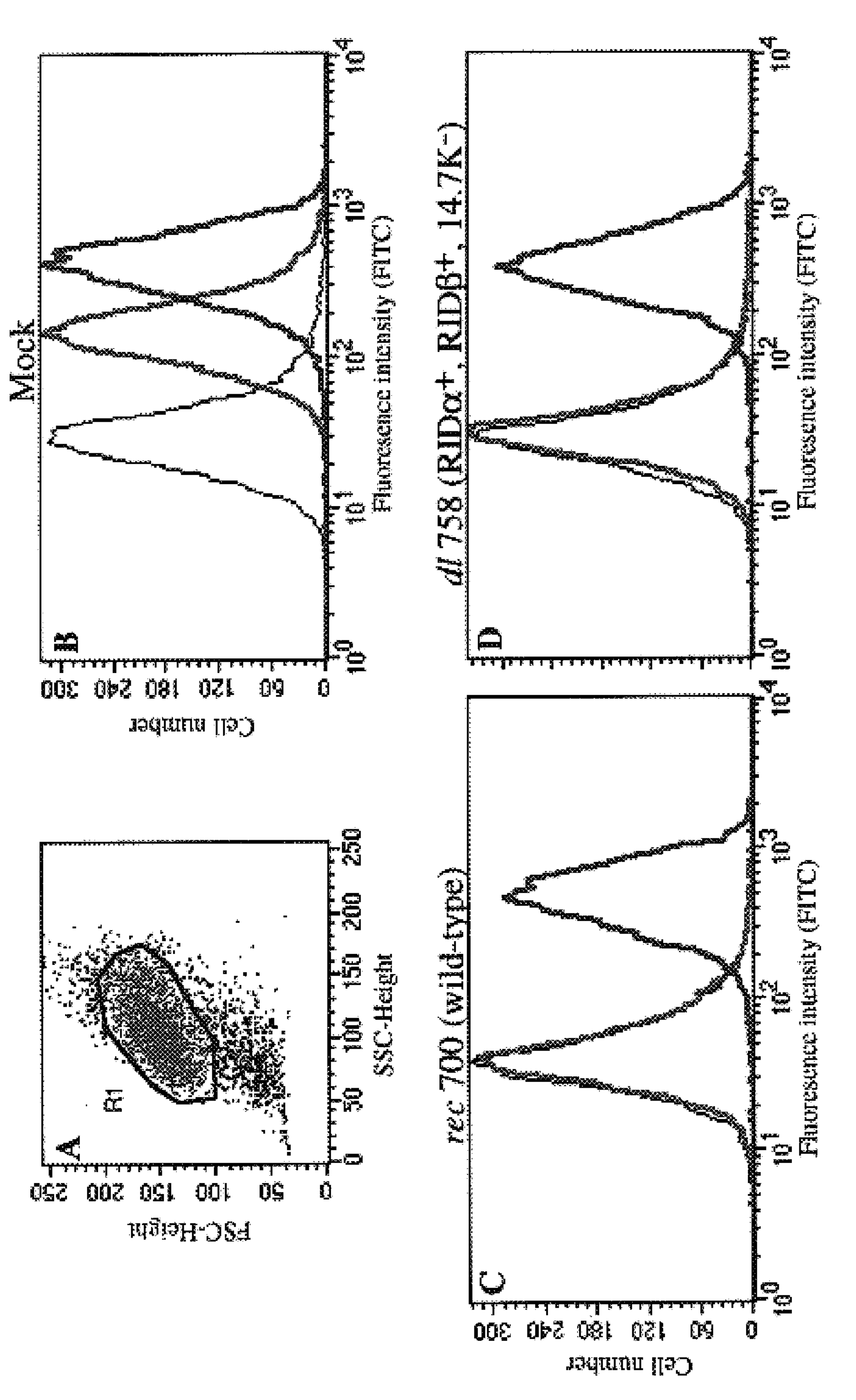
FIG. 8 shows flow cytometry tracings of A549 cells which were mock-infected (FIG. 8B) or infected with wild-type Ad (rec700) (FIG. 8C) or with the indicated Ad E3 mutant (FIGS. 7D–7H) and then incubated with antibodies to Fas (red trace), transferrin receptor (blue trace), or control IgG (black trace), with the cell pattern for mock-infected cells shown in FIG. 8A and R1 indicating the cells that were gated for the analysis.
Figure 8:
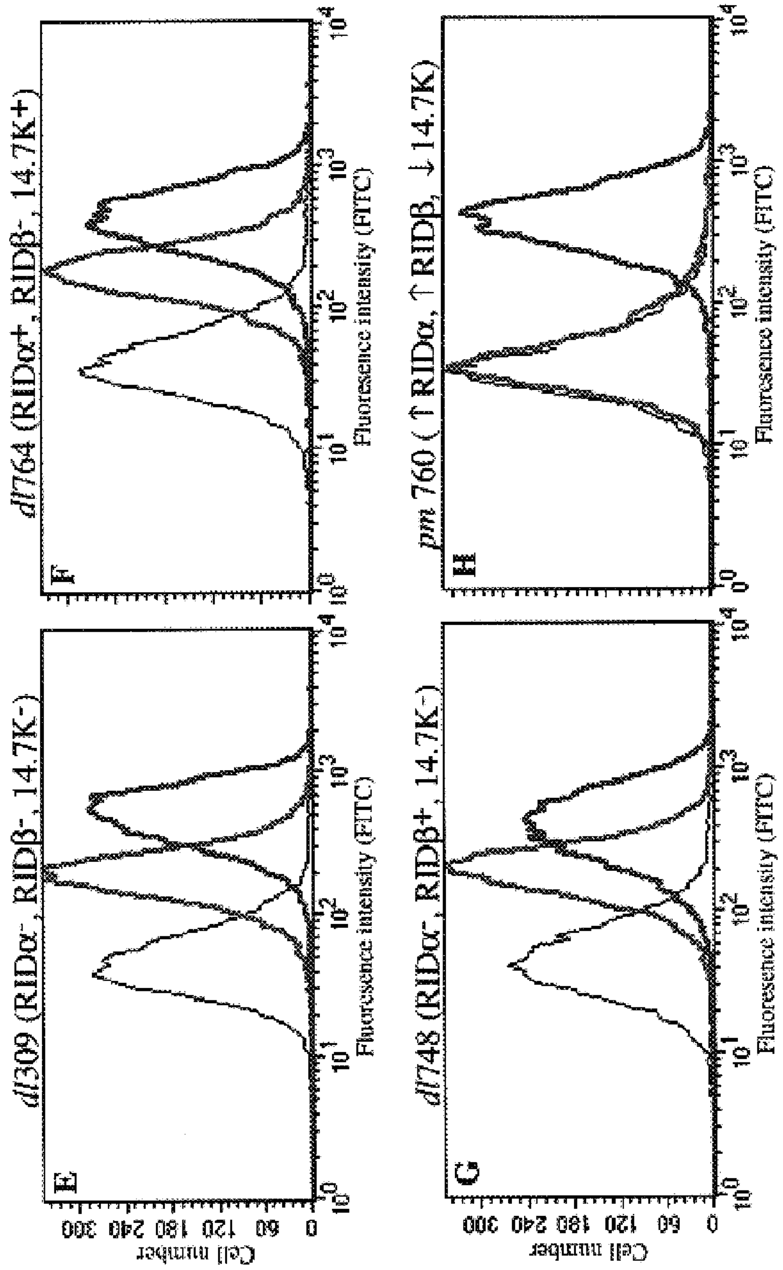

With mock-infected cells (FIG. 8B), there was strong staining for both Fas (the red trace in FIG. 8) and transferrin receptor (the blue trace in FIG. 8). With rec700 or pm760, a virus mutant that overexpresses RID (i.e., RIDα plus RIDβ) and underexpresses other Ad E3 proteins, Fas was completely cleared from the cell surface whereas the transferrin receptor was not affected (FIGS. 8C, 8H). With three virus mutants that lack both RIDα and RIDβ (dl309), RIDβ only (dl764), or RIDα (dl748), Fas was not cleared from the cell surface (FIG. 8, Panels E, F, and G). With dl758, a mutant that lacks only E3-14.7K and that expresses RIDα and RIDβ, Fas was down-regulated to the same extent as with rec700 and pm760. Therefore, the E3-14.7K protein is not required to down-regulate cell surface Fas. Recently, RID was reported to clear Fas from the cell surface in two. other human cell lines, HT-29.14S and ME-180 (Shisler et al., *J. Virol.* 71:8299–8306, 1997). These results have been confirmed with HT-29.14S and ME-180 cells (data not shown). Thus, RID stimulates the removal of Fas from the cell surface of at least four different cell types, MCF7-Fas, A549, HT-29.14S, and ME-180 cells.

EXAMPLE 5

This example illustrates that Fas molecules removed from the cell surface by RID are internalized into vesicles and then degraded in lysosomes.

Many receptors are internalized into endosomes. Accordingly, MCF7-Fas cells were mock-infected or infected with rec700 or with an E3 Ad mutant. MCF7 cells were mock-infected as a control. At 19 h p.i., cells were fixed in methanol and stained for Fas using the ZB4 mAb (Panvera) and goat anti-mouse IgG (Texas red conjugate). The results are shown in FIG. 9.

Figure 9A:
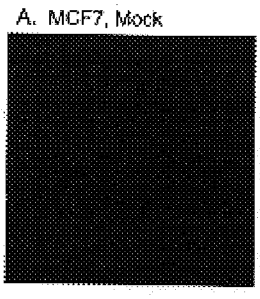
FIG. 9 shows photographs of mock-infected MCF7 cells (FIG. 9A) or MCF7-Fas cells mock-infected (FIG. 9B) or infected with the indicated viruses (FIGS. 9C–9H) and then analyzed for Fas by immunofluorescence, with the speckled pattern in FIGS. 9C, 9G, and 9H representing putative endosomes and lysosomes containing Fas.
Figure 9B:
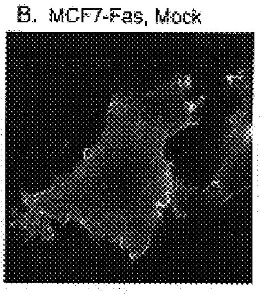
Figure 9C:
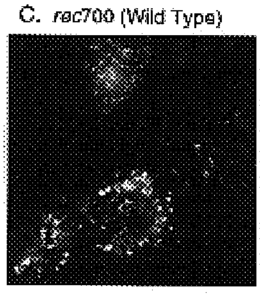
Figure 9D:
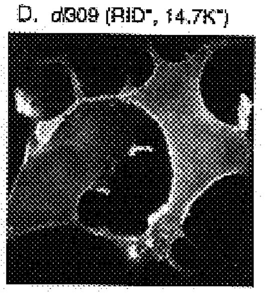
Figure 9E:
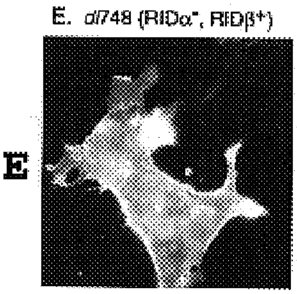
Figure 9F:
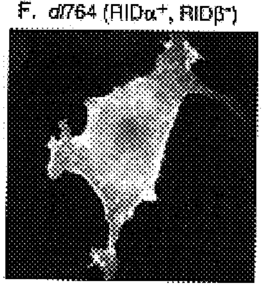
Figure 9G:
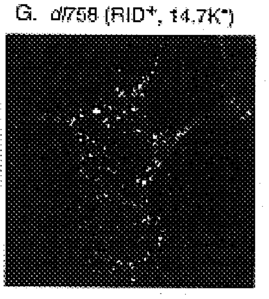
Figure 9H:
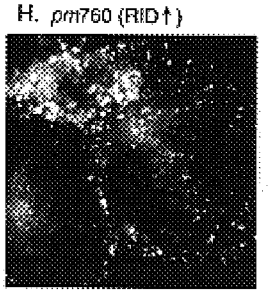

Fas was not detected in mock-infected parental MCF7 cells (FIG. 9A), but was readily apparent on the surface of MCF7-Fas cells (FIG. 9B). In cells infected with rec700, Fas was in numerous vesicles and there was no cell surface staining (FIG. 9C). These vesicles are likely to be endosomes and lysosomes containing Fas. These vesicles were not observed with dl309, dl748, or dl764 (lack RIDα and/or RIDβ), whereas in each case, strong Fas staining was apparent at the plasma membrane (FIGS. 9D–9F). Vesicles staining for Fas were seen with dl758 and pm760, both of which express RID (FIGS. 9G, 9H).

Figure 10:
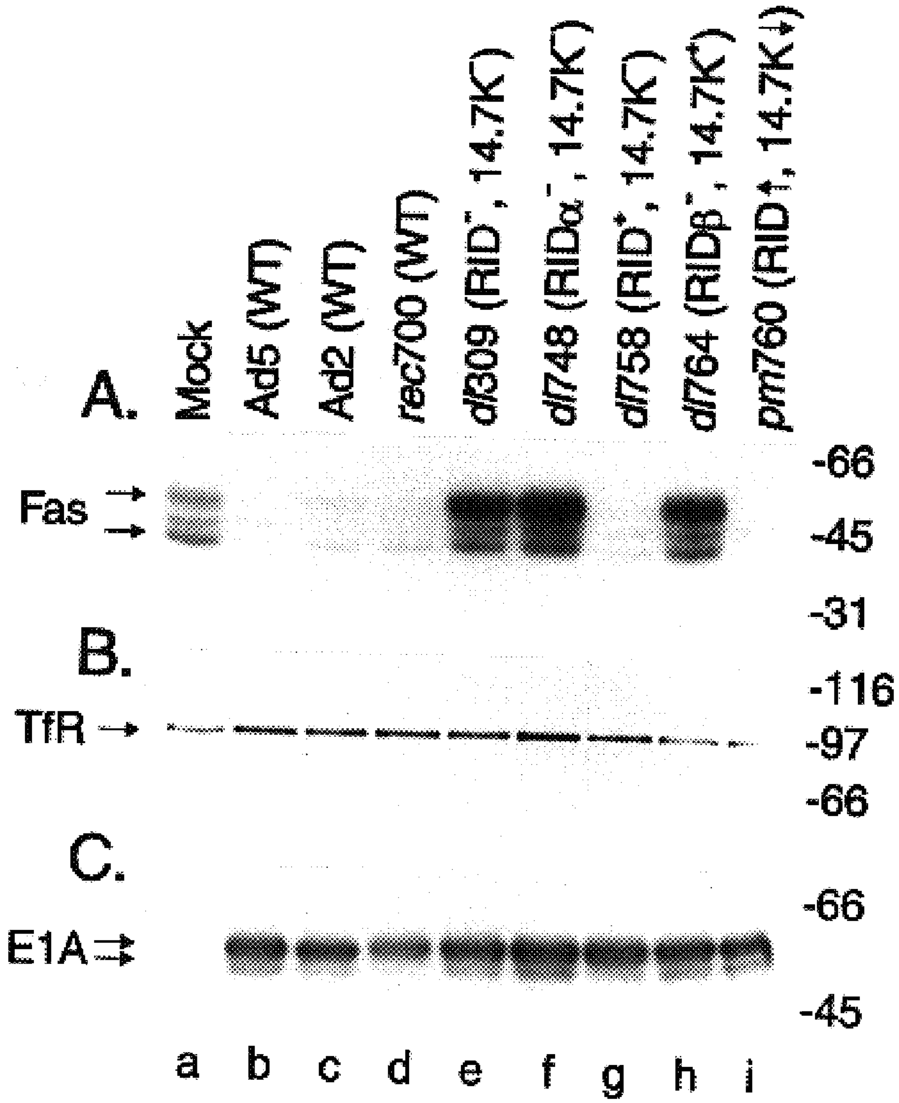
FIG. 10 shows an immunoblot of proteins extracted from MCF-7 Fas cells following mock-infection or infection with the indicated wild-type and mutant Ads and stained for Fas (FIG. 10A), transferrin receptor (FIG. 10B) or Ad E1A (FIG. 10C), with molecular weight markers indicated on the right.

Some receptor types internalized into endosomes are targeted to lysosomes where they are degraded. To determine whether Fas was degraded in Ad-infected cells expressing RID, MCF7-Fas cells were mock-infected or infected with wild-type Ad or an E3 mutant lacking expression of one or more of RIDα, RIDβ, and 14.7K proteins, then at 27 h p.i. proteins were extracted, separated by sodium dodecyl sulfate polyacrylamide gel electrophoresis (SDS-PAGE), and blotted onto an Immobilon-P membrane. After blocking, membranes were incubated with rabbit anti-Fas antiserum (Santa Cruz Biotechnology, Inc., Santa Cruz, Calif.), mouse anti-transferrin receptor mAb OKT9 (ATCC), or mouse anti-E1A mAb M73. Membranes were incubated with the appropriate peroxidase-conjugated secondary antibody (ICN). Proteins were detected with ECL reagents (Amersham Life Sciences, Arlington Heights, Ill.) and the results are shown in FIG. 10.

Fas was degraded in cells infected with viruses that express both RlDα and RIDβ (Ad5, Ad2, rec700, dl75 8,pm760) (FIG. 10A). Transferrin receptor was not degraded in these same extracts (FIG. 10B). Fas expression was actually stimulated in cells infected with mutants that lack RIDα and/or RIDβ (FIG. 10A, compare Mock with dl309, dl748, and dl764). The Ad-coded E1A proteins were expressed at similar levels (FIG. 10C), indicating that all infections were equivalent. These and the above results establish that RID (i.e. RIDα and RIDβ) functions in the internalization of Fas into putative endosomes, the degradation of Fas, and the inhibition of Fas-induced apoptosis.

RID has been reported to stimulate the internalization of EGFR into vesicles and its degradation in lysosomes (Carlin et al., *Cell* 5 7:135–144, 1989; Tollefson et al., *J. Virol.* 65:3095–3105, 1991). VWhen the epidermal growth factor receptor (EGFR) interacts with its ligand, EGF, EGFR is internalized into early endosomes which are transported to late endosomes which fuse with lysosomes, where EGFR is degraded. This process results in attenuation of signal transduction through EGFR. Many receptors are degraded by the endosome-lysosome pathway in response to ligand. To determine if RID-induced degradation of Fas is occurring through this pathway, the following experiments were performed.

The first experiment, which was described in the copending provisional application, examined Fas localization in COS cells transiently co-transfected with combinations of expression plasmids for Fas, RID α and RIDβ. The following plasmids were used, the pMT2-RIDα and pMT2-RIDβ plasmid vectors described in Example 2, and pcDNA3-Fas, which expresses Fas frem the human cytomegalovirus promoter (CMV). COS7 cells were transfected (Mazzarella, R. A. & Green, M. *J. Biol. Chem.* 262:8875–8883, 1987) with 1 μg each of pMT2-RIDα plus pcDNA3-Fas, pMT2-RIDβ plus pcDNA3-Fas, or pMT2-RIDα, pMT2-RIDβ, and pcDNA3-Fas. After 30 h, cells were fixed in methanol with DAPI and stained for Fas using the ZB4 mAb, for RIDα using the rabbit P77–91 antipeptide antiserum, or for RIDβ using the rabbit P118–132 antipeptide antiserum (Tollefson et al., *J. Virol.* 64:794–801, 1990; Tollefson et al., *Virology* 175:19–29, 1990). The results are shown in FIG. 11.

Figures 11E, 11F, 11G, 11H:
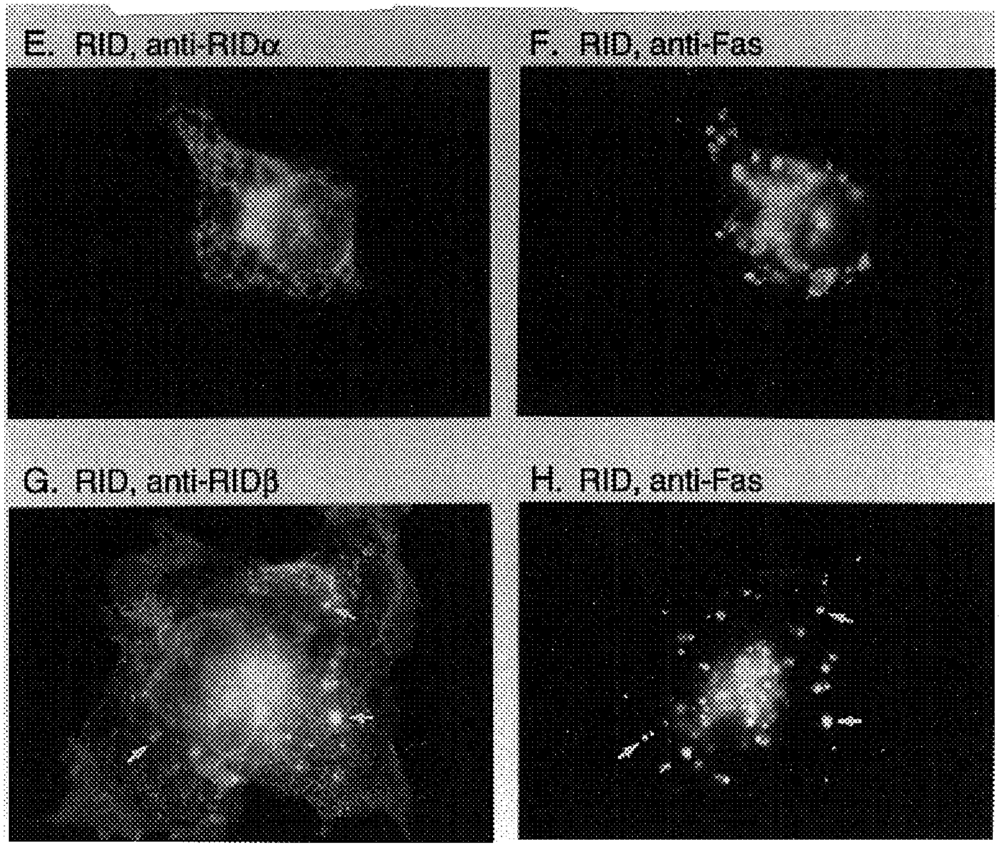
FIG. 11 shows photographs of COS7 cells transfected with expression plasmids for Fas and RIDα (FIGS. 11A, 11B), Fas and RIDβ (FIGS. 11C, 11D), or Fas, RIDα, and RIDβ (FIGS. 11E–11H) and double-stained for RIDα and Fas (FIGS. 11A, 11B, 11E, 11F) or for RIDβ and Fas (FIGS. 11C, 11D, 11G, 11H) with arrow in FIGS. 11G and H indicate vesicles that appear to contain both RIDβ and Fas.
Figure 12A:
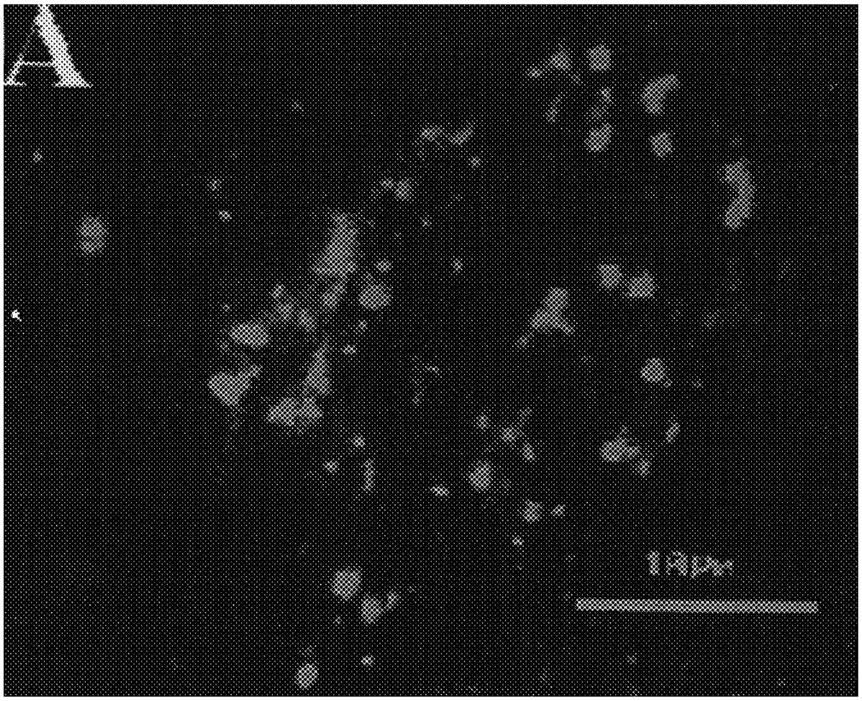
FIG. 12 shows photographs of rec700-infected A549 cells double-stained for Fas and a lysosomal protein, LAMP1 and examined by confocal microscopy, with FIG. 12A showing cells labeled with rabbit anti-Fas antibody and fluoroscein isothiocyanate (FITC), FIG. 12B showing cells labeled with mouse anti-LAMP-1 antibody and rhodamine isothiocyanate (RITC), FIG. 12C showing the combined images of FIGS. 12A and 12B, and FIG. 12D showing a perpendicular view of the image in FIG. 12C (arrows), 1 μm thick, where green indicates Fas, red indicates LAMP-1 and yellow indicates colocalization of Fas and LAMP1 and the bar indicating a distance of 10 μm.
Figure 12B:
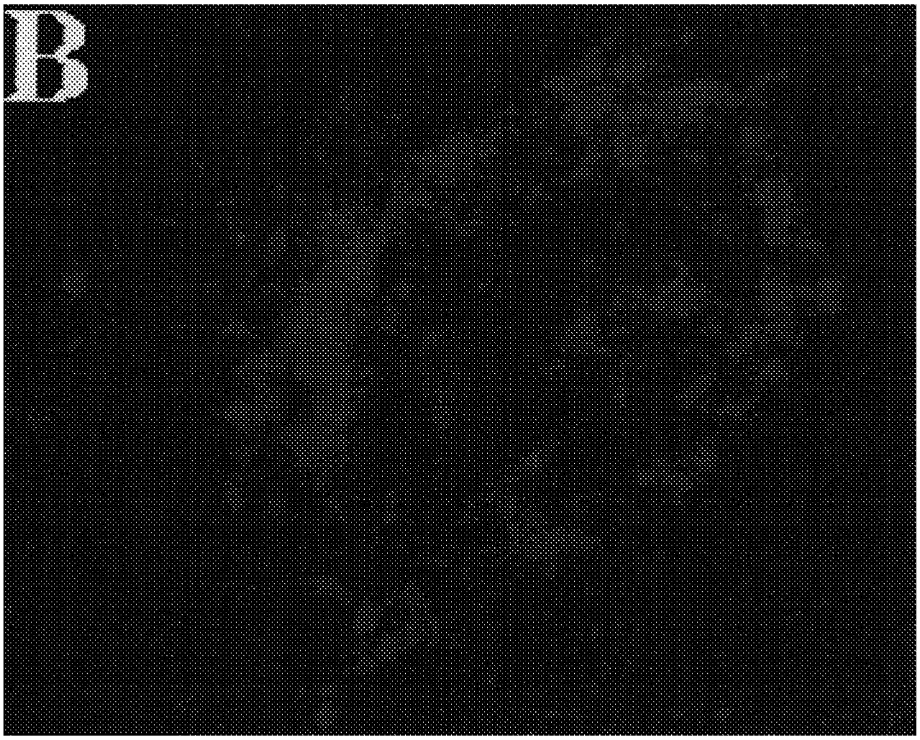
Figure 12C:
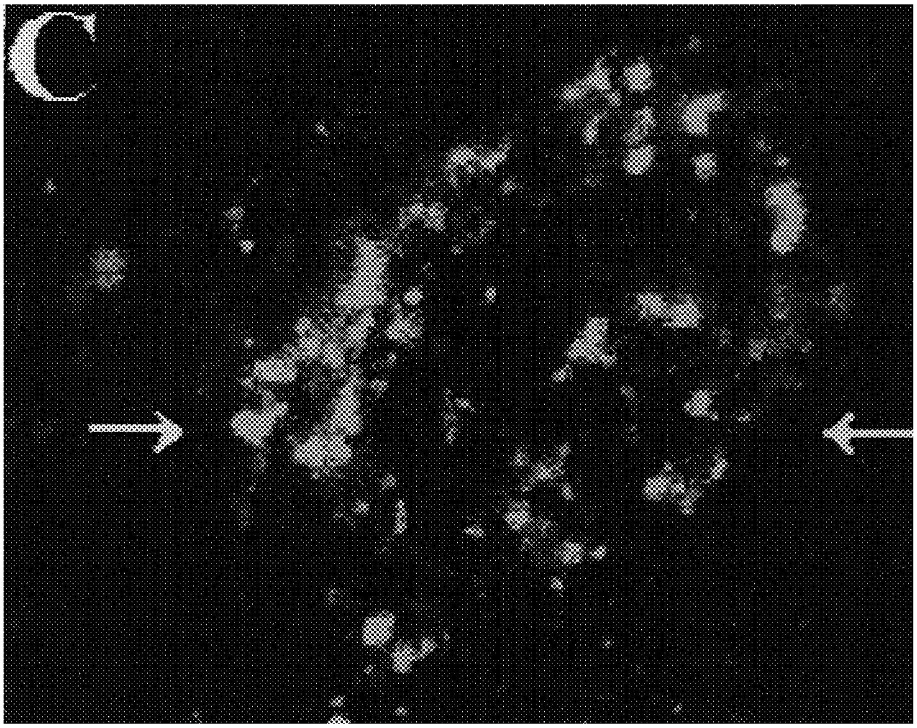
Figure 12D:
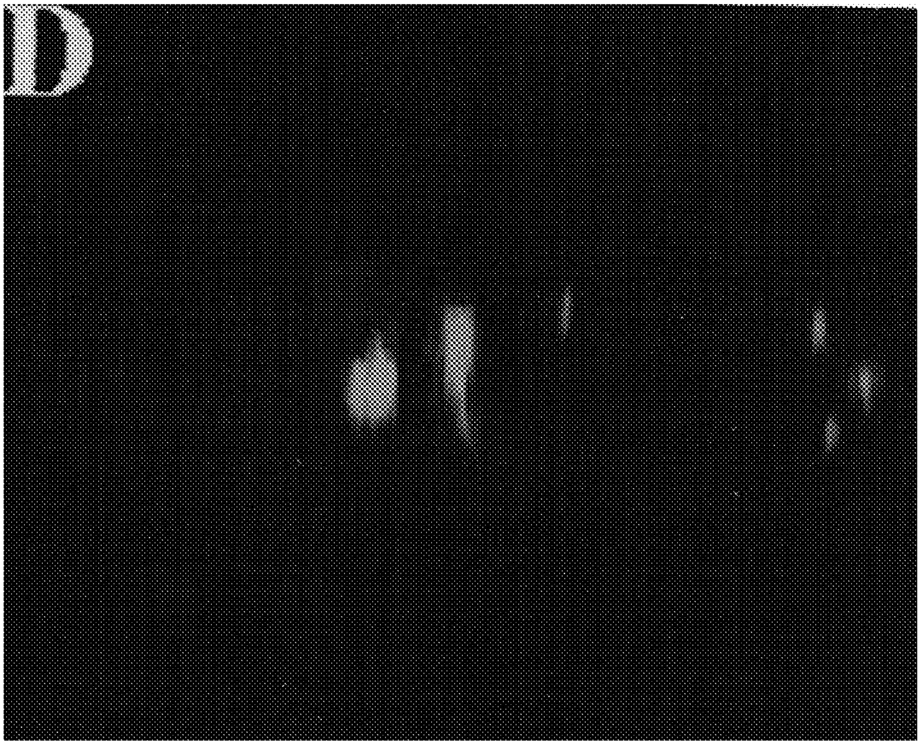

With cells co-transfected with expression plasmids for RIDα plus Fas, or RIDβ plus Fas, Fas was localized on the cell surface (FIGS. 11B, 11D). In contrast, with cells triple-transfected with expression plasmids for RIDα, RIDβ, and Fas, Fas was in vesicles rather than the cell surface (FIGS. 11F, 11H). RIDβ staining was typical of the endoplasmic reticulum (ER) and plasma membrane, a probable site of RID action (Stewart et al., *J. Virol.* 69:172–181, 1995); many vesicles containing RIDβ appeared to co-localize with vesicles containing Fas (arrows in FIGS. 11G and 11H). Distribution to the ER was also characteristic of RIDα (FIG. 11E), and in some cells the plasma membrane was stained (not shown). RIDα: did not co-localize with Fas-coniaining vesicles. Thus, RID (i.e. RIDα plus RIDβ) is sufficient to internalize Fas into vesicles.

In a second experiment, Fas localization was examined in Ad-infected cells. Human A549 cells were infected with rec700 fixed using 3.7% paraformaldehyde followed by methanol/DAPI (4,6-diamidino-2-phenylindole). Cells were double-stained for Fas and LAMP1, which is a lysosomal protein (Carlsson et al., *J. Biol. Chem.* 15:18911–18919, 1988), using a rabbit anti-Fas antibody (Santa Cruz Biotechnology) and the BB6 mouse anti-human-LAMP-1 monoclonal antibody (Carlsson et al., supra), followed by goat anti-rabbit IgG-FITC and goat anti-mouse IgG-RITC (rhodamine isothiocyanate) (Cappel ICN). Cells were examined using a Zeiss LSM 410 scanning laser confocal microscope with LSM 410 software. The results are shown in FIG. 12.

Green, red, and yellow vesicles contain Fas (FIG. 12A), LAMP1 (FIG. 12B), or both Fas and LAMP1(FIGS. 12C, 12D), respectively. The many yellow vesicles establish that Fas co-localizes with LAMP1 in lysosomes. The Fas-containing green vesicles may be endosomes. Similar results were obtained with another lysosomal protein, CD63 (data not shown).

To obtain additional evidence supporting the involvement of the endosome-lysosome pathway in RID-induced Fas degradation in Ad-infected cells, the effect of Bafilomycin A1 (Baf) treatment was investigated. Baf specifically inhibits the vacuolar-type $H^+$-ATPase, preventing vesicle acidification and trafficking of receptors from late endosomes to lysosomes (Yoshimori et al., *J. Biol. Chem.* 266:17707–17712, 1991; van Weert et al, *J. Cell. Biol.* 130:821–834, 1995). A549 cells were mock-infected or infected with rec700 or dl309 (lacks RID). At 13 h after infection, cells were treated with Baf (0.1 μM) for 12 h and then immunostained for Fas. In a separate experiment, cells were treated with Baf at 6 h after infection and processed for immunoblot analysis 18 h later. The results are shown in FIG. 13.

Figure 13A:
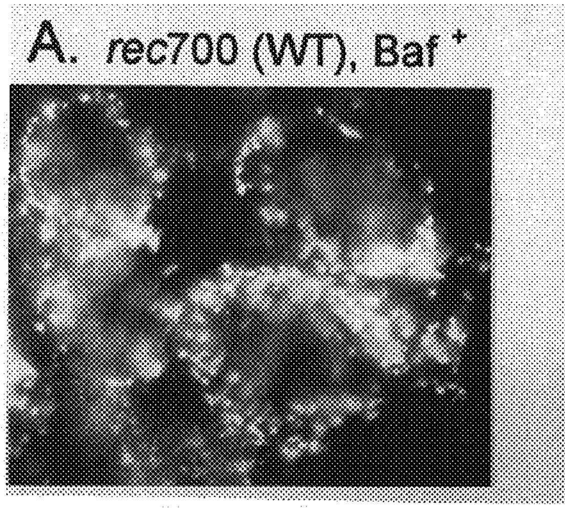
FIGS. 13A–13C show photographs of immunofluorescence labeling of Fas in rec700-infected cells treated (FIG. 13A) or not treated (FIG. 13B) with bafilomycin A1 (Baf), or in dl309 ($RID^-$)-infected cells treated with Baf (FIG. 13C)
Figure 13B:
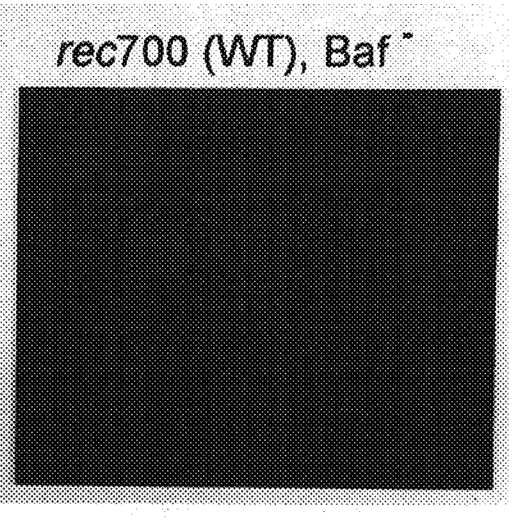
Figure 13C:
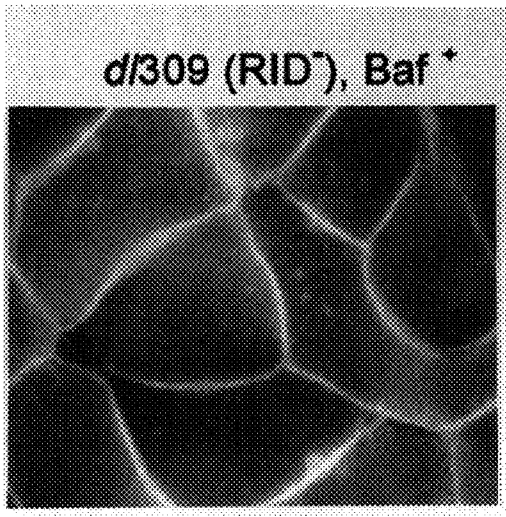
Figure 13D:
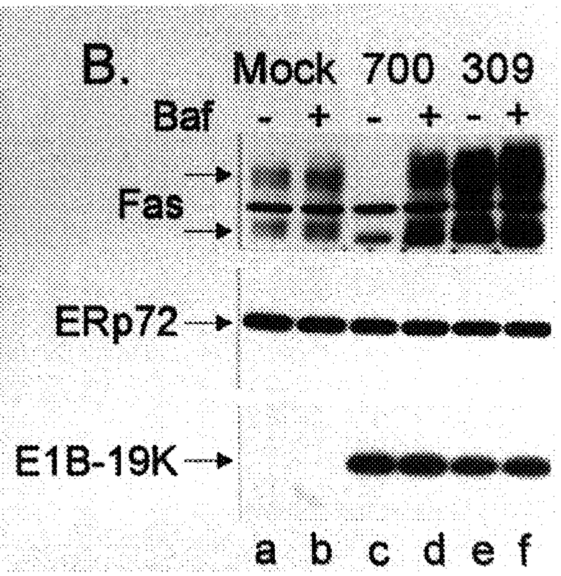
FIG. 13D shows an immunoblot of proteins extracted from mock-, rec700- or dl309-infected cells treated (+) or not treated (–) with bafilomycin A1 (Baf) and stained for Fas, ERp72, or Ad protein E1B-19K.
Figure 13E:
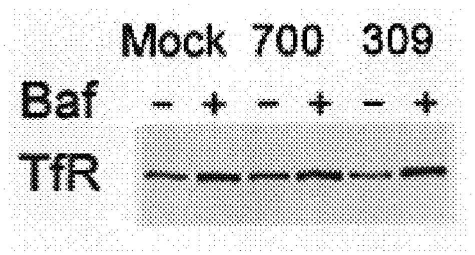
FIG. 13E shows the immunoblot of FIG. 13D following removal of antibody and restaining for transferrin receptor (TfR)

When wild-type Ad-infected cells were treated with Baf, Fas was cleared from the cell surface but it accumulated in vesicles (FIG. 13A) rather than being degraded as in untreated cells (FIG. 13B). Baf did not affect cell surface Fas in cells infected with a mutant lacking RID (dl309)(FIG. 13C). Immunoblot analysis of proteins extracted from these cells indicated that Baf blocked the degradation of Fas in wild-type Ad-infected cells (FIG. 13D). Baf did not affect the abundance of Fas in mock-infected cells or in cells infected with the RID-minus mutant. Neither virus infection nor Baf affected the abundance of Erp72 (FIG. 13D), a cellular protein localized in the endoplasmic reticulum (Mazzarella et al., 1990). Also, neither virus infection nor Baf significantly affected the level of another cellular protein, the transferrin receptor (FIG. 13E). The infections were equivalent as indicated by the E1B-19K levels of the Ad-encoded protein (FIG. 13D). These confocal microscopy and Baf data provide strong evidence that RID causes Fas to be degraded in lysosomes in Ad-infected cells.

EXAMPLE 6

This example illustrates that the RID proteins are sufficient to promote the degradation of Fas.

COS cells were transiently transfected with different combinations of pMT2-RIDα, MT2-RIDβ, pcDNA3-Fas, and pBUC-Shp-1, which expresses a mammalian cell protein named Shp-1. At 36 h post-transfection, cells were treated with cycloheximide (25 μg/ml) for 12 h and at 48 h post-transfection, proteins were extracted and analyzed for Fas, Shp-1, or ERp72 by immunoblot using rabbit antisera to Fas (Santa Cruz), Erp72 (Mazzarella et al., 1990), or Shp-1 (Plas et al., 1996) (Tollefson et al., Nature 392:726–730 (1998)). The results are shown in FIG. 14.

Figure 14:
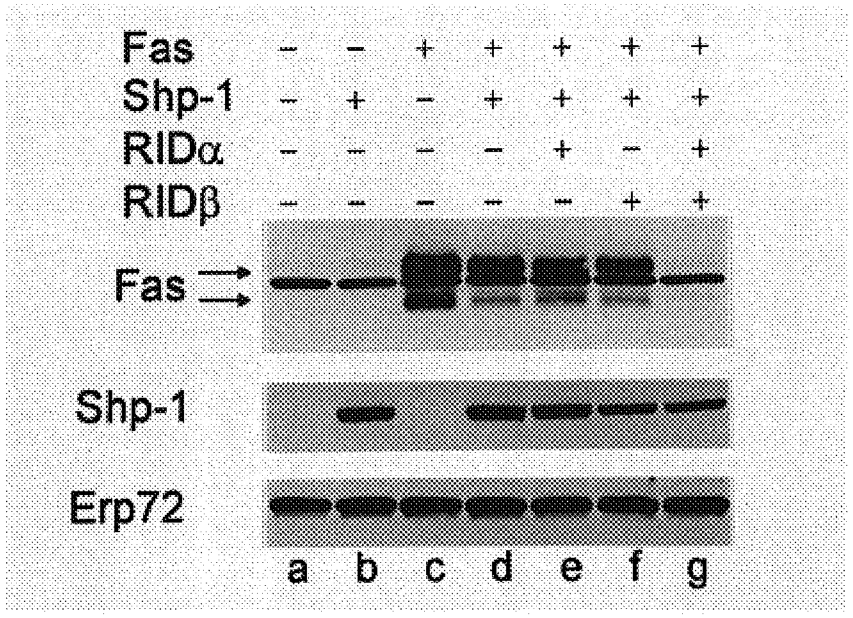
FIG. 14 shows an immunoblot of proteins extracted from COS7 cells transfected with various combinations of plasmids expressing Fas, Shp-1, RIDα or RIDβ as indicated by the "–" and "+" signs and stained for Fas, Erp72 or Shp-1 using appropriate antisera, with the arrows indicating two groupings of bands which correspond to differently glycosylated species of Fas.

In cells transfected with pcDNA3-Fas and/or pBUC-Shp-1, expression of Fas and/or Shp-1 proteins was readily detected by immunoblot (FIG. 14, lanes b–d). For Fas, two groupings of bands were detected (indicated by the arrows), which represent differentially glycosylated species of Fas. The anti-Fas antibody also reacted with an unknown cellular protein that migrated between the two sets of Fas protein bands. When pMT2-RIDα or pMT2-RIDβ were co-transfected with pcDNA3-Fas and pBUC-Shp-1, there was a marginal decrease in Fas and Shp-1 (FIG. 14, lanes e and f). However, when both pMT2-RIDα and pMT2-RIDβ were co-transfected with pcDNA3-Fas and pBUC-Shp-1, the Fas bands were reduced to nearly undeiectable levels, whereas the Shp-1 band was only marginally decreased (FIG. 14, lane g). The levels of the endogenous cellular protein, Erp72, were equivalent in all of the transfected cells. These results indicate that the RID complex (i.e. RIDα plus RIDβ), but not RIDα or RIDβ alone, is sufficient to induce degradation of Fas.

Figure 15:
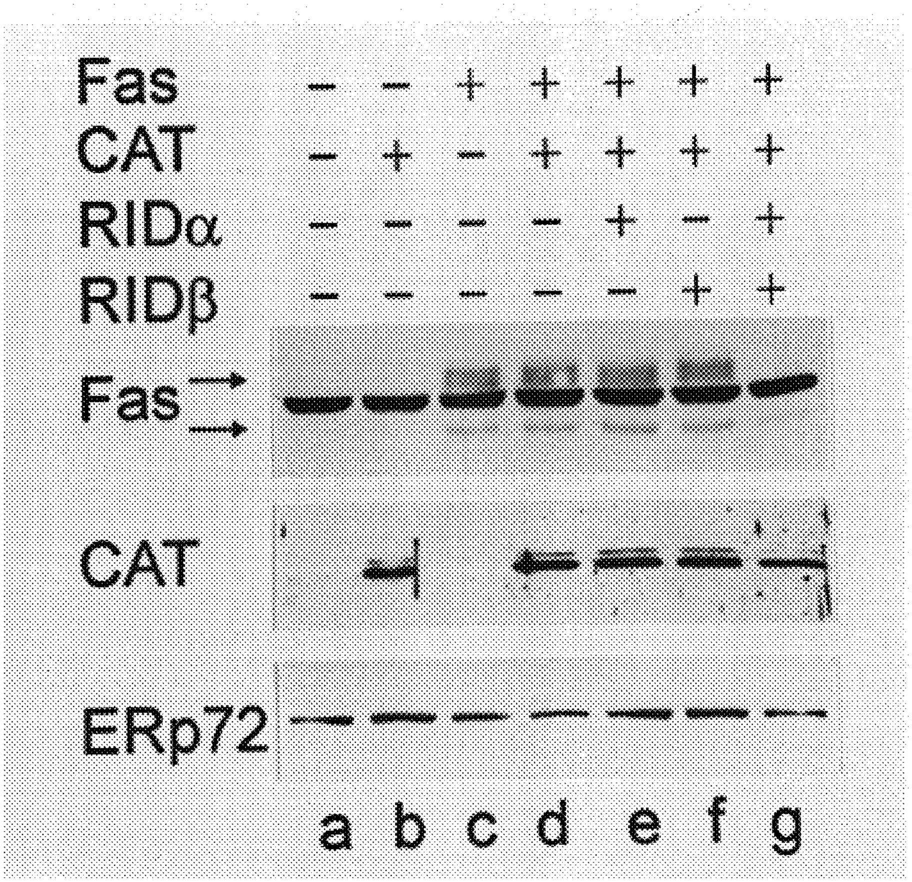
FIG. 15 shows an immunoblot of proteins extracted from COS7 cells transfected with various combinations of plasmids expressing Fas, chloramphenical acetyl-transferase (CAT), RIDα or RIDβ as indicated by the "–" and "+" signs and stained for Fas, Erp72 or CAT using appropriate antisera, with the arrows indicating two groupings of bands which correspond to differently glycosylated species of Fas.

A similar experiment was conducted except that cells were transfected with the pcDNA3.1-CAT (InVitrogen, Carlsbad, Calif.) plasmid expressing chloramphenicol acetyl transferase (CAT) instead of pBUC-Shp-1. Since CAT is a bacterial protein, it is not possible for RID to have evolved in Ad to exert a specific biological effect on CAT. Expression of this protein was detected by immunoblot using anti-CAT antiserum obtained from 5 prime-3 prime. The results of the experiment were similar to those with Shp-1, i.e. Fas was greatly reduced in the presence of RID, whereas CAT was only marginally affected (FIG. 15).

These experiments demonstrate that the RID complex is sufficient to induce the internalization of cell-surface Fas into vesicles, presumably endosomes and lysosomes, to induce degradation of Fas, presumably in lysosomes, and to inhibit apoptosis triggered by an anti-Fas agonist monoclonal antibody.

EXAMPLE 7

This example illustrates that RID inhibits killing of Ad-infected cells by natural killer cells and cytotoxic lymphocytes.

Natural killer (NK) cells and cytotoxic T-lymphocytes (CTL) play an important role in the destruction of vinis-infected cells during the early innate phase and the late immune-specific stages, respectively, of the host anti-viral response. Both NK and CTL kill targets via two major pathways. In one major pathway, perforin generates holes in the target and granzymes are introduced to induce apoptosis of the target cell. In another major pathway, Fas ligand on the surface of the CTL engages Fas on the target cell and induces apoptosis through activation of the pro-apoptotic caspases. CTL can also kill cells through a third minor pathway, in which TNF expressed on the surface of CTL (or secreted by CTL) engages TNFR1 on targets and induces apoptosis via the caspases. In cell culture, TNF-mediated killing by CTL is observable in long terrn (>24 h) killing assays. To investigate whether RID inhibits NK- and CTL-lcilling through Fas, the following experiments were conducted.

Figure 16A:
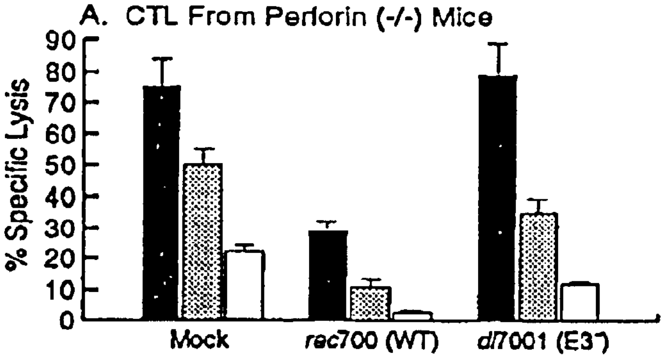
FIGS. 16A and 16B are graphs of the amount of lysis of mock-, rec700- or dl7001-infected Fas-positive mouse P815 cells by activated cytotoxic lymphocyetes (CTL) from perforin (–/–) mice (FIG. 16A) or matched perforin (+/+) mice (FIG. 16B) at effector lymphocyte:target ratios of 60:1 (black bars), 20:1 (stippled bars), or 6:1 (open bars)
Figure 16B:
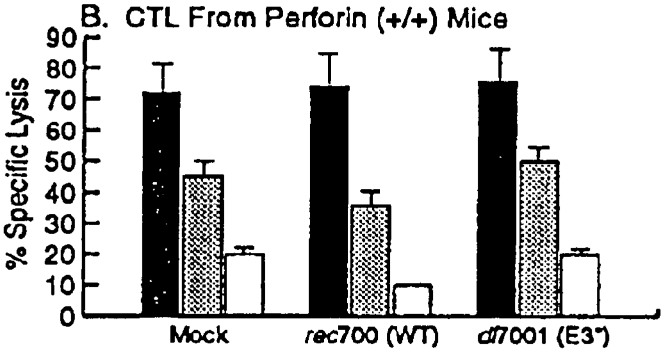
Figure 16C:
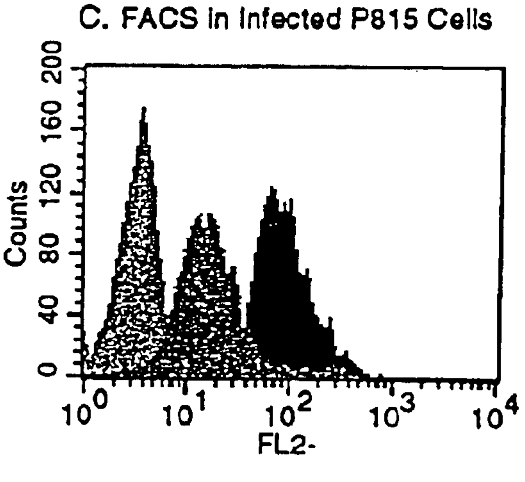
FIG. 16C shows flow cytometry tracings of P815 cells infected with rec700 (middle plot) or dl7000 (right dark plot) and then stained for Fas, with the left plot showing the IgG control.

In the first experiment, which was described in the copending provisional application, the effect of Ad proteins on CTL-killing was assessed by performing a short-term CD3-dependent redirected cell assay (Azuma et al., *J. Exp. Med.* 175:353–360, 1992), using lymphocytes from perforin (−/−) mice (Kagi et al., *Science* 265:528–530, 1994) and from wild-type perform (+/+) C57BL/6J mice acutely infected with influenza virus. Influenza virus enhances the expression of Fas ligand in activated lymphocytes (Clark et al., *Immunol. Rev.* 146:33–44, 1995). In brief, mice were primed by intranasal infection of 50 HAU of HkX31 influenza A virus (Topham et al., *J. Virol.* 70:1288–1291, 1996; Tripp et al., *J. Immunol.* 154:6013–6021, 1995). CTL were isolated from the spleens of the infected mice, irradiated, and effector CTL generated by secondary in vitro re-stimulation. These CTL were further activated by incubation with the 145-2C11 anti-CD3ε mAb for 30 min on ice. Mouse Fas and Fc receptor-positive P815 cells ($1\times10^6$) were mock-infected or infected with 1000 PFU per cell of rec700 or dl7001 and labeled overnight with 100 μCi of $Na_2{}^{51}CrO_4$. These $^{51}Cr$-labeled P815 target cells were washed, resuspended in DME, and then incubated with the activated anti-CD3ε-trealted CTL using effector lymphocyte:target ratios of 60:1, 20:1 or 6:1. Cell lysis was determined 6 h later from a standard $^{51}Cr$ release assay and the results are shown in FIGS. 16A and 16B. The presence of Fas on the surface of P815 cells infected with rec700 or dl7000 was also examined by flow cytometry and the results are shown in FIG. 16C.

The perforin (−/−) CTL lysed mock-infected P815 cells efficiently (FIG. 16A). Lysis was inhibited by rec700 but not by dl7001 (lacks all E3 genes). Since the mice lack perforin, it follows that the CTL were killing the mock- and mutant-infected cells through the Fas pathway and that the E3 region is required to inhibit killing through this pathway. The CTL from perforin (+/+) mice killed mock-, rec700-, or dl700 1-infected P815 cells with similar high efficiency (FIG. 16B). Cell surface Fas was diminished on P815 cells infected with rec700 but not with dl700 (lacks all E3 genes except for E3-14.7K) (FIG. 16C). These results indicate that E3 proteins expressed by rec700 but not dl7000, presumably RID, inhibit CTL killing through the Fas pathway by down-regulating Fas from the cell surface.

A second experiment was conducted to investigate the role of RID in inhibiting killing of Ad-infected cells by NK cells. Human A549 cells were mock-infected or infected with rec700 (wild-type Ad) or dl764, a virus mutant that lacks only RIDβ and then labeled with 100 μCi of $Na_2{}^{51}CrO_4$. These $^{51}Cr$-labeled A549 target cells were washed, resuspended in DME, and then incubated with a semi-permanent line of human NK cells. After 24 h, cell lysis was measured based on release of $^{51}Cr$ from the cells as described elsewhere (Tollefson et al., Nature 392:726–730 (1998)) and the results are shown in FIG. 17.

Figure 17:
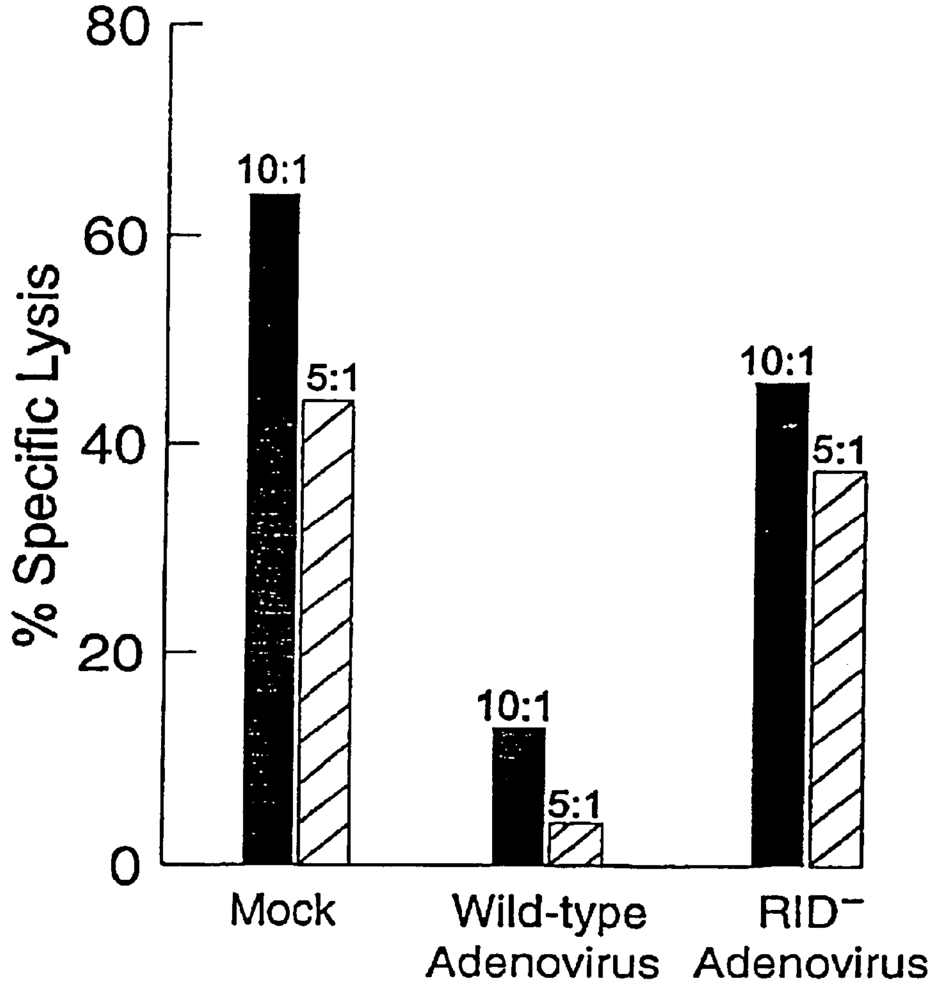
FIG. 17 is a graph of the amount of lysis of mock- or Ad-infected Fas-positive human A549 cells by natural killer (NK) cells at NK:A549 cell ratios of 10:1(black bar) and 5:1 (striped bar)

Mock-infected cells were lysed efficiently at NK:A549 cell ratios of 10:1 and 5:1 (FIG. 17). This lysis was dramatically inhibited by infection with rec700, but it was only marginally reduced by infection with dl764 (FIG. 17). Since the only protein not expressed by dl764 is RIDβ, it is believed that RID is required to inhibit killing of Ad-infected cells by NK cells. Most likely RID inhibits killing by NK cells by blocking the Fas pathway. However, a RID effect on the perforin-granzyme pathway cannot be excluded.

In summary, RID inhibits killing of Ad-infected cells by NK cells and by CTL. Thus, RID should protect infected cells from attack by killer cells that are active in both the early innate phase and the late immune-specific phase of the anti-viral immune response. Similarly, transplanted cells and tissues are destroyed by NK cells and CTL. Therefore, RID should be useful to inhibit killing of transplanted cells or tissues by NK cells and CTL.

EXAMPLE 8

This example illustrates that RID is required and probably sufficient to remove the TNFR1 from the cell surface.

Figure 18:
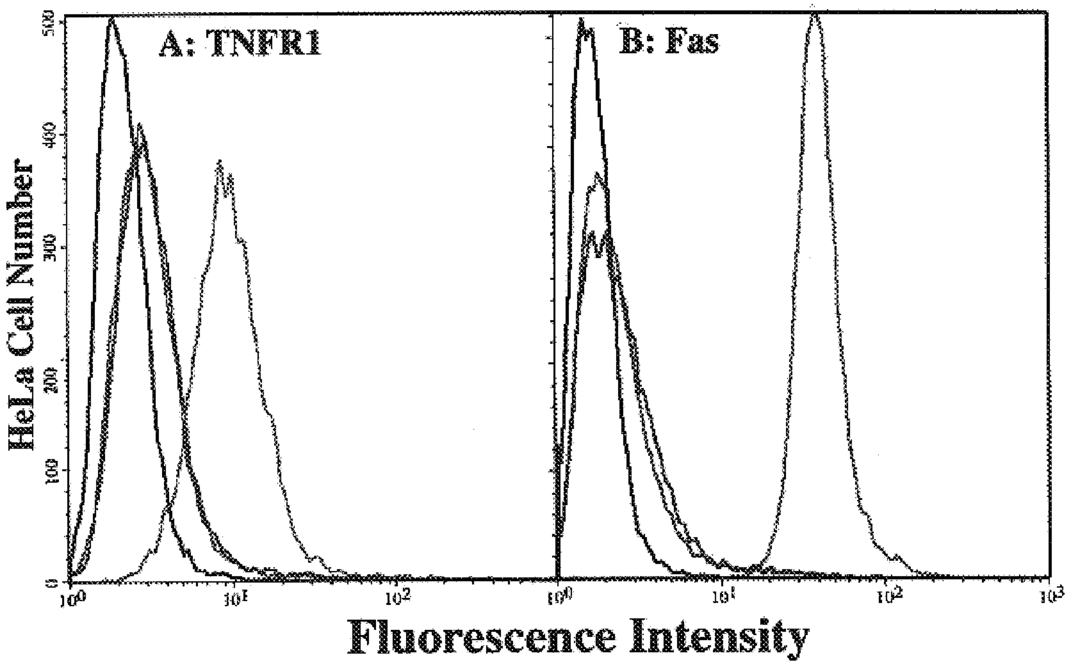
FIG. 18 shows flow cytometry tracings of human HeLa cells mock-infected (green trace) or infected with rec700 (red trace) or dl712, a mutant that overexpresses RID and E3-14.7K (blue trace) and then stained for TNFR1 (FIG. 18A) or Fas (FIG. 18B), with the percentage of cells that stained positive for TNFR1 or Fas indicated at the bottom.

Human HeLa cells were mock-infected or infected with 50 PFU/cell of rec700 (wild-type) or dl712, which is a rec700-derived mutant with a deletion in the adp gene in the E3 region that results in overexpression of both RID (i.e. RIDα and RIDβ) and E3-14.7K, and only trace amounts of other E3 proteins (Tollefson et al., *J. Virol.* 64,794–801, 1990; Tollefson et al., *Virol.* 175:19–29, 190; Gooding et al., *Cell* 53:341–346, 1988). At 26 h p.i., cells were analyzed by flow cytometry (Tollefson et al., Nature 392:726–730 (1998)) using the B/O:Feb. 18, 1991 rabbit antiserum against TNFR1 (obtained from Immunex Corp.) and PE-conjugated goat anti-rabbit IgG (Caltag). Fas was detected in the same experiment using supernatants from the M38 anti-Fas hybridoma cell line (obtained from the American Type Culture Collection) and FITC-conjugated goat anti-mouse IgG. The results are shown in FIG. 18.

As shown in FIG. 18A, TNFR1 was removed from the surface of most cells infected with rec700 (red trace) or dl712 (blue trace). The percentage of mock-infected cells that were stained for TNTR1 was 93%, as compared to 16% and 18%, respectively, for rec700 and dl712. In this same experiment, cell surface Fas was also internalized by rec700 and dl712 (FIG. 18B). Thus, Ad infection removes TNFR1 from the cell surface, as is the case with Fas.

Figure 19:
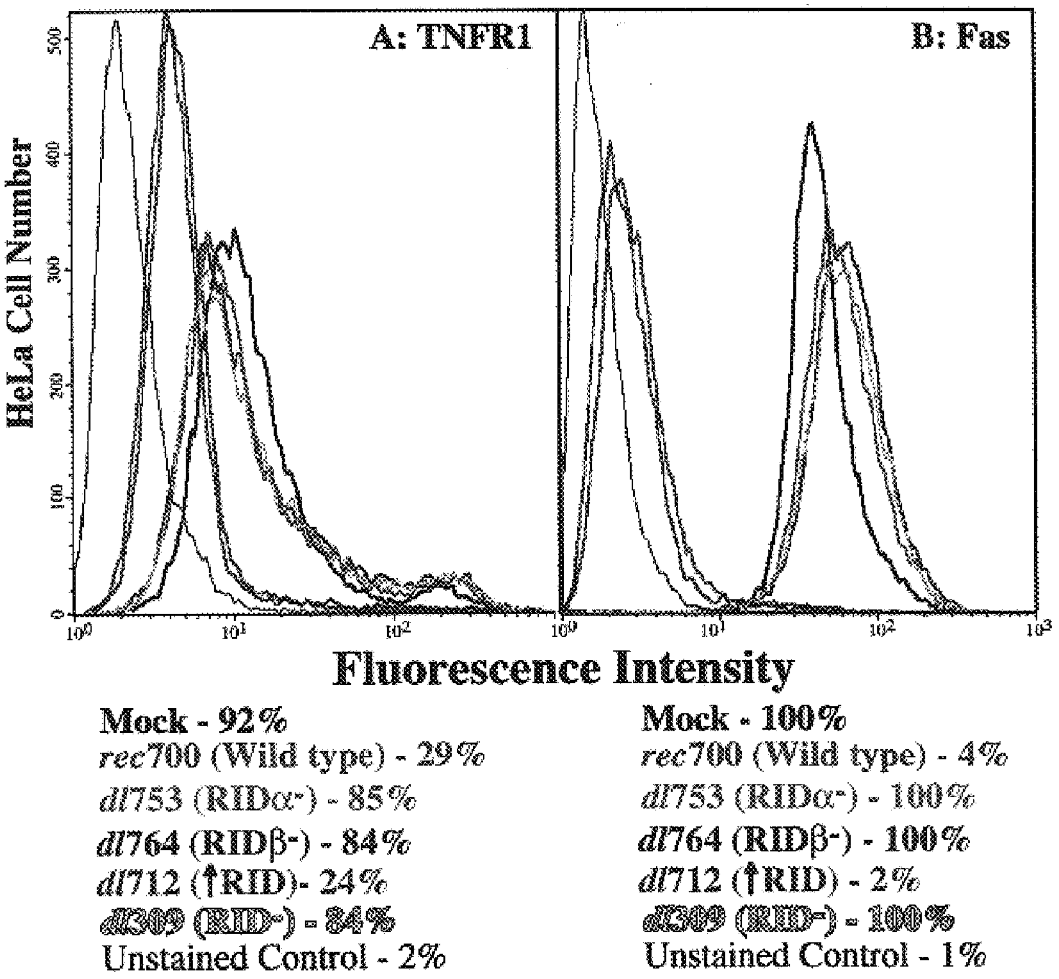
FIG. 19 shows flow cytometry tracings of human HeLa cells mock-infected (black trace) or infected with rec700 (red trace), dl753 (light blue trace), dl764 (dark blue trace), dl712 (green trace), dl309 (pink trace) and then stained for TNFR1 (FIG. 19A) or Fas (FIG. 19B), with the genotype of each virus and the percentage of cells that stained positive for TNFR1 or Fas indicated at the bottom.

The mutant used in the above experiment, dl712, overexpresses RID and E3-14.7K, and expresses very little of the other E3 proteins. To determine whether RID and/or E314.K is involved in internalization of TNFR1 in Ad-infected HeLa cells, the same experiment was performed using dl712 and additional E3 mutants: dl309, which lacks RIDα, RIDβ, and E3-14.7K; dl753, which lacks RIDα but expresses RIDβ and E3-14.7K; and d1764, which lacks RIDβ but expresses RIDα and E3-14.7K. The deletions in these mutants do not affect expression of any other Ad proteins. The results are shown in FIG. 19.

With rec700 and d1712, TNFR1 was removed from the cell surface such that only 29% and 24%, respectively, of cells were stained for TNFRI as compared to 92% with mock-infected cells (FIG. 19A). With dl309, dl753, and dl764 infected cells, 84%, 85%, and 84%, respectively, were stained for TNFR1, indicating that these mutants did not induce removal of TNFR1 from the cell surface. Cell surface Fas was also examined in this same experiment. rec700 and dl712 cleared Fas whereas dl309, dl753, and dl764 did not (FIG. 19B). Thus, RID is required to remove TNFR1 from the surface of Ad-infected cells, as is the case with Fas.

As a means to determine whether RID is sufficient to remove TNFR1 from the cell surface, HeLa cells were infected with the Ad vector named 231-10. This vector will be described in detail in Example 10 below. In brief, 231-10 lacks the E1A, E1B, and E3 transcription units. The deleted E1A plus E1B regions are replaced with an expression cassette wherein all the E3 proteins are expressed from the human cytomegalovirus (CMV) promoter. Because 231-10 lacks E1A, viral genes in the vector backbone are not expressed; only the E3 proteins are expressed from the CMV promoter. Thus, the vector serves as an essentially inert vehicle by which E3 genes can be delivered into cells and the properties of their proteins studied.

Figure 20:
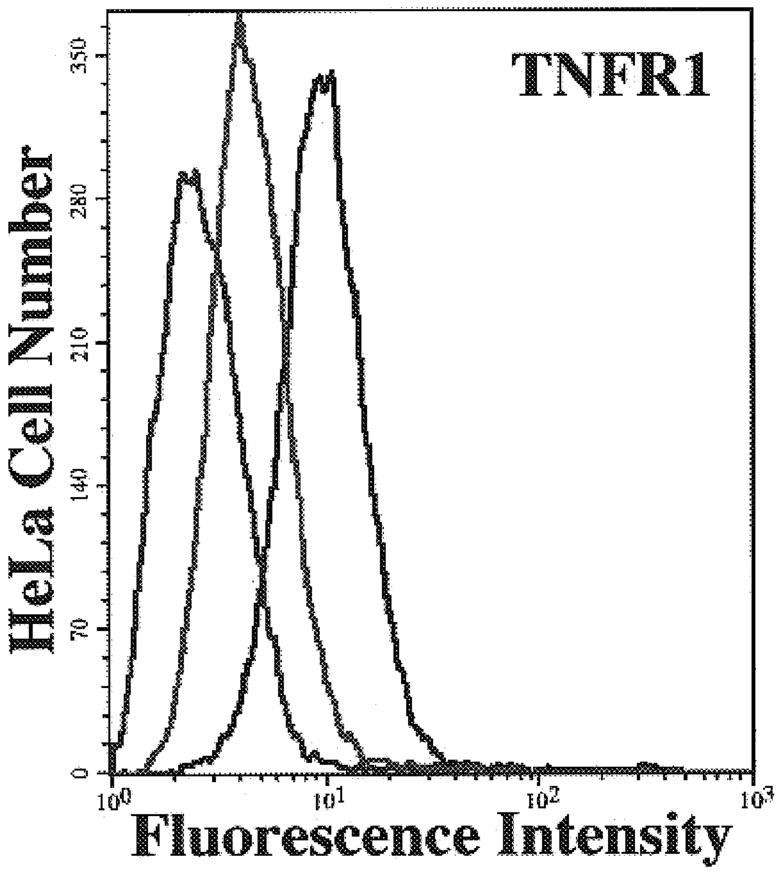
FIG. 20 shows flow cytometry tracings of human HeLa cells mock-infected (black trace) or infected with the 231-10 vector, which expresses only the E3 proteins, and then stained for TNFR1 at 24 hr. p.i. (red trace) or 48 hr. p.i. (blue trace)

HeLa cells were mock-infected or infected with the 231-10 vector, and cell surface TNFR1 was examined by flow cytometry at 24 h and 48 h p.i. as described above. At 24 h p.i., the percentage of cells bearing TNFR1 was reduced from 93% to 35%, and by 48 h the percentage was reduced to 11% (FIG. 20). This time course of TNFRI down-regulation correlates with expression of the E3 proteins. In a parallel experiment, Fas was nearly completely cleared by 24, 36, and 48 h p.i. (data not shown). Thus, TNFR1 and Fas are removed from the cell surface by the E3 proteins expressed by 231-10. RID is undoubtedly the E3 protein responsible for the removal of these death receptors.

The ability of Ad and the RID protein to remove TNFR1 from the cell surface was examined using the biotin-streptavidin system (Stewart et al., 1995) to detect TNFR1. Multiple dishes of A54, cells were mock-infected or infected with 50 PFU/cell of rec700 (wild-type). At 16 h p.i., cell surface proteins in mock- and Ad-infected cells were labeled using biotin. Ad-infected cells in other dishes were also labeled with biotin at 18, 20, 22, 24, and 30 h p.i. Proteins were extracted using buffer containing 0.5% NP-40, and were incubated with protein At-Sepharose CL-4B attached to the B/O:Feb. 18, 1991 rabbit antiserum against TNFR1. After washing, proteins were solubilized, subjected to SDS-PAGE, and transferred to membranes. Membranes were incubated with peroxidase-conjugated streptavidin (Sigma), and proteins were visualized using ECL (Amersham).

Figure 21:
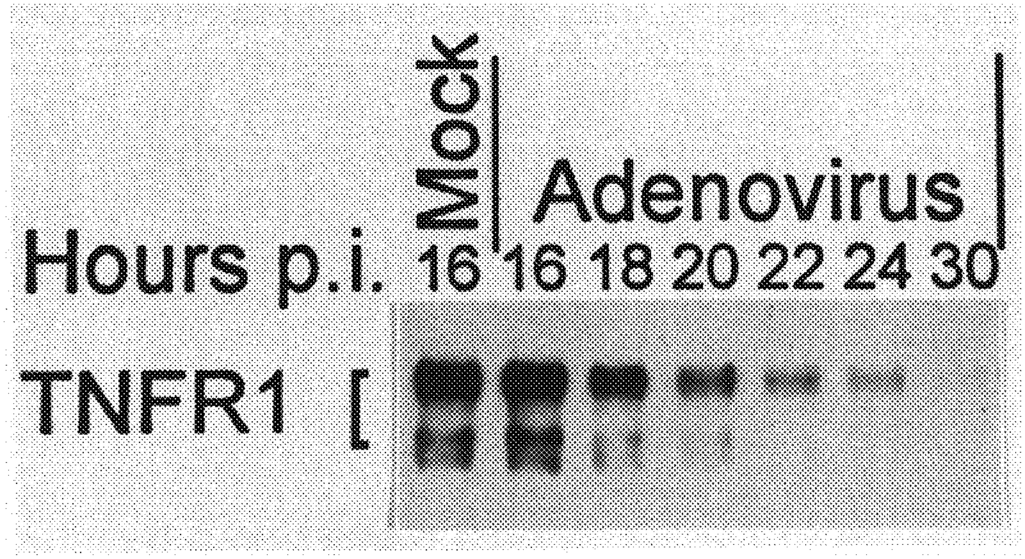
FIG. 21 shows an immunoblot of TNFR1 extracted from A549 cells mock-infected or infected with rec700 in which cell surface proteins were labeled by incubation with biotin at the indicated hour p.i.

In this assay, if Ad infection has resulted in the removal of TNFR1 from the cell surface, then TNFR1 will not be available for biotinylation and therefore TNFR1will not be detected. As shown in FIG. 21, similar amounts of TNFR1 were obtained from mock- or rec700-infected cells at 16 h p.i. With rec700, TNFR1 declined from 18 to 30 h p.i. until only small amounts were detected. Thus, as was the case when TNFR1 was detected by flow cytometry, Ad infection results in markedly decreased amounts of cell surface TNFR1.

Figure 22:
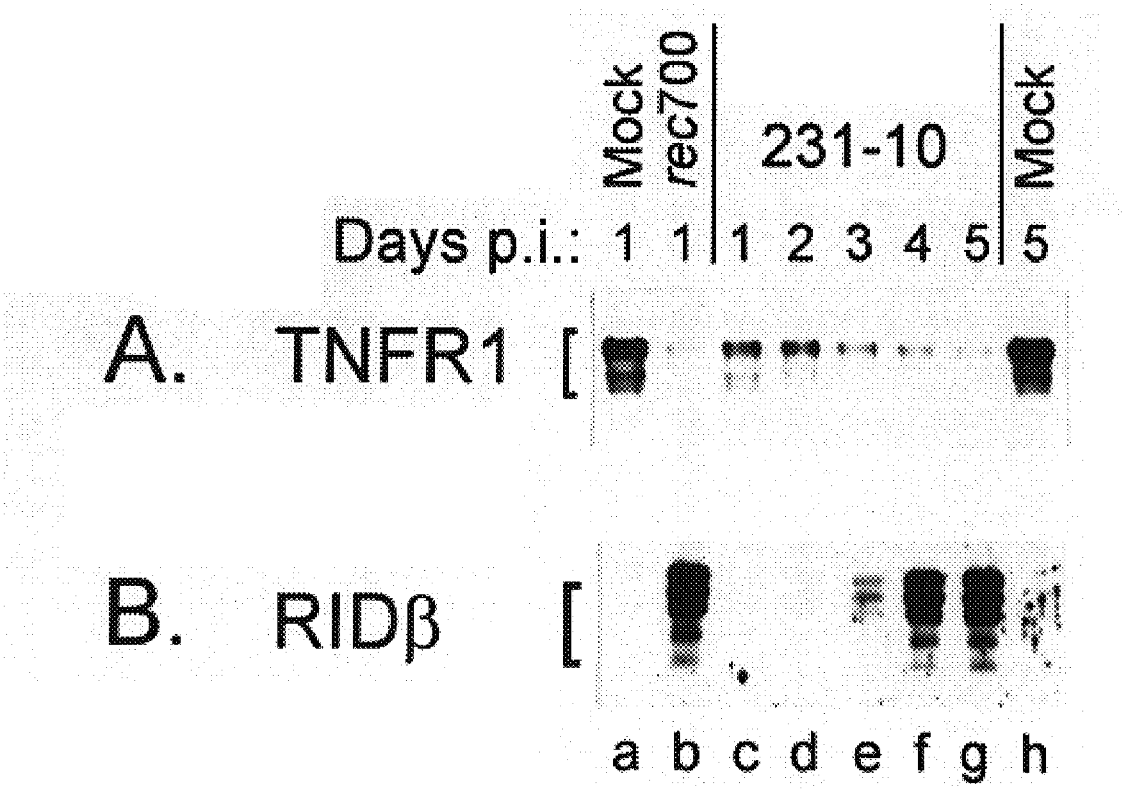
FIG. 22 shows an immunoblot of TNFR1 (FIG. 22A) and RIDβ (FIG. 22B) extracted from A549 cells mock-infected or infected with rec700 or the 231-10 vector in which cell surface proteins were labeled by incubation with biotin at the indicated hour p.i.

The ability of the 231-10 Ad vector to down-regulate cell surface TNFR1 as determined with the biotin-streptavidin assay was also examined. As discussed above, 231-10 expresses only Ad E3 proteins. Cells were mock-infected, infected with 50 PFU/cell of rec700 (wild-type), or infected with 250 PFU/cell of 231-10. At different days p.i., cells were biotinylated and TNFR1 detected as described above. As expected, most of the TNFR1 was cleared by rec700 at 1 day p.i. (FIG. 22A, compare lanes a and b). With 231-10, reduced amounts of TNFR1 were detected by 1 day p.i., and by 5 days p.i. the TNFR1 levels declined to those of rec700. The levels of TNFR1 in mock-infected cells were similar after 5 days to those after 1 day (FIG. 22A, compare lane h with lane a). Therefore, the reduction at 5 days seen with 231-10 is not due to a non-viral event associated with maintaining the cells in dishes for 5 days. These results indicate that the E3 proteins expressed by the 231-10 vector, presumably RID, are sufficient to clear TNFR1 from the cell surface.

The accumulation of RIDβ in these same cell extracts was also examined by standard immunoblot using the rabbit P118–132 antiserum (Stewart et al., 1995). With rec700, RIDβ was abundant after 1 day (FIG. 22B, lane b). The multiple bands on RIDβ are species of RIDβ that are differentially O-glycosylated and phosphorylated. With 231-10, RIDβ was detected after 2 days, and it increased dramatically in abundance from days 3–5 (FIG. 22B, lanes c–g). Therefore, as expected, the accumulation of RIDβ in this experiment correlated inversely with the decline in cell-surface TNFR1.

These results obtained using the B/O:Feb. 18, 1991 antibody in the biotin-streptavidin and flow cytometry assays to detect TNFR1 are consistent. Thus, it is believed that RID is necessary to efficiently down-regulate cell surface TNFR1 in Ad-infected cells. The results with 231-10 indicate that RID is sufficient to down-regulate TNFR1, with the caveat that the E3 14.7K and gp9K proteins, and possibly the E3 12.5K and 6.7K proteins, are expressed by 231-10.

To determine if RID is responsible for clearance of cell-surface TNFR1, the following Ad E3 mutants were used: dl748, which overexpresses RIDβ but lacks RIDα; and dl798, which overexpresses RIDα but lacks RIDβ. A549 cells were mock-infected or infected with 50 PFU/cell of rec700, dl748, or dl798, or infected with 25 PFU/cell each of dl748 and dl798. At 26 h p.i. cells were biotinylated and TNFR1 examined as described above. As a positive control, a dish of mock-infected cells was treated with TNF, and the cell extract was examined for TNFR1. As expected, TNF removed most of the TNFR1 from the cell surface (FIG. 23A, lanes a and b).

Figure 23:
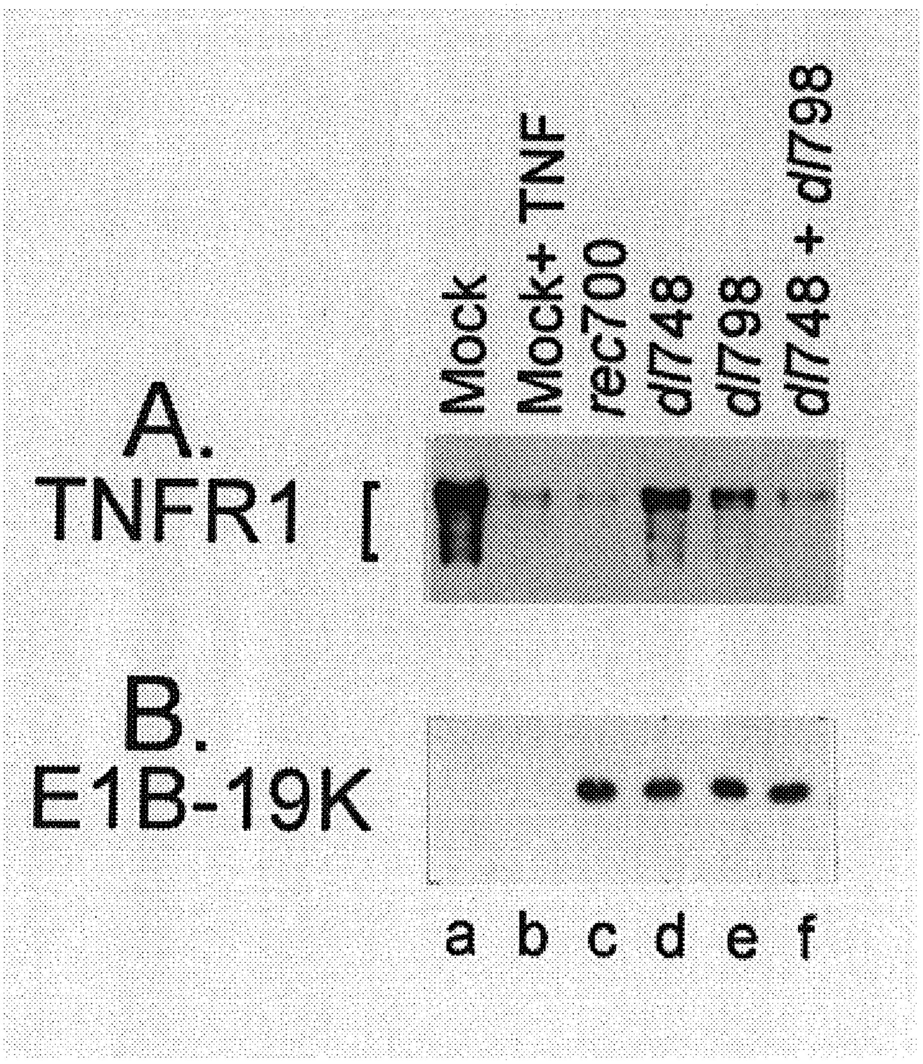
FIG. 23A shows an immunoblot of TNFR1 extracted from A549 cells mock-infected or infected with the indicated virus in which cell surface proteins were labeled by incubation with biotin at 26 h p.i.
FIG. 23B shows an immunoblot of Ad E1B-19K protein extracted from the same cells used in FIG. 23A.

The results with the viruses are shown in FIG. 23A, lanes c–f. With rec700 (wild-type)-infected cells, only small amounts of TNFR1 were detected (lane c). With dl748 (RIDα–, RIDβ$^+$) and dl798 (RIDα$^+$, RIDβ–), high to intermediate levels of TNFR1 were observed, indicating that RIDα and RIDβ are required for efficient clearance of TNFR1. When cells were co-infected with dl748 and dl798, TNFR1 was reduced to levels comparable to rec700-infected cells (lanes f and c). This result indicates that the mutants complement (dl748 provides RIDβ, dl798 provides RIDα), and that both RIDα and RIDβ are required for efficient removal of TNFR1 from the cell surface. FIG. 23B shows a standard immunoblot for E1B-19K from the same extracts that were analyzed for biotinylated TNFR1. Similar amounts of E1B-19K were detected with all viruses. Therefore, differences in TNFR1 levels seen with these viruses are not due to differences in infection efficiency by the viruses.

The partial clearance of TNFR1 observed with these RIDα$^-$ and RIDβ$^-$ mutants is consistent with the flow cytometry data in FIG. 19. These results suggest that there may be a mechanism in addition to RID that down-regulates cell-surface TNFR1 in Ad-infected cells. However, clearly, most of the down-regulation of TNFR1 requires RID.

In summary, RID is required to remove TNFR1 from the surface of Ad-infected cells. RID is also sufficient for removal of TNFR1 as indicated by the experiment with the 231-10 vector, with the caveat that the 231-10 vector also expresses other E3 proteins. RID expressed by the 231-10 vector is also sufficient to remove Fas from the cell surface, again, with the same caveat. However, the down-regulation of TNFR1 and Fas by 231-10 is almost certainly due to RID, because the mutant mapping data with E3 mutants have provided no indication that other E3 proteins play any role in down-regulating these death receptors.

EXAMPLE 9

This example demonstrates that the 231-10 vector prevents rejection of human cancer cells transplanted into irmmunocompetent mice.

Cells or tissues transplanted into immunocompetent recipients are usually destroyed (rejected) by immune killer cells of the recipient. Rejection begins within 1–2 days, and therefore is mediated by the innate immune system including macrophages and NK cells. Specific CTL formed after about 5–7 days also play a major role in transplant rejection. As discussed above in Example 7, RID inhibits NK- and CTL-killing of Ad-infected cells and thus should also be able to inhibit NK- and CTL-mediated rejection of transplanted cells or tissues.

This idea was tested by determining whether the E3 proteins expressed by the 231-10 vector will permit human cancer A549 cells to grow as a tumor in immunocompetent C57BL/6 (H-$2^b$) mice. Human cancer cells normally will be rejected when transplanted in C57BL/6 mice. However, RID should inhibit rejection by removing Fas and TNFR1 from the transplanted cells. E3-14.7K may also prevent rejection.

Figure 24:
FIG. 24 shows a photograph of exposed skin and muscle of the hind flanks of a female C57B1/6 mouse sacrificed 18 days after the flanks were subcutaneously injected with human cancer A549 cells infected with the 231-10 vector, with A549 tumors appearing as whitish-tan masses on each flank.
Figure 25:
FIG. 25 shows a closer view of the tumor on the right flank of the mouse in FIG. 24.

A549 cells mock-infected or infected with 50 PFU/cell of 231-10. After 48 h, $2\times10^6$ cells (in 100 μl) were injected subcutaneously into each hind limb flank of female C57BL/6 mice. At 18 days post-injection, the mice were sacrificed and the site of injection was examined following removal of the skin. With mice that received mock-infected cells, there was a pin-point mass on one flank, and no mass at all on the other flank (data not shown). With the 231-10-infected cells, there were significant tumor masses on both flanks (FIG. 24). The tumors were opaque and ellipsoid in shape. The left-flank tumor was attached to the muscle. The right-flank tumor, which is shown in higher magnification in FIG. 25, was attached to both the muscle and skin. The size of the tumor obtained with 231-10-infected cells was many times larger than what would be observed from the initial bolus of cells injected ($2\times10^6$ cells are barely visible to the naked eye). Thus, the cells grew into a tumor.

In the second experiment, mock-infected and 231-10-infected A549 cells (at 2 days p.i. in culture, 50 PFU/cell) were used, both live cells as well as cells that were killed by freezing and thawing. These cells were injected into each hind limb of C57BL/6 and Balb/c mice, $2\times10^7$ cells per injection. As is the case with C57BL/6, the Balb/c mice are fully immunocompetent. There were four mice of each strain. Mouse I received killed uninfected A549 cells, mouse 2 received live A549 cells, mouse 3 received killed 231-10-infected cells, and mouse 4 received live 231-10-infected cells. Mice were harvested at 15 days following injection. No tumors were observed in either mouse strain with killed cells. With the C57BL/6 mouse that received uninfected live cells, there was no growth on one flank and a very small mass on the other flank. With the Balb/c mouse that received live uninfected cells, there were small flat masses on each flank. However, with both the C57BL/6 and the Balb/c mouse that received 231-10-infected cells, there were much larger elipsoid masses (tumors) on both hind flanks. These tumors resembled the tumors shown in FIGS. 24 and 25. Therefore, as was the case in the first experiment, the 231-10 vector allowed A549 cells to form tumors in immunocompetent mice.

Figure 26:
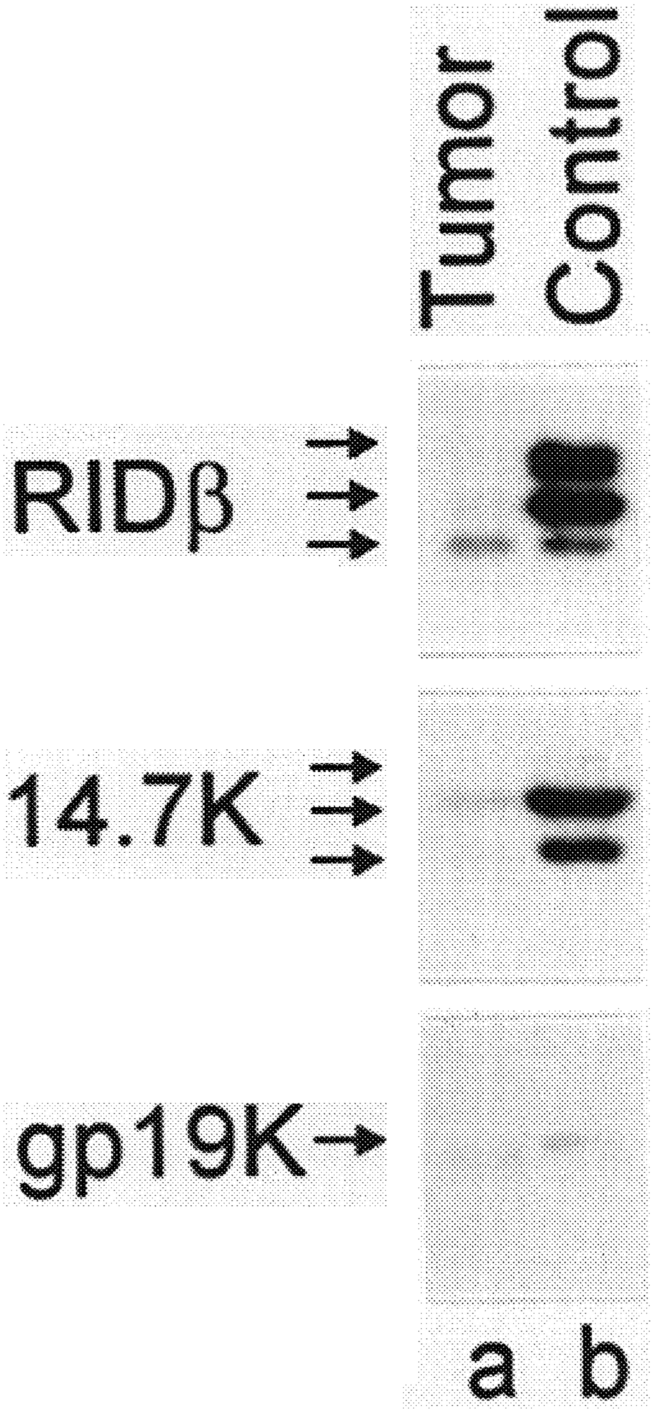
FIG. 26 shows an immunoblot of proteins extracted from an A549 tumor grown in a mouse such as described in FIG. 24.

One of the 231-infected cell tumors from the C57BL/6 mouse was examined for expression of the E3 proteins known to be synthesized in cultured cells by 231-10. Proteins were extracted from the tumor, and the RIDβ, 14.7K, and gp19K proteins assayed by immunoblot. As shown in FIG. 26, all three proteins were detected. This result provides very strong evidence that the cells originally infected with 231-10, at the very minimum, persisted in the mouse. It is very likely that these cells grew as well, considering that tumors were formed. It is not likely that the 231-10 vector replicated in these cells, because the vector lacks the E1A gene. Most likely, as the A549 cells proliferated in the mouse, a portion of the input vector was segregated into the daughter cells.

In summary, the E3 proteins expressed from the 231-10 vector have permitted the growth of human A549 cancer cells to form tumors in C57BL/6 and Balb/c mice. The tumors would not have been able to form unless they were protected from destruction by the immune system. These results argue strongly that the E3 proteins should prevent immune rejection of other types of transplanted cells and tissues. Thus, the 231-10 vector has the potential to be used in tissue or cell transplants to prevent rejection of the tissues or cells.

EXAMPLE 10

This example illustrates the construction and properties of the 231-10 vector.

Features of 231-10

The 231-10 vector is a human adenovirus serotype 5 (Ad5) vector. It can be viewed as a "transient transfection" system, analogous to that obtained when a plasmid expression vector is transfected into cells. The basic features of the 231-10 vector are outlined in the schematic shown in FIG. 27 and the entire DNA sequence of the genome of 231-10 is given in FIG. 28.

Figure 27:
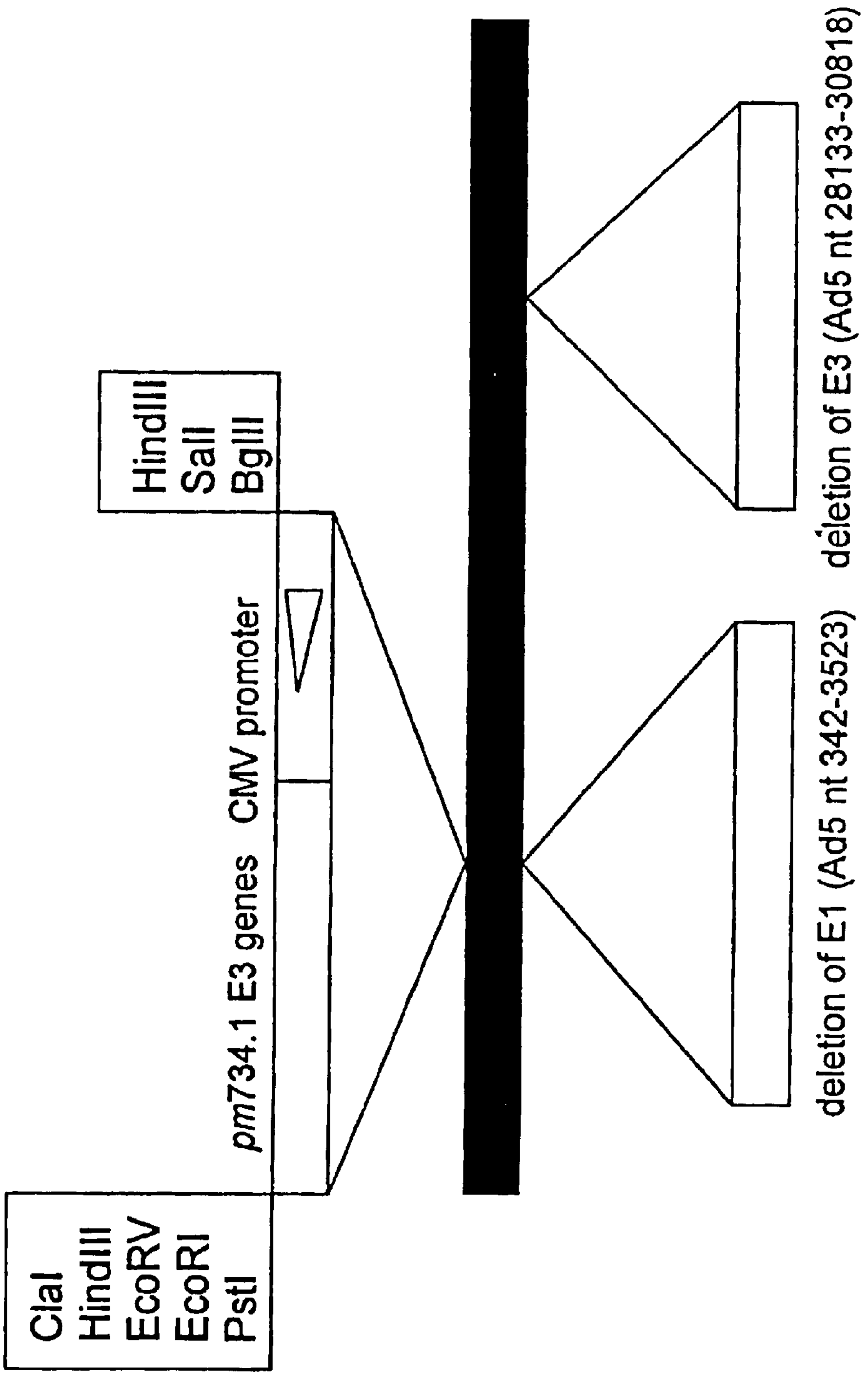
FIG. 27 is a schematic illustration of the structure of the genome of the Ad 231-10 vector, with the black horizontal bar representing the backbone of the AdS genome, from which the E1 and E3 regions are deleted, as indicated by the triangles below the black bar, and containing an expression cassette with the CMV promoter controlling the E3 genes inserted into the deleted E1 region, as indicated by the triangle to the left, above the black bar, with the transcription unit oriented from right to left as indicated by the arrowhead and restriction endonuclease cleavage sites flanking the CMV-E3 cassette indicated.
Figure 28T:
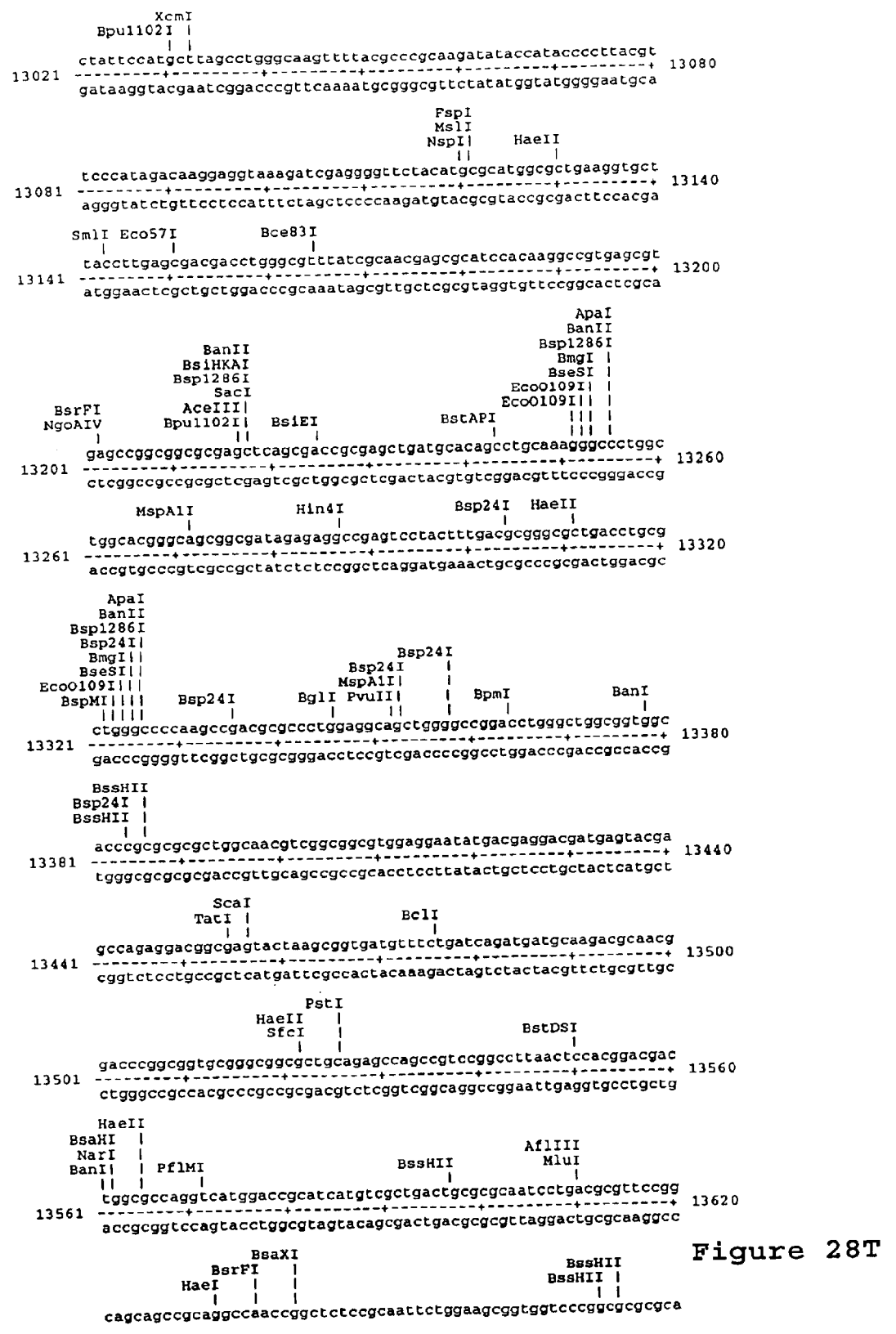

The horizontal bar in FIG. 27 depicts the linear double-stranded DNA genome. The base pairs (nucleotides) are numbered from 1 to 34427 (see FIG. 28), from left to right in FIG. 27. Nucleotides 342–3523 are deleted, removing all the genes in the Ad E1A and E1B transcription units (collectively known as E1). Nucleotides 28133–30818 are also deleted, removing all the genes in the E3 transcription unit. In place of E1, an expression cassette has been inserted, in which the E3 genes are expressed from the human cytomegalovirus immediate early promoter-enhancer (CMV). This E3 expression cassette contains the E3 genes from the virus named pm734.1, which is a derivative of the virus named rec700 (Tollefson et al., *Virol.* 220:152–162, 1996). rec700 is an Ad5-Ad2-Ad recombinant that has the Ad2 version of the E3 genes for the 12.5K, 6.7K, gp19K, and RIDα proteins, and the Ad5 version of the E3 genes for the RIDβ and 14.7K proteins. The E3 cassette in 231-10 contains all the E3 genes from pin734.1. Notably, there are two missense mutations in the adp gene (which encodes the Adenovirus Death Protein [ADP], previously named E3-11.6K) (Tollefson et al., supra). These two mutations eliminate the first two methionine codons in the adp gene, thereby precluding synthesis of functional ADP (Tollefson et al., supra).

The 231-10 vector was designed to have the following properties. First, since the E1A genes are lacking, the vector should not replicate (efficiently) on most cell lines. Therefore, Ad early and late proteins will not be expressed and Ad DNA will not replicate. (It is known that Ad mutants lacking E1A do replicate their DNA and express late proteins at low levels when high multiplicities of infection are used and the infection is allowed to proceed for several days. This is also true for 231-10 [not shown].) Second, the E3 proteins should be expressed in an E1A-independent manner from the CMV promoter/enhancer. Thus, 231-10 is an essentially inert vehicle that can deliver the Ad E3 proteins into cells without having other Ad proteins expressed, at least for the first approximately 3 days following infection. Even after 3 days, other Ad proteins should be expressed only in very small amounts, much less than the E3 proteins.

Construction of Ad 231-10

(a) The genes of the E3 transcription unit were excised from pm734. 1 (pm734.1 is rec700 with mutations of the Met1 and Met41 codons in the adp gene. rec700 is the same as Ad5 but with the Ad2 EcoRI-D fragment substituted for the corresponding AdS EcoRI-C fragment). The pm734.1 SrfI-NdeI-D fragment (3560 bp) was blunt-end using the Klenow enzyme and cloned into the SmaI site of the pBluescriptSK(+) vector (Stratagene), resulting in plasmid p1721 which has the whole E3 transcription unit of pm734.1 (−39 to 3521) flanked by SalI-BstXI-SacII-NotI-XbaI-SpeI-BamHI sites situated upstream from the E3 sequences and PstI-EcoRI-EcoRV-HindIII-ClaI-SalI-XhoI sites situated downstream from the E3 sequences.

(b) The BamHI-SalI-A fragment (3605 bp) of p1721 was subcloned between the BamHI-XhoI sites of plasmid pCDNA3.1zeo(+) (Invitrogen), resulting in plasmid p181 in which E3 genes are under control of the CMV promoter-enhancer.

(c) The MfeI-ClaI fragment of p 181 (4328 bp), corresponding to the CMV promoter-E3 genes from the pm734.1 expression cassette, was subcloned between the EcoRI-ClaI sites of plasmid pΔE1sp1A (Microbix Biosystems Inc., Toronto), resulting in plasmid p231 which has the CMV-E3 expression cassette flanked by Ad5 genomic sequences (Ad5 map units 0–1 and 9.8–16.1). The orientation of the CMV-E3 expression cassette is right-to-left (opposite to the Ad E1 and major late transcription units).

(d) Plasmid p231 was cotransfected along with plasmid pBHG10 (Microbix Biosystems Inc., Toronto) into 293 cells resulting in plaques of recombinant virus 231-10. The virus has deletions of E1 (Ad5 nt 342–3523) and E3 (Ad5 nt 28133–30818), and has the CMV-E3 expression cassette in place of the E1 deletion.

The 231-10 Vector Expresses the E3 RID, 14.7K, and gp19K Proteins.

Figure 29:
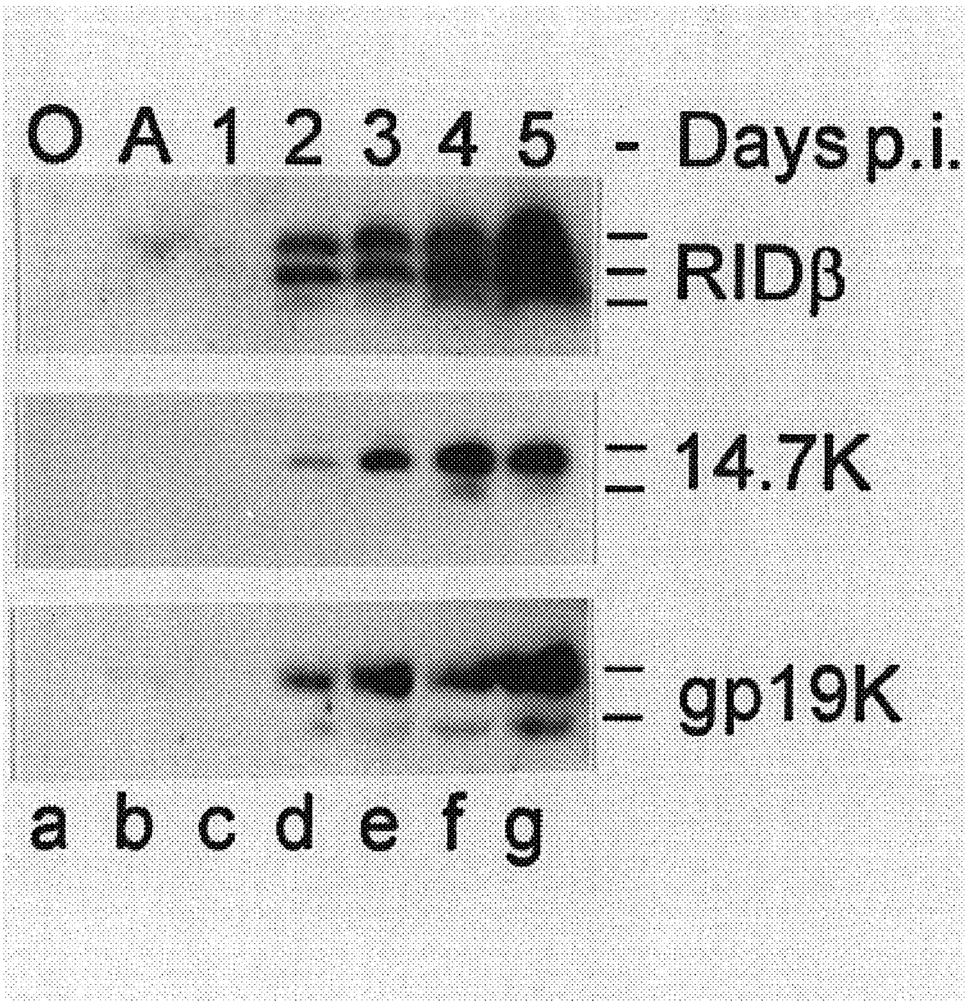
FIG. 29 shows an immunoblot of E3 RIDβ, 14.7K, and gp19K proteins expressed in A549 cells infected with the 231-10 vector and detected at the days p.i. indicated, with lane A containing proteins extracted from 231-10-infected cells at 1 day p.i. following treatment with 1-β-D-arabinofuransylcytosine (araC) at 2 h p.i.

The E3 proteins are expected to be synthesized from the E3 expression cassette in 231-10. To demonstrate that this is so, separate dishes of A549 cells were infected with 250 PFU/cell of 231-10, then at 0–5 days p.i. protein extracts were examined for the E3 RID, 14.7K, and gp19K proteins using standard immunoblot procedures (Tollefson et al., Nature 392:726–730 (1998)). In one dish, 231-10-infected cells were treated with 1-β-D-arabinofuransylcytosine (araC) at 2 h p.i., then proteins were extracted at 1 day p.i. RIDβ, 14.7K, and gp19K were readily detected at 2 days p.i., and their abundance increased until the end of the experiment at 5 days p.i. (FIG. 29, lanes d–g). On longer exposures of the gel shown in FIG. 29, a trace of RIDβ, 14.7K, and gp19K can be seen at 1 day p.i. (not shown).

In the experiment shown in FIG. 29, one dish of cells was treated with araC. AraC inhibits Ad DNA replication, and therefore Ad late genes cannot be expressed. As shown in FIG. 29, small amounts of RIDβ and gp19K were detected in the araC-treated cells; 14.7K was also detected in longer exposures of the gel (lane A). Therefore, as expected, E3 proteins are synthesized by 231-10 without replication of the vector Ad DNA.

These results demonstrate that the RIDβ, 14.7K, and gp19K proteins are expressed in 231-10-infected cells. En another experiment, the levels of RIDβ at 4 or 5 days p.i. were roughly similar to those of rec700-infected cells at 1 day p.i. (see FIG. 22). Bearing in mind that rec700 has replicated by 1 day p.i. and therefore has expressed higher levels of RIDβ from more templates, the quantities of RIDβ, 14.7K, and gp19K observed with 231-10, which does not replicate (or only replicates in small amounts at 4 or 5 days p.i.), are quite high. The synthesis of the E3 12.5K and 6.7K proteins by 231-10 has not been examined. Although not shown directly in FIG. 29, the RIDβ polypeptide is also expressed by 231-10. This can be deduced from the observation that 231-10 exhibits the expected functions of RID, namely it clears Fas and TNFR1 from the surface of infected cells (see Example 8.). These functions require both RIDα and RIDβ.

Figure 30A:
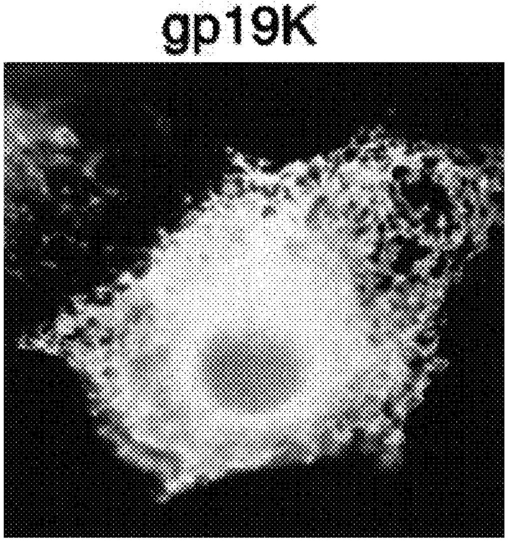
FIG. 30 shows a photograph of A549 cells infected with the 231-10 vector(SEQ ID NO:5) and gp19K, RIDβ, and 14.7K proteins detected by indirect immunoflourescence.
Figure 30B:
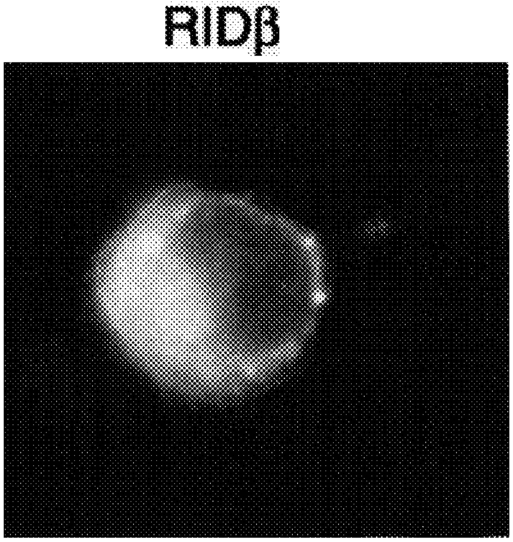
Figure 30C:
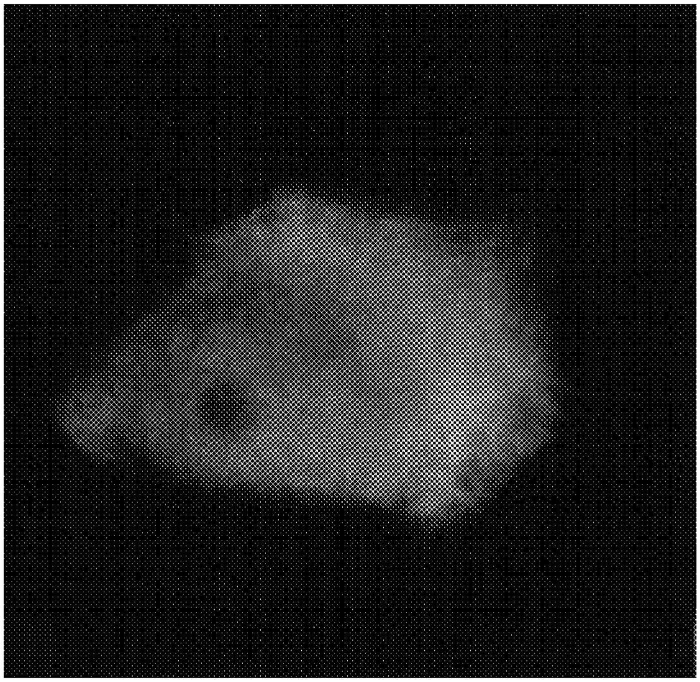

Indirect immunofluorescence was also used to study the expression of the gp19K, RIDβ, and 14.7K proteins in A549 cells infected with 231-10. At 2 days p.i., the gp19K and RIDβ proteins were visualized as described previously (Tollefson et al., *Nature* 392:726–730 (1998); Hermiston et al., *J. Virol.* 67:5289–5298 (1993)) and the 14.7K protein was stained using a rabbit antiserum directed against a TrpE-14.7K fusion protein (Tollefson and Wold, *J. Virol.* 62:33–39 (1988)). Strong staining of gp19K was observed in a pattern typical of the endoplasmic reticulum (FIG. 30A), as has been observed with rec700 (Hermiston et al., supra). The pattern for RIDβ was also similar to that seen with rec700, i.e. staining of the Golgi, other membranes, and the plasma membrane (FIG. 30B; Tollefson et al., *Nature* 392:726–730 (1998)). The 14.7K protein staining was diffuse in the cytoplasm (FIG. 30C), which again is typical of rec700 (unpublished results). These results establish that the E3 gp19K, RID, and 14.7K proteins localize to the same or similar intracellular compartments as they do in wild-type Ad-infected cells.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. A method for inhibiting apoptosis of a cell comprising contacting the cell ex vivo with a recombinant adenovirus comprising a polynucleotide encoding a RIDα-S polypeptide, a RIDα-L polypeptide and a RIDβ polypeptide, as disclosed in SEQ ID NO: 1, SEQ ID NO:2 and SEQ ID NO:4, wherein (a) the polynucleotide is operably linked to a cytomegalovirus ("CMV") promoter, (b) the adenovirus enters the cell and delivers the polynucleotide to the cell, (c) the RIDα-S polypeptide, RIDα-L polypeptide and RIDβ polypeptide are expressed in the cell in an amount sufficient to inhibit apoptosis of the cell, (d) the cell expresses Fas, DR3, TRAIL-R1, or TRAIL-R2, (e) the adenovirus lacks at least one functional E1 gene and (f) the apoptosis is not mediated by TNF activity.

2. The method of claim 1 wherein the recombinant adenovirus vector consist of a polynucleotide having a sequence set forth in SEQ ID NO: 5.

3. A composition comprising a pharmaceutically acceptable excipient and a recombinant adenovirus that comprises a polynucleotide encoding a RIDα-S polypeptide, a RIDα-L polypeptide and a RIDβ polypeptide, as disclosed in SEQ ID NO: 1, SEQ ID NO:2 and SEQ ID NO:4, wherein the polynucleotide is operably linked to a cytomegalovirus ("CMV") promoter.

4. A recombinant adenovirus vector comprising a polynucleotide encoding a RIDα-S polypeptide, a RIDα-L polypeptide and a RIDβ polypeptide, as disclosed in SEQ ID NO: 1, SEQ ID NO:2 and SEQ ID NO:4, wherein (a) the polynucleotide is operably linked to a cytomegalovirus ("CMV") promoter (b), the adenovirus is replication defective and (c) the polynucleotide is expressed upon infection of a eukaryotic cell with the adenovirus.

5. The recombinant adenovirus vector of claim 4 consisting of 231-10.

6. A method for decreasing the rejection of transplanted cells comprising contacting the cells ex vivo with a recombinant adenovirus comprising a polynucleotide encoding a RIDα-S polypeptide, a RIDα-L polypeptide and a RIDβ polypeptide, as disclosed in SEQ ID NO:1, SEQ ID NO:2 and SEQ ID NO:4, wherein (a) the polynucleotide is operably linked to a cytomegalovirus ("CMV") promoter, (b) the adenovirus enters the cell and delivers the polynucleotide to the cell, (c) the RIDα-S polypeptide RIDα-L polypeptide and RIDβ polypeptide are expressed in the cell in an amount sufficient to inhibit apoptosis of the cell, (d) the cell expresses Fas, DR3, TRAIL-R1, or TRAIL-R2, (e) the adenovirus lacks at least one functional E1 gene and (f) the rejection is mediated by Fas receptor activity; wherein the recombinant adenovirus vector consists of a polynucleotide having a sequence set forth in SEQ ID NO:5; and wherein the transplanted cells are in a mouse.

* * * * *

```
                        SEQUENCE LISTING

<160> NUMBER OF SEQ ID NOS:  5

<210> SEQ ID NO 1
<211> LENGTH: 91
<212> TYPE: PRT
<213> ORGANISM: Adenovirus

<400> SEQUENCE: 1

Met Ile Pro Arg Val Leu Ile Leu Leu Thr Leu Val Ala Leu Phe Cys
  1               5                  10                  15

Ala Cys Ser Thr Leu Ala Ala Val Ala His Ile Glu Val Asp Cys Ile
             20                  25                  30

Pro Pro Phe Thr Val Tyr Leu Leu Tyr Gly Phe Val Thr Leu Ile Leu
         35                  40                  45

Ile Cys Ser Leu Val Thr Val Val Ile Ala Phe Ile Gln Phe Ile Asp
     50                  55                  60

Trp Val Cys Val Arg Ile Ala Tyr Leu Arg His His Pro Gln Tyr Arg
 65                  70                  75                  80

Asp Arg Thr Ile Ala Asp Leu Leu Arg Ile Leu
                 85                  90


<210> SEQ ID NO 2
<211> LENGTH: 69
<212> TYPE: PRT
<213> ORGANISM: Adenovirus

<400> SEQUENCE: 2

Ala Val Ala His Ile Glu Val Asp Cys Ile Pro Pro Phe Thr Val Tyr
  1               5                  10                  15

Leu Leu Tyr Gly Phe Val Thr Leu Ile Leu Ile Cys Ser Leu Val Thr
             20                  25                  30

Val Val Ile Ala Phe Ile Gln Phe Ile Asp Trp Val Cys Val Arg Ile
         35                  40                  45

Ala Tyr Leu Arg His His Pro Gln Tyr Arg Asp Arg Thr Ile Ala Asp
     50                  55                  60

Leu Leu Arg Ile Leu
 65
```

-continued

<210> SEQ ID NO 3
<211> LENGTH: 132
<212> TYPE: PRT
<213> ORGANISM: Adenovirus

<400> SEQUENCE: 3

```
Met Lys Phe Thr Val Thr Phe Leu Leu Ile Ile Cys Thr Leu Ser Ala
  1               5                  10                  15

Phe Cys Ser Pro Thr Ser Lys Pro Gln Arg His Ile Ser Cys Arg Phe
             20                  25                  30

Thr Arg Ile Trp Asn Ile Pro Ser Cys Tyr Asn Glu Lys Ser Asp Leu
         35                  40                  45

Ser Glu Ala Trp Leu Tyr Ala Ile Ile Ser Val Met Val Phe Cys Ser
     50                  55                  60

Thr Ile Leu Ala Leu Ala Ile Tyr Pro Tyr Leu Asp Ile Gly Trp Asn
 65                  70                  75                  80

Ala Ile Asp Ala Met Asn His Pro Thr Phe Pro Ala Pro Ala Met Leu
                 85                  90                  95

Pro Leu Gln Gln Val Val Ala Gly Gly Phe Val Pro Ala Asn Gln Pro
            100                 105                 110

Arg Pro Pro Ser Pro Thr Pro Thr Glu Ile Ser Tyr Phe Asn Leu Thr
        115                 120                 125

Gly Gly Asp Asp
    130
```

<210> SEQ ID NO 4
<211> LENGTH: 114
<212> TYPE: PRT
<213> ORGANISM: Adenovirus

<400> SEQUENCE: 4

```
Ser Pro Thr Ser Lys Pro Gln Arg His Ile Ser Cys Arg Phe Thr Arg
  1               5                  10                  15

Ile Trp Asn Ile Pro Ser Cys Tyr Asn Glu Lys Ser Asp Leu Ser Glu
             20                  25                  30

Ala Trp Leu Tyr Ala Ile Ile Ser Val Met Val Phe Cys Ser Thr Ile
         35                  40                  45

Leu Ala Leu Ala Ile Tyr Pro Tyr Leu Asp Ile Gly Trp Asn Ala Ile
     50                  55                  60

Asp Ala Met Asn His Pro Thr Phe Pro Ala Pro Ala Met Leu Pro Leu
 65                  70                  75                  80

Gln Gln Val Val Ala Gly Gly Phe Val Pro Ala Asn Gln Pro Arg Pro
                 85                  90                  95

Pro Ser Pro Thr Pro Thr Glu Ile Ser Tyr Phe Asn Leu Thr Gly Gly
            100                 105                 110
Asp Asp
```

<210> SEQ ID NO 5
<211> LENGTH: 34427
<212> TYPE: DNA
<213> ORGANISM: Artificial Sequence
<220> FEATURE:
<223> OTHER INFORMATION: Description of Artificial Sequence:  Plasmid
      Combining E.coli and Adenovirus Sequences

<400> SEQUENCE: 5

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120
```

-continued

```
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatcgataag cttgatatcg    360
aattcctgca gccctatgga tacacggggt tgaaggtatc ttcagacggt cttgcgcgct    420
tcatctgcaa caacatgaag atagtgggtg cggatggaca ggaacaggag gaaactgaca    480
ttccatttag attgtggaga aagtttgcag ccaggaggaa gctgcaatac cagagctggg    540
aggagggcaa ggaggtgctg ctgaataaac tggacagaaa tttgctaact gattttaagt    600
aagtgatgct ttattatttt tttttattag ttaaagggaa taagatcttt gagaccgcac    660
agggtcttaa taagggtgca gagatcctca ggtccttgac aaggtgagtg aatgcagcct    720
tcggtttcta ccgagtgctg agttatggta atgggctttt ctcccaccat gaccaccaat    780
ttctgacgct tggttggcaa cttgtagcta aggcggtgtc cggtggtatt actgtcgtag    840
gtgactttgg cctgctttac cagacaaaag ataccccttt tgcactggtg caagttaacc    900
atgtcttgga gctcttgatt catgcgctgt tgctcggccg ctgccctgcg tctttctagc    960
aggcgctgct ctgtaataat tccgtccatt tctagatcta gggtgtcagt catctcctcc   1020
tgttagatta aagtagctga tttcagtggg ggtgggagaa gtggggcgag gctgattggc   1080
tgggacaaag ccgccggcaa caacttgttg cagtggaagc atagcgggcg cggggaaagt   1140
tgggtggttc atggcatcta ttcgtttcca gccaatgtca aggtagggat atatagctag   1200
ggctaagatg gtactgcaga acaccataac agagatgatt gcatataacc aggcttcgga   1260
aagatcgctt ttttcattgt agcaacttgg aatattccat atacgagtga atctgcatga   1320
tatatgtctt tgaggcttgg aggtcgggga acaaaacgca gatagggtgc aaataatcag   1380
cagaaaagtc acagtaaatt tcataattaa agaattctga gaagatcagc tatagtcctg   1440
tctctgtatt gcggatggtg cctgaggtac gcaatgcgca cacaaaccca gtcaatgaac   1500
tgaatgaagg cgatgactac agtgacgagg ctgcagatga ggataagggt gacaaatccg   1560
taaagcaggt aaactgtgaa aggtgggatg caatctactt cgatgtgagc gaccgcggcc   1620
aatgtagagc acgcacagaa aagcgcaaca agggtcaata atataagaac tcgaggaatc   1680
atgtctcatt taatcatact gtaaaagaag agaacatggt ttcagaccgt ccaatctatg   1740
aatttttttca ttgtgtgggt tgagcacaat gataggccta tagatggggg gtctggcgcg   1800
tctgcgcttt aggcaacaaa taagccacat aataataagg caaacaaaca taagcgctat   1860
ggaaaaccac cacaagtcca agctcgccca gtcattgaca aaggcatgaa cttggggtaa   1920
atttagggca gatgttagtc cggtagcagt ggtgttgcga tagtccgttg tgggcgcgat   1980
ggttgagccg gtcaactctg gagcaggcaa gctgaagctg ggtttgatca aatttgcagt   2040
gcaggcgctg gcagaaatca ggcgctaacg tccaggaaag tttgatttga aggttgtggg   2100
tataatcttg cccgcctgga gcatatccca catagagtaa attgtccagg ggaatacaag   2160
caagcggaaa atcaaggcat ttcttttca tcaataaaac tgcgtctgct tttgtatttg   2220
agataaagta aggtacatac caaagcaagc gctgtaataa gcagagcggt ggaacaaaag   2280
gtgccagtgt tctctaaaca cttttgtggg ggccacaact tgtactgttt gctcatgtac   2340
atggtaatat cgcacatttc ataaaatgga aatttataca taaaagtttt acgattttca   2400
ccttggaaga ctgtgacatt atagtcgtta gtgtcacctg gctgccaaat agcatataca   2460
gcatacttgc caattttgtc tttgtggcga ataataagct tttcatgttc tgtggtgcat   2520
```

-continued

```
tttataagag tagtgcattc attagcttct gatttaaatg taacattgca agctggttcc   2580
ttaaactcaa cctttttggc agcgctgcag actgccgcaa gggcgagcaa gcctaaaatc   2640
atgtacctca tcttggatgt tgcccccagc gtttaaaaag ctgacaatag gtacaaacgt   2700
gcgtgcagca ggcggcaacc ctaaggcaca gaagtgctag tataagaata aacagaatta   2760
caagagtaag gataaccccg accccaattc cagaaaaatt agacaagctt gtagagttac   2820
ttgaattgct catatactta attaaaaaat cccagcaccc cgcaaaatgc ttttttgacc   2880
tgagttccgg gagttgagct cacctcctgt tttggaaaaa tgggagtaat gtctggttac   2940
gctcaggctg taggtgtggg cgcagcaacc ggtgacgcac tcgtacgttc ccggcaggtg   3000
aggagggtgg tggtggtggt gtttttcttg acggtgtagt tgaagccgag aaggttgtgt   3060
ggcaaactta cttcgtctcg ctggaaactg ttgtaaatta caaatgaaga gccgttaaag   3120
taccaggtaa ggtacttatt ggcccgcttg tgcaaaccgg aggtgaggtt tgctttggtc   3180
tgctttgggt gggtaaaaac ggtggcgttc acaggatggc gacaggagcc ccagtagatt   3240
ctaatttctg tatttattat actcagcaca gagatgacaa caaagatctt gatgtaatcc   3300
agggttagga cagttgcaaa ccacggtcag aacacaggga ccccgctccc gctccactag   3360
cagggggcgc ttggtaaact cccgaatcag gctacgtgta agctctacct gggtggtgag   3420
ccggacgccg tgcgccgggc cctcgatatg ctcttcgggc aattcaaagt aacaaaactc   3480
accggagccg cgggcaaagc acttgtggcg gcggcagtgg tcgaggtgtg tcaggcgcag   3540
tcgctctgcc tctccactgg tcattcagtc gtagccgtcc gccgagtctt tcaccgcgtc   3600
aaagttggga ataaactggt ccgggtagtg gccgggaggt ccagaaaagg ggttgaagta   3660
aaccgaaggc acgaactcct caataaattg tagagttcca atgcctccgg agcgcggctc   3720
cgaggacgag gtctgcagag ttaggatcgc ctgacggggc gtaaatgaag agcggccagc   3780
gccgccgatc tgaaatgtcc cgtccggacg gagaccaaga gaggagctca ccgactcgtc   3840
gttgagctga atacctcgcc ctctgatttt caggtgagtt ataccctgcc cggggggggat   3900
ccgagctcgg taccaagctt aagtttaaac gctagccagc ttgggtctcc ctatagtgag   3960
tcgtattaat ttcgataagc cagtaagcag tgggttctct agttagccag agagctctgc   4020
ttatatagac ctcccaccgt acacgcctac cgcccatttg cgtcaatggg gcggagttgt   4080
tacgacattt tggaaagtcc cgttgatttt ggtgccaaaa caaactccca ttgacgtcaa   4140
tggggtggag acttggaaat ccccgtgagt caaaccgcta tccacgccca ttgatgtact   4200
gccaaaaccg catcaccatg gtaatagcga tgactaatac gtagatgtac tgccaagtag   4260
gaaagtccca taaggtcatg tactgggcat aatgccaggc gggccattta ccgtcattga   4320
cgtcaatagg gggcgtactt ggcatatgat acacttgatg tactgccaag tgggcagttt   4380
accgtaaata gtccacccat tgacgtcaat ggaaagtccc tattggcgtt actatgggaa   4440
catacgtcat tattgacgtc aatgggcggg ggtcgttggg cggtcagcca ggcgggccat   4500
ttaccgtaag ttatgtaacg cggaactcca tatatgggct atgaactaat gaccccgtaa   4560
ttgattacta ttaataacta gtcaataatc aatgtcaacg cgtatatctg gcccgtacat   4620
cgcgaagcag cgcaaaacgc ctaaccctaa gcagattctt catgcaattc aagcttgtcg   4680
acagatcttg ggcgtggctt aagggtggga aagaatatat aaggtggggg tcttatgtag   4740
ttttgtatct gttttgcagc agccgccgcc gccatgagca ccaactcgtt tgatggaagc   4800
attgtgagct catatttgac aacgcgcatg cccccatggg ccggggtgcg tcagaatgtg   4860
```

-continued

```
atgggctcca gcattgatgg tcgccccgtc ctgcccgcaa actctactac cttgacctac   4920

gagaccgtgt ctggaacgcc gttggagact gcagcctccg ccgccgcttc agccgctgca   4980

gccaccgccc gcgggattgt gactgacttt gctttcctga gcccgcttgc aagcagtgca   5040

gcttcccgtt catccgcccg cgatgacaag ttgacggctc ttttggcaca attggattct   5100

ttgacccggg aacttaatgt cgtttctcag cagctgttgg atctgcgcca gcaggtttct   5160

gccctgaagg cttcctcccc tcccaatgcg gtttaaaaca taaataaaaa accagactct   5220

gtttggattt ggatcaagca agtgtcttgc tgtctttatt taggggtttt gcgcgcgcgg   5280

taggcccggg accagcggtc tcggtcgttg agggtcctgt gtattttttc caggacgtgg   5340

taaaggtgac tctggatgtt cagatacatg ggcataagcc cgtctctggg gtggaggtag   5400

caccactgca gagcttcatg ctgcggggtg gtgttgtaga tgatccagtc gtagcaggag   5460

cgctgggcgt ggtgcctaaa aatgtctttc agtagcaagc tgattgccag gggcaggccc   5520

ttggtgtaag tgtttacaaa gcggttaagc tgggatgggt gcatacgtgg ggatatgaga   5580

tgcatcttgg actgtatttt taggttggct atgttcccag ccatatccct ccggggattc   5640

atgttgtgca gaaccaccag cacagtgtat ccggtgcact tgggaaattt gtcatgtagc   5700

ttagaaggaa atgcgtggaa gaacttggag acgcccttgt gacctccaag attttccatg   5760

cattcgtcca taatgatggc aatgggccca cgggcggcgg cctgggcgaa gatatttctg   5820

ggatcactaa cgtcatagtt gtgttccagg atgagatcgt cataggccat ttttacaaag   5880

cgcgggcgga gggtgccaga ctgcggtata atggttccat ccggcccagg ggcgtagtta   5940

ccctcacaga tttgcatttc ccacgctttg agttcagatg gggggatcat gtctacctgc   6000

ggggcgatga agaaaacggt ttccggggta ggggagatca gctgggaaga aagcaggttc   6060

ctgagcagct gcgacttacc gcagccggtg ggcccgtaaa tcacacctat taccgggtgc   6120

aactggtagt taagagagct gcagctgccg tcatccctga gcaggggggc cacttcgtta   6180

agcatgtccc tgactcgcat gttttccctg accaaatccg ccagaaggcg ctcgccgccc   6240

agcgatagca gttcttgcaa ggaagcaaag tttttcaacg gtttgagacc gtccgccgta   6300

ggcatgcttt tgagcgtttg accaagcagt tccaggcggt cccacagctc ggtcacctgc   6360

tctacggcat ctcgatccag catatctcct cgtttcgcgg gttggggcgg ctttcgctgt   6420

acggcagtag tcggtgctcg tccagacggg ccagggtcat gtctttccac gggcgcaggg   6480

tcctcgtcag cgtagtctgg gtcacggtga aggggtgcgc tccgggctgc gcgctggcca   6540

gggtgcgctt gaggctggtc ctgctggtgc tgaagcgctg ccggtcttcg ccctgcgcgt   6600

cggccaggta gcatttgacc atggtgtcat agtccagccc ctccgcggcg tggcccttgg   6660

cgcgcagctt gcccttggag gaggcgccgc acgaggggca gtgcagactt ttgagggcgt   6720

agagcttggg cgcgagaaat accgattccg gggagtaggc atccgcgccg caggccccgc   6780

agacggtctc gcattccacg agccaggtga gctctggccg ttcggggtca aaaaccaggt   6840

ttcccccatg ctttttgatg cgtttcttac ctctggtttc catgagccgg tgtccacgct   6900

cggtgacgaa aaggctgtcc gtgtccccgt atacagactt gagaggcctg tcctcgagcg   6960

gtgttccgcg gtcctcctcg tatagaaact cggaccactc tgagacaaag gctcgcgtcc   7020

aggccagcac gaaggaggct aagtgggagg ggtagcggtc gttgtccact agggggtcca   7080

ctcgctccag ggtgtgaaga cacatgtcgc cctcttcggc atcaaggaag gtgattggtt   7140

tgtaggtgta ggccacgtga ccgggtgttc ctgaaggggg gctataaaag ggggtggggg   7200

cgcgttcgtc ctcactctct tccgcatcgc tgtctgcgag ggccagctgt tggggtgagt   7260
```

-continued

```
actccctctg aaaagcgggc atgacttctg cgctaagatt gtcagtttcc aaaaacgagg   7320
aggatttgat attcacctgg cccgcggtga tgcctttgag ggtggccgca tccatctggt   7380
cagaaaagac aatctttttg ttgtcaagct tggtggcaaa cgacccgtag agggcgttgg   7440
acagcaactt ggcgatggag cgcagggttt ggtttttgtc gcgatcggcg cgctccttgg   7500
ccgcgatgtt tagctgcacg tattcgcgcg caacgcaccg ccattcggga aagacggtgg   7560
tgcgctcgtc gggcaccagg tgcacgcgcc aaccgcggtt gtgcagggtg acaaggtcaa   7620
cgctggtggc tacctctccg cgtaggcgct cgttggtcca gcagaggcgg ccgcccttgc   7680
gcgagcagaa tggcggtagg gggtctagct gcgtctcgtc cggggggtct gcgtccacgg   7740
taaagacccc gggcagcagg cgcgcgtcga agtagtctat cttgcatcct tgcaagtcta   7800
gcgcctgctg ccatgcgcgg gcggcaagcg cgcgctcgta tgggttgagt gggggacccc   7860
atggcatggg gtgggtgagc gcggaggcgt acatgccgca aatgtcgtaa acgtagaggg   7920
gctctctgag tattccaaga tatgtagggt agcatcttcc accgcggatg ctggcgcgca   7980
cgtaatcgta tagttcgtgc gagggagcga ggaggtcggg accgaggttg ctacgggcgg   8040
gctgctctgc tcggaagact atctgcctga agatggcatg tgagttggat gatatggttg   8100
gacgctggaa gacgttgaag ctggcgtctg tgagacctac cgcgtcacgc acgaaggagg   8160
cgtaggagtc gcgcagcttg ttgaccagct cggcggtgac ctgcacgtct agggcgcagt   8220
agtccagggt ttccttgatg atgtcatact tatcctgtcc cttttttttc cacagctcgc   8280
ggttgaggac aaactcttcg cggtctttcc agtactcttg gatcggaaac ccgtcggcct   8340
ccgaacggta agagcctagc atgtagaact ggttgacggc ctggtaggcg cagcatccct   8400
tttctacggg tagcgcgtat gcctgcgcgg ccttccggag cgaggtgtgg gtgagcgcaa   8460
aggtgtccct gaccatgact ttgaggtact ggtatttgaa gtcagtgtcg tcgcatccgc   8520
cctgctccca gagcaaaaag tccgtgcgct ttttggaacg cggatttggc agggcgaagg   8580
tgacatcgtt gaagagtatc tttcccgcgc gaggcataaa gttgcgtgtg atgcggaagg   8640
gtcccggcac ctcggaacgg ttgttaatta cctgggcggc gagcacgatc tcgtcaaagc   8700
cgttgatgtt gtggcccaca atgtaaagtt ccaagaagcg cgggatgccc ttgatggaag   8760
gcaatttttt aagttcctcg taggtgagct cttcagggga gctgagcccg tgctctgaaa   8820
gggcccagtc tgcaagatga gggttggaag cgacgaatga gctccacagg tcacgggcca   8880
ttagcatttg caggtggtcg cgaaaggtcc taaactggcg acctatggcc atttttctg    8940
gggtgatgca gtagaaggta agcgggtctt gttcccagcg gtcccatcca aggttcgcgg   9000
ctaggtctcg cgcggcagtc actagaggct catctccgcc gaacttcatg accagcatga   9060
agggcacgag ctgcttccca aaggccccca tccaagtata ggtctctaca tcgtaggtga   9120
caaagagacg ctcggtgcga ggatgcgagc cgatcgggaa gaactggatc tcccgccacc   9180
aattggagga gtggctattg atgtggtgaa agtagaagtc cctgcgacgg gccgaacact   9240
cgtgctggct tttgtaaaaa cgtgcgcagt actggcagcg gtgcacgggc tgtacatcct   9300
gcacgaggtt gacctgacga ccgcgcacaa ggaagcagag tgggaatttg agcccctcgc   9360
ctggcgggtt tggctggtgg tcttctactt cggctgcttg tccttgaccg tctggctgct   9420
cgaggggagt tacggtggat cggaccacca cgccgcgcga gcccaaagtc cagatgtccg   9480
cgcgcggcgg tcggagcttg atgacaacat cgcgcagatg ggagctgtcc atggtctgga   9540
gctcccgcgg cgtcaggtca ggcgggagct cctgcaggtt tacctcgcat agacgggtca   9600
```

-continued

```
gggcgcgggc tagatccagg tgatacctaa tttccagggg ctggttggtg gcggcgtcga   9660
tggcttgcaa gaggccgcat ccccgcggcg cgactacggt accgcgcggc gggcggtggg   9720
ccgcgggggt gtccttggat gatgcatcta aaagcggtga cgcgggcgag cccccggagg   9780
taggggggc tccggacccg ccgggagagg gggcaggggc acgtcggcgc cgcgcgcggg   9840
caggagctgg tgctgcgcgc gtaggttgct ggcgaacgcg acgacgcggc ggttgatctc   9900
ctgaatctgg cgcctctgcg tgaagacgac gggcccggtg agcttgagcc tgaaagagag   9960
ttcgacagaa tcaatttcgg tgtcgttgac ggcggcctgg cgcaaaatct cctgcacgtc  10020
tcctgagttg tcttgatagg cgatctcggc catgaactgc tcgatctctt cctcctggag  10080
atctccgcgt ccggctcgct ccacggtggc ggcgaggtcg ttggaaatgc gggccatgag  10140
ctgcgagaag gcgttgaggc ctccctcgtt ccagacgcgg ctgtagacca cgcccccttc  10200
ggcatcgcgg gcgcgcatga ccacctgcgc gagattgagc tccacgtgcc gggcgaagac  10260
ggcgtagttt cgcaggcgct gaaagaggta gttgagggtg gtggcggtgt gttctgccac  10320
gaagaagtac ataacccagc gtcgcaacgt ggattcgttg atatccccca aggcctcaag  10380
gcgctccatg gcctcgtaga agtccacggc gaagttgaaa aactgggagt tgcgcgccga  10440
cacggttaac tcctcctcca gaagacggat gagctcggcg acagtgtcgc gcacctcgcg  10500
ctcaaaggct acaggggcct cttcttcttc ttcaatctcc tcttccataa gggcctcccc  10560
ttcttcttct tctggcggcg gtgggggagg ggggacacgg cggcgacgac ggcgcaccgg  10620
gaggcggtcg acaaagcgct cgatcatctc cccgcggcga cggcgcatgg tctcggtgac  10680
ggcgcggccg ttctcgcggg ggcgcagttg gaagacgccg cccgtcatgt cccggttatg  10740
ggttggcggg ggctgccat gcggcaggga tacggcgcta acgatgcatc tcaacaattg  10800
ttgtgtaggt actccgccgc cgagggacct gagcgagtcc gcatcgaccg gatcggaaaa  10860
cctctcgaga aaggcgtcta accagtcaca gtcgcaaggt aggctgagca ccgtggcggg  10920
cggcagcggg cggcggtcgg ggttgtttct ggcggaggtg ctgctgatga tgtaattaaa  10980
gtaggcggtc ttgagacggc ggatggtcga cagaagcacc atgtccttgg gtccggcctg  11040
ctgaatgcgc aggcggtcgg ccatgcccca ggcttcgttt tgacatcggc gcaggtcttt  11100
gtagtagtct tgcatgagcc tttctaccgg cacttcttct tctccttcct cttgtcctgc  11160
atctcttgca tctatcgctg cggcggcggc ggagtttggc cgtaggtggc gccctcttcc  11220
tcccatgcgt gtgaccccga agcccctcat cggctgaagc agggctaggt cggcgacaac  11280
gcgctcggct aatatggcct gctgcacctg cgtgagggta gactggaagt catccatgtc  11340
cacaaagcgg tggtatgcgc ccgtgttgat ggtgtaagtg cagttggcca taacggacca  11400
gttaacggtc tggtgacccg gctgcgagag ctcggtgtac ctgagacgcg agtaagccct  11460
cgagtcaaat acgtagtcgt tgcaagtccg caccaggtac tggtatccca ccaaaaagtg  11520
cggcggcggc tggcggtaga ggggccagcg tagggtggcc ggggctccgg gggcgagatc  11580
ttccaacata aggcgatgat atccgtagat gtacctggac atccaggtga tgccggcggc  11640
ggtggtggag gcgcgcggaa agtcgcggac gcggttccag atgttgcgca gcggcaaaaa  11700
gtgctccatg gtcgggacgc tctggccggt caggcgcgcg caatcgttga cgctctagac  11760
cgtgcaaaag gagagcctgt aagcgggcac tcttccgtgg tctggtggat aaattcgcaa  11820
gggtatcatg gcggacgacc ggggttcgag ccccgtatcc ggccgtccgc cgtgatccat  11880
gcggttaccg cccgcgtgtc gaacccaggt gtgcgacgtc agacaacggg ggagtgctcc  11940
ttttggcttc cttccaggcg cggcggctgc tgcgctagct tttttggcca ctggccgcgc  12000
```

-continued

```
gcagcgtaag cggttaggct ggaaagcgaa agcattaagt ggctcgctcc ctgtagccgg  12060
agggttattt tccaagggtt gagtcgcggg acccccggtt cgagtctcgg accggccgga  12120
ctgcggcgaa cgggggtttg cctccccgtc atgcaagacc ccgcttgcaa attcctccgg  12180
aaacagggac gagccccttt tttgcttttc ccagatgcat ccggtgctgc ggcagatgcg  12240
ccccctcct cagcagcggc aagagcaaga gcagcggcag acatgcaggg caccctcccc  12300
tcctcctacc gcgtcaggag gggcgacatc cgcggttgac gcggcagcag atggtgatta  12360
cgaacccccg cggcgccggg cccggcacta cctggacttg gaggagggcg agggcctggc  12420
gcggctagga gcgccctctc ctgagcggta cccaagggtg cagctgaagc gtgatacgcg  12480
tgaggcgtac gtgccgcggc agaacctgtt tcgcgaccgc gagggagagg agcccgagga  12540
gatgcgggat cgaaagttcc acgcagggcg cgagctgcgg catggcctga atcgcgagcg  12600
gttgctgcgc gaggaggact ttgagcccga cgcgcgaacc gggattagtc ccgcgcgcgc  12660
acacgtggcg gccgccgacc tggtaaccgc atacgagcag acggtgaacc aggagattaa  12720
ctttcaaaaa agctttaaca accacgtgcg tacgcttgtg gcgcgcgagg aggtggctat  12780
aggactgatg catctgtggg actttgtaag cgcgctggag caaaacccaa atagcaagcc  12840
gctcatggcg cagctgttcc ttatagtgca gcacagcagg gacaacgagg cattcaggga  12900
tgcgctgcta aacatagtag agcccgaggg ccgctggctg ctcgatttga taaacatcct  12960
gcagagcata gtggtgcagg agcgcagctt gagcctggct gacaaggtgg ccgccatcaa  13020
ctattccatg cttagcctgg gcaagtttta cgcccgcaag atataccata ccccttacgt  13080
tcccatagac aaggaggtaa agatcgaggg gttctacatg cgcatggcgc tgaaggtgct  13140
taccttgagc gacgacctgg gcgtttatcg caacgagcgc atccacaagg ccgtgagcgt  13200
gagccggcgg cgcgagctca gcgaccgcga gctgatgcac agcctgcaaa gggccctggc  13260
tggcacgggc agcggcgata gagaggccga gtcctacttt gacgcgggcg ctgacctgcg  13320
ctgggcccca agccgacgcg ccctggaggc agctggggcc ggacctgggc tggcggtggc  13380
acccgcgcgc gctggcaacg tcggcggcgt ggaggaatat gacgaggacg atgagtacga  13440
gccagaggac ggcgagtact aagcggtgat gtttctgatc agatgatgca agacgcaacg  13500
gacccggcgg tgcgggcggc gctgcagagc cagccgtccg gccttaactc cacggacgac  13560
tggcgccagg tcatggaccg catcatgtcg ctgactgcgc gcaatcctga cgcgttccgg  13620
cagcagccgc aggccaaccg gctctccgca attctggaag cggtggtccc ggcgcgcgca  13680
aaccccacgc acgagaaggt gctggcgatc gtaaacgcgc tggccgaaaa cagggccatc  13740
cggcccgacg aggccggcct ggtctacgac gcgctgcttc agcgcgtggc tcgttacaac  13800
agcggcaacg tgcagaccaa cctggaccgg ctggtggggg atgtgcgcga ggccgtggcg  13860
cagcgtgagc gcgcgcagca gcagggcaac ctgggctcca tggttgcact aaacgccttc  13920
ctgagtacac agcccgccaa cgtgccgcgg ggacaggagg actacaccaa ctttgtgagc  13980
gcactgcggc taatggtgac tgagacaccg caaagtgagg tgtaccagtc tgggccagac  14040
tatttttcc agaccagtag acaaggcctg cagaccgtaa acctgagcca ggctttcaaa  14100
aacttgcagg ggctgtgggg ggtgcgggct cccacaggcg accgcgcgac cgtgtctagc  14160
ttgctgacgc ccaactcgcg cctgttgctg ctgctaatag cgcccttcac ggacagtggc  14220
agcgtgtccc gggacacata cctaggtcac ttgctgacac tgtaccgcga ggccataggt  14280
caggcgcatg tggacgagca tactttccag gagattacaa gtgtcagccg cgcgctgggg  14340
```

-continued

```
caggaggaca cgggcagcct ggaggcaacc ctaaactacc tgctgaccaa ccggcggcag  14400
aagatcccct cgttgcacag tttaaacagc gaggaggagc gcattttgcg ctacgtgcag  14460
cagagcgtga gccttaacct gatgcgcgac ggggtaacgc ccagcgtggc gctggacatg  14520
accgcgcgca acatggaacc gggcatgtat gcctcaaacc ggccgtttat caaccgccta  14580
atggactact tgcatcgcgc ggccgccgtg aaccccgagt atttcaccaa tgccatcttg  14640
aacccgcact ggctaccgcc ccctggtttc tacaccgggg gattcgaggt gcccgagggt  14700
aacgatggat tcctctggga cgacatagac gacagcgtgt tttccccgca accgcagacc  14760
ctgctagagt tgcaacagcg cgagcaggca gaggcggcgc tgcgaaagga aagcttccgc  14820
aggccaagca gcttgtccga tctaggcgct gcggccccgc ggtcagatgc tagtagccca  14880
tttccaagct tgatagggtc tcttaccagc actcgcacca cccgcccgcg cctgctgggc  14940
gaggaggagt acctaaacaa ctcgctgctg cagccgcagc gcgaaaaaaa cctgcctccg  15000
gcatttccca acaacgggat agagagccta gtggacaaga tgagtagatg gaagacgtac  15060
gcgcaggagc acagggacgt gccaggcccg cgcccgccca cccgtcgtca aaggcacgac  15120
cgtcagcggg gtctggtgtg ggaggacgat gactcggcag acgacagcag cgtcctggat  15180
ttgggaggga gtggcaaccc gtttgcgcac cttcgcccca ggctggggag aatgttttaa  15240
aaaaaaaaaa gcatgatgca aaataaaaaa ctcaccaagg ccatggcacc gagcgttggt  15300
tttcttgtat tccccttagt atgcggcgcg cggcgatgta tgaggaaggt cctcctccct  15360
cctacgagag tgtggtgagc gcggcgccag tggcggcggc gctgggttct cccttcgatg  15420
ctcccctgga cccgccgttt gtgcctccgc ggtacctgcg gcctaccggg gggagaaaca  15480
gcatccgtta ctctgagttg gcacccctat tcgacaccac ccgtgtgtac ctggtggaca  15540
acaagtcaac ggatgtggca tccctgaact accagaacga ccacagcaac tttctgacca  15600
cggtcattca aaacaatgac tacagcccgg gggaggcaag cacacagacc atcaatcttg  15660
acgaccggtc gcactggggc ggcgacctga aaaccatcct gcataccaac atgccaaatg  15720
tgaacgagtt catgtttacc aataagttta aggcgcgggt gatggtgtcg cgcttgccta  15780
ctaaggacaa tcaggtggag ctgaaatacg agtgggtgga gttcacgctg cccgagggca  15840
actactccga gaccatgacc atagacctta tgaacaacgc gatcgtggag cactacttga  15900
aagtgggcag acagaacggg gttctggaaa gcgacatcgg ggtaaagttt gacacccgca  15960
acttcagact ggggtttgac ccgtcactg gtcttgtcat gcctggggta tatacaaacg  16020
aagccttcca tccagacatc attttgctgc caggatgcgg ggtggacttc acccacagcc  16080
gcctgagcaa cttgttgggc atccgcaagc ggcaaccctt ccaggagggc tttaggatca  16140
cctacgatga tctggagggt ggtaacattc ccgcactgtt ggatgtggac gcctaccagg  16200
cgagcttgaa agatgacacc gaacagggcg ggggtggcgc aggcggcagc aacagcagtg  16260
gcagcggcgc ggaagagaac tccaacgcgg cagccgcggc aatgcagccg gtggaggaca  16320
tgaacgatca tgccattcgc ggcgacacct ttgccacacg ggctgaggag aagcgcgctg  16380
aggccgaagc agcggccgaa gctgccgccc ccgctgcgca acccgaggtc gagaagcctc  16440
agaagaaacc ggtgatcaaa cccctgacag aggacagcaa gaaacgcagt tacaacctaa  16500
taagcaatga cagcaccttc acccagtacc gcagctggta ccttgcatac aactacggcg  16560
accctcagac cggaatccgc tcatggaccc tgctttgcac tcctgacgta acctgcggct  16620
cggagcaggt ctactggtcg ttgccagaca tgatgcaaga ccccgtgacc ttccgctcca  16680
cgcgccagat cagcaacttt ccggtggtgg gcgccgagct gttgcccgtg cactccaaga  16740
```

-continued

```
gcttctacaa cgaccaggcc gtctactccc aactcatccg ccagtttacc tctctgaccc  16800
acgtgttcaa tcgctttccc gagaaccaga ttttggcgcg cccgccagcc cccaccatca  16860
ccaccgtcag tgaaaacgtt cctgctctca cagatcacgg gacgctaccg ctgcgcaaca  16920
gcatcggagg agtccagcga gtgaccatta ctgacgccag acgccgcacc tgcccctacg  16980
tttacaaggc cctgggcata gtctcgccgc gcgtcctatc gagccgcact ttttgagcaa  17040
gcatgtccat ccttatatcg cccagcaata acacaggctg gggcctgcgc ttcccaagca  17100
agatgtttgg cggggccaag aagcgctccg accaacaccc agtgcgcgtg cgcgggcact  17160
accgcgcgcc ctggggcgcg cacaaacgcg gccgcactgg gcgcaccacc gtcgatgacg  17220
ccatcgacgc ggtggtggag gaggcgcgca actacacgcc cacgccgcca ccagtgtcca  17280
cagtggacgc ggccattcag accgtggtgc gcggagcccg gcgctatgct aaaatgaaga  17340
gacggcggag gcgcgtagca cgtcgccacc gccgccgacc cggcactgcc gcccaacgcg  17400
cggcggcggc cctgcttaac cgcgcacgtc gcaccggccg acgggcggcc atgcgggccg  17460
ctcgaaggct ggccgcgggt attgtcactg tgcccccag gtccaggcga cgagcggccg  17520
ccgcagcagc cgcggccatt agtgctatga ctcagggtcg caggggcaac gtgtattggg  17580
tgcgcgactc ggttagcggc ctgcgcgtgc ccgtgcgcac ccgcccccg cgcaactaga  17640
ttgcaagaaa aaactactta gactcgtact gttgtatgta tccagcggcg gcggcgcgca  17700
acgaagctat gtccaagcgc aaaatcaaag aagagatgct ccaggtcatc gcgccggaga  17760
tctatggccc cccgaagaag gaagagcagg attacaagcc ccgaaagcta aagcgggtca  17820
aaaagaaaaa gaaagatgat gatgatgaac ttgacgacga ggtggaactg ctgcacgcta  17880
ccgcgcccag gcgacgggta cagtggaaag gtcgacgcgt aaaacgtgtt ttgcgacccg  17940
gcaccaccgt agtctttacg cccggtgagc gctccacccg cacctacaag cgcgtgtatg  18000
atgaggtgta cggcgacgag gacctgcttg agcaggccaa cgagcgcctc ggggagtttg  18060
cctacggaaa gcggcataag gacatgctgg cgttgccgct ggacgagggc aacccaacac  18120
ctagcctaaa gcccgtaaca ctgcagcagg tgctgcccgc gcttgcaccg tccgaagaaa  18180
agcgcggcct aaagcgcgag tctggtgact tggcacccac cgtgcagctg atggtaccca  18240
agcgccagcg actggaagat gtcttggaaa aaatgaccgt ggaacctggg ctggagcccg  18300
aggtccgcgt gcggccaatc aagcaggtgg cgccgggact gggcgtgcag accgtggacg  18360
ttcagatacc cactaccagt agcaccagta ttgccaccgc cacagagggc atggagacac  18420
aaacgtcccc ggttgcctca gcggtggcgg atgccgcggt gcaggcggtc gctgcggccg  18480
cgtccaagac ctctacggag gtgcaaacgg acccgtggat gtttcgcgtt tcagcccccc  18540
ggcgcccgcg cggttcgagg aagtacggcg ccgccagcgc gctactgccc gaatatgccc  18600
tacatccttc cattgcgcct acccccggct atcgtggcta cacctaccgc cccagaagac  18660
gagcaactac ccgacgccga accaccactg gaacccgccg ccgccgtcgc cgtcgccagc  18720
ccgtgctggc cccgatttcc gtgcgcaggg tggctcgcga aggaggcagg accctggtgc  18780
tgccaacagc gcgctaccac cccagcatcg tttaaaagcc ggtctttgtg gttcttgcag  18840
atatggccct cacctgccgc ctccgtttcc cggtgccggg attccgagga agaatgcacc  18900
gtaggagggg catggccggc cacggcctga cgggcggcat gcgtcgtgcg caccaccggc  18960
ggcggcgcgc gtcgcaccgt cgcatgcgcg gcggtatcct gcccctcctt attccactga  19020
tcgccgcggc gattggcgcc gtgcccggaa ttgcatccgt ggccttgcag gcgcagagac  19080
```

-continued

```
actgattaaa aacaagttgc atgtggaaaa atcaaaataa aaagtctgga ctctcacgct  19140
cgcttggtcc tgtaactatt ttgtagaatg gaagacatca actttgcgtc tctggccccg  19200
cgacacggct cgcgcccgtt catgggaaac tggcaagata tcggcaccag caatatgagc  19260
ggtggcgcct tcagctgggg ctcgctgtgg agcggcatta aaaatttcgg ttccaccgtt  19320
aagaactatg gcagcaaggc ctggaacagc agcacaggcc agatgctgag ggataagttg  19380
aaagagcaaa atttccaaca aaaggtggta gatggcctgg cctctggcat tagcggggtg  19440
gtggacctgg ccaaccaggc agtgcaaaat aagattaaca gtaagcttga tccccgccct  19500
cccgtagagg agcctccacc ggccgtggag acagtgtctc cagaggggcg tggcgaaaag  19560
cgtccgcgcc ccgacaggga agaaactctg gtgacgcaaa tagacgagcc tccctcgtac  19620
gaggaggcac taaagcaagg cctgcccacc acccgtccca tcgcgcccat ggctaccgga  19680
gtgctgggcc agcacacacc cgtaacgctg gacctgcctc cccccgccga cacccagcag  19740
aaacctgtgc tgccaggccc gaccgccgtt gttgtaaccc gtcctagccg cgcgtccctg  19800
cgccgcgccg ccagcggtcc gcgatcgttg cggcccgtag ccagtggcaa ctggcaaagc  19860
acactgaaca gcatcgtggg tctgggggtg caatccctga agcgccgacg atgcttctga  19920
atagctaacg tgtcgtatgt gtgtcatgta tgcgtccatg tcgccgccag aggagctgct  19980
gagccgccgc gcgcccgctt tccaagatgg ctaccccttc gatgatgccg cagtggtctt  20040
acatgcacat ctcgggccag gacgcctcgg agtacctgag ccccgggctg gtgcagtttg  20100
cccgcgccac cgagacgtac ttcagcctga ataacaagtt tagaaacccc acggtggcgc  20160
ctacgcacga cgtgaccaca gaccggtccc agcgtttgac gctgcggttc atccctgtgg  20220
accgtgagga tactgcgtac tcgtacaagg cgcggttcac cctagctgtg ggtgataacc  20280
gtgtgctgga catggcttcc acgtactttg acatccgcgg cgtgctggac aggggcccta  20340
cttttaagcc ctactctggc actgcctaca acgccctggc tcccaagggt gccccaaatc  20400
cttgcgaatg ggatgaagct gctactgctc ttgaaataaa cctagaagaa gaggacgatg  20460
acaacgaaga cgaagtagac gagcaagctg agcagcaaaa aactcacgta tttgggcagg  20520
cgccttattc tggtataaat attacaaagg agggtattca aataggtgtc gaaggtcaaa  20580
cacctaaata tgccgataaa acatttcaac ctgaacctca aataggagaa tctcagtggt  20640
acgaaactga aattaatcat gcagctggga gagtccttaa aaagactacc ccaatgaaac  20700
catgttacgg ttcatatgca aaacccacaa atgaaaatgg agggcaaggc attcttgtaa  20760
agcaacaaaa tggaaagcta gaaagtcaag tggaaatgca atttttctca actactgagg  20820
cgaccgcagg caatggtgat aacttgactc ctaaagtggt attgtacagt gaagatgtag  20880
atatagaaac cccagacact catatttctt acatgcccac tattaaggaa ggtaactcac  20940
gagaactaat gggccaacaa tctatgccca acaggcctaa ttacattgct tttagggaca  21000
attttattgg tctaatgtat tacaacagca cgggtaatat gggtgttctg gcgggccaag  21060
catcgcagtt gaatgctgtt gtagatttgc aagacagaaa cacagagctt tcataccagc  21120
ttttgcttga ttccattggt gatagaacca ggtacttttc tatgtggaat caggctgttg  21180
acagctatga tccagatgtt agaattattg aaaatcatgg aactgaagat gaacttccaa  21240
attactgctt tccactggga ggtgtgatta atacagagac tcttaccaag gtaaaaccta  21300
aaacaggtca ggaaaatgga tgggaaaaag atgctacaga attttcagat aaaaatgaaa  21360
taagagttgg aaataatttt gccatggaaa tcaatctaaa tgccaacctg tggagaaatt  21420
tcctgtactc caacatagcg ctgtatttgc ccgacaagct aaagtacagt ccttccaacg  21480
```

-continued

```
taaaaatttc tgataaccca aacacctacg actacatgaa caagcgagtg gtggctcccg  21540
ggttagtgga ctgctacatt aaccttggag cacgctggtc ccttgactat atggacaacg  21600
tcaacccatt taaccaccac cgcaatgctg gcctgcgcta ccgctcaatg ttgctgggca  21660
atggtcgcta tgtgcccttc cacatccagg tgcctcagaa gttctttgcc attaaaaacc  21720
tccttctcct gccgggctca tacacctacg agtggaactt caggaaggat gttaacatgg  21780
ttctgcagag ctccctagga aatgacctaa gggttgacgg agccagcatt aagtttgata  21840
gcatttgcct ttacgccacc ttcttcccca tggcccacaa caccgcctcc acgcttgagg  21900
ccatgcttag aaacgacacc aacgaccagt cctttaacga ctatctctcc gccgccaaca  21960
tgctctaccc tatacccgcc aacgctacca acgtgcccat atccatcccc tcccgcaact  22020
gggcggcttt ccgcggctgg gccttcacgc gccttaagac taaggaaacc ccatcactgg  22080
gctcgggcta cgacccttat tacacctact ctggctctat accctaccta gatggaacct  22140
tttacctcaa ccacaccttt aagaaggtgg ccattacctt tgactcttct gtcagctggc  22200
ctggcaatga ccgcctgctt acccccaacg agtttgaaat taagcgctca gttgacgggg  22260
agggttacaa cgttgcccag tgtaacatga ccaaagactg gttcctggta caaatgctag  22320
ctaactacaa cattggctac cagggcttct atatcccaga gagctacaag gaccgcatgt  22380
actccttctt tagaaacttc cagcccatga gccgtcaggt ggtggatgat actaaataca  22440
aggactacca acaggtgggc atcctacacc aacacaacaa ctctggattt gttggctacc  22500
ttgcccccac catgcgcgaa ggacaggcct accctgctaa cttcccctat ccgcttatag  22560
gcaagaccgc agttgacagc attacccaga aaaagtttct ttgcgatcgc accctttggc  22620
gcatcccatt ctccagtaac tttatgtcca tgggcgcact cacagacctg ggccaaaacc  22680
ttctctacgc caactccgcc cacgcgctag acatgacttt tgaggtggat cccatggacg  22740
agcccaccct tctttatgtt ttgtttgaag tctttgacgt ggtccgtgtg caccggccgc  22800
accgcggcgt catcgaaacc gtgtacctgc gcacgccctt ctcggccggc aacgccacaa  22860
cataaagaag caagcaacat caacaacagc tgccgccatg ggctccagtg agcaggaact  22920
gaaagccatt gtcaaagatc ttggttgtgg gccatatttt ttgggcacct atgacaagcg  22980
ctttccaggc tttgtttctc cacacaagct cgcctgcgcc atagtcaata cggccggtcg  23040
cgagactggg ggcgtacact ggatggcctt tgcctggaac ccgcactcaa aaacatgcta  23100
cctctttgag ccctttggct ttctgacca gcgactcaag caggtttacc agtttgagta  23160
cgagtcactc ctgcgccgta gcgccattgc ttcttccccc gaccgctgta taacgctgga  23220
aaagtccacc caaagcgtac aggggcccaa ctcggccgcc tgtggactat tctgctgcat  23280
gtttctccac gcctttgcca actggcccca aactcccatg gatcacaacc ccaccatgaa  23340
ccttattacc ggggtaccca actccatgct caacagtccc caggtacagc ccaccctgcg  23400
tcgcaaccag gaacagctct acagcttcct ggagcgccac tcgccctact tccgcagcca  23460
cagtgcgcag attaggagcg ccacttcttt ttgtcacttg aaaaacatgt aaaaataatg  23520
tactagagac actttcaata aaggcaaatg cttttatttg tacactctcg ggtgattatt  23580
tacccccacc cttgccgtct gcgccgttta aaaatcaaag ggttctgcc gcgcatcgct  23640
atgcgccact ggcagggaca cgttgcgata ctggtgttta gtgctccact taaactcagg  23700
cacaaccatc cgcggcagct cggtgaagtt ttcactccac aggctgcgca ccatcaccaa  23760
cgcgtttagc aggtcgggcg ccgatatctt gaagtcgcag ttggggcctc cgccctgcgc  23820
```

-continued

```
gcgcgagttg cgatacacag ggttgcagca ctggaacact atcagcgccg ggtggtgcac  23880
gctggccagc acgctcttgt cggagatcag atccgcgtcc aggtcctccg cgttgctcag  23940
ggcgaacgga gtcaactttg gtagctgcct tcccaaaaag ggcgcgtgcc caggctttga  24000
gttgcactcg caccgtagtg gcatcaaaag gtgaccgtgc ccggtctggg cgttaggata  24060
cagcgcctgc ataaaagcct tgatctgctt aaaagccacc tgagcctttg cgccttcaga  24120
gaagaacatg ccgcaagact tgccggaaaa ctgattggcc ggacaggccg cgtcgtgcac  24180
gcagcacctt gcgtcggtgt tggagatctg caccacattt cggccccacc ggttcttcac  24240
gatcttggcc ttgctagact gctccttcag cgcgcgctgc ccgttttcgc tcgtcacatc  24300
catttcaatc acgtgctcct tatttatcat aatgcttccg tgtagacact taagctcgcc  24360
ttcgatctca gcgcagcggt gcagccacaa cgcgcagccc gtgggctcgt gatgcttgta  24420
ggtcacctct gcaaacgact gcaggtacgc ctgcaggaat cgccccatca tcgtcacaaa  24480
ggtcttgttg ctggtgaagg tcagctgcaa cccgcggtgc tcctcgttca gccaggtctt  24540
gcatacggcc gccagagctt ccacttggtc aggcagtagt ttgaagttcg cctttagatc  24600
gttatccacg tggtacttgt ccatcagcgc gcgcgcagcc tccatgccct tctcccacgc  24660
agacacgatc ggcacactca gcgggttcat caccgtaatt tcactttccg cttcgctggg  24720
ctcttcctct tcctcttgcg tccgcatacc acgcgccact gggtcgtctt cattcagccg  24780
ccgcactgtg cgcttacctc ctttgccatg cttgattagc accggtgggt tgctgaaacc  24840
caccatttgt agcgccacat cttctctttc ttcctcgctg tccacgatta cctctggtga  24900
tggcgggcgc tcgggcttgg gagaagggcg cttctttttc ttcttgggcg caatggccaa  24960
atccgccgcc gaggtcgatg gccgcgggct gggtgtgcgc ggcaccagcg cgtcttgtga  25020
tgagtcttcc tcgtcctcgg actcgatacg ccgcctcatc cgcttttttg ggggcgcccg  25080
gggaggcggc ggcgacgggg acggggacga cacgtcctcc atggttgggg gacgtcgcgc  25140
cgcaccgcgt ccgcgctcgg gggtggtttc gcgctgctcc tcttcccgac tggccatttc  25200
cttctcctat aggcagaaaa agatcatgga gtcagtcgag aagaaggaca gcctaaccgc  25260
cccctctgag ttcgccacca ccgcctccac cgatgccgcc aacgcgccta ccaccttccc  25320
cgtcgaggca cccccgcttg aggaggagga agtgattatc gagcaggacc caggttttgt  25380
aagcgaagac gacgaggacc gctcagtacc aacagaggat aaaaagcaag accaggacaa  25440
cgcagaggca aacgaggaac aagtcgggcg gggggacgaa aggcatggcg actacctaga  25500
tgtgggagac gacgtgctgt tgaagcatct gcagcgccag tgcgccatta tctgcgacgc  25560
gttgcaagag cgcagcgatg tgcccctcgc catagcggat gtcagccttg cctacgaacg  25620
ccacctattc tcaccgcgcg taccccccaa acgccaagaa aacggcacat gcgagcccaa  25680
cccgcgcctc aacttctacc ccgtatttgc cgtgccagag gtgcttgcca cctatcacat  25740
ctttttccaa aactgcaaga taccccctatc ctgccgtgcc aaccgcagcc gagcggacaa  25800
gcagctggcc ttgcggcagg gcgctgtcat acctgatatc gcctcgctca acgaagtgcc  25860
aaaaatcttt gagggtcttg gacgcgacga gaagcgcgcg gcaaacgctc tgcaacagga  25920
aaacagcgaa aatgaaagtc actctggagt gttggtggaa ctcgagggtg acaacgcgcg  25980
cctagccgta ctaaaacgca gcatcgaggt cacccacttt gcctacccgg cacttaacct  26040
accccccaag gtcatgagca cagtcatgag tgagctgatc gtgcgccgtg cgcagcccct  26100
ggagagggat gcaaatttgc aagaacaaac agaggagggc ctacccgcag ttggcgacga  26160
gcagctagcg cgctggcttc aaacgcgcga gcctgccgac ttggaggagc gacgcaaact  26220
```

-continued

```
aatgatggcc gcagtgctcg ttaccgtgga gcttgagtgc atgcagcggt tctttgctga  26280
cccggagatg cagcgcaagc tagaggaaac attgcactac acctttcgac agggctacgt  26340
acgccaggcc tgcaagatct ccaacgtgga gctctgcaac ctggtctcct accttggaat  26400
tttgcacgaa aaccgccttg ggcaaaacgt gcttcattcc acgctcaagg gcgaggcgcg  26460
ccgcgactac gtccgcgact gcgtttactt atttctatgc tacacctggc agacggccat  26520
gggcgtttgg cagcagtgct tggaggagtg caacctcaag gagctgcaga aactgctaaa  26580
gcaaaacttg aaggacctat ggacggcctt caacgagcgc tccgtggccg cgcacctggc  26640
ggacatcatt ttccccgaac gcctgcttaa aaccctgcaa cagggtctgc cagacttcac  26700
cagtcaaagc atgttgcaga actttaggaa ctttatccta gagcgctcag gaatcttgcc  26760
cgccacctgc tgtgcacttc ctagcgactt tgtgcccatt aagtaccgcg aatgccctcc  26820
gccgctttgg ggccactgct accttctgca gctagccaac taccttgcct accactctga  26880
cataatggaa gacgtgagcg gtgacggtct actggagtgt cactgtcgct gcaacctatg  26940
caccccgcac cgctccctgg tttgcaattc gcagctgctt aacgaaagtc aaattatcgg  27000
tacctttgag ctgcagggtc cctcgcctga cgaaaagtcc gcggctccgg ggttgaaact  27060
cactccgggg ctgtggacgt cggcttacct tcgcaaattt gtacctgagg actaccacgc  27120
ccacgagatt aggttctacg aagaccaatc ccgcccgcca aatgcggagc ttaccgcctg  27180
cgtcattacc cagggccaca ttcttggcca attgcaagcc atcaacaaag cccgccaaga  27240
gtttctgcta cgaaagggac ggggggttta cttggacccc cagtccggcg aggagctcaa  27300
cccaatcccc ccgccgccgc agccctatca gcagcagccg cgggcccttg cttcccagga  27360
tggcacccaa aaagaagctg cagctgccgc cgccacccac ggacgaggag gaatactggg  27420
acagtcaggc agaggaggtt ttggacgagg aggaggagga catgatggaa gactgggaga  27480
gcctagacga ggaagcttcc gaggtcgaag aggtgtcaga cgaaacaccg tcaccctcgg  27540
tcgcattccc ctcgccggcg ccccagaaat cggcaaccgg ttccagcatg gctacaacct  27600
ccgctcctca ggcgccgccg gcactgcccg ttcgccgacc caaccgtaga tgggacacca  27660
ctggaaccag ggccggtaag tccaagcagc cgccgccgtt agcccaagag caacaacagc  27720
gccaaggcta ccgctcatgg cgcgggcaca agaacgccat agttgcttgc ttgcaagact  27780
gtgggggcaa catctccttc gcccgccgct ttcttctcta ccatcacggc gtggccttcc  27840
cccgtaacat cctgcattac taccgtcatc tctacagccc atactgcacc ggcggcagcg  27900
gcagcggcag caacagcagc ggccacacag aagcaaaggc gaccggatag caagactctg  27960
acaaagccca agaaatccac agcggcggca gcagcaggag gaggagcgct gcgtctggcg  28020
cccaacgaac ccgtatcgac ccgcgagctt agaaacagga tttttcccac tctgtatgct  28080
atatttcaac agagcagggg ccaagaacaa gagctgaaaa taaaaaacag gtctctgcga  28140
tccctcaccc gcagctgcct gtatcacaaa agcgaagatc agcttcggcg cacgctggaa  28200
gacgcggagg ctctcttcag taaatactgc gcgctgactc ttaaggacta gtttcgcgcc  28260
ctttctcaaa tttaagcgcg aaaactacgt catctccagc ggccacaccc ggcgccagca  28320
cctgtcgtca gcgccattat gagcaaggaa attcccacgc cctacatgtg gagttaccag  28380
ccacaaatgg gacttgcggc tggagctgcc caagactact caacccgaat aaactacatg  28440
agcgcgggac cccacatgat atcccgggtc aacggaatcc gcgcccaccg aaaccgaatt  28500
ctcttggaac aggcggctat taccaccaca cctcgtaata accttaatcc ccgtagttgg  28560
```

-continued

```
cccgctgccc tggtgtacca ggaaagtccc gctcccacca ctgtggtact tcccagagac  28620
gcccaggccg aagttcagat gactaactca ggggcgcagc ttgcgggcgg ctttcgtcac  28680
agggtgcggt cgcccgggca gggtataact cacctgacaa tcagagggcg aggtattcag  28740
ctcaacgacg agtcggtgag ctcctcgctt ggtctccgtc cggacgggac atttcagatc  28800
ggcggcgccg gccgtccttc attcacgcct cgtcaggcaa tcctaactct gcagacctcg  28860
tcctctgagc cgcgctctgg aggcattgga actctgcaat ttattgagga gtttgtgcca  28920
tcggtctact ttaacccctt ctcgggacct cccggccact atccggatca atttattcct  28980
aactttgacg cggtaaagga ctcggcggac ggctacgact gaatgttaag tggagaggca  29040
gagcaactgc gcctgaaaca cctggtccac tgtcgccgcc acaagtgctt tgcccgcgac  29100
tccggtgagt tttgctactt tgaattgccc gaggatcata tcgagggccc ggcgcacggc  29160
gtccggctta ccgcccaggg agagcttgcc cgtagcctga ttcgggagtt tacccagcgc  29220
cccctgctag ttgagcggga caggggaccc tgtgttctca ctgtgatttg caactgtcct  29280
aaccttggat tacatcaaga tcttaattaa gatcttattc cctttaacta ataaaaaaaa  29340
ataataaagc atcacttact taaaatcagt tagcaaattt ctgtccagtt tattcagcag  29400
cacctccttg ccctcctccc agctctggta ttgcagcttc ctcctggctg caaactttct  29460
ccacaatcta aatggaatgt cagtttcctc ctgttcctgt ccatccgcac ccactatctt  29520
catgttgttg cagatgaagc gcgcaagacc gtctgaagat accttcaacc ccgtgtatcc  29580
atatgacacg gaaaccggtc ctccaactgt gccttttctt actcctccct ttgtatcccc  29640
caatgggttt caagagagtc cccctggggt actctctttg cgcctatccg aacctctagt  29700
tacctccaat ggcatgcttg cgctcaaaat gggcaacggc ctctctctgg acgaggccgg  29760
caaccttacc tcccaaaatg taaccactgt gagcccacct ctcaaaaaaa ccaagtcaaa  29820
cataaacctg gaaatatctg cacccctcac agttacctca gaagccctaa ctgtggctgc  29880
cgccgcacct ctaatggtcg cgggcaacac actcaccatg caatcacagg ccccgctaac  29940
cgtgcacgac tccaaactta gcattgccac ccaaggaccc ctcacagtgt cagaaggaaa  30000
gctagccctg caaacatcag gcccctcac caccaccgat agcagtaccc ttactatcac  30060
tgcctcaccc cctctaacta ctgccactgg tagcttgggc attgacttga aagagcccat  30120
ttatacacaa aatggaaaac taggactaaa gtacggggct cctttgcatg taacagacga  30180
cctaaacact ttgaccgtag caactggtcc aggtgtgact attaataata cttccttgca  30240
aactaaagtt actggagcct tgggttttga ttcacaaggc aatatgcaac ttaatgtagc  30300
aggaggacta aggattgatt ctcaaaacag acgccttata cttgatgtta gttatccgtt  30360
tgatgctcaa aaccaactaa atctaagact aggacagggc cctcttttta taaactcagc  30420
ccacaacttg gatattaact acaacaaagg cctttacttg tttacagctt caaacaattc  30480
caaaaagctt gaggttaacc taagcactgc caaggggttg atgtttgacg ctacagccat  30540
agccattaat gcaggagatg ggcttgaatt tggttcacct aatgcaccaa acacaaatcc  30600
cctcaaaaca aaaattggcc atggcctaga atttgattca aacaaggcta tggttcctaa  30660
actaggaact ggccttagtt ttgacagcac aggtgccatt acagtaggaa acaaaaataa  30720
tgataagcta actttgtgga ccacaccagc tccatctcct aactgtagac taaatgcaga  30780
gaaagatgct aaactcactt tggtcttaac aaaatgtggc agtcaaatac ttgctacagt  30840
ttcagttttg gctgttaaag gcagtttggc tccaatatct ggaacagttc aaagtgctca  30900
tcttattata agatttgacg aaaatggagt gctactaaac aattccttcc tggacccaga  30960
```

-continued

```
atattggaac tttagaaatg gagatcttac tgaaggcaca gcctatacaa acgctgttgg  31020
atttatgcct aacctatcag cttatccaaa atctcacggt aaaactgcca aaagtaacat  31080
tgtcagtcaa gtttacttaa acggagacaa aactaaacct gtaacactaa ccattacact  31140
aaacggtaca caggaaacag gagacacaac tccaagtgca tactctatgt cattttcatg  31200
ggactggtct ggccacaact acattaatga aatatttgcc acatcctctt acactttttc  31260
atacattgcc caagaataaa gaatcgtttg tgttatgttt caacgtgttt atttttcaat  31320
tgcagaaaat ttcaagtcat ttttcattca gtagtatagc cccaccacca catagcttat  31380
acagatcacc gtaccttaat caaactcaca gaaccctagt attcaacctg ccacctccct  31440
cccaacacac agagtacaca gtcctttctc cccggctggc cttaaaaagc atcatatcat  31500
gggtaacaga catattctta ggtgttatat tccacacggt ttcctgtcga gccaaacgct  31560
catcagtgat attaataaac tccccgggca gctcacttaa gttcatgtcg ctgtccagct  31620
gctgagccac aggctgctgt ccaacttgcg gttgcttaac gggcggcgaa ggagaagtcc  31680
acgcctacat gggggtagag tcataatcgt gcatcaggat agggcggtgg tgctgcagca  31740
gcgcgcgaat aaactgctgc cgccgccgct ccgtcctgca ggaatacaac atggcagtgg  31800
tctcctcagc gatgattcgc accgcccgca gcataaggcg ccttgtcctc cgggcacagc  31860
agcgcaccct gatctcactt aaatcagcac agtaactgca gcacagcacc acaatattgt  31920
tcaaaatccc acagtgcaag gcgctgtatc caaagctcat ggcggggacc acagaaccca  31980
cgtggccatc ataccacaag cgcaggtaga ttaagtggcg acccctcata aacacgctgg  32040
acataaacat tacctctttt ggcatgttgt aattcaccac ctcccggtac catataaacc  32100
tctgattaaa catggcgcca tccaccacca tcctaaacca gctggccaaa acctgcccgc  32160
cggctataca ctgcagggaa ccgggactgg aacaatgaca gtggagagcc caggactcgt  32220
aaccatggat catcatgctc gtcatgatat caatgttggc acaacacagg cacacgtgca  32280
tacacttcct caggattaca agctcctccc gcgttagaac catatcccag ggaacaaccc  32340
attcctgaat cagcgtaaat cccacactgc agggaagacc tcgcacgtaa ctcacgttgt  32400
gcattgtcaa agtgttacat tcgggcagca gcggatgatc ctccagtatg gtagcgcggg  32460
tttctgtctc aaaaggaggt agacgatccc tactgtacgg agtgcgccga gacaaccgag  32520
atcgtgttgg tcgtagtgtc atgccaaatg gaacgccgga cgtagtcata tttcctgaag  32580
caaaaccagg tgcgggcgtg acaaacagat ctgcgtctcc ggtctcgccg cttagatcgc  32640
tctgtgtagt agttgtagta tatccactct ctcaaagcat ccaggcgccc cctggcttcg  32700
ggttctatgt aaactccttc atgcgccgct gccctgataa catccaccac cgcagaataa  32760
gccacaccca gccaacctac acattcgttc tgcgagtcac acacgggagg agcgggaaga  32820
gctggaagaa ccatgttttt ttttttattc caaaagatta tccaaaacct caaaatgaag  32880
atctattaag tgaacgcgct cccctccggt ggcgtggtca aactctacag ccaaagaaca  32940
gataatggca tttgtaagat gttgcacaat ggcttccaaa aggcaaacgg ccctcacgtc  33000
caagtggacg taaaggctaa acccttcagg gtgaatctcc tctataaaca ttccagcacc  33060
ttcaaccatg cccaaataat tctcatctcg ccaccttctc aatatatctc taagcaaatc  33120
ccgaatatta agtccggcca ttgtaaaaat ctgctccaga gcgccctcca ccttcagcct  33180
caagcagcga atcatgattg caaaaattca ggttcctcac agacctgtat aagattcaaa  33240
agcggaacat taacaaaaat accgcgatcc cgtaggtccc ttcgcagggc cagctgaaca  33300
```

-continued

```
taatcgtgca ggtctgcacg gaccagcgcg gccacttccc cgccaggaac cttgacaaaa  33360

gaacccacac tgattatgac acgcatactc ggagctatgc taaccagcgt agccccgatg  33420

taagctttgt tgcatgggcg gcgatataaa atgcaaggtg ctgctcaaaa aatcaggcaa  33480

agcctcgcgc aaaaaagaaa gcacatcgta gtcatgctca tgcagataaa ggcaggtaag  33540

ctccggaacc accacagaaa aagacaccat ttttctctca aacatgtctg cgggtttctg  33600

cataaacaca aaataaaata acaaaaaaac atttaaacat tagaagcctg tcttacaaca  33660

ggaaaaacaa cccttataag cataagacgg actacggcca tgccggcgtg accgtaaaaa  33720

aactggtcac cgtgattaaa aagcaccacc gacagctcct cggtcatgtc cggagtcata  33780

atgtaagact cggtaaacac atcaggttga ttcatcggtc agtgctaaaa agcgaccgaa  33840

atagcccggg ggaatacata cccgcaggcg tagagacaac attacagccc ccataggagg  33900

tataacaaaa ttaataggag agaaaaacac ataaacacct gaaaaaccct cctgcctagg  33960

caaaatagca ccctcccgct ccagaacaac atacagcgct tcacagcggc agcctaacag  34020

tcagccttac cagtaaaaaa gaaaacctat taaaaaaaca ccactcgaca cggcaccagc  34080

tcaatcagtc acagtgtaaa aaagggccaa gtgcagagcg agtatatata ggactaaaaa  34140

atgacgtaac ggttaaagtc cacaaaaaac acccagaaaa ccgcacgcga acctacgccc  34200

agaaacgaaa gccaaaaaac ccacaacttc ctcaaatcgt cacttccgtt ttcccacgtt  34260

acgtaacttc ccattttaag aaaactacaa ttcccaacac atacaagtta ctccgcccta  34320

aaacctacgt cacccgcccc gttcccacgc cccgcgccac gtcacaaact ccacccccctc  34380

attatcatat tggcttcaat ccaaaataag gtatattatt gatgatg              34427
```